(12) United States Patent
Domon et al.

(10) Patent No.: US 7,776,555 B1
(45) Date of Patent: Aug. 17, 2010

(54) COLON DISEASE TARGETS AND USES THEREOF

(75) Inventors: Bruno Domon, Zurich (CH); Steve Ruben, Brookeville, MD (US); Charles E. Birse, North Potomac, MD (US); Yeoun Jin Kim, Germantown, MD (US); Tao He, North Potomac, MD (US); Ian McCaffery, Moorpark, CA (US)

(73) Assignee: Celera Corporation, Alameda, CA (US)

( * ) Notice: Subject to any disclaimer, the term of this patent is extended or adjusted under 35 U.S.C. 154(b) by 278 days.

(21) Appl. No.: 11/822,094

(22) Filed: Jul. 2, 2007

Related U.S. Application Data

(63) Continuation of application No. 11/191,273, filed on Jul. 28, 2005, now abandoned.

(60) Provisional application No. 60/592,189, filed on Jul. 30, 2004.

(51) Int. Cl.
*G01N 33/53* (2006.01)

(52) U.S. Cl. ................................................ 435/7.1

(58) Field of Classification Search ................ None
See application file for complete search history.

(56) References Cited

U.S. PATENT DOCUMENTS 5,874,222 A * 2/1999 Jirtle et al. ................. 435/6

OTHER PUBLICATIONS

Tockman et al (Cancer Res., 1992, 52:2711s-2718s).*
Stein et al (Cancer Research, Apr. 2004, 64:2805-2816).*
Charalambous et al (Br J Cancer, May 2003, 88(10): 1598-1604).*

* cited by examiner

*Primary Examiner*—Sean E Aeder

(57) ABSTRACT

The present invention provides a method for diagnosing and detecting diseases associated with colon. The present invention provides one or more proteins or fragments thereof, peptides or nucleic acid molecules differentially expressed in colon diseases (CCAT) and antibodies binds to CCAT. The present invention provides that CCAT is used as targets for screening agents that modulates the CCAT activities. Further the present invention provides methods for treating diseases associated with colon.

3 Claims, No Drawings

SEQUENCE LISTING

```
<160> NUMBER OF SEQ ID NOS: 145

<210> SEQ ID NO 1
<211> LENGTH: 686
<212> TYPE: PRT
<213> ORGANISM: Homo sapiens

<400> SEQUENCE: 1

Met Arg Leu Pro Asp Leu Arg Pro Trp Thr Ser Leu Leu Val Asp
 1               5                  10                  15

Ala Ala Leu Leu Trp Leu Leu Gln Gly Pro Leu Gly Thr Leu Leu Pro
                20                  25                  30

Gln Gly Leu Pro Gly Leu Trp Leu Glu Gly Thr Leu Arg Leu Gly Gly
            35                  40                  45

Leu Trp Gly Leu Leu Lys Leu Arg Gly Leu Leu Gly Phe Val Gly Thr
```

```
         50              55              60
Leu Leu Leu Pro Leu Cys Leu Ala Thr Pro Leu Thr Val Ser Leu Arg
 65              70              75              80

Ala Leu Val Ala Gly Ala Ser Arg Ala Pro Pro Ala Arg Val Ala Ser
             85              90              95

Ala Pro Trp Ser Trp Leu Leu Val Gly Tyr Gly Ala Ala Gly Leu Ser
         100             105             110

Trp Ser Leu Trp Ala Val Leu Ser Pro Pro Gly Ala Gln Glu Lys Glu
         115             120             125

Gln Asp Gln Val Asn Asn Lys Val Leu Met Trp Arg Leu Leu Lys Leu
130             135             140

Ser Arg Pro Asp Leu Pro Leu Leu Val Ala Ala Phe Phe Phe Leu Val
145             150             155             160

Leu Ala Val Leu Gly Glu Thr Leu Ile Pro His Tyr Ser Gly Arg Val
             165             170             175

Ile Asp Ile Leu Gly Gly Asp Phe Asp Pro His Ala Phe Ala Ser Ala
             180             185             190

Ile Phe Phe Met Cys Leu Phe Ser Phe Gly Ser Ser Leu Ser Ala Gly
             195             200             205

Cys Arg Gly Gly Cys Phe Thr Tyr Thr Met Ser Arg Ile Asn Leu Arg
210             215             220

Ile Arg Glu Gln Leu Phe Ser Ser Leu Leu Arg Gln Asp Leu Gly Phe
225             230             235             240

Phe Gln Glu Thr Lys Thr Gly Glu Leu Asn Ser Arg Leu Ser Ser Asp
             245             250             255

Thr Thr Leu Met Ser Asn Trp Leu Pro Leu Asn Ala Asn Val Leu Leu
             260             265             270

Arg Ser Leu Val Lys Val Gly Leu Tyr Gly Phe Met Leu Ser Ile
             275             280             285

Ser Pro Arg Leu Thr Leu Leu Ser Leu Leu His Met Pro Phe Thr Ile
             290             295             300

Ala Ala Glu Lys Val Tyr Asn Thr Arg His Gln Glu Val Leu Arg Glu
305             310             315             320

Ile Gln Asp Ala Val Ala Arg Ala Gly Gln Val Val Arg Glu Ala Val
             325             330             335

Gly Gly Leu Gln Thr Val Arg Ser Phe Gly Ala Glu Glu His Glu Val
             340             345             350

Cys Arg Tyr Lys Glu Ala Leu Glu Gln Cys Arg Gln Leu Tyr Trp Arg
             355             360             365

Arg Asp Leu Glu Arg Ala Leu Tyr Leu Leu Val Arg Arg Val Leu His
370             375             380

Leu Gly Val Gln Met Leu Met Leu Ser Cys Gly Leu Gln Gln Met Gln
385             390             395             400

Asp Gly Glu Leu Thr Gln Gly Ser Leu Leu Ser Phe Met Ile Tyr Gln
             405             410             415

Glu Ser Val Gly Ser Tyr Val Gln Thr Leu Val Tyr Ile Tyr Gly Asp
             420             425             430

Met Leu Ser Asn Val Gly Ala Ala Glu Lys Val Phe Ser Tyr Met Asp
             435             440             445

Arg Gln Pro Asn Leu Pro Ser Pro Gly Thr Leu Ala Pro Thr Thr Leu
             450             455             460

Gln Gly Val Val Lys Phe Gln Asp Val Ser Phe Ala Tyr Pro Asn Arg
465             470             475             480
```

-continued

```
Pro Asp Arg Pro Val Leu Lys Gly Leu Thr Phe Thr Leu Arg Pro Gly
            485                 490                 495
Glu Val Thr Ala Leu Val Gly Pro Asn Gly Ser Gly Lys Ser Thr Val
        500                 505                 510
Ala Ala Leu Leu Gln Asn Leu Tyr Gln Pro Thr Gly Gly Gln Val Leu
    515                 520                 525
Leu Asp Glu Lys Pro Ile Ser Gln Tyr Glu His Cys Tyr Leu His Ser
530                 535                 540
Gln Val Val Ser Val Gly Gln Glu Pro Val Leu Phe Ser Gly Ser Val
545                 550                 555                 560
Arg Asn Asn Ile Ala Tyr Gly Leu Gln Ser Cys Glu Asp Asp Lys Val
                565                 570                 575
Met Ala Ala Gln Ala Ala His Ala Asp Asp Phe Ile Gln Glu Met
            580                 585                 590
Glu His Gly Ile Tyr Thr Asp Val Gly Glu Lys Gly Ser Gln Leu Ala
        595                 600                 605
Ala Gly Gln Lys Gln Arg Leu Ala Ile Ala Arg Ala Leu Val Arg Asp
    610                 615                 620
Pro Arg Val Leu Ile Leu Asp Glu Ala Thr Ser Ala Leu Asp Val Gln
625                 630                 635                 640
Cys Glu Gln Ala Leu Gln Asp Trp Asn Ser Arg Gly Asp Arg Thr Val
                645                 650                 655
Leu Val Ile Ala His Arg Leu Gln Thr Val Gln Arg Ala His Gln Ile
            660                 665                 670
Leu Val Leu Gln Glu Gly Lys Leu Gln Lys Leu Ala Gln Leu
        675                 680                 685

<210> SEQ ID NO 2
<211> LENGTH: 686
<212> TYPE: PRT
<213> ORGANISM: Homo sapiens

<400> SEQUENCE: 2

Met Arg Leu Pro Asp Leu Arg Pro Trp Thr Ser Leu Leu Leu Val Asp
1               5                   10                  15
Ala Ala Leu Leu Trp Leu Leu Gln Gly Pro Leu Gly Thr Leu Leu Pro
            20                  25                  30
Gln Gly Leu Pro Gly Leu Trp Leu Glu Gly Thr Leu Arg Leu Gly Gly
        35                  40                  45
Leu Trp Gly Leu Leu Lys Leu Arg Gly Leu Leu Gly Phe Val Gly Thr
    50                  55                  60
Leu Leu Leu Pro Leu Cys Leu Ala Thr Pro Leu Thr Val Ser Leu Arg
65                  70                  75                  80
Ala Leu Val Ala Gly Ala Ser Arg Ala Pro Pro Ala Arg Val Ala Ser
                85                  90                  95
Ala Pro Trp Ser Trp Leu Leu Val Gly Tyr Gly Ala Ala Gly Leu Ser
            100                 105                 110
Trp Ser Leu Trp Ala Val Leu Ser Pro Pro Gly Ala Gln Glu Lys Glu
        115                 120                 125
Gln Asp Gln Val Asn Asn Lys Val Leu Met Trp Arg Leu Leu Lys Leu
    130                 135                 140
Ser Arg Pro Asp Leu Pro Leu Leu Val Ala Ala Phe Phe Phe Leu Val
145                 150                 155                 160
Leu Ala Val Leu Gly Glu Thr Leu Ile Pro His Tyr Ser Gly Arg Val
```

-continued

```
                165                 170                 175
Ile Asp Ile Leu Gly Gly Asp Phe Asp Pro His Ala Phe Ala Ser Ala
            180                 185                 190
Ile Phe Phe Met Cys Leu Phe Ser Phe Gly Ser Ser Leu Ser Ala Gly
            195                 200                 205
Cys Arg Gly Gly Cys Phe Thr Tyr Thr Met Ser Arg Ile Asn Leu Arg
            210                 215                 220
Ile Arg Glu Gln Leu Phe Ser Ser Leu Leu Arg Gln Asp Leu Gly Phe
225                 230                 235                 240
Phe Gln Glu Thr Lys Thr Gly Glu Leu Asn Ser Arg Leu Ser Ser Asp
            245                 250                 255
Thr Thr Leu Met Ser Asn Trp Leu Pro Leu Asn Ala Asn Val Leu Leu
            260                 265                 270
Arg Ser Leu Val Lys Val Gly Leu Tyr Gly Phe Met Leu Ser Ile
            275                 280                 285
Ser Pro Arg Leu Thr Leu Leu Ser Leu Leu His Met Pro Phe Thr Ile
            290                 295                 300
Ala Ala Glu Lys Val Tyr Asn Thr Arg His Gln Glu Val Leu Arg Glu
305                 310                 315                 320
Ile Gln Asp Ala Val Ala Arg Ala Gly Gln Val Val Arg Glu Ala Val
            325                 330                 335
Gly Gly Leu Gln Thr Val Arg Ser Phe Gly Ala Glu Glu His Glu Val
            340                 345                 350
Cys Arg Tyr Lys Glu Ala Leu Glu Gln Cys Arg Gln Leu Tyr Trp Arg
            355                 360                 365
Arg Asp Leu Glu Arg Ala Leu Tyr Leu Leu Val Arg Arg Val Leu His
            370                 375                 380
Leu Gly Val Gln Met Leu Met Leu Ser Cys Gly Leu Gln Gln Met Gln
385                 390                 395                 400
Asp Gly Glu Leu Thr Gln Gly Ser Leu Leu Ser Phe Met Ile Tyr Gln
            405                 410                 415
Glu Ser Val Gly Ser Tyr Val Gln Thr Leu Val Tyr Ile Tyr Gly Asp
            420                 425                 430
Met Leu Ser Asn Val Gly Ala Ala Glu Lys Val Phe Ser Tyr Met Asp
            435                 440                 445
Arg Gln Pro Asn Leu Pro Ser Pro Gly Thr Leu Ala Pro Thr Thr Leu
            450                 455                 460
Gln Gly Val Val Lys Phe Gln Asp Val Ser Phe Ala Tyr Pro Asn Arg
465                 470                 475                 480
Pro Asp Arg Pro Val Leu Lys Gly Leu Thr Phe Thr Leu Arg Pro Gly
            485                 490                 495
Glu Val Thr Ala Leu Val Gly Pro Asn Gly Ser Gly Lys Ser Thr Val
            500                 505                 510
Ala Ala Leu Leu Gln Asn Leu Tyr Gln Pro Thr Gly Gly Gln Val Leu
            515                 520                 525
Leu Asp Glu Lys Pro Ile Ser Gln Tyr Glu His Cys Tyr Leu His Ser
            530                 535                 540
Gln Val Val Ser Val Gly Gln Glu Pro Val Leu Phe Ser Gly Ser Val
545                 550                 555                 560
Arg Asn Asn Ile Ala Tyr Gly Leu Gln Ser Cys Glu Asp Asp Lys Val
            565                 570                 575
Met Ala Ala Ala Gln Ala Ala His Ala Asp Asp Phe Ile Gln Glu Met
            580                 585                 590
```

Glu His Gly Ile Tyr Thr Asp Val Gly Glu Lys Gly Ser Gln Leu Ala
            595                 600                 605

Ala Gly Gln Lys Gln Arg Leu Ala Ile Ala Arg Ala Leu Val Arg Asp
            610                 615                 620

Pro Arg Val Leu Ile Leu Asp Glu Ala Thr Ser Ala Leu Asp Val Gln
625                 630                 635                 640

Cys Glu Gln Ala Leu Gln Asp Trp Asn Ser Arg Gly Asp Arg Thr Val
            645                 650                 655

Leu Val Ile Ala His Arg Leu Gln Thr Val Gln Arg Ala His Gln Ile
            660                 665                 670

Leu Val Leu Gln Glu Gly Lys Leu Gln Lys Leu Ala Gln Leu
            675                 680                 685

<210> SEQ ID NO 3
<211> LENGTH: 653
<212> TYPE: PRT
<213> ORGANISM: Homo sapiens

<400> SEQUENCE: 3

Met Arg Leu Pro Asp Leu Arg Pro Trp Thr Ser Leu Leu Leu Val Asp
  1               5                  10                  15

Ala Ala Leu Leu Trp Leu Leu Gln Gly Pro Leu Gly Thr Leu Leu Pro
             20                  25                  30

Gln Gly Leu Pro Gly Leu Trp Leu Glu Gly Thr Leu Arg Leu Gly Gly
             35                  40                  45

Leu Trp Gly Leu Leu Lys Leu Arg Gly Leu Leu Gly Phe Val Gly Thr
 50                  55                  60

Leu Leu Leu Pro Leu Cys Leu Ala Thr Pro Leu Thr Val Ser Leu Arg
 65                  70                  75                  80

Ala Leu Val Ala Gly Ala Ser Arg Ala Pro Pro Ala Arg Val Ala Ser
             85                  90                  95

Ala Pro Trp Ser Trp Leu Leu Val Gly Tyr Gly Ala Ala Gly Leu Ser
            100                 105                 110

Trp Ser Leu Trp Ala Val Leu Ser Pro Pro Gly Ala Gln Glu Lys Glu
            115                 120                 125

Gln Asp Gln Val Asn Asn Lys Val Leu Met Trp Arg Leu Leu Lys Leu
            130                 135                 140

Ser Arg Pro Asp Leu Pro Leu Leu Val Ala Ala Phe Phe Phe Leu Val
145                 150                 155                 160

Leu Ala Val Leu Gly Glu Thr Leu Ile Pro His Tyr Ser Gly Arg Val
            165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
            195                 200                 205

Cys Arg Gly Gly Cys Phe Thr Tyr Thr Met Ser Arg Ile Asn Leu Arg
            210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
            245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile

```
                275                 280                 285
Ser Pro Arg Leu Thr Leu Leu Ser Leu Leu His Met Pro Phe Thr Ile
    290                 295                 300
Ala Ala Glu Lys Val Tyr Asn Thr Arg His Gln Glu Val Leu Arg Glu
305                 310                 315                 320
Ile Gln Asp Ala Val Ala Arg Ala Gly Gln Val Val Arg Glu Ala Val
                325                 330                 335
Gly Gly Leu Gln Thr Val Arg Ser Phe Gly Ala Glu Glu His Glu Val
                340                 345                 350
Cys Arg Tyr Lys Glu Ala Leu Glu Gln Cys Arg Gln Leu Tyr Trp Arg
                355                 360                 365
Arg Asp Leu Glu Arg Ala Leu Tyr Leu Leu Ile Arg Arg Val Leu His
            370                 375                 380
Leu Gly Val Gln Met Leu Met Leu Ser Cys Gly Leu Gln Gln Met Gln
385                 390                 395                 400
Asp Gly Glu Leu Thr Gln Gly Ser Leu Leu Ser Phe Met Ile Tyr Gln
                405                 410                 415
Glu Ser Val Gly Ser Tyr Val Gln Thr Leu Val Tyr Ile Tyr Gly Asp
            420                 425                 430
Met Leu Ser Asn Val Gly Ala Ala Glu Lys Val Phe Ser Tyr Met Asp
            435                 440                 445
Arg Gln Pro Asn Leu Pro Ser Pro Gly Thr Leu Ala Pro Thr Thr Leu
        450                 455                 460
Gln Gly Val Val Lys Phe Gln Asp Val Ser Phe Ala Tyr Pro Asn Arg
465                 470                 475                 480
Pro Asp Arg Pro Val Leu Lys Gly Leu Thr Phe Thr Leu Arg Pro Gly
                485                 490                 495
Glu Val Thr Ala Leu Val Gly Pro Asn Gly Ser Gly Lys Ser Thr Val
                500                 505                 510
Ala Ala Leu Leu Gln Asn Leu Tyr Gln Pro Thr Gly Gly Gln Val Leu
            515                 520                 525
Leu Asp Glu Lys Pro Ile Ser Gln Tyr Glu His Cys Tyr Leu His Ser
        530                 535                 540
Gln Val Val Ser Val Gly Gln Glu Pro Val Leu Phe Ser Gly Ser Val
545                 550                 555                 560
Arg Asn Asn Ile Ala Tyr Gly Leu Gln Ser Cys Glu Asp Asp Lys Val
                565                 570                 575
Met Ala Ala Ala Gln Ala Ala His Ala Asp Asp Phe Ile Gln Glu Met
            580                 585                 590
Glu His Gly Ile Tyr Thr Asp Val Gly Glu Lys Gly Ser Gln Leu Ala
        595                 600                 605
Ala Gly Gln Lys Gln Arg Leu Ala Ile Ala Arg Ala Leu Val Arg Asp
    610                 615                 620
Pro Arg Val Leu Ile Leu Asp Glu Ala Thr Ser Ala Leu Asp Val Gln
625                 630                 635                 640
Cys Glu Gln Ala Lys Thr Leu Trp Lys Phe Met Ile Phe
                645                 650

<210> SEQ ID NO 4
<211> LENGTH: 653
<212> TYPE: PRT
<213> ORGANISM: Homo sapiens

<400> SEQUENCE: 4
```

```
Met Arg Leu Pro Asp Leu Arg Pro Trp Thr Ser Leu Leu Val Asp
 1               5                  10                  15

Ala Ala Leu Leu Trp Leu Leu Gln Gly Pro Leu Gly Thr Leu Leu Pro
                 20                  25                  30

Gln Gly Leu Pro Gly Leu Trp Leu Glu Gly Thr Leu Arg Leu Gly Gly
             35                  40                  45

Leu Trp Gly Leu Leu Lys Leu Arg Gly Leu Leu Gly Phe Val Gly Thr
 50                  55                  60

Leu Leu Leu Pro Leu Cys Leu Ala Thr Pro Leu Thr Val Ser Leu Arg
 65                  70                  75                  80

Ala Leu Val Ala Gly Ala Ser Arg Ala Pro Pro Ala Arg Val Ala Ser
                 85                  90                  95

Ala Pro Trp Ser Trp Leu Leu Val Gly Tyr Gly Ala Ala Gly Leu Ser
                100                 105                 110

Trp Ser Leu Trp Ala Val Leu Ser Pro Pro Gly Ala Gln Glu Lys Glu
            115                 120                 125

Gln Asp Gln Val Asn Asn Lys Val Leu Met Trp Arg Leu Leu Lys Leu
        130                 135                 140

Ser Arg Pro Asp Leu Pro Leu Val Ala Ala Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
            195                 200                 205

Cys Arg Gly Gly Cys Phe Thr Tyr Thr Met Ser Arg Ile Asn Leu Arg
210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile
275                 280                 285

Ser Pro Arg Leu Thr Leu Leu Ser Leu Leu His Met Pro Phe Thr Ile
        290                 295                 300

Ala Ala Glu Lys Val Tyr Asn Thr Arg His Gln Glu Val Leu Arg Glu
305                 310                 315                 320

Ile Gln Asp Ala Val Ala Arg Ala Gly Gln Val Val Arg Glu Ala Val
                325                 330                 335

Gly Gly Leu Gln Thr Val Arg Ser Phe Gly Ala Glu Glu His Glu Val
            340                 345                 350

Cys Arg Tyr Lys Glu Ala Leu Glu Gln Cys Arg Gln Leu Tyr Trp Arg
        355                 360                 365

Arg Asp Leu Glu Arg Ala Leu Tyr Leu Leu Val Arg Arg Val Leu His
        370                 375                 380

Leu Gly Val Gln Met Leu Met Leu Ser Cys Gly Leu Gln Gln Met Gln
385                 390                 395                 400

Asp Gly Glu Leu Thr Gln Gly Ser Leu Leu Ser Phe Met Ile Tyr Gln
                405                 410                 415

Glu Ser Val Gly Ser Tyr Val Gln Thr Leu Val Tyr Ile Tyr Gly Asp
```

-continued

```
                420                 425                 430
Met Leu Ser Asn Val Gly Ala Ala Glu Lys Val Phe Ser Tyr Met Asp
            435                 440                 445

Arg Gln Pro Asn Leu Pro Ser Pro Gly Thr Leu Ala Pro Thr Thr Leu
        450                 455                 460

Gln Gly Val Val Lys Phe Gln Asp Val Ser Phe Ala Tyr Pro Asn Arg
465                 470                 475                 480

Pro Asp Arg Pro Val Leu Lys Gly Leu Thr Phe Thr Leu Arg Pro Gly
                485                 490                 495

Glu Val Thr Ala Leu Val Gly Pro Asn Gly Ser Gly Lys Ser Thr Val
            500                 505                 510

Ala Ala Leu Leu Gln Asn Leu Tyr Gln Pro Thr Gly Gly Gln Val Leu
        515                 520                 525

Leu Asp Glu Lys Pro Ile Ser Gln Tyr Glu His Cys Tyr Leu His Ser
530                 535                 540

Gln Val Val Ser Val Gly Gln Glu Pro Val Leu Phe Ser Gly Ser Val
                545                 550                 555                 560

Arg Asn Asn Ile Ala Tyr Gly Leu Gln Ser Cys Glu Asp Asp Lys Val
            565                 570                 575

Met Ala Ala Gln Ala Ala His Ala Asp Asp Phe Ile Gln Glu Met
        580                 585                 590

Glu His Gly Ile Tyr Thr Asp Val Gly Glu Lys Gly Ser Gln Leu Ala
            595                 600                 605

Ala Gly Gln Lys Gln Arg Leu Ala Ile Ala Arg Ala Leu Val Arg Asp
        610                 615                 620

Pro Arg Val Leu Ile Leu Asp Glu Ala Thr Ser Ala Leu Asp Val Gln
625                 630                 635                 640

Cys Glu Gln Ala Lys Thr Leu Trp Lys Phe Met Ile Phe
                645                 650
```

<210> SEQ ID NO 5
<211> LENGTH: 703
<212> TYPE: PRT
<213> ORGANISM: Homo sapiens

<400> SEQUENCE: 5

```
Met Arg Leu Pro Asp Leu Arg Pro Trp Thr Ser Leu Leu Leu Val Asp
  1               5                  10                  15

Ala Ala Leu Leu Trp Leu Leu Gln Gly Pro Leu Gly Thr Leu Leu Pro
            20                  25                  30

Gln Gly Leu Pro Gly Leu Trp Leu Glu Gly Thr Leu Arg Leu Gly Gly
        35                  40                  45

Leu Trp Gly Leu Leu Lys Leu Arg Gly Leu Leu Gly Phe Val Gly Thr
    50                  55                  60

Leu Leu Leu Pro Leu Cys Leu Ala Thr Pro Leu Thr Val Ser Leu Arg
65                  70                  75                  80

Ala Leu Val Ala Gly Ala Ser Arg Ala Pro Pro Ala Arg Val Ala Ser
                85                  90                  95

Ala Pro Trp Ser Trp Leu Leu Val Gly Tyr Gly Ala Ala Gly Leu Ser
            100                 105                 110

Trp Ser Leu Trp Ala Val Leu Ser Pro Pro Gly Ala Gln Glu Lys Glu
        115                 120                 125

Gln Asp Gln Val Asn Asn Lys Val Leu Met Trp Arg Leu Leu Lys Leu
    130                 135                 140
```

```
Ser Arg Pro Asp Leu Pro Leu Val Ala Ala Phe Phe Phe Leu Val
145                 150                 155                 160

Leu Ala Val Leu Gly Glu Thr Leu Ile Pro His Tyr Ser Gly Arg Val
            165                 170                 175

Ile Asp Ile Leu Gly Gly Asp Phe Asp Pro His Ala Phe Ala Ser Ala
        180                 185                 190

Ile Phe Phe Met Cys Leu Phe Ser Phe Gly Ser Ser Leu Ser Ala Gly
            195                 200                 205

Cys Arg Gly Gly Cys Phe Thr Tyr Thr Met Ser Arg Ile Asn Leu Arg
        210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile
        275                 280                 285

Ser Pro Arg Leu Thr Leu Leu Ser Leu Leu His Met Pro Phe Thr Ile
290                 295                 300

Ala Ala Glu Lys Val Tyr Asn Thr Arg His Gln Glu Val Leu Arg Glu
305                 310                 315                 320

Ile Gln Asp Ala Val Ala Arg Ala Gly Gln Val Val Arg Glu Ala Val
                325                 330                 335

Gly Gly Leu Gln Thr Val Arg Ser Phe Gly Ala Glu Glu His Glu Val
            340                 345                 350

Cys Arg Tyr Lys Glu Ala Leu Glu Gln Cys Arg Gln Leu Tyr Trp Arg
        355                 360                 365

Arg Asp Leu Glu Arg Ala Leu Tyr Leu Leu Ile Arg Arg Val Leu His
        370                 375                 380

Leu Gly Val Gln Met Leu Met Leu Ser Cys Gly Leu Gln Gln Met Gln
385                 390                 395                 400

Asp Gly Glu Leu Thr Gln Gly Ser Leu Leu Ser Phe Met Ile Tyr Gln
                405                 410                 415

Glu Ser Val Gly Ser Tyr Val Gln Thr Leu Val Tyr Ile Tyr Gly Asp
            420                 425                 430

Met Leu Ser Asn Val Gly Ala Ala Glu Lys Val Phe Ser Tyr Met Asp
        435                 440                 445

Arg Gln Pro Asn Leu Pro Ser Pro Gly Thr Leu Ala Pro Thr Thr Leu
        450                 455                 460

Gln Gly Val Val Lys Phe Gln Asp Val Ser Phe Ala Tyr Pro Asn Arg
465                 470                 475                 480

Pro Asp Arg Pro Val Leu Lys Gly Leu Thr Phe Thr Leu Arg Pro Gly
                485                 490                 495

Glu Val Thr Ala Leu Val Gly Pro Asn Gly Ser Gly Lys Ser Thr Val
            500                 505                 510

Ala Ala Leu Leu Gln Asn Leu Tyr Gln Pro Thr Gly Gly Gln Val Leu
        515                 520                 525

Leu Asp Glu Lys Pro Ile Ser Gln Tyr Glu His Cys Tyr Leu His Ser
        530                 535                 540

Gln Val Val Ser Val Gly Gln Glu Pro Val Leu Phe Ser Gly Ser Val
545                 550                 555                 560

Arg Asn Asn Ile Ala Tyr Gly Leu Gln Ser Cys Glu Asp Asp Lys Val
```

```
                  565                 570                 575
Met Ala Ala Gln Ala His Ala Asp Asp Phe Ile Gln Glu Met
            580                 585                 590

Glu His Gly Ile Tyr Thr Asp Val Gly Glu Lys Gly Ser Gln Leu Ala
            595                 600                 605

Ala Gly Gln Lys Gln Arg Leu Ala Ile Ala Arg Ala Leu Val Arg Asp
            610                 615                 620

Pro Arg Val Leu Ile Leu Asp Glu Ala Thr Ser Ala Leu Asp Val Gln
625                 630                 635                 640

Cys Glu Gln Ala Leu Gln Asp Trp Asn Ser Arg Gly Asp Arg Thr Val
            645                 650                 655

Leu Val Ile Ala His Arg Leu Gln Ala Val Gln Arg Ala His Gln Ile
            660                 665                 670

Leu Val Leu Gln Glu Gly Lys Leu Gln Lys Leu Ala Gln Leu Gln Glu
            675                 680                 685

Gly Gln Asp Leu Tyr Ser Arg Leu Val Gln Gln Arg Leu Met Asp
            690                 695                 700
```

<210> SEQ ID NO 6
<211> LENGTH: 254
<212> TYPE: PRT
<213> ORGANISM: Homo sapiens

<400> SEQUENCE: 6

```
Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
            35                  40                  45

Phe Asp Phe Asp Gly Asp Glu Ile Phe His Val Asp Met Ala Lys Lys
        50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
            85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
            115                 120                 125

Val Leu Ile Cys Phe Ile Asp Lys Phe Thr Pro Pro Val Val Asn Val
        130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
            165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
        210                 215                 220

Thr Val Gly Leu Val Gly Ile Ile Ile Gly Thr Ile Phe Ile Ile Lys
225                 230                 235                 240
```

```
Gly Val Arg Lys Ser Asn Ala Ala Glu Arg Arg Gly Pro Leu
                245                 250
```

```
<210> SEQ ID NO 7
<211> LENGTH: 254
<212> TYPE: PRT
<213> ORGANISM: Homo sapiens

<400> SEQUENCE: 7

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
                20                  25                  30

Ile Gln Ala Glu Phe Tyr Leu Asn Pro Asp Gln Ser Gly Glu Phe Met
            35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240

Gly Val Arg Lys Ser Asn Ala Ala Glu Arg Arg Gly Pro Leu
                245                 250
```

```
<210> SEQ ID NO 8
<211> LENGTH: 268
<212> TYPE: PRT
<213> ORGANISM: Homo sapiens

<400> SEQUENCE: 8

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
                20                  25                  30

Ile Gln Ala Glu Phe Tyr Leu Asn Pro Asp Gln Ser Gly Glu Phe Met
            35                  40                  45

Phe Asp Phe Asp Gly Asp Glu Ile Phe His Val Asp Met Ala Lys Lys
    50                  55                  60
```

```
Glu Thr Val Trp Arg Leu Glu Phe Gly Arg Phe Ala Ser Phe Glu
 65                  70                  75                  80

Ala Gln Gly Ala Leu Ala Asn Ile Ala Val Asp Lys Ala Asn Leu Glu
             85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
            115                 120                 125

Val Leu Ile Cys Phe Ile Asp Lys Phe Thr Pro Pro Val Val Asn Val
            130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
                180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
210                 215                 220

Thr Val Gly Leu Val Gly Ile Ile Gly Thr Ile Phe Ile Ile Lys
225                 230                 235                 240

Gly Val Met Val Phe Leu Arg Glu Lys Ile Thr Glu Thr Ser Ala
                245                 250                 255

Leu Met Thr Leu Gln Ser Trp Gln Tyr Tyr Asn Pro
                260                 265

<210> SEQ ID NO 9
<211> LENGTH: 207
<212> TYPE: PRT
<213> ORGANISM: Homo sapiens

<400> SEQUENCE: 9

Met Phe Asp Phe Asp Gly Asp Glu Ile Phe His Val Asp Met Ala Lys
 1                   5                  10                  15

Lys Glu Thr Val Trp Arg Leu Glu Glu Phe Gly Arg Phe Ala Ser Phe
                 20                  25                  30

Glu Ala Gln Gly Ala Leu Ala Asn Ile Ala Val Asp Lys Ala Asn Leu
             35                  40                  45

Glu Ile Met Thr Lys Arg Ser Asn Tyr Thr Pro Ile Thr Asn Val Pro
 50                  55                  60

Pro Glu Val Thr Val Leu Thr Asn Ser Pro Val Glu Leu Arg Glu Pro
 65                  70                  75                  80

Asn Val Leu Ile Cys Phe Ile Asp Lys Phe Thr Pro Pro Val Val Asn
                 85                  90                  95

Val Thr Trp Leu Arg Asn Gly Lys Pro Val Thr Thr Gly Val Ser Glu
            100                 105                 110

Thr Val Phe Leu Pro Arg Glu Asp His Leu Phe Arg Lys Phe His Tyr
            115                 120                 125

Leu Pro Phe Leu Pro Ser Thr Glu Asp Val Tyr Asp Cys Arg Val Glu
            130                 135                 140

His Trp Gly Leu Asp Glu Pro Leu Leu Lys His Trp Glu Phe Asp Ala
145                 150                 155                 160

Pro Ser Pro Leu Pro Glu Thr Thr Glu Asn Val Val Cys Ala Leu Gly
                165                 170                 175
```

```
Leu Thr Val Gly Leu Val Gly Ile Ile Ile Gly Thr Ile Phe Ile Ile
            180                 185                 190

Lys Gly Val Arg Lys Ser Asn Ala Ala Glu Arg Arg Gly Pro Leu
        195                 200                 205

<210> SEQ ID NO 10
<211> LENGTH: 675
<212> TYPE: PRT
<213> ORGANISM: Homo sapiens

<400> SEQUENCE: 10

Met Ala Ala Ala Lys Val Ala Leu Thr Lys Arg Ala Asp Pro Ala Glu
  1               5                  10                  15

Leu Arg Thr Ile Phe Leu Lys Tyr Ala Ser Ile Glu Lys Asn Gly Glu
             20                  25                  30

Phe Phe Met Ser Pro Asn Asp Phe Val Thr Arg Tyr Leu Asn Ile Phe
         35                  40                  45

Gly Glu Ser Gln Pro Asn Pro Lys Thr Val Glu Leu Leu Ser Gly Val
     50                  55                  60

Val Asp Gln Thr Lys Asp Gly Leu Ile Ser Phe Gln Glu Phe Val Ala
 65                  70                  75                  80

Phe Glu Ser Val Leu Cys Ala Pro Asp Ala Leu Phe Met Val Ala Phe
                 85                  90                  95

Gln Leu Phe Asp Lys Ala Gly Lys Gly Glu Val Thr Phe Glu Asp Val
            100                 105                 110

Lys Gln Val Phe Gly Gln Thr Thr Ile His Gln His Ile Pro Phe Asn
        115                 120                 125

Trp Asp Ser Glu Phe Val Gln Leu His Phe Gly Lys Glu Arg Lys Arg
    130                 135                 140

His Leu Thr Tyr Ala Glu Phe Thr Gln Phe Leu Leu Glu Ile Gln Leu
145                 150                 155                 160

Glu His Ala Lys Gln Ala Phe Val Gln Arg Asp Asn Ala Arg Thr Gly
                165                 170                 175

Arg Val Thr Ala Ile Asp Phe Arg Asp Ile Met Val Thr Ile Arg Pro
            180                 185                 190

His Val Leu Thr Pro Phe Val Glu Glu Cys Leu Val Ala Ala Ala Gly
        195                 200                 205

Gly Thr Thr Ser His Gln Val Ser Phe Ser Tyr Phe Asn Gly Phe Asn
    210                 215                 220

Ser Leu Leu Asn Asn Met Glu Leu Ile Arg Lys Ile Tyr Ser Thr Leu
225                 230                 235                 240

Ala Gly Thr Arg Lys Asp Val Glu Val Thr Lys Glu Glu Phe Val Leu
                245                 250                 255

Ala Ala Gln Lys Phe Gly Gln Val Thr Pro Met Glu Val Asp Ile Leu
            260                 265                 270

Phe Gln Leu Ala Asp Leu Tyr Glu Pro Arg Gly Arg Met Thr Leu Ala
        275                 280                 285

Asp Ile Glu Arg Ile Ala Pro Leu Glu Glu Gly Thr Leu Pro Phe Asn
    290                 295                 300

Leu Ala Glu Ala Gln Arg Gln Lys Ala Ser Gly Asp Ser Ala Arg Pro
305                 310                 315                 320

Val Leu Leu Gln Val Ala Glu Ser Ala Tyr Arg Phe Gly Leu Gly Ser
                325                 330                 335

Val Ala Gly Ala Val Gly Ala Thr Ala Val Tyr Pro Ile Asp Leu Val
```

```
            340                 345                 350
Lys Thr Arg Met Gln Asn Gln Arg Ser Thr Gly Ser Phe Val Gly Glu
        355                 360                 365

Leu Met Tyr Lys Asn Ser Phe Asp Cys Phe Lys Lys Val Leu Arg Tyr
    370                 375                 380

Glu Gly Phe Phe Gly Leu Tyr Arg Gly Leu Leu Pro Gln Leu Leu Gly
385                 390                 395                 400

Val Ala Pro Glu Lys Ala Ile Lys Leu Thr Val Asn Asp Phe Val Arg
                405                 410                 415

Asp Lys Phe Met His Lys Asp Gly Ser Val Pro Leu Ala Ala Glu Ile
            420                 425                 430

Leu Ala Gly Gly Cys Ala Gly Gly Ser Gln Val Ile Phe Thr Asn Pro
        435                 440                 445

Leu Glu Ile Val Lys Ile Arg Leu Gln Val Ala Gly Glu Ile Thr Thr
    450                 455                 460

Gly Pro Arg Val Ser Ala Leu Ser Val Val Arg Asp Leu Gly Phe Phe
465                 470                 475                 480

Gly Ile Tyr Lys Gly Ala Lys Ala Cys Phe Leu Arg Asp Ile Pro Phe
                485                 490                 495

Ser Ala Ile Tyr Phe Pro Cys Tyr Ala His Val Lys Ala Ser Phe Ala
            500                 505                 510

Asn Glu Asp Gly Gln Val Ser Pro Gly Ser Leu Leu Leu Ala Gly Ala
        515                 520                 525

Ile Ala Gly Met Pro Ala Ala Ser Leu Val Thr Pro Ala Asp Val Ile
    530                 535                 540

Lys Thr Arg Leu Gln Val Ala Ala Arg Ala Gly Gln Thr Thr Tyr Ser
545                 550                 555                 560

Gly Val Ile Asp Cys Phe Arg Lys Ile Leu Arg Glu Gly Pro Lys
                565                 570                 575

Ala Leu Trp Lys Gly Ala Gly Ala Arg Val Phe Arg Ser Ser Pro Gln
            580                 585                 590

Phe Gly Val Thr Leu Leu Thr Tyr Glu Leu Leu Gln Arg Trp Phe Tyr
        595                 600                 605

Ile Asp Phe Gly Gly Val Lys Pro Met Gly Ser Glu Pro Val Pro Lys
    610                 615                 620

Ser Arg Ile Asn Leu Pro Ala Pro Asn Pro Asp His Val Gly Gly Tyr
625                 630                 635                 640

Lys Leu Ala Val Ala Thr Phe Ala Gly Ile Glu Asn Lys Phe Gly Leu
                645                 650                 655

Tyr Leu Pro Leu Phe Lys Pro Ser Val Ser Thr Ser Lys Ala Ile Gly
            660                 665                 670

Gly Gly Pro
        675

<210> SEQ ID NO 11
<211> LENGTH: 675
<212> TYPE: PRT
<213> ORGANISM: Homo sapiens

<400> SEQUENCE: 11

Met Ala Ala Ala Lys Val Ala Leu Thr Lys Arg Ala Asp Pro Ala Glu
 1               5                  10                  15

Leu Arg Thr Ile Phe Leu Lys Tyr Ala Ser Ile Glu Lys Asn Gly Glu
            20                  25                  30
```

```
Phe Phe Met Ser Pro Asn Asp Phe Val Thr Arg Tyr Leu Asn Ile Phe
         35                  40                  45

Gly Glu Ser Gln Pro Asn Pro Lys Thr Val Glu Leu Leu Ser Gly Val
     50                  55                  60

Val Asp Gln Thr Lys Asp Gly Leu Ile Ser Phe Gln Glu Phe Val Ala
65                   70                  75                  80

Phe Glu Ser Val Leu Cys Ala Pro Asp Ala Leu Phe Met Val Ala Phe
                 85                  90                  95

Gln Leu Phe Asp Lys Ala Gly Lys Gly Glu Val Thr Phe Glu Asp Val
             100                 105                 110

Lys Gln Val Phe Gly Gln Thr Thr Ile His Gln His Ile Pro Phe Asn
         115                 120                 125

Trp Asp Ser Glu Phe Val Gln Leu His Phe Gly Lys Glu Arg Lys Arg
     130                 135                 140

His Leu Thr Tyr Ala Glu Phe Thr Gln Phe Leu Leu Glu Ile Gln Leu
145                 150                 155                 160

Glu His Ala Lys Gln Ala Phe Val Gln Arg Asp Asn Ala Arg Thr Gly
                 165                 170                 175

Arg Val Thr Ala Ile Asp Phe Arg Asp Ile Met Val Thr Ile Arg Pro
             180                 185                 190

His Val Leu Thr Pro Phe Val Glu Glu Cys Leu Val Ala Ala Ala Gly
         195                 200                 205

Gly Thr Thr Ser His Gln Val Ser Phe Ser Tyr Phe Asn Gly Phe Asn
     210                 215                 220

Ser Leu Leu Asn Asn Met Glu Leu Ile Arg Lys Ile Tyr Ser Thr Leu
225                 230                 235                 240

Ala Gly Thr Arg Lys Asp Val Glu Val Thr Lys Glu Glu Phe Val Leu
                 245                 250                 255

Ala Ala Gln Lys Phe Gly Gln Val Thr Pro Met Glu Val Asp Ile Leu
             260                 265                 270

Phe Gln Leu Ala Asp Leu Tyr Glu Pro Arg Gly Arg Met Thr Leu Ala
         275                 280                 285

Asp Ile Glu Arg Ile Ala Pro Leu Glu Glu Gly Thr Leu Pro Phe Asn
     290                 295                 300

Leu Ala Glu Ala Gln Arg Gln Lys Ala Ser Gly Asp Ser Ala Arg Pro
305                 310                 315                 320

Val Leu Leu Gln Val Ala Glu Ser Ala Tyr Arg Phe Gly Leu Gly Ser
                 325                 330                 335

Val Ala Gly Ala Val Gly Ala Thr Ala Val Tyr Pro Ile Asp Leu Val
             340                 345                 350

Lys Thr Arg Met Gln Asn Gln Arg Ser Thr Gly Ser Phe Val Gly Glu
         355                 360                 365

Leu Met Tyr Lys Asn Ser Phe Asp Cys Phe Lys Lys Val Leu Arg Tyr
     370                 375                 380

Glu Gly Phe Phe Gly Leu Tyr Arg Gly Leu Leu Pro Gln Leu Leu Gly
385                 390                 395                 400

Val Ala Pro Glu Lys Ala Ile Lys Leu Thr Val Asn Asp Phe Val Arg
                 405                 410                 415

Asp Lys Phe Met His Lys Asp Gly Ser Val Pro Leu Ala Ala Glu Ile
             420                 425                 430

Leu Ala Gly Gly Cys Ala Gly Gly Ser Gln Val Ile Phe Thr Asn Pro
         435                 440                 445

Leu Glu Ile Val Lys Ile Arg Leu Gln Val Ala Gly Glu Ile Thr Thr
```

```
                450             455             460
Gly Pro Arg Val Ser Ala Leu Ser Val Val Arg Asp Leu Gly Phe Phe
465                 470             475                 480

Gly Ile Tyr Lys Gly Ala Lys Ala Cys Phe Leu Arg Asp Ile Pro Phe
                485             490             495

Ser Ala Ile Tyr Phe Pro Cys Tyr Ala His Val Lys Ala Ser Phe Ala
                500             505             510

Asn Glu Asp Gly Gln Val Ser Pro Gly Ser Leu Leu Ala Gly Ala
            515             520             525

Ile Ala Gly Met Pro Ala Ala Ser Leu Val Thr Pro Ala Asp Val Ile
530             535             540

Lys Thr Arg Leu Gln Val Ala Ala Arg Ala Gly Gln Thr Thr Tyr Ser
545             550             555             560

Gly Val Ile Asp Cys Phe Arg Lys Ile Leu Arg Glu Gly Pro Lys
                565             570             575

Ala Leu Trp Lys Gly Ala Gly Ala Arg Val Phe Arg Ser Ser Pro Gln
            580             585             590

Phe Gly Val Thr Leu Leu Thr Tyr Glu Leu Leu Gln Arg Trp Phe Tyr
            595             600             605

Ile Asp Phe Gly Gly Val Lys Pro Met Gly Ser Glu Pro Val Pro Lys
610             615             620

Ser Arg Ile Asn Leu Pro Ala Pro Asn Pro Asp His Val Gly Gly Tyr
625             630             635             640

Lys Leu Ala Val Ala Thr Phe Ala Gly Ile Glu Asn Lys Phe Gly Leu
                645             650             655

Tyr Leu Pro Leu Phe Lys Pro Ser Val Ser Thr Ser Lys Ala Ile Gly
                660             665             670

Gly Gly Pro
        675

<210> SEQ ID NO 12
<211> LENGTH: 701
<212> TYPE: PRT
<213> ORGANISM: Homo sapiens

<400> SEQUENCE: 12

Met Arg Asp Ser Gly Ser Lys Ala Ala Thr Asp Ala Gln Asp Ala Asn
 1               5              10              15

Gln Cys Cys Thr Ser Cys Glu Asp Asn Ala Pro Ala Thr Ser Tyr Cys
                20              25              30

Val Glu Cys Ser Glu Pro Leu Cys Glu Thr Cys Val Glu Ala His Gln
            35              40              45

Arg Val Lys Tyr Thr Lys Asp His Thr Val Arg Ser Thr Gly Pro Ala
    50              55              60

Lys Ser Arg Asp Gly Glu Arg Thr Val Tyr Cys Asn Val His Lys His
65              70              75              80

Glu Pro Leu Val Leu Phe Cys Glu Ser Cys Asp Thr Leu Thr Cys Arg
                85              90              95

Asp Cys Gln Leu Asn Ala His Lys Asp His Gln Tyr Gln Phe Leu Glu
                100             105             110

Asp Ala Val Arg Asn Gln Arg Lys Leu Leu Ala Ser Leu Val Lys Arg
            115             120             125

Leu Gly Asp Lys His Ala Thr Leu Gln Lys Ser Thr Lys Glu Val Arg
    130             135             140
```

-continued

```
Ser Ser Ile Arg Gln Val Ser Asp Val Gln Lys Arg Val Gln Val Asp
145                 150                 155                 160
Val Lys Met Ala Ile Leu Gln Ile Met Lys Glu Leu Asn Lys Arg Gly
                165                 170                 175
Arg Val Leu Val Asn Asp Ala Gln Lys Val Thr Glu Gly Gln Gln Glu
            180                 185                 190
Arg Leu Glu Arg Gln His Trp Thr Met Thr Lys Ile Gln Lys His Gln
        195                 200                 205
Glu His Ile Leu Arg Phe Ala Ser Trp Ala Leu Glu Ser Asp Asn Asn
    210                 215                 220
Thr Ala Leu Leu Leu Ser Lys Lys Leu Ile Tyr Phe Gln Leu His Arg
225                 230                 235                 240
Ala Leu Lys Met Ile Val Asp Pro Val Glu Pro His Gly Glu Met Lys
                245                 250                 255
Phe Gln Trp Asp Leu Asn Ala Trp Thr Lys Ser Ala Glu Ala Phe Gly
            260                 265                 270
Lys Ile Val Ala Glu Arg Pro Gly Thr Asn Ser Thr Gly Pro Ala Pro
        275                 280                 285
Met Ala Pro Pro Arg Ala Pro Gly Pro Leu Ser Lys Gln Gly Ser Gly
    290                 295                 300
Ser Ser Gln Pro Met Glu Val Gln Glu Gly Tyr Gly Phe Gly Ser Gly
305                 310                 315                 320
Asp Asp Pro Tyr Ser Ser Ala Glu Pro His Val Ser Gly Val Lys Arg
                325                 330                 335
Ser Arg Ser Gly Glu Gly Glu Val Ser Gly Leu Met Arg Lys Val Pro
            340                 345                 350
Arg Val Ser Leu Glu Arg Leu Asp Leu Asp Leu Thr Ala Asp Ser Gln
        355                 360                 365
Pro Pro Val Phe Lys Val Phe Pro Gly Ser Thr Thr Glu Asp Tyr Asn
    370                 375                 380
Leu Ile Val Ile Glu Arg Gly Ala Ala Ala Ala Thr Gly Gln Pro
385                 390                 395                 400
Gly Thr Ala Pro Ala Gly Thr Pro Gly Ala Pro Pro Leu Ala Gly Met
                405                 410                 415
Ala Ile Val Lys Glu Glu Glu Thr Glu Ala Ala Ile Gly Ala Pro Pro
            420                 425                 430
Thr Ala Thr Glu Gly Pro Glu Thr Lys Pro Val Leu Met Ala Leu Ala
        435                 440                 445
Glu Gly Pro Gly Ala Glu Gly Pro Arg Leu Ala Ser Pro Ser Gly Ser
    450                 455                 460
Thr Ser Ser Gly Leu Glu Val Val Ala Pro Glu Gly Thr Ser Ala Pro
465                 470                 475                 480
Gly Gly Gly Pro Gly Thr Leu Asp Asp Ser Ala Thr Ile Cys Arg Val
                485                 490                 495
Cys Gln Lys Pro Gly Asp Leu Val Met Cys Asn Gln Cys Glu Phe Cys
            500                 505                 510
Phe His Leu Asp Cys His Leu Pro Ala Leu Gln Asp Val Pro Gly Glu
        515                 520                 525
Glu Trp Ser Cys Ser Leu Cys His Val Leu Pro Asp Leu Lys Glu Glu
    530                 535                 540
Asp Gly Ser Leu Ser Leu Asp Gly Ala Asp Ser Thr Gly Val Val Ala
545                 550                 555                 560
Lys Leu Ser Pro Ala Asn Gln Arg Lys Cys Glu Arg Val Leu Leu Ala
```

```
                         565                 570                 575
Leu Phe Cys His Glu Pro Cys Arg Pro Leu His Gln Leu Ala Thr Asp
                580                 585                 590
Ser Thr Phe Ser Leu Asp Gln Pro Gly Gly Thr Leu Asp Leu Thr Leu
            595                 600                 605
Ile Arg Ala Arg Leu Gln Glu Lys Leu Ser Pro Pro Tyr Ser Ser Pro
        610                 615                 620
Gln Glu Phe Ala Gln Asp Val Gly Arg Met Phe Lys Gln Phe Asn Lys
625                 630                 635                 640
Leu Thr Glu Asp Lys Ala Asp Val Gln Ser Ile Ile Gly Leu Gln Arg
                645                 650                 655
Phe Phe Glu Thr Arg Met Asn Glu Ala Phe Gly Asp Thr Lys Phe Ser
            660                 665                 670
Ala Val Leu Val Glu Pro Pro Met Ser Leu Pro Gly Ala Gly Leu
        675                 680                 685
Ser Ser Gln Glu Leu Ser Gly Gly Pro Gly Asp Gly Pro
    690                 695                 700

<210> SEQ ID NO 13
<211> LENGTH: 753
<212> TYPE: PRT
<213> ORGANISM: Homo sapiens

<400> SEQUENCE: 13

Met Ala Ala Ser Ala Ala Ala Ser Ala Ala Ala Ser Ala Ala
1               5                   10                  15
Ser Gly Ser Pro Gly Pro Gly Glu Gly Ser Ala Gly Gly Glu Lys Arg
                20                  25                  30
Ser Thr Ala Pro Ser Ala Ala Ala Ser Ala Ser Ala Ser Ala Ala Ala
            35                  40                  45
Ser Ser Pro Ala Gly Gly Ala Glu Ala Leu Glu Leu Leu Glu His
        50                  55                  60
Cys Gly Val Cys Arg Glu Arg Leu Arg Pro Glu Arg Glu Pro Arg Leu
65                  70                  75                  80
Leu Pro Cys Leu His Ser Ala Cys Ser Ala Cys Leu Gly Pro Ala Ala
                85                  90                  95
Pro Ala Ala Asn Ser Ser Gly Asp Gly Ala Ala Gly Asp Gly
            100                 105                 110
Thr Gly Pro Ala Lys Ser Arg Asp Gly Glu Arg Thr Val Tyr Cys Asn
        115                 120                 125
Val His Lys His Glu Pro Leu Val Leu Phe Cys Glu Ser Cys Asp Thr
130                 135                 140
Leu Thr Cys Arg Asp Cys Gln Leu Asn Ala His Lys Asp His Gln Tyr
145                 150                 155                 160
Gln Phe Leu Glu Asp Ala Val Arg Asn Gln Arg Lys Leu Leu Ala Ser
                165                 170                 175
Leu Val Lys Arg Leu Gly Asp Lys His Ala Thr Leu Gln Lys Ser Thr
            180                 185                 190
Lys Glu Val Arg Ser Ser Ile Arg Gln Val Ser Asp Val Gln Lys Arg
        195                 200                 205
Val Gln Val Asp Val Lys Met Ala Ile Leu Gln Ile Met Lys Glu Leu
    210                 215                 220
Asn Lys Arg Gly Arg Val Leu Val Asn Asp Ala Gln Lys Val Thr Glu
225                 230                 235                 240
```

-continued

```
Gly Gln Gln Glu Arg Leu Glu Arg Gln His Trp Thr Met Thr Lys Ile
            245                 250                 255
Gln Lys His Gln Glu His Ile Leu Arg Phe Ala Ser Trp Ala Leu Glu
        260                 265                 270
Ser Asp Asn Asn Thr Ala Leu Leu Leu Ser Lys Lys Leu Ile Tyr Phe
            275                 280                 285
Gln Leu His Arg Ala Leu Lys Met Ile Val Asp Pro Val Glu Pro His
        290                 295                 300
Gly Glu Met Lys Phe Gln Trp Asp Leu Asn Ala Trp Thr Lys Ser Ala
305                 310                 315                 320
Glu Ala Phe Gly Lys Ile Val Ala Glu Arg Pro Gly Thr Asn Ser Thr
                325                 330                 335
Gly Pro Ala Pro Met Ala Pro Pro Arg Ala Pro Gly Pro Leu Ser Lys
            340                 345                 350
Gln Gly Ser Gly Ser Ser Gln Pro Met Glu Val Gln Glu Gly Tyr Gly
        355                 360                 365
Phe Gly Ser Gly Asp Asp Pro Tyr Ser Ser Ala Glu Pro His Val Ser
    370                 375                 380
Gly Val Lys Arg Ser Arg Ser Gly Glu Gly Glu Val Ser Gly Leu Met
385                 390                 395                 400
Arg Lys Val Pro Arg Val Ser Leu Glu Arg Leu Asp Leu Asp Leu Thr
                405                 410                 415
Ala Asp Ser Gln Pro Pro Val Phe Lys Val Phe Pro Gly Ser Thr Thr
            420                 425                 430
Glu Asp Tyr Asn Leu Ile Val Ile Glu Arg Gly Ala Ala Ala Ala Ala
        435                 440                 445
Thr Gly Gln Pro Gly Thr Ala Pro Ala Gly Thr Pro Gly Ala Pro Pro
    450                 455                 460
Leu Ala Gly Met Ala Ile Val Lys Glu Glu Thr Glu Ala Ala Ile
465                 470                 475                 480
Gly Ala Pro Pro Thr Ala Thr Glu Gly Pro Glu Thr Lys Pro Val Leu
                485                 490                 495
Met Ala Leu Ala Glu Gly Pro Gly Ala Glu Gly Pro Arg Leu Ala Ser
            500                 505                 510
Pro Ser Gly Ser Thr Ser Ser Gly Leu Glu Val Val Ala Pro Glu Gly
        515                 520                 525
Thr Ser Ala Pro Gly Gly Pro Gly Thr Leu Asp Asp Ser Ala Thr
    530                 535                 540
Ile Cys Arg Val Cys Gln Lys Pro Gly Asp Leu Val Met Cys Asn Gln
545                 550                 555                 560
Cys Glu Phe Cys Phe His Leu Asp Cys His Leu Pro Ala Leu Gln Asp
                565                 570                 575
Val Pro Gly Glu Glu Trp Ser Cys Ser Leu Cys His Val Leu Pro Asp
            580                 585                 590
Leu Lys Glu Glu Asp Gly Ser Leu Ser Leu Asp Gly Ala Asp Ser Thr
        595                 600                 605
Gly Val Val Ala Lys Leu Ser Pro Ala Asn Gln Arg Lys Cys Glu Arg
    610                 615                 620
Val Leu Leu Ala Leu Phe Cys His Glu Pro Cys Arg Pro Leu His Gln
625                 630                 635                 640
Leu Ala Thr Asp Ser Thr Phe Ser Leu Asp Gln Pro Gly Gly Thr Leu
                645                 650                 655
Asp Leu Thr Leu Ile Arg Ala Arg Leu Gln Glu Lys Leu Ser Pro Pro
```

-continued

```
                        660                 665                 670
Tyr Ser Ser Pro Gln Glu Phe Ala Gln Asp Val Gly Arg Met Phe Lys
            675                 680                 685
Gln Phe Asn Lys Leu Thr Glu Asp Lys Ala Asp Val Gln Ser Ile Ile
        690                 695                 700
Gly Leu Gln Arg Phe Phe Glu Thr Arg Met Asn Glu Ala Phe Gly Asp
705                 710                 715                 720
Thr Lys Phe Ser Ala Val Leu Val Glu Pro Pro Met Ser Leu Pro
                725                 730                 735
Gly Ala Gly Leu Ser Ser Gln Glu Leu Ser Gly Gly Pro Gly Asp Gly
            740                 745                 750
Pro

<210> SEQ ID NO 14
<211> LENGTH: 835
<212> TYPE: PRT
<213> ORGANISM: Homo sapiens

<400> SEQUENCE: 14

Met Ala Ala Ser Ala Ala Ala Ala Ser Ala Ala Ala Ser Ala Ala
 1               5                  10                  15
Ser Gly Ser Pro Gly Pro Gly Glu Gly Ser Ala Gly Gly Glu Lys Arg
            20                  25                  30
Ser Thr Ala Pro Ser Ala Ala Ala Ser Ala Ser Ala Ala Ala
        35                  40                  45
Ser Ser Pro Ala Gly Gly Gly Ala Glu Ala Leu Glu Leu Leu Glu His
    50                  55                  60
Cys Gly Val Cys Arg Glu Arg Leu Arg Pro Glu Arg Glu Pro Arg Leu
65                  70                  75                  80
Leu Pro Cys Leu His Ser Ala Cys Ser Ala Cys Leu Gly Pro Ala Ala
                85                  90                  95
Pro Ala Ala Ala Asn Ser Ser Gly Asp Gly Gly Ala Ala Gly Asp Gly
            100                 105                 110
Thr Val Val Asp Cys Pro Val Cys Lys Gln Gln Cys Phe Ser Lys Asp
        115                 120                 125
Ile Val Glu Asn Tyr Phe Met Arg Asp Ser Gly Ser Lys Ala Ala Thr
    130                 135                 140
Asp Ala Gln Asp Ala Asn Gln Cys Cys Thr Ser Cys Glu Asp Asn Ala
145                 150                 155                 160
Pro Ala Thr Ser Tyr Cys Val Glu Cys Ser Glu Pro Leu Cys Glu Thr
                165                 170                 175
Cys Val Glu Ala His Gln Arg Val Lys Tyr Thr Lys Asp His Thr Val
            180                 185                 190
Arg Ser Thr Gly Pro Ala Lys Ser Arg Asp Gly Glu Arg Thr Val Tyr
        195                 200                 205
Cys Asn Val His Lys His Glu Pro Leu Val Leu Phe Cys Glu Ser Cys
    210                 215                 220
Asp Thr Leu Thr Cys Arg Asp Cys Gln Leu Asn Ala His Lys Asp His
225                 230                 235                 240
Gln Tyr Gln Phe Leu Glu Asp Ala Val Arg Asn Gln Arg Lys Leu Leu
                245                 250                 255
Ala Ser Leu Val Lys Arg Leu Gly Asp Lys His Ala Thr Leu Gln Lys
            260                 265                 270
Ser Thr Lys Glu Val Arg Ser Ser Ile Arg Gln Val Ser Asp Val Gln
```

-continued

```
                275                 280                 285
Lys Arg Val Gln Val Asp Val Lys Met Ala Ile Leu Gln Ile Met Lys
            290                 295                 300
Glu Leu Asn Lys Arg Gly Arg Val Leu Val Asn Asp Ala Gln Lys Val
305                 310                 315                 320
Thr Glu Gly Gln Gln Glu Arg Leu Glu Arg Gln His Trp Thr Met Thr
                325                 330                 335
Lys Ile Gln Lys His Gln Glu His Ile Leu Arg Phe Ala Ser Trp Ala
            340                 345                 350
Leu Glu Ser Asp Asn Asn Thr Ala Leu Leu Ser Lys Lys Leu Ile
            355                 360                 365
Tyr Phe Gln Leu His Arg Ala Leu Lys Met Ile Val Asp Pro Val Glu
370                 375                 380
Pro His Gly Glu Met Lys Phe Gln Trp Asp Leu Asn Ala Trp Thr Lys
385                 390                 395                 400
Ser Ala Glu Ala Phe Gly Lys Ile Val Ala Glu Arg Pro Gly Thr Asn
                405                 410                 415
Ser Thr Gly Pro Ala Pro Met Ala Pro Pro Arg Ala Pro Gly Pro Leu
            420                 425                 430
Ser Lys Gln Gly Ser Gly Ser Ser Gln Pro Met Glu Val Gln Glu Gly
            435                 440                 445
Tyr Gly Phe Gly Ser Gly Asp Asp Pro Tyr Ser Ser Ala Glu Pro His
            450                 455                 460
Val Ser Gly Val Lys Arg Ser Arg Ser Gly Glu Gly Glu Val Ser Gly
465                 470                 475                 480
Leu Met Arg Lys Val Pro Arg Val Ser Leu Glu Arg Leu Asp Leu Asp
                485                 490                 495
Leu Thr Ala Asp Ser Gln Pro Pro Val Phe Lys Val Phe Pro Gly Ser
            500                 505                 510
Thr Thr Glu Asp Tyr Asn Leu Ile Val Ile Glu Arg Gly Ala Ala Ala
            515                 520                 525
Ala Ala Thr Gly Gln Pro Gly Thr Ala Pro Ala Gly Thr Pro Gly Ala
            530                 535                 540
Pro Pro Leu Ala Gly Met Ala Ile Val Lys Glu Glu Thr Glu Ala
545                 550                 555                 560
Ala Ile Gly Ala Pro Pro Thr Ala Thr Glu Gly Pro Glu Thr Lys Pro
                565                 570                 575
Val Leu Met Ala Leu Ala Glu Gly Pro Gly Ala Glu Gly Pro Arg Leu
            580                 585                 590
Ala Ser Pro Ser Gly Ser Thr Ser Ser Gly Leu Glu Val Val Ala Pro
            595                 600                 605
Glu Gly Thr Ser Ala Pro Gly Gly Pro Gly Thr Leu Asp Asp Ser
            610                 615                 620
Ala Thr Ile Cys Arg Val Cys Gln Lys Pro Gly Asp Leu Val Met Cys
625                 630                 635                 640
Asn Gln Cys Glu Phe Cys Phe His Leu Asp Cys His Leu Pro Ala Leu
                645                 650                 655
Gln Asp Val Pro Gly Glu Glu Trp Ser Cys Ser Leu Cys His Val Leu
            660                 665                 670
Pro Asp Leu Lys Glu Glu Asp Gly Ser Leu Ser Leu Asp Gly Ala Asp
            675                 680                 685
Ser Thr Gly Val Val Ala Lys Leu Ser Pro Ala Asn Gln Arg Lys Cys
            690                 695                 700
```

-continued

```
Glu Arg Val Leu Leu Ala Leu Phe Cys His Glu Pro Cys Arg Pro Leu
705                 710                 715                 720

His Gln Leu Ala Thr Asp Ser Thr Phe Ser Leu Asp Gln Pro Gly Gly
                725                 730                 735

Thr Leu Asp Leu Thr Leu Ile Arg Ala Arg Leu Gln Glu Lys Leu Ser
            740                 745                 750

Pro Pro Tyr Ser Ser Pro Gln Glu Phe Ala Gln Asp Val Gly Arg Met
        755                 760                 765

Phe Lys Gln Phe Asn Lys Leu Thr Glu Asp Lys Ala Asp Val Gln Ser
770                 775                 780

Ile Ile Gly Leu Gln Arg Phe Phe Glu Thr Arg Met Asn Glu Ala Phe
785                 790                 795                 800

Gly Asp Thr Lys Phe Ser Ala Val Leu Val Glu Pro Pro Met Ser
                805                 810                 815

Leu Pro Gly Ala Gly Leu Ser Ser Gln Glu Leu Ser Gly Gly Pro Gly
            820                 825                 830

Asp Gly Pro
        835

<210> SEQ ID NO 15
<211> LENGTH: 835
<212> TYPE: PRT
<213> ORGANISM: Homo sapiens

<400> SEQUENCE: 15

Met Ala Ala Ser Ala Ala Ala Ser Ala Ala Ala Ser Ala Ala
1               5                   10                  15

Ser Gly Ser Pro Gly Pro Gly Glu Gly Ser Ala Gly Gly Glu Lys Arg
            20                  25                  30

Ser Thr Ala Pro Ser Ala Ala Ser Ala Ser Ala Ser Ala Ala Ala
            35                  40                  45

Ser Ser Pro Ala Gly Gly Ala Glu Ala Leu Glu Leu Leu Glu His
    50                  55                  60

Cys Gly Val Cys Arg Glu Arg Leu Arg Pro Glu Arg Glu Pro Arg Leu
65                  70                  75                  80

Leu Pro Cys Leu His Ser Ala Cys Ser Ala Cys Leu Gly Pro Ala Ala
                85                  90                  95

Pro Ala Ala Ala Asn Ser Ser Gly Asp Gly Gly Ala Ala Gly Asp Gly
                100                 105                 110

Thr Val Val Asp Cys Pro Val Cys Lys Gln Gln Cys Phe Ser Lys Asp
            115                 120                 125

Ile Val Glu Asn Tyr Phe Met Arg Asp Ser Gly Ser Lys Ala Ala Thr
    130                 135                 140

Asp Ala Gln Asp Ala Asn Gln Cys Cys Thr Ser Cys Glu Asp Asn Ala
145                 150                 155                 160

Pro Ala Thr Ser Tyr Cys Val Glu Cys Ser Glu Pro Leu Cys Glu Thr
                165                 170                 175

Cys Val Glu Ala His Gln Arg Val Lys Tyr Thr Lys Asp His Thr Val
                180                 185                 190

Arg Ser Thr Gly Pro Ala Lys Ser Arg Asp Gly Glu Arg Thr Val Tyr
            195                 200                 205

Cys Asn Val His Lys His Glu Pro Leu Val Leu Phe Cys Glu Ser Cys
    210                 215                 220

Asp Thr Leu Thr Cys Arg Asp Cys Gln Leu Asn Ala His Lys Asp His
```

-continued

```
              225                 230                 235                 240
        Gln Tyr Gln Phe Leu Glu Asp Ala Val Arg Asn Gln Arg Lys Leu Leu
                        245                 250                 255

Ala Ser Leu Val Lys Arg Leu Gly Asp Lys His Ala Thr Leu Gln Lys
                    260                 265                 270

Ser Thr Lys Glu Val Arg Ser Ile Arg Gln Val Ser Asp Val Gln
                275                 280                 285

Lys Arg Val Gln Val Asp Val Lys Met Ala Ile Leu Gln Ile Met Lys
            290                 295                 300

Glu Leu Asn Lys Arg Gly Arg Val Leu Val Asn Asp Ala Gln Lys Val
        305                 310                 315                 320

Thr Glu Gly Gln Gln Glu Arg Leu Glu Arg Gln His Trp Thr Met Thr
                        325                 330                 335

Lys Ile Gln Lys His Gln Glu His Ile Leu Arg Phe Ala Ser Trp Ala
                    340                 345                 350

Leu Glu Ser Asp Asn Asn Thr Ala Leu Leu Ser Lys Lys Leu Ile
                355                 360                 365

Tyr Phe Gln Leu His Arg Ala Leu Lys Met Ile Val Asp Pro Val Glu
            370                 375                 380

Pro His Gly Glu Met Lys Phe Gln Trp Asp Leu Asn Ala Trp Thr Lys
        385                 390                 395                 400

Ser Ala Glu Ala Phe Gly Lys Ile Val Ala Glu Arg Pro Gly Thr Asn
                        405                 410                 415

Ser Thr Gly Pro Ala Pro Met Ala Pro Arg Ala Gly Pro Leu
                    420                 425                 430

Ser Lys Gln Gly Ser Gly Ser Gln Pro Met Glu Val Gln Glu Gly
                435                 440                 445

Tyr Gly Phe Gly Ser Gly Asp Asp Pro Tyr Ser Ser Ala Glu Pro His
            450                 455                 460

Val Ser Gly Val Lys Arg Ser Arg Ser Gly Glu Gly Glu Val Ser Gly
        465                 470                 475                 480

Leu Met Arg Lys Val Pro Arg Val Ser Leu Glu Arg Leu Asp Leu Asp
                        485                 490                 495

Leu Thr Ala Asp Ser Gln Pro Val Phe Lys Val Phe Pro Gly Ser
                    500                 505                 510

Thr Thr Glu Asp Tyr Asn Leu Ile Val Ile Glu Arg Gly Ala Ala Ala
                515                 520                 525

Ala Ala Thr Gly Gln Pro Gly Thr Ala Pro Ala Gly Thr Pro Gly Ala
            530                 535                 540

Pro Pro Leu Ala Gly Met Ala Ile Val Lys Glu Glu Thr Glu Ala
        545                 550                 555                 560

Ala Ile Gly Ala Pro Pro Thr Ala Thr Glu Gly Pro Glu Thr Lys Pro
                        565                 570                 575

Val Leu Met Ala Leu Ala Glu Gly Pro Gly Ala Glu Gly Pro Arg Leu
                    580                 585                 590

Ala Ser Pro Ser Gly Ser Thr Ser Ser Gly Leu Glu Val Val Ala Pro
                595                 600                 605

Glu Gly Thr Ser Ala Pro Gly Gly Pro Gly Thr Leu Asp Asp Ser
            610                 615                 620

Ala Thr Ile Cys Arg Val Cys Gln Lys Pro Gly Asp Leu Val Met Cys
        625                 630                 635                 640

Asn Gln Cys Glu Phe Cys Phe His Leu Asp Cys His Leu Pro Ala Leu
                        645                 650                 655
```

-continued

Gln Asp Val Pro Gly Glu Glu Trp Ser Cys Ser Leu Cys His Val Leu
            660                 665                 670

Pro Asp Leu Lys Glu Glu Asp Gly Ser Leu Ser Leu Asp Gly Ala Asp
            675                 680                 685

Ser Thr Gly Val Val Ala Lys Leu Ser Pro Ala Asn Gln Arg Lys Cys
            690                 695                 700

Glu Arg Val Leu Leu Ala Leu Phe Cys His Glu Pro Cys Arg Pro Leu
705                 710                 715                 720

His Gln Leu Ala Thr Asp Ser Thr Phe Ser Leu Asp Gln Pro Gly Gly
            725                 730                 735

Thr Leu Asp Leu Thr Leu Ile Arg Ala Arg Leu Gln Glu Lys Leu Ser
            740                 745                 750

Pro Pro Tyr Ser Ser Pro Gln Glu Phe Ala Gln Asp Val Gly Arg Met
            755                 760                 765

Phe Lys Gln Phe Asn Lys Leu Thr Glu Asp Lys Ala Asp Val Gln Ser
            770                 775                 780

Ile Ile Gly Leu Gln Arg Phe Phe Glu Thr Arg Met Asn Glu Ala Phe
785                 790                 795                 800

Gly Asp Thr Lys Phe Ser Ala Val Leu Val Glu Pro Pro Met Ser
            805                 810                 815

Leu Pro Gly Ala Gly Leu Ser Ser Gln Glu Leu Ser Gly Pro Gly
            820                 825                 830

Asp Gly Pro
        835

<210> SEQ ID NO 16
<211> LENGTH: 2491
<212> TYPE: PRT
<213> ORGANISM: Homo sapiens

<400> SEQUENCE: 16

Met Gly Ala Ala Ala Gly Arg Ser Pro His Leu Gly Pro Ala Pro Ala
1               5                   10                  15

Arg Arg Pro Gln Arg Ser Leu Leu Leu Gln Leu Leu Leu Leu Val
            20                  25                  30

Ala Ala Pro Gly Ser Thr Gln Ala Gln Ala Ala Pro Phe Pro Glu Leu
            35                  40                  45

Cys Ser Tyr Thr Trp Glu Ala Val Asp Thr Lys Asn Asn Val Leu Tyr
        50                  55                  60

Lys Ile Asn Ile Cys Gly Ser Val Asp Ile Val Gln Cys Gly Pro Ser
65                  70                  75                  80

Ser Ala Val Cys Met His Asp Leu Lys Thr Arg Thr Tyr His Ser Val
            85                  90                  95

Gly Asp Ser Val Leu Arg Ser Ala Thr Arg Ser Leu Leu Glu Phe Asn
            100                 105                 110

Thr Thr Val Ser Cys Asp Gln Gln Gly Thr Asn His Arg Val Gln Ser
            115                 120                 125

Ser Ile Ala Phe Leu Cys Gly Lys Thr Leu Gly Thr Pro Glu Phe Val
        130                 135                 140

Thr Ala Thr Glu Cys Val His Tyr Phe Glu Trp Arg Thr Thr Ala Ala
145                 150                 155                 160

Cys Lys Lys Asp Ile Phe Lys Ala Asn Lys Glu Val Pro Cys Tyr Val
            165                 170                 175

Phe Asp Glu Glu Leu Arg Lys His Asp Leu Asn Pro Leu Ile Lys Leu

-continued

```
              180                 185                 190
Ser Gly Ala Tyr Leu Val Asp Asp Ser Asp Pro Asp Thr Ser Leu Phe
            195                 200                 205

Ile Asn Val Cys Arg Asp Ile Asp Thr Leu Arg Asp Pro Gly Ser Gln
210                 215                 220

Leu Arg Ala Cys Pro Pro Gly Thr Ala Ala Cys Leu Val Arg Gly His
225                 230                 235                 240

Gln Ala Phe Asp Val Gly Gln Pro Arg Asp Gly Leu Lys Leu Val Arg
                245                 250                 255

Lys Asp Arg Leu Val Leu Ser Tyr Val Arg Glu Glu Ala Gly Lys Leu
            260                 265                 270

Asp Phe Cys Asp Gly His Ser Pro Ala Val Thr Ile Thr Phe Val Cys
            275                 280                 285

Pro Ser Glu Arg Arg Glu Gly Thr Ile Pro Lys Leu Thr Ala Lys Ser
290                 295                 300

Asn Cys Arg Tyr Glu Ile Glu Trp Ile Thr Glu Tyr Ala Cys His Arg
305                 310                 315                 320

Asp Tyr Leu Glu Ser Lys Thr Cys Ser Leu Ser Gly Glu Gln Gln Asp
                325                 330                 335

Val Ser Ile Asp Leu Thr Pro Leu Ala Gln Ser Gly Gly Ser Ser Tyr
            340                 345                 350

Ile Ser Asp Gly Lys Glu Tyr Leu Phe Tyr Leu Asn Val Cys Gly Glu
            355                 360                 365

Thr Glu Ile Gln Phe Cys Asn Lys Lys Gln Ala Ala Val Cys Gln Val
370                 375                 380

Lys Lys Ser Asp Thr Ser Gln Val Lys Ala Ala Gly Arg Tyr His Asn
385                 390                 395                 400

Gln Thr Leu Arg Tyr Ser Asp Gly Asp Leu Thr Leu Ile Tyr Phe Gly
                405                 410                 415

Gly Asp Glu Cys Ser Ser Gly Phe Gln Arg Met Ser Val Ile Asn Phe
            420                 425                 430

Glu Cys Asn Lys Thr Ala Gly Asn Asp Gly Lys Gly Thr Pro Val Phe
            435                 440                 445

Thr Gly Glu Val Asp Cys Thr Tyr Phe Phe Thr Trp Asp Thr Glu Tyr
450                 455                 460

Ala Cys Val Lys Glu Lys Glu Asp Leu Leu Cys Gly Ala Thr Asp Gly
465                 470                 475                 480

Lys Lys Arg Tyr Asp Leu Ser Ala Leu Val Arg His Ala Glu Pro Glu
                485                 490                 495

Gln Asn Trp Glu Ala Val Asp Gly Ser Gln Thr Glu Thr Glu Lys Lys
            500                 505                 510

His Phe Phe Ile Asn Ile Cys His Arg Val Leu Gln Glu Gly Lys Ala
            515                 520                 525

Arg Gly Cys Pro Glu Asp Ala Ala Val Cys Ala Val Asp Lys Asn Gly
            530                 535                 540

Ser Lys Asn Leu Gly Lys Phe Ile Ser Ser Pro Met Lys Glu Lys Gly
545                 550                 555                 560

Asn Ile Gln Leu Ser Tyr Ser Asp Gly Asp Cys Gly His Gly Lys
                565                 570                 575

Lys Ile Lys Thr Asn Ile Thr Leu Val Cys Lys Pro Gly Asp Leu Glu
            580                 585                 590

Ser Ala Pro Val Leu Arg Thr Ser Gly Glu Gly Gly Cys Phe Tyr Glu
            595                 600                 605
```

-continued

```
Phe Glu Trp Arg Thr Ala Ala Cys Val Leu Ser Lys Thr Glu Gly
    610                 615                 620

Glu Asn Cys Thr Val Phe Asp Ser Gln Ala Gly Phe Ser Phe Asp Leu
625                 630                 635                 640

Ser Pro Leu Thr Lys Lys Asn Gly Ala Tyr Lys Val Glu Thr Lys Lys
                645                 650                 655

Tyr Asp Phe Tyr Ile Asn Val Cys Gly Pro Val Ser Val Ser Pro Cys
                660                 665                 670

Gln Pro Asp Ser Gly Ala Cys Gln Val Ala Lys Ser Asp Glu Lys Thr
            675                 680                 685

Trp Asn Leu Gly Leu Ser Asn Ala Lys Leu Ser Tyr Tyr Asp Gly Met
690                 695                 700

Ile Gln Leu Asn Tyr Arg Gly Gly Thr Pro Tyr Asn Asn Glu Arg His
705                 710                 715                 720

Thr Pro Arg Ala Thr Leu Ile Thr Phe Leu Cys Asp Arg Asp Ala Gly
                725                 730                 735

Val Gly Phe Pro Glu Tyr Gln Glu Asp Asn Ser Thr Tyr Asn Phe
            740                 745                 750

Arg Trp Tyr Thr Ser Tyr Ala Cys Pro Glu Glu Pro Leu Glu Cys Val
                755                 760                 765

Val Thr Asp Pro Ser Thr Leu Glu Gln Tyr Asp Leu Ser Ser Leu Ala
770                 775                 780

Lys Ser Glu Gly Gly Leu Gly Gly Asn Trp Tyr Ala Met Asp Asn Ser
785                 790                 795                 800

Gly Glu His Val Thr Trp Arg Lys Tyr Tyr Ile Asn Val Cys Arg Pro
                805                 810                 815

Leu Asn Pro Val Pro Gly Cys Asn Arg Tyr Ala Ser Ala Cys Gln Met
                820                 825                 830

Lys Tyr Glu Lys Asp Gln Gly Ser Phe Thr Glu Val Val Ser Ile Ser
            835                 840                 845

Asn Leu Gly Met Ala Lys Thr Gly Pro Val Val Glu Asp Ser Gly Ser
850                 855                 860

Leu Leu Leu Glu Tyr Val Asn Gly Ser Ala Cys Thr Thr Ser Asp Gly
865                 870                 875                 880

Arg Gln Thr Thr Tyr Thr Thr Arg Ile His Leu Val Cys Ser Arg Gly
                885                 890                 895

Arg Leu Asn Ser His Pro Ile Phe Ser Leu Asn Trp Glu Cys Val Val
            900                 905                 910

Ser Phe Leu Trp Asn Thr Glu Ala Ala Cys Pro Ile Gln Thr Thr Thr
    915                 920                 925

Asp Thr Asp Gln Ala Cys Ser Ile Arg Asp Pro Asn Ser Gly Phe Val
930                 935                 940

Phe Asn Leu Asn Pro Leu Asn Ser Ser Gln Gly Tyr Asn Val Ser Gly
945                 950                 955                 960

Ile Gly Lys Ile Phe Met Phe Asn Val Cys Gly Thr Met Pro Val Cys
                965                 970                 975

Gly Thr Ile Leu Gly Lys Pro Ala Ser Gly Cys Glu Ala Glu Thr Gln
            980                 985                 990

Thr Glu Glu Leu Lys Asn Trp Lys Pro Ala Arg Pro Val Gly Ile Glu
            995                1000                1005

Lys Ser Leu Gln Leu Ser Thr Glu Gly Phe Ile Thr Leu Thr Tyr Lys
        1010                1015                1020
```

-continued

```
Gly Pro Leu Ser Ala Lys Gly Thr Ala Asp Ala Phe Ile Val Arg Phe
1025                1030                1035                1040

Val Cys Asn Asp Asp Val Tyr Ser Gly Pro Leu Lys Phe Leu His Gln
            1045                1050                1055

Asp Ile Asp Ser Gly Gln Gly Ile Arg Asn Thr Tyr Phe Glu Phe Glu
        1060                1065                1070

Thr Ala Leu Ala Cys Val Pro Ser Pro Val Asp Cys Gln Val Thr Asp
    1075                1080                1085

Leu Ala Gly Asn Glu Tyr Asp Leu Thr Gly Leu Ser Thr Val Arg Lys
1090                1095                1100

Pro Trp Thr Ala Val Asp Thr Ser Val Asp Gly Arg Lys Arg Thr Phe
1105                1110                1115                1120

Tyr Leu Ser Val Cys Asn Pro Leu Pro Tyr Ile Pro Gly Cys Gln Gly
            1125                1130                1135

Ser Ala Val Gly Ser Cys Leu Val Ser Glu Gly Asn Ser Trp Asn Leu
        1140                1145                1150

Gly Val Val Gln Met Ser Pro Gln Ala Ala Ala Asn Gly Ser Leu Ser
    1155                1160                1165

Ile Met Tyr Val Asn Gly Asp Lys Cys Gly Asn Gln Arg Phe Ser Thr
1170                1175                1180

Arg Ile Thr Phe Glu Cys Ala Gln Ile Ser Gly Ser Pro Ala Phe Gln
1185                1190                1195                1200

Leu Gln Asp Gly Cys Glu Tyr Val Phe Ile Trp Arg Thr Val Glu Ala
            1205                1210                1215

Cys Pro Val Val Arg Val Glu Gly Asp Asn Cys Glu Val Lys Asp Pro
        1220                1225                1230

Arg His Gly Asn Leu Tyr Asp Leu Lys Pro Leu Gly Leu Asn Asp Thr
    1235                1240                1245

Ile Val Ser Ala Gly Glu Tyr Thr Tyr Phe Arg Val Cys Gly Lys
1250                1255                1260

Leu Ser Ser Asp Val Cys Pro Thr Ser Asp Lys Ser Lys Val Val Ser
1265                1270                1275                1280

Ser Cys Gln Glu Lys Arg Glu Pro Gln Gly Phe His Lys Val Ala Gly
            1285                1290                1295

Leu Leu Thr Gln Lys Leu Thr Tyr Glu Asn Gly Leu Leu Lys Met Asn
        1300                1305                1310

Phe Thr Gly Gly Asp Thr Cys His Lys Val Tyr Gln Arg Ser Thr Ala
    1315                1320                1325

Ile Phe Phe Tyr Cys Asp Arg Gly Thr Gln Arg Pro Val Phe Leu Lys
1330                1335                1340

Glu Thr Ser Asp Cys Ser Tyr Leu Phe Glu Trp Arg Thr Gln Tyr Ala
1345                1350                1355                1360

Cys Pro Pro Phe Asp Leu Thr Glu Cys Ser Phe Lys Asp Gly Ala Gly
            1365                1370                1375

Asn Ser Phe Asp Leu Ser Ser Leu Ser Arg Tyr Ser Asp Asn Trp Glu
        1380                1385                1390

Ala Ile Thr Gly Thr Gly Asp Pro Glu His Tyr Leu Ile Asn Val Cys
    1395                1400                1405

Lys Ser Leu Ala Pro Gln Ala Gly Thr Glu Pro Cys Pro Pro Glu Ala
    1410                1415                1420

Ala Ala Cys Leu Leu Gly Gly Ser Lys Pro Val Asn Leu Gly Arg Val
1425                1430                1435                1440

Arg Asp Gly Pro Gln Trp Arg Asp Gly Ile Ile Val Leu Lys Tyr Val
```

-continued

```
                1445                1450                1455
Asp Gly Asp Leu Cys Pro Asp Gly Ile Arg Lys Lys Ser Thr Thr Ile
            1460                1465                1470
Arg Phe Thr Cys Ser Glu Ser Gln Val Asn Ser Arg Pro Met Phe Ile
            1475                1480                1485
Ser Ala Val Glu Asp Cys Glu Tyr Thr Phe Ala Trp Pro Thr Ala Thr
            1490                1495                1500
Ala Cys Pro Met Lys Ser Asn Glu His Asp Asp Cys Gln Val Thr Asn
1505                1510                1515                1520
Pro Ser Thr Gly His Leu Phe Asp Leu Ser Ser Leu Ser Gly Arg Ala
            1525                1530                1535
Gly Phe Thr Ala Ala Tyr Ser Glu Lys Gly Leu Val Tyr Met Ser Ile
            1540                1545                1550
Cys Gly Glu Asn Glu Asn Cys Pro Pro Gly Val Gly Ala Cys Phe Gly
            1555                1560                1565
Gln Thr Arg Ile Ser Val Gly Lys Ala Asn Lys Arg Leu Arg Tyr Val
            1570                1575                1580
Asp Gln Val Leu Gln Leu Val Tyr Lys Asp Gly Ser Pro Cys Pro Ser
1585                1590                1595                1600
Lys Ser Gly Leu Ser Tyr Lys Ser Val Ile Ser Phe Val Cys Arg Pro
            1605                1610                1615
Glu Ala Gly Pro Thr Asn Arg Pro Met Leu Ile Ser Leu Asp Lys Gln
            1620                1625                1630
Thr Cys Thr Leu Phe Phe Ser Trp His Thr Pro Leu Ala Cys Glu Gln
            1635                1640                1645
Ala Thr Glu Cys Ser Val Arg Asn Gly Ser Ser Ile Val Asp Leu Ser
            1650                1655                1660
Pro Leu Ile His Arg Thr Gly Gly Tyr Glu Ala Tyr Asp Glu Ser Glu
1665                1670                1675                1680
Asp Asp Ala Ser Asp Thr Asn Pro Asp Phe Tyr Ile Asn Ile Cys Gln
            1685                1690                1695
Pro Leu Asn Pro Met His Ala Val Pro Cys Pro Ala Gly Ala Ala Val
            1700                1705                1710
Cys Lys Val Pro Ile Asp Gly Pro Pro Ile Asp Ile Gly Arg Val Ala
            1715                1720                1725
Gly Pro Pro Ile Leu Asn Pro Ile Ala Asn Glu Ile Tyr Leu Asn Phe
            1730                1735                1740
Glu Ser Ser Thr Pro Cys Leu Ala Asp Lys His Phe Asn Tyr Thr Ser
1745                1750                1755                1760
Leu Ile Ala Phe His Cys Lys Arg Gly Val Ser Met Gly Thr Pro Lys
            1765                1770                1775
Leu Leu Arg Thr Ser Glu Cys Asp Phe Val Phe Glu Trp Glu Thr Pro
            1780                1785                1790
Val Val Cys Pro Asp Glu Val Arg Met Asp Gly Cys Thr Leu Thr Asp
            1795                1800                1805
Glu Gln Leu Leu Tyr Ser Phe Asn Leu Ser Ser Leu Ser Thr Ser Thr
            1810                1815                1820
Phe Lys Val Thr Arg Asp Ser Arg Thr Tyr Ser Val Gly Val Cys Thr
1825                1830                1835                1840
Phe Ala Val Gly Pro Glu Gln Gly Gly Cys Lys Asp Gly Gly Val Cys
            1845                1850                1855
Leu Leu Ser Gly Thr Lys Gly Ala Ser Phe Gly Arg Leu Gln Ser Met
            1860                1865                1870
```

```
Lys Leu Asp Tyr Arg His Gln Asp Glu Ala Val Val Leu Ser Tyr Val
        1875                1880                1885
Asn Gly Asp Arg Cys Pro Pro Glu Thr Asp Asp Gly Val Pro Cys Val
        1890                1895                1900
Phe Pro Phe Ile Phe Asn Gly Lys Ser Tyr Glu Glu Cys Ile Ile Glu
1905                1910                1915                1920
Ser Arg Ala Lys Leu Trp Cys Ser Thr Thr Ala Asp Tyr Asp Arg Asp
        1925                1930                1935
His Glu Trp Gly Phe Cys Arg His Ser Asn Ser Tyr Arg Thr Ser Ser
        1940                1945                1950
Ile Ile Phe Lys Cys Asp Glu Asp Ile Gly Arg Pro Gln Val
        1955                1960                1965
Phe Ser Glu Val Arg Gly Cys Asp Val Thr Phe Glu Trp Lys Thr Lys
        1970                1975                1980
Val Val Cys Pro Pro Lys Lys Leu Glu Cys Lys Phe Val Gln Lys His
1985                1990                1995                2000
Lys Thr Tyr Asp Leu Arg Leu Leu Ser Ser Leu Thr Gly Ser Trp Ser
        2005                2010                2015
Leu Val His Asn Gly Val Ser Tyr Tyr Ile Asn Leu Cys Gln Lys Ile
        2020                2025                2030
Tyr Lys Gly Pro Leu Gly Cys Ser Glu Arg Ala Ser Ile Cys Arg Arg
        2035                2040                2045
Thr Thr Thr Gly Asp Val Gln Val Leu Gly Leu Val His Thr Gln Lys
        2050                2055                2060
Leu Gly Val Ile Gly Asp Lys Val Val Thr Tyr Ser Lys Gly Tyr
2065                2070                2075                2080
Pro Cys Gly Gly Asn Lys Thr Ala Ser Ser Val Ile Glu Leu Thr Cys
        2085                2090                2095
Thr Lys Thr Val Gly Arg Pro Ala Phe Lys Arg Phe Asp Ile Asp Ser
        2100                2105                2110
Cys Thr Tyr Tyr Phe Ser Trp Asp Ser Arg Ala Ala Cys Ala Val Lys
        2115                2120                2125
Pro Gln Glu Val Gln Met Val Asn Gly Thr Ile Thr Asn Pro Ile Asn
        2130                2135                2140
Gly Lys Ser Phe Ser Leu Gly Asp Ile Tyr Phe Lys Leu Phe Arg Ala
2145                2150                2155                2160
Ser Gly Asp Met Arg Thr Asn Gly Asp Asn Tyr Leu Tyr Glu Ile Gln
        2165                2170                2175
Leu Ser Ser Ile Thr Ser Ser Arg Asn Pro Ala Cys Ser Gly Ala Asn
        2180                2185                2190
Ile Cys Gln Val Lys Pro Asn Asp Gln His Phe Ser Arg Lys Val Gly
        2195                2200                2205
Thr Ser Asp Lys Thr Lys Tyr Tyr Leu Gln Asp Gly Asp Leu Asp Val
        2210                2215                2220
Val Phe Ala Ser Ser Ser Lys Cys Gly Lys Asp Lys Thr Lys Ser Val
2225                2230                2235                2240
Ser Ser Thr Ile Phe Phe His Cys Asp Pro Leu Val Glu Asp Gly Ile
        2245                2250                2255
Pro Glu Phe Ser His Glu Thr Ala Asp Cys Gln Tyr Leu Phe Ser Trp
        2260                2265                2270
Tyr Thr Ser Ala Val Cys Pro Leu Gly Val Gly Phe Asp Ser Glu Asn
        2275                2280                2285
```

-continued

```
Pro Gly Asp Asp Gly Gln Met His Lys Gly Leu Ser Glu Arg Ser Gln
    2290                2295                2300

Ala Val Gly Ala Val Leu Ser Leu Leu Val Ala Leu Thr Cys Cys
2305                2310                2315                2320

Leu Leu Ala Leu Leu Leu Tyr Lys Lys Glu Arg Arg Glu Thr Val Ile
                2325                2330                2335

Ser Lys Leu Thr Thr Cys Cys Arg Arg Ser Ser Asn Val Ser Tyr Lys
                2340                2345                2350

Tyr Ser Lys Val Asn Lys Glu Glu Thr Asp Glu Asn Glu Thr Glu
                2355                2360                2365

Trp Leu Met Glu Glu Ile Gln Leu Pro Pro Arg Gln Gly Lys Glu
                2370                2375                2380

Gly Gln Glu Asn Gly His Ile Thr Thr Lys Ser Val Lys Ala Leu Ser
2385                2390                2395                2400

Ser Leu His Gly Asp Asp Gln Asp Ser Glu Asp Glu Val Leu Thr Ile
                2405                2410                2415

Pro Glu Val Lys Val His Ser Gly Arg Gly Ala Gly Ala Glu Ser Ser
                2420                2425                2430

His Pro Val Arg Asn Ala Gln Ser Asn Ala Leu Gln Glu Arg Glu Asp
                2435                2440                2445

Asp Arg Val Gly Leu Val Arg Gly Glu Lys Ala Arg Lys Gly Lys Ser
                2450                2455                2460

Ser Ser Ala Gln Gln Lys Thr Val Ser Ser Thr Lys Leu Val Ser Phe
2465                2470                2475                2480

His Asp Asp Ser Asp Glu Asp Leu Leu His Ile
                2485                2490

<210> SEQ ID NO 17
<211> LENGTH: 2491
<212> TYPE: PRT
<213> ORGANISM: Homo sapiens

<400> SEQUENCE: 17

Met Gly Ala Ala Ala Gly Arg Ser Pro His Leu Gly Pro Ala Pro Ala
1               5                   10                  15

Arg Arg Pro Gln Arg Ser Leu Leu Leu Gln Leu Leu Leu Leu Val
                20                  25                  30

Ala Ala Pro Gly Ser Thr Gln Ala Gln Ala Ala Pro Phe Pro Glu Leu
                35                  40                  45

Cys Ser Tyr Thr Trp Glu Ala Val Asp Thr Lys Asn Asn Val Leu Tyr
    50                  55                  60

Lys Ile Asn Ile Cys Gly Ser Val Asp Ile Val Gln Cys Gly Pro Ser
65                  70                  75                  80

Ser Ala Val Cys Met His Asp Leu Lys Thr Arg Thr Tyr His Ser Val
                85                  90                  95

Gly Asp Ser Val Leu Arg Ser Ala Thr Arg Ser Leu Leu Glu Phe Asn
                100                 105                 110

Thr Thr Val Ser Cys Asp Gln Gln Gly Thr Asn His Arg Val Gln Ser
                115                 120                 125

Ser Ile Ala Phe Leu Cys Gly Lys Thr Leu Gly Thr Pro Glu Phe Val
                130                 135                 140

Thr Ala Thr Glu Cys Val His Tyr Phe Glu Trp Arg Thr Thr Ala Ala
145                 150                 155                 160

Cys Lys Lys Asp Ile Phe Lys Ala Asn Lys Glu Val Pro Cys Tyr Val
                165                 170                 175
```

-continued

Phe Asp Glu Glu Leu Arg Lys His Asp Leu Asn Pro Leu Ile Lys Leu
            180                 185                 190

Ser Gly Ala Tyr Leu Val Asp Ser Asp Pro Asp Thr Ser Leu Phe
        195                 200                 205

Ile Asn Val Cys Arg Asp Ile Asp Thr Leu Arg Asp Pro Gly Ser Gln
    210                 215                 220

Leu Arg Ala Cys Pro Pro Gly Thr Ala Ala Cys Leu Val Arg Gly His
225                 230                 235                 240

Gln Ala Phe Asp Val Gly Gln Pro Arg Asp Gly Leu Lys Leu Val Arg
                245                 250                 255

Lys Asp Arg Leu Val Leu Ser Tyr Val Arg Glu Ala Gly Lys Leu
            260                 265                 270

Asp Phe Cys Asp Gly His Ser Pro Ala Val Thr Ile Thr Phe Val Cys
        275                 280                 285

Pro Ser Glu Arg Arg Glu Gly Thr Ile Pro Lys Leu Thr Ala Lys Ser
    290                 295                 300

Asn Cys Arg Tyr Glu Ile Glu Trp Ile Thr Glu Tyr Ala Cys His Arg
305                 310                 315                 320

Asp Tyr Leu Glu Ser Lys Thr Cys Ser Leu Ser Gly Glu Gln Gln Asp
                325                 330                 335

Val Ser Ile Asp Leu Thr Pro Leu Ala Gln Ser Gly Gly Ser Ser Tyr
            340                 345                 350

Ile Ser Asp Gly Lys Glu Tyr Leu Phe Tyr Leu Asn Val Cys Gly Glu
        355                 360                 365

Thr Glu Ile Gln Phe Cys Asn Lys Lys Gln Ala Ala Val Cys Gln Val
    370                 375                 380

Lys Lys Ser Asp Thr Ser Gln Val Lys Ala Ala Gly Arg Tyr His Asn
385                 390                 395                 400

Gln Thr Leu Arg Tyr Ser Asp Gly Asp Leu Thr Leu Ile Tyr Phe Gly
                405                 410                 415

Gly Asp Glu Cys Ser Ser Gly Phe Gln Arg Met Ser Val Ile Asn Phe
            420                 425                 430

Glu Cys Asn Lys Thr Ala Gly Asn Asp Gly Lys Gly Thr Pro Val Phe
        435                 440                 445

Thr Gly Glu Val Asp Cys Thr Tyr Phe Phe Thr Trp Asp Thr Glu Tyr
    450                 455                 460

Ala Cys Val Lys Glu Lys Glu Asp Leu Leu Cys Gly Ala Thr Asp Gly
465                 470                 475                 480

Lys Lys Arg Tyr Asp Leu Ser Ala Leu Val Arg His Ala Glu Pro Glu
                485                 490                 495

Gln Asn Trp Glu Ala Val Asp Gly Ser Gln Thr Glu Thr Glu Lys Lys
            500                 505                 510

His Phe Phe Ile Asn Ile Cys His Arg Val Leu Gln Glu Gly Lys Ala
        515                 520                 525

Arg Gly Cys Pro Glu Asp Ala Ala Val Cys Ala Val Asp Lys Asn Gly
    530                 535                 540

Ser Lys Asn Leu Gly Lys Phe Ile Ser Ser Pro Met Lys Glu Lys Gly
545                 550                 555                 560

Asn Ile Gln Leu Ser Tyr Ser Asp Gly Asp Asp Cys Gly His Gly Lys
                565                 570                 575

Lys Ile Lys Thr Asn Ile Thr Leu Val Cys Lys Pro Gly Asp Leu Glu
            580                 585                 590

-continued

```
Ser Ala Pro Val Leu Arg Thr Ser Gly Glu Gly Cys Phe Tyr Glu
        595                 600                 605
Phe Glu Trp His Thr Ala Ala Cys Val Leu Ser Lys Thr Glu Gly
    610                 615                 620
Glu Asn Cys Thr Val Phe Asp Ser Gln Ala Gly Phe Ser Phe Asp Leu
625                 630                 635                 640
Ser Pro Leu Thr Lys Lys Asn Gly Ala Tyr Lys Val Glu Thr Lys Lys
                645                 650                 655
Tyr Asp Phe Tyr Ile Asn Val Cys Gly Pro Val Ser Val Ser Pro Cys
                660                 665                 670
Gln Pro Asp Ser Gly Ala Cys Gln Val Ala Lys Ser Asp Glu Lys Thr
            675                 680                 685
Trp Asn Leu Gly Leu Ser Asn Ala Lys Leu Ser Tyr Tyr Asp Gly Met
    690                 695                 700
Ile Gln Leu Asn Tyr Arg Gly Gly Thr Pro Tyr Asn Asn Glu Arg His
705                 710                 715                 720
Thr Pro Arg Ala Thr Leu Ile Thr Phe Leu Cys Asp Arg Asp Ala Gly
                725                 730                 735
Val Gly Phe Pro Glu Tyr Gln Glu Glu Asp Asn Ser Thr Tyr Asn Phe
            740                 745                 750
Arg Trp Tyr Thr Ser Tyr Ala Cys Pro Glu Glu Pro Leu Glu Cys Val
    755                 760                 765
Val Thr Asp Pro Ser Thr Leu Glu Gln Tyr Asp Leu Ser Ser Leu Ala
    770                 775                 780
Lys Ser Glu Gly Gly Leu Gly Gly Asn Trp Tyr Ala Met Asp Asn Ser
785                 790                 795                 800
Gly Glu His Val Thr Trp Arg Lys Tyr Tyr Ile Asn Val Cys Arg Pro
                805                 810                 815
Leu Asn Pro Val Pro Gly Cys Asn Arg Tyr Ala Ser Ala Cys Gln Met
            820                 825                 830
Lys Tyr Glu Lys Asp Gln Gly Ser Phe Thr Glu Val Val Ser Ile Ser
    835                 840                 845
Asn Leu Gly Met Ala Lys Thr Gly Pro Val Val Glu Asp Ser Gly Ser
    850                 855                 860
Leu Leu Leu Glu Tyr Val Asn Gly Ser Ala Cys Thr Thr Ser Asp Gly
865                 870                 875                 880
Arg Gln Thr Thr Tyr Thr Thr Arg Ile His Leu Val Cys Ser Arg Gly
                885                 890                 895
Arg Leu Asn Ser His Pro Ile Phe Ser Leu Asn Trp Glu Cys Val Val
            900                 905                 910
Ser Phe Leu Trp Asn Thr Glu Ala Ala Cys Pro Ile Gln Thr Thr Thr
    915                 920                 925
Asp Thr Asp Gln Ala Cys Ser Ile Arg Asp Pro Asn Ser Gly Phe Val
    930                 935                 940
Phe Asn Leu Asn Pro Leu Asn Ser Ser Gln Gly Tyr Asn Val Ser Gly
945                 950                 955                 960
Ile Gly Lys Ile Phe Met Phe Asn Val Cys Gly Thr Met Pro Val Cys
                965                 970                 975
Gly Thr Ile Leu Gly Lys Pro Ala Ser Gly Cys Glu Ala Glu Thr Gln
            980                 985                 990
Thr Glu Glu Leu Lys Asn Trp Lys Pro Ala Arg Pro Val Gly Ile Glu
    995                 1000                1005
Lys Ser Leu Gln Leu Ser Thr Glu Gly Phe Ile Thr Leu Thr Tyr Lys
```

-continued

```
            1010                1015                1020
Gly Pro Leu Ser Ala Lys Gly Thr Ala Asp Ala Phe Ile Val Arg Phe
1025                1030                1035                1040

Val Cys Asn Asp Asp Val Tyr Ser Gly Pro Leu Lys Phe Leu His Gln
                1045                1050                1055

Asp Ile Asp Ser Gly Gln Gly Ile Arg Asn Thr Tyr Phe Glu Phe Glu
                1060                1065                1070

Thr Ala Leu Ala Cys Val Pro Ser Pro Val Asp Cys Gln Val Thr Asp
                1075                1080                1085

Leu Ala Gly Asn Glu Tyr Asp Leu Thr Gly Leu Ser Thr Val Arg Lys
                1090                1095                1100

Pro Trp Thr Ala Val Asp Thr Ser Val Asp Gly Arg Lys Arg Thr Phe
1105                1110                1115                1120

Tyr Leu Ser Val Cys Asn Pro Leu Pro Tyr Ile Pro Gly Cys Gln Gly
                1125                1130                1135

Ser Ala Val Gly Ser Cys Leu Val Ser Glu Gly Asn Ser Trp Asn Leu
                1140                1145                1150

Gly Val Val Gln Met Ser Pro Gln Ala Ala Asn Gly Ser Leu Ser
                1155                1160                1165

Ile Met Tyr Val Asn Gly Asp Lys Cys Gly Asn Gln Arg Phe Ser Thr
                1170                1175                1180

Arg Ile Thr Phe Glu Cys Ala Gln Ile Ser Gly Ser Pro Ala Phe Gln
1185                1190                1195                1200

Leu Gln Asp Gly Cys Glu Tyr Val Phe Ile Trp Arg Thr Val Glu Ala
                1205                1210                1215

Cys Pro Val Val Arg Val Glu Gly Asp Asn Cys Glu Val Lys Asp Pro
                1220                1225                1230

Arg His Gly Asn Leu Tyr Asp Leu Lys Pro Leu Gly Leu Asn Asp Thr
                1235                1240                1245

Ile Val Ser Ala Gly Glu Tyr Thr Tyr Tyr Phe Arg Val Cys Gly Lys
                1250                1255                1260

Leu Ser Ser Asp Val Cys Pro Thr Ser Asp Lys Ser Lys Val Val Ser
1265                1270                1275                1280

Ser Cys Gln Glu Lys Arg Glu Pro Gln Gly Phe His Lys Val Ala Gly
                1285                1290                1295

Leu Leu Thr Gln Lys Leu Thr Tyr Glu Asn Gly Leu Leu Lys Met Asn
                1300                1305                1310

Phe Thr Gly Gly Asp Thr Cys His Lys Val Tyr Gln Arg Ser Thr Ala
                1315                1320                1325

Ile Phe Phe Tyr Cys Asp Arg Gly Thr Gln Arg Pro Val Phe Leu Lys
                1330                1335                1340

Glu Thr Ser Asp Cys Ser Tyr Leu Phe Glu Trp Arg Thr Gln Tyr Ala
1345                1350                1355                1360

Cys Pro Pro Phe Asp Leu Thr Glu Cys Ser Phe Lys Asp Gly Ala Gly
                1365                1370                1375

Asn Ser Phe Asp Leu Ser Ser Leu Ser Arg Tyr Ser Asp Asn Trp Glu
                1380                1385                1390

Ala Ile Thr Gly Thr Gly Asp Pro Glu His Tyr Leu Ile Asn Val Cys
                1395                1400                1405

Lys Ser Leu Ala Pro Gln Ala Gly Thr Glu Pro Cys Pro Pro Glu Ala
                1410                1415                1420

Ala Ala Cys Leu Leu Gly Gly Ser Lys Pro Val Asn Leu Gly Arg Val
1425                1430                1435                1440
```

```
Arg Asp Gly Pro Gln Trp Arg Asp Gly Ile Ile Val Leu Lys Tyr Val
            1445                1450                1455

Asp Gly Asp Leu Cys Pro Asp Gly Ile Arg Lys Lys Ser Thr Thr Ile
            1460                1465                1470

Arg Phe Thr Cys Ser Glu Ser Gln Val Asn Ser Arg Pro Met Phe Ile
            1475                1480                1485

Ser Ala Val Glu Asp Cys Glu Tyr Thr Phe Ala Trp Pro Thr Ala Thr
            1490                1495                1500

Ala Cys Pro Met Lys Ser Asn Glu His Asp Asp Cys Gln Val Thr Asn
1505                1510                1515                1520

Pro Ser Thr Gly His Leu Phe Asp Leu Ser Ser Leu Ser Gly Arg Ala
            1525                1530                1535

Gly Phe Thr Ala Ala Tyr Ser Glu Lys Gly Leu Val Tyr Met Ser Ile
            1540                1545                1550

Cys Gly Glu Asn Glu Asn Cys Pro Pro Gly Val Gly Ala Cys Phe Gly
            1555                1560                1565

Gln Thr Arg Ile Ser Val Gly Lys Ala Asn Lys Arg Leu Arg Tyr Val
            1570                1575                1580

Asp Gln Val Leu Gln Leu Val Tyr Lys Asp Gly Ser Pro Cys Pro Ser
1585                1590                1595                1600

Lys Ser Gly Leu Ser Tyr Lys Ser Val Ile Ser Phe Val Cys Arg Pro
            1605                1610                1615

Glu Ala Gly Pro Thr Asn Arg Pro Met Leu Ile Ser Leu Asp Lys Gln
            1620                1625                1630

Thr Cys Thr Leu Phe Phe Ser Trp His Thr Pro Leu Ala Cys Glu Gln
            1635                1640                1645

Ala Thr Glu Cys Ser Val Arg Asn Gly Ser Ser Ile Val Asp Leu Ser
            1650                1655                1660

Pro Leu Ile His Arg Thr Gly Gly Tyr Glu Ala Tyr Asp Glu Ser Glu
1665                1670                1675                1680

Asp Asp Ala Ser Asp Thr Asn Pro Asp Phe Tyr Ile Asn Ile Cys Gln
            1685                1690                1695

Pro Leu Asn Pro Met His Gly Val Pro Cys Pro Ala Gly Ala Ala Val
            1700                1705                1710

Cys Lys Val Pro Ile Asp Gly Pro Pro Ile Asp Ile Gly Arg Val Ala
            1715                1720                1725

Gly Pro Pro Ile Leu Asn Pro Ile Ala Asn Glu Ile Tyr Leu Asn Phe
            1730                1735                1740

Glu Ser Ser Thr Pro Cys Leu Ala Asp Lys His Phe Asn Tyr Thr Ser
1745                1750                1755                1760

Leu Ile Ala Phe His Cys Lys Arg Gly Val Ser Met Gly Thr Pro Lys
            1765                1770                1775

Leu Leu Arg Thr Ser Glu Cys Asp Phe Val Phe Glu Trp Glu Thr Pro
            1780                1785                1790

Val Val Cys Pro Asp Glu Val Arg Met Asp Gly Cys Thr Leu Thr Asp
            1795                1800                1805

Glu Gln Leu Leu Tyr Ser Phe Asn Leu Ser Ser Leu Ser Thr Ser Thr
            1810                1815                1820

Phe Lys Val Thr Arg Asp Ser Arg Thr Tyr Ser Val Gly Val Cys Thr
1825                1830                1835                1840

Phe Ala Val Gly Pro Glu Gln Gly Gly Cys Lys Asp Gly Gly Val Cys
            1845                1850                1855
```

```
Leu Leu Ser Gly Thr Lys Gly Ala Ser Phe Gly Arg Leu Gln Ser Met
        1860                1865                1870

Lys Leu Asp Tyr Arg His Gln Asp Glu Ala Val Val Leu Ser Tyr Val
        1875                1880                1885

Asn Gly Asp Arg Cys Pro Glu Thr Asp Asp Gly Val Pro Cys Val
    1890                1895                1900

Phe Pro Phe Ile Phe Asn Gly Lys Ser Tyr Glu Glu Cys Ile Ile Glu
1905            1910                1915                1920

Ser Arg Ala Lys Leu Trp Cys Ser Thr Thr Ala Asp Tyr Asp Arg Asp
                1925                1930                1935

His Glu Trp Gly Phe Cys Arg His Ser Asn Ser Tyr Arg Thr Ser Ser
            1940                1945                1950

Ile Ile Phe Lys Cys Asp Glu Asp Ile Gly Arg Pro Gln Val
        1955                1960                1965

Phe Ser Glu Val Arg Gly Cys Asp Val Thr Phe Glu Trp Lys Thr Lys
    1970                1975                1980

Val Val Cys Pro Pro Lys Lys Leu Glu Cys Lys Phe Val Gln Lys His
1985                1990                1995                2000

Lys Thr Tyr Asp Leu Arg Leu Leu Ser Ser Leu Thr Gly Ser Trp Ser
            2005                2010                2015

Leu Val His Asn Gly Val Ser Tyr Tyr Ile Asn Leu Cys Gln Lys Ile
        2020                2025                2030

Tyr Lys Gly Pro Leu Gly Cys Ser Glu Arg Ala Ser Ile Cys Arg Arg
            2035                2040                2045

Thr Thr Thr Gly Asp Val Gln Val Leu Gly Leu Val His Thr Gln Lys
        2050                2055                2060

Leu Gly Val Ile Gly Asp Lys Val Val Val Thr Tyr Ser Lys Gly Tyr
2065                2070                2075                2080

Pro Cys Gly Gly Asn Lys Thr Ala Ser Ser Val Ile Glu Leu Thr Cys
            2085                2090                2095

Thr Lys Thr Val Gly Arg Pro Ala Phe Lys Arg Phe Asp Ile Asp Ser
        2100                2105                2110

Cys Thr Tyr Tyr Phe Ser Trp Asp Ser Arg Ala Ala Cys Ala Val Lys
        2115                2120                2125

Pro Gln Glu Val Gln Met Val Asn Gly Thr Ile Thr Asn Pro Ile Asn
        2130                2135                2140

Gly Lys Ser Phe Ser Leu Gly Asp Ile Tyr Phe Lys Leu Phe Arg Ala
2145                2150                2155                2160

Ser Gly Asp Met Arg Thr Asn Gly Asp Asn Tyr Leu Tyr Glu Ile Gln
            2165                2170                2175

Leu Ser Ser Ile Thr Ser Ser Arg Asn Pro Ala Cys Ser Gly Ala Asn
        2180                2185                2190

Ile Cys Gln Val Lys Pro Asn Asp Gln His Phe Ser Arg Lys Val Gly
            2195                2200                2205

Thr Ser Asp Lys Thr Lys Tyr Tyr Leu Gln Asp Gly Asp Leu Asp Val
        2210                2215                2220

Val Phe Ala Ser Ser Ser Lys Cys Gly Lys Asp Lys Thr Lys Ser Val
2225                2230                2235                2240

Ser Ser Thr Ile Phe Phe His Cys Asp Pro Leu Val Glu Asp Gly Ile
            2245                2250                2255

Pro Glu Phe Ser His Glu Thr Ala Asp Cys Gln Tyr Leu Phe Ser Trp
        2260                2265                2270

Tyr Thr Ser Ala Val Cys Pro Leu Gly Val Gly Phe Asp Ser Glu Asn
```

-continued

```
                2275                2280                2285
Pro Gly Asp Asp Gly Gln Met His Lys Gly Leu Ser Glu Arg Ser Gln
    2290                2295                2300

Ala Val Gly Ala Val Leu Ser Leu Leu Val Ala Leu Thr Cys Cys
2305                2310                2315                2320

Leu Leu Ala Leu Leu Leu Tyr Lys Lys Glu Arg Arg Glu Thr Val Ile
                2325                2330                2335

Ser Lys Leu Thr Thr Cys Cys Arg Arg Ser Ser Asn Val Ser Tyr Lys
                2340                2345                2350

Tyr Ser Lys Val Asn Lys Glu Glu Thr Asp Glu Asn Glu Thr Glu
        2355                2360                2365

Trp Leu Met Glu Glu Ile Gln Leu Pro Pro Arg Gln Gly Lys Glu
    2370                2375                2380

Gly Gln Glu Asn Gly His Ile Thr Thr Lys Ser Val Lys Ala Leu Ser
2385                2390                2395                2400

Ser Leu His Gly Asp Asp Gln Asp Ser Glu Asp Glu Val Leu Thr Ile
            2405                2410                2415

Pro Glu Val Lys Val His Ser Gly Arg Gly Ala Gly Ala Glu Ser Ser
        2420                2425                2430

His Pro Val Arg Asn Ala Gln Ser Asn Ala Leu Gln Glu Arg Glu Asp
        2435                2440                2445

Asp Arg Val Gly Leu Val Arg Gly Glu Lys Ala Arg Lys Gly Lys Ser
    2450                2455                2460

Ser Ser Ala Gln Gln Lys Thr Val Ser Thr Lys Leu Val Ser Phe
2465                2470                2475                2480

His Asp Asp Ser Asp Glu Asp Leu Leu His Ile
            2485                2490

<210> SEQ ID NO 18
<211> LENGTH: 1500
<212> TYPE: PRT
<213> ORGANISM: Homo sapiens

<400> SEQUENCE: 18

Met Thr Arg Ile Leu Thr Ala Phe Lys Val Val Arg Thr Leu Lys Thr
 1               5                  10                  15

Gly Phe Gly Phe Thr Asn Val Thr Ala His Gln Lys Trp Lys Phe Ser
                20                  25                  30

Arg Pro Gly Ile Arg Leu Leu Ser Val Lys Ala Gln Thr Ala His Ile
            35                  40                  45

Val Leu Glu Asp Gly Thr Lys Met Lys Gly Tyr Ser Phe Gly His Pro
        50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
    130                 135                 140

Ala Thr Lys Ser Leu Gly Gln Trp Leu Gln Glu Glu Lys Val Pro Ala
145                 150                 155                 160
```

-continued

```
Ile Tyr Gly Val Asp Thr Arg Met Leu Thr Lys Ile Ile Arg Asp Lys
                165                 170                 175
Gly Thr Met Leu Gly Lys Ile Glu Phe Glu Gly Gln Pro Val Asp Phe
            180                 185                 190
Val Asp Pro Asn Lys Gln Asn Leu Ile Ala Glu Val Ser Thr Lys Asp
        195                 200                 205
Val Lys Val Tyr Gly Lys Gly Asn Pro Thr Lys Val Ala Val Asp
    210                 215                 220
Cys Gly Ile Lys Asn Asn Val Ile Arg Leu Leu Val Lys Arg Gly Ala
225                 230                 235                 240
Glu Val His Leu Val Pro Trp Asn His Asp Phe Thr Lys Met Glu Tyr
                245                 250                 255
Asp Gly Ile Leu Ile Ala Gly Gly Pro Gly Asn Pro Ala Leu Ala Glu
            260                 265                 270
Pro Leu Ile Gln Asn Val Arg Lys Ile Leu Glu Ser Asp Arg Lys Glu
        275                 280                 285
Pro Leu Phe Gly Ile Ser Thr Gly Asn Leu Ile Thr Gly Leu Ala Ala
    290                 295                 300
Gly Ala Lys Thr Tyr Lys Met Ser Met Ala Asn Arg Gly Gln Asn Gln
305                 310                 315                 320
Pro Val Leu Asn Ile Thr Asn Lys Gln Ala Phe Ile Thr Ala Gln Asn
                325                 330                 335
His Gly Tyr Ala Leu Asp Asn Thr Leu Pro Ala Gly Trp Lys Pro Leu
            340                 345                 350
Phe Val Asn Val Asn Asp Gln Thr Asn Glu Gly Ile Met His Glu Ser
        355                 360                 365
Lys Pro Phe Phe Ala Val Gln Phe His Pro Glu Val Thr Pro Gly Pro
    370                 375                 380
Ile Asp Thr Glu Tyr Leu Phe Asp Ser Phe Phe Ser Leu Ile Lys Lys
385                 390                 395                 400
Gly Lys Ala Thr Thr Ile Thr Ser Val Leu Pro Lys Pro Ala Leu Val
                405                 410                 415
Ala Ser Arg Val Glu Val Ser Lys Val Leu Ile Leu Gly Ser Gly Gly
            420                 425                 430
Leu Ser Ile Gly Gln Ala Gly Glu Phe Asp Tyr Ser Gly Ser Gln Ala
        435                 440                 445
Val Lys Ala Met Lys Glu Glu Asn Val Lys Thr Val Leu Met Asn Pro
    450                 455                 460
Asn Ile Ala Ser Val Gln Thr Asn Glu Val Gly Leu Lys Gln Ala Asp
465                 470                 475                 480
Thr Val Tyr Phe Leu Pro Ile Thr Pro Gln Phe Val Thr Glu Val Ile
                485                 490                 495
Lys Ala Glu Gln Pro Asp Gly Leu Ile Leu Gly Met Gly Gly Gln Thr
            500                 505                 510
Ala Leu Asn Cys Gly Val Glu Leu Phe Lys Arg Gly Val Leu Lys Glu
        515                 520                 525
Tyr Gly Val Lys Val Leu Gly Thr Ser Val Glu Ser Ile Met Ala Thr
    530                 535                 540
Glu Asp Arg Gln Leu Phe Ser Asp Lys Leu Asn Glu Ile Asn Glu Lys
545                 550                 555                 560
Ile Ala Pro Ser Phe Ala Val Glu Ser Ile Glu Asp Ala Leu Lys Ala
                565                 570                 575
Ala Asp Thr Ile Gly Tyr Pro Val Met Ile Arg Ser Ala Tyr Ala Leu
```

-continued

```
                580                 585                 590
Gly Gly Leu Gly Ser Gly Ile Cys Pro Asn Arg Glu Thr Leu Met Asp
            595                 600                 605
Leu Ser Thr Lys Ala Phe Ala Met Thr Asn Gln Ile Leu Val Glu Lys
            610                 615                 620
Ser Val Thr Gly Trp Lys Glu Ile Glu Tyr Glu Val Arg Asp Ala
625                 630                 635                 640
Asp Asp Asn Cys Val Thr Val Cys Asn Met Glu Asn Val Asp Ala Met
                    645                 650                 655
Gly Val His Thr Gly Asp Ser Val Val Ala Pro Ala Gln Thr Leu
                660                 665                 670
Ser Asn Ala Glu Phe Gln Met Leu Arg Arg Thr Ser Ile Asn Val Val
            675                 680                 685
Arg His Leu Gly Ile Val Gly Glu Cys Asn Ile Gln Phe Ala Leu His
        690                 695                 700
Pro Thr Ser Met Glu Tyr Cys Ile Ile Glu Val Asn Ala Arg Leu Ser
705                 710                 715                 720
Arg Ser Ser Ala Leu Ala Ser Lys Ala Thr Gly Tyr Pro Leu Ala Phe
                725                 730                 735
Ile Ala Ala Lys Ile Ala Leu Gly Ile Pro Leu Pro Glu Ile Lys Asn
            740                 745                 750
Val Val Ser Gly Lys Thr Ser Ala Cys Phe Glu Pro Ser Leu Asp Tyr
755                 760                 765
Met Val Thr Lys Ile Pro Arg Trp Asp Leu Asp Arg Phe His Gly Thr
        770                 775                 780
Ser Ser Arg Ile Gly Ser Ser Met Lys Ser Val Gly Glu Val Met Ala
785                 790                 795                 800
Ile Gly Arg Thr Phe Glu Glu Ser Phe Gln Lys Ala Leu Arg Met Cys
                    805                 810                 815
His Pro Ser Ile Glu Gly Phe Thr Pro Arg Leu Pro Met Asn Lys Glu
                820                 825                 830
Trp Pro Ser Asn Leu Asp Leu Arg Lys Glu Leu Ser Glu Pro Ser Ser
            835                 840                 845
Thr Arg Ile Tyr Ala Ile Ala Lys Ala Ile Asp Asp Asn Met Ser Leu
        850                 855                 860
Asp Glu Ile Glu Lys Leu Thr Tyr Ile Asp Lys Trp Phe Leu Tyr Lys
865                 870                 875                 880
Met Arg Asp Ile Leu Asn Met Glu Lys Thr Leu Lys Gly Leu Asn Ser
                    885                 890                 895
Glu Ser Met Thr Glu Glu Thr Leu Lys Arg Ala Lys Glu Ile Gly Phe
                900                 905                 910
Ser Asp Lys Gln Ile Ser Lys Cys Leu Gly Leu Thr Glu Ala Gln Thr
            915                 920                 925
Arg Glu Leu Arg Leu Lys Lys Asn Ile His Pro Trp Val Lys Gln Ile
        930                 935                 940
Asp Thr Leu Ala Ala Glu Tyr Pro Ser Val Thr Asn Tyr Leu Tyr Val
945                 950                 955                 960
Thr Tyr Asn Gly Gln Glu His Asp Val Asn Phe Asp Asp His Gly Met
                    965                 970                 975
Met Val Leu Gly Cys Gly Pro Tyr His Ile Gly Ser Ser Val Glu Phe
                980                 985                 990
Asp Trp Cys Ala Val Ser Ser Ile Arg Thr Leu Arg Gln Leu Gly Lys
            995                 1000                1005
```

```
Lys Thr Val Val Val Asn Cys Asn Pro Glu Thr Val Ser Thr Asp Phe
    1010                1015                1020

Asp Glu Cys Asp Lys Leu Tyr Phe Glu Glu Leu Ser Leu Glu Arg Ile
1025                1030                1035                1040

Leu Asp Ile Tyr His Gln Glu Ala Cys Gly Gly Cys Ile Ile Ser Val
            1045                1050                1055

Gly Gly Gln Ile Pro Asn Asn Leu Ala Val Pro Leu Tyr Lys Asn Gly
        1060                1065                1070

Val Lys Ile Met Gly Thr Ser Pro Leu Gln Ile Asp Arg Ala Glu Asp
    1075                1080                1085

Arg Ser Ile Phe Ser Ala Val Leu Asp Glu Leu Lys Val Ala Gln Ala
1090                1095                1100

Pro Trp Lys Ala Val Asn Thr Leu Asn Glu Ala Leu Glu Phe Ala Lys
1105                1110                1115                1120

Ser Val Asp Tyr Pro Cys Leu Leu Arg Pro Ser Tyr Val Leu Ser Gly
            1125                1130                1135

Ser Ala Met Asn Val Val Phe Ser Glu Asp Glu Met Lys Lys Phe Leu
            1140                1145                1150

Glu Glu Ala Thr Arg Val Ser Gln Glu His Pro Val Leu Thr Lys
        1155                1160                1165

Phe Val Glu Gly Ala Arg Glu Val Glu Met Asp Ala Val Gly Lys Asp
    1170                1175                1180

Gly Arg Val Ile Ser His Ala Ile Ser Glu His Val Glu Asp Ala Gly
1185                1190                1195                1200

Val His Ser Gly Asp Ala Thr Leu Met Leu Pro Thr Gln Thr Ile Ser
                1205                1210                1215

Gln Gly Ala Ile Glu Lys Val Lys Asp Ala Thr Arg Lys Ile Ala Lys
            1220                1225                1230

Ala Phe Ala Ile Ser Gly Pro Phe Asn Val Gln Phe Leu Val Lys Gly
        1235                1240                1245

Asn Asp Val Leu Val Ile Glu Cys Asn Leu Arg Ala Ser Arg Ser Phe
    1250                1255                1260

Pro Phe Val Ser Lys Thr Leu Gly Val Asp Phe Ile Asp Val Ala Thr
1265                1270                1275                1280

Lys Val Met Ile Gly Glu Asn Val Asp Glu Lys His Leu Pro Thr Leu
                1285                1290                1295

Asp His Pro Ile Ile Pro Ala Asp Tyr Val Ala Ile Lys Ala Pro Met
            1300                1305                1310

Phe Ser Trp Pro Arg Leu Arg Asp Ala Asp Pro Ile Leu Arg Cys Glu
        1315                1320                1325

Met Ala Ser Thr Gly Glu Val Ala Cys Phe Gly Glu Gly Ile His Thr
    1330                1335                1340

Ala Phe Leu Lys Ala Met Leu Ser Thr Gly Phe Lys Ile Pro Gln Lys
1345                1350                1355                1360

Gly Ile Leu Ile Gly Ile Gln Gln Ser Phe Arg Pro Arg Phe Leu Gly
            1365                1370                1375

Val Ala Glu Gln Leu His Asn Glu Gly Phe Lys Leu Phe Ala Thr Glu
            1380                1385                1390

Ala Thr Ser Asp Trp Leu Asn Ala Asn Asn Val Pro Ala Thr Pro Val
        1395                1400                1405

Ala Trp Pro Ser Gln Glu Gly Gln Asn Pro Ser Leu Ser Ser Ile Arg
    1410                1415                1420
```

-continued

Lys Leu Ile Arg Asp Gly Ser Ile Asp Leu Val Ile Asn Leu Pro Asn
1425                1430                1435                1440

Asn Asn Thr Lys Phe Val His Asp Asn Tyr Val Ile Arg Arg Thr Ala
            1445                1450                1455

Val Asp Ser Gly Ile Pro Leu Leu Thr Asn Phe Gln Val Thr Lys Leu
        1460                1465                1470

Phe Ala Glu Ala Val Gln Lys Ser Arg Lys Val Asp Ser Lys Ser Leu
    1475                1480                1485

Phe His Tyr Arg Gln Tyr Ser Ala Gly Lys Ala Ala
    1490                1495                1500

<210> SEQ ID NO 19
<211> LENGTH: 1500
<212> TYPE: PRT
<213> ORGANISM: Homo sapiens

<400> SEQUENCE: 19

Met Thr Arg Ile Leu Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
    50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
    130                 135                 140

Ala Thr Lys Ser Leu Gly Gln Trp Leu Gln Glu Glu Lys Val Pro Ala
145                 150                 155                 160

Ile Tyr Gly Val Asp Thr Arg Met Leu Thr Lys Ile Ile Arg Asp Lys
                165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
        195                 200                 205

Val Lys Val Tyr Gly Lys Gly Asn Pro Thr Lys Val Val Ala Val Asp
    210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
        275                 280                 285

Pro Leu Phe Gly Ile Ser Thr Gly Asn Leu Ile Thr Gly Leu Ala Ala
    290                 295                 300

```
Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
            340                 345                 350

Phe Val Asn Val Asn Asp Gln Thr Asn Glu Gly Ile Met His Glu Ser
        355                 360                 365

Lys Pro Phe Phe Ala Val Gln Phe His Pro Glu Val Thr Pro Gly Pro
    370                 375                 380

Ile Asp Thr Glu Tyr Leu Phe Asp Ser Phe Phe Ser Leu Ile Lys Lys
385                 390                 395                 400

Gly Lys Ala Thr Thr Ile Thr Ser Val Leu Pro Lys Pro Ala Leu Val
                405                 410                 415

Ala Ser Arg Val Glu Val Ser Lys Val Leu Ile Leu Gly Ser Gly Gly
            420                 425                 430

Leu Ser Ile Gly Gln Ala Gly Glu Phe Asp Tyr Ser Gly Ser Gln Ala
        435                 440                 445

Val Lys Ala Met Lys Glu Glu Asn Val Lys Thr Val Leu Met Asn Pro
    450                 455                 460

Asn Ile Ala Ser Val Gln Thr Asn Glu Val Gly Leu Lys Gln Ala Asp
465                 470                 475                 480

Thr Val Tyr Phe Leu Pro Ile Thr Pro Gln Phe Val Thr Glu Val Ile
                485                 490                 495

Lys Ala Glu Gln Pro Asp Gly Leu Ile Leu Gly Met Gly Gly Gln Thr
            500                 505                 510

Ala Leu Asn Cys Gly Val Glu Leu Phe Lys Arg Gly Val Leu Lys Glu
        515                 520                 525

Tyr Gly Val Lys Val Leu Gly Thr Ser Val Glu Ser Ile Met Ala Thr
    530                 535                 540

Glu Asp Arg Gln Leu Phe Ser Asp Lys Leu Asn Glu Ile Asn Glu Lys
545                 550                 555                 560

Ile Ala Pro Ser Phe Ala Val Glu Ser Ile Glu Asp Ala Leu Lys Ala
                565                 570                 575

Ala Asp Thr Ile Gly Tyr Pro Val Met Ile Arg Ser Ala Tyr Ala Leu
            580                 585                 590

Gly Gly Leu Gly Ser Gly Ile Cys Pro Asn Arg Glu Thr Leu Met Asp
        595                 600                 605

Leu Ser Thr Lys Ala Phe Ala Met Thr Asn Gln Ile Leu Val Glu Lys
    610                 615                 620

Ser Val Thr Gly Trp Lys Glu Ile Glu Tyr Glu Val Val Arg Asp Ala
625                 630                 635                 640

Asp Asp Asn Cys Val Thr Val Cys Asn Met Glu Asn Val Asp Ala Met
                645                 650                 655

Gly Val His Thr Gly Asp Ser Val Val Val Ala Pro Ala Gln Thr Leu
            660                 665                 670

Ser Asn Ala Glu Phe Gln Met Leu Arg Arg Thr Ser Ile Asn Val Val
        675                 680                 685

Arg His Leu Gly Ile Val Gly Glu Cys Asn Ile Gln Phe Ala Leu His
    690                 695                 700

Pro Thr Ser Met Glu Tyr Cys Ile Ile Glu Val Asn Ala Arg Leu Ser
705                 710                 715                 720
```

```
Arg Ser Ser Ala Leu Ala Ser Lys Ala Thr Gly Tyr Pro Leu Ala Phe
            725                 730                 735

Ile Ala Ala Lys Ile Ala Leu Gly Ile Pro Leu Pro Glu Ile Lys Asn
            740                 745                 750

Val Val Ser Gly Lys Thr Ser Ala Cys Phe Glu Pro Ser Leu Asp Tyr
            755                 760                 765

Met Val Thr Lys Ile Pro Arg Trp Asp Leu Asp Arg Phe His Gly Thr
            770                 775                 780

Ser Ser Arg Ile Gly Ser Ser Met Lys Ser Val Gly Glu Val Met Ala
785                 790                 795                 800

Ile Gly Arg Thr Phe Glu Glu Ser Phe Gln Lys Ala Leu Arg Met Cys
            805                 810                 815

His Pro Ser Ile Glu Gly Phe Thr Pro Arg Leu Pro Met Asn Lys Glu
            820                 825                 830

Trp Pro Ser Asn Leu Asp Leu Arg Lys Glu Leu Ser Glu Pro Ser Ser
            835                 840                 845

Thr Arg Ile Tyr Ala Ile Ala Lys Ala Ile Asp Asp Asn Met Ser Leu
            850                 855                 860

Asp Glu Ile Glu Lys Leu Thr Tyr Ile Asp Lys Trp Phe Leu Tyr Lys
865                 870                 875                 880

Met Arg Asp Ile Leu Asn Met Glu Lys Thr Leu Lys Gly Leu Asn Ser
            885                 890                 895

Glu Ser Met Thr Glu Thr Leu Lys Arg Ala Lys Glu Ile Gly Phe
            900                 905                 910

Ser Asp Lys Gln Ile Ser Lys Cys Leu Gly Leu Thr Glu Ala Gln Thr
            915                 920                 925

Arg Glu Leu Arg Leu Lys Lys Asn Ile His Pro Trp Val Lys Gln Ile
            930                 935                 940

Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp His Gly Met
            965                 970                 975

Met Val Leu Gly Cys Gly Pro Tyr His Ile Gly Ser Ser Val Glu Phe
            980                 985                 990

Asp Trp Cys Ala Val Ser Ser Ile Arg Thr Leu Arg Gln Leu Gly Lys
            995                 1000                1005

Lys Thr Val Val Val Asn Cys Asn Pro Glu Thr Val Ser Thr Asp Phe
    1010                1015                1020

Asp Glu Cys Asp Lys Leu Tyr Phe Glu Glu Leu Ser Leu Glu Arg Ile
1025                1030                1035                1040

Leu Asp Ile Tyr His Gln Glu Ala Cys Gly Gly Cys Ile Ile Ser Val
            1045                1050                1055

Gly Gly Gln Ile Pro Asn Asn Leu Ala Val Pro Leu Tyr Lys Asn Gly
            1060                1065                1070

Val Lys Ile Met Gly Thr Ser Pro Leu Gln Ile Asp Arg Ala Glu Asp
            1075                1080                1085

Arg Ser Ile Phe Ser Ala Val Leu Asp Glu Leu Lys Val Ala Gln Ala
            1090                1095                1100

Pro Trp Lys Ala Val Asn Thr Leu Asn Glu Ala Leu Glu Phe Ala Lys
1105                1110                1115                1120

Ser Val Asp Tyr Pro Cys Leu Leu Arg Pro Ser Tyr Val Leu Ser Gly
            1125                1130                1135

Ser Ala Met Asn Val Val Phe Ser Glu Asp Glu Met Lys Lys Phe Leu
```

```
                    1140                1145                1150
Glu Glu Ala Thr Arg Val Ser Gln Glu His Pro Val Val Leu Thr Lys
        1155                1160                1165

Phe Val Glu Gly Ala Arg Glu Val Met Asp Ala Val Gly Lys Asp
    1170                1175                1180

Gly Arg Val Ile Ser His Ala Ile Ser Glu His Val Glu Asp Ala Gly
1185                1190                1195                1200

Val His Ser Gly Asp Ala Thr Leu Met Leu Pro Thr Gln Thr Ile Ser
        1205                1210                1215

Gln Gly Ala Ile Glu Lys Val Lys Asp Ala Thr Arg Lys Ile Ala Lys
        1220                1225                1230

Ala Phe Ala Ile Ser Gly Pro Phe Asn Val Gln Phe Leu Val Lys Gly
        1235                1240                1245

Asn Asp Val Leu Val Ile Glu Cys Asn Leu Arg Ala Ser Arg Ser Phe
        1250                1255                1260

Pro Phe Val Ser Lys Thr Leu Gly Val Asp Phe Ile Asp Val Ala Thr
1265                1270                1275                1280

Lys Val Met Ile Gly Glu Asn Val Asp Glu Lys His Leu Pro Thr Leu
        1285                1290                1295

Asp His Pro Ile Ile Pro Ala Asp Tyr Val Ala Ile Lys Ala Pro Met
        1300                1305                1310

Phe Ser Trp Pro Arg Leu Arg Asp Ala Asp Pro Ile Leu Arg Cys Glu
        1315                1320                1325

Met Ala Ser Thr Gly Glu Val Ala Cys Phe Gly Glu Gly Ile His Thr
        1330                1335                1340

Ala Phe Leu Lys Ala Met Leu Ser Thr Gly Phe Lys Ile Pro Gln Lys
1345                1350                1355                1360

Gly Ile Leu Ile Gly Ile Gln Gln Ser Phe Arg Pro Arg Phe Leu Gly
        1365                1370                1375

Val Ala Glu Gln Leu His Asn Glu Gly Phe Lys Leu Phe Ala Thr Glu
        1380                1385                1390

Ala Thr Ser Asp Trp Leu Asn Ala Asn Asn Val Pro Ala Thr Pro Val
        1395                1400                1405

Ala Trp Pro Ser Gln Glu Gly Gln Asn Pro Ser Leu Ser Ser Ile Arg
        1410                1415                1420

Lys Leu Ile Arg Asp Gly Ser Ile Asp Leu Val Ile Asn Leu Pro Asn
1425                1430                1435                1440

Asn Asn Thr Lys Phe Val His Asp Asn Tyr Val Ile Arg Arg Thr Ala
        1445                1450                1455

Val Asp Ser Gly Ile Pro Leu Leu Thr Asn Phe Gln Val Thr Lys Leu
        1460                1465                1470

Phe Ala Glu Ala Val Gln Lys Ser Arg Lys Val Asp Ser Lys Ser Leu
        1475                1480                1485

Phe His Tyr Arg Gln Tyr Ser Ala Gly Lys Ala Ala
        1490                1495                1500

<210> SEQ ID NO 20
<211> LENGTH: 1500
<212> TYPE: PRT
<213> ORGANISM: Homo sapiens

<400> SEQUENCE: 20

Met Thr Arg Ile Leu Thr Ala Phe Lys Val Val Arg Thr Leu Lys Thr
1               5                   10                  15
```

```
Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
            35                  40                  45

Val Leu Glu Asp Gly Thr Lys Met Lys Gly Tyr Ser Phe Gly His Pro
 50                  55                  60

Ser Ser Val Ala Gly Glu Val Val Phe Asn Thr Gly Leu Gly Gly Tyr
 65                  70                  75                  80

Pro Glu Ala Ile Thr Asp Pro Ala Tyr Lys Gly Gln Ile Leu Thr Met
            85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
            115                 120                 125

Ser Gly Leu Leu Val Leu Asp Tyr Ser Lys Asp Tyr Asn His Trp Leu
130                 135                 140

Ala Thr Lys Ser Leu Gly Gln Trp Leu Gln Glu Glu Lys Val Pro Ala
145                 150                 155                 160

Ile Tyr Gly Val Asp Thr Arg Met Leu Thr Lys Ile Ile Arg Asp Lys
            165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
            195                 200                 205

Val Lys Val Tyr Gly Lys Gly Asn Pro Thr Lys Val Val Ala Val Asp
            210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
            245                 250                 255

Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
            275                 280                 285

Pro Leu Phe Gly Ile Ser Thr Gly Asn Leu Ile Thr Gly Leu Ala Ala
            290                 295                 300

Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
            325                 330                 335

His Gly Tyr Ala Leu Asp Asn Thr Leu Pro Ala Gly Trp Lys Pro Leu
            340                 345                 350

Phe Val Asn Val Asn Asp Gln Thr Asn Glu Gly Ile Met His Glu Ser
            355                 360                 365

Lys Pro Phe Phe Ala Val Gln Phe His Pro Glu Val Thr Pro Gly Pro
            370                 375                 380

Ile Asp Thr Glu Tyr Leu Phe Asp Ser Phe Phe Ser Leu Ile Lys Lys
385                 390                 395                 400

Gly Lys Ala Thr Thr Ile Thr Ser Val Leu Pro Lys Pro Ala Leu Val
            405                 410                 415

Ala Ser Arg Val Glu Val Ser Lys Val Leu Ile Leu Gly Ser Gly Gly
            420                 425                 430

Leu Ser Ile Gly Gln Ala Gly Glu Phe Asp Tyr Ser Gly Ser Gln Ala
```

-continued

```
            435                 440                 445
Val Lys Ala Met Lys Glu Glu Asn Val Lys Thr Val Leu Met Asn Pro
    450                 455                 460

Asn Ile Ala Ser Val Gln Thr Asn Glu Val Gly Leu Lys Gln Ala Asp
465                 470                 475                 480

Thr Val Tyr Phe Leu Pro Ile Thr Pro Gln Phe Val Thr Glu Val Ile
                485                 490                 495

Lys Ala Glu Gln Pro Asp Gly Leu Ile Leu Gly Met Gly Gly Gln Thr
                500                 505                 510

Ala Leu Asn Cys Gly Val Glu Leu Phe Lys Arg Gly Val Leu Lys Glu
                515                 520                 525

Tyr Gly Val Lys Val Leu Gly Thr Ser Val Glu Ser Ile Met Ala Thr
    530                 535                 540

Glu Asp Arg Gln Leu Phe Ser Asp Lys Leu Asn Glu Ile Asn Glu Lys
545                 550                 555                 560

Ile Ala Pro Ser Phe Ala Val Glu Ser Ile Glu Asp Ala Leu Lys Ala
                565                 570                 575

Ala Asp Thr Ile Gly Tyr Pro Val Met Ile Arg Ser Ala Tyr Ala Leu
                580                 585                 590

Gly Gly Leu Gly Ser Gly Ile Cys Pro Asn Arg Glu Thr Leu Met Asp
                595                 600                 605

Leu Ser Thr Lys Ala Phe Ala Met Thr Asn Gln Ile Leu Val Glu Lys
    610                 615                 620

Ser Val Thr Gly Trp Lys Glu Ile Glu Tyr Glu Val Val Arg Asp Ala
625                 630                 635                 640

Asp Asp Asn Cys Val Thr Val Cys Asn Met Glu Asn Val Asp Ala Met
                645                 650                 655

Gly Val His Thr Gly Asp Ser Val Val Val Ala Pro Ala Gln Thr Leu
                660                 665                 670

Ser Asn Ala Glu Phe Gln Met Leu Arg Arg Thr Ser Ile Asn Val Val
                675                 680                 685

Arg His Leu Gly Ile Val Gly Glu Cys Asn Ile Gln Phe Ala Leu His
    690                 695                 700

Pro Thr Ser Met Glu Tyr Cys Ile Ile Glu Val Asn Ala Arg Leu Ser
705                 710                 715                 720

Arg Ser Ser Ala Leu Ala Ser Lys Ala Thr Gly Tyr Pro Leu Ala Phe
                725                 730                 735

Ile Ala Ala Lys Ile Ala Leu Gly Ile Pro Leu Pro Glu Ile Lys Asn
                740                 745                 750

Val Val Ser Gly Lys Thr Ser Ala Cys Phe Glu Pro Ser Leu Asp Tyr
                755                 760                 765

Met Val Thr Lys Ile Pro Arg Trp Asp Leu Asp Arg Phe His Gly Thr
    770                 775                 780

Ser Ser Arg Ile Gly Ser Ser Met Lys Ser Val Gly Glu Val Met Ala
785                 790                 795                 800

Ile Gly Arg Thr Phe Glu Glu Ser Phe Gln Lys Ala Leu Arg Met Cys
                805                 810                 815

His Pro Ser Ile Glu Gly Phe Thr Pro Arg Leu Pro Met Asn Lys Glu
                820                 825                 830

Trp Pro Ser Asn Leu Asp Leu Arg Lys Glu Leu Ser Glu Pro Ser Ser
                835                 840                 845

Thr Arg Ile Tyr Ala Ile Ala Lys Ala Ile Asp Asp Asn Met Ser Leu
    850                 855                 860
```

```
Asp Glu Ile Glu Lys Leu Thr Tyr Ile Asp Lys Trp Phe Leu Tyr Lys
865                 870                 875                 880

Met Arg Asp Ile Leu Asn Met Glu Lys Thr Leu Lys Gly Leu Asn Ser
            885                 890                 895

Glu Ser Met Thr Glu Thr Leu Lys Arg Ala Lys Glu Ile Gly Phe
        900                 905                 910

Ser Asp Lys Gln Ile Ser Lys Cys Leu Gly Leu Thr Glu Ala Gln Thr
            915                 920                 925

Arg Glu Leu Arg Leu Lys Lys Asn Ile His Pro Trp Val Lys Gln Ile
    930                 935                 940

Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp Asp His Gly Met
                965                 970                 975

Met Val Leu Gly Cys Gly Pro Tyr His Ile Gly Ser Ser Val Glu Phe
            980                 985                 990

Asp Trp Cys Ala Val Ser Ser Ile Arg Thr Leu Arg Gln Leu Gly Lys
    995                 1000                1005

Lys Thr Val Val Val Asn Cys Asn Pro Glu Thr Val Ser Thr Asp Phe
    1010                1015                1020

Asp Glu Cys Asp Lys Leu Tyr Phe Glu Glu Leu Ser Leu Glu Arg Ile
1025                1030                1035                1040

Leu Asp Ile Tyr His Gln Glu Ala Cys Gly Gly Cys Ile Ile Ser Val
            1045                1050                1055

Gly Gly Gln Ile Pro Asn Asn Leu Ala Val Pro Leu Tyr Lys Asn Gly
        1060                1065                1070

Val Lys Ile Met Gly Thr Ser Pro Leu Gln Ile Asp Arg Ala Glu Asp
            1075                1080                1085

Arg Ser Ile Phe Ser Ala Val Leu Asp Glu Leu Lys Val Ala Gln Ala
    1090                1095                1100

Pro Trp Lys Ala Val Asn Thr Leu Asn Glu Ala Leu Glu Phe Ala Lys
1105                1110                1115                1120

Ser Val Asp Tyr Pro Cys Leu Leu Arg Pro Ser Tyr Val Leu Ser Gly
            1125                1130                1135

Ser Ala Met Asn Val Val Phe Ser Glu Asp Glu Met Lys Lys Phe Leu
        1140                1145                1150

Glu Glu Ala Thr Arg Val Ser Gln Glu His Pro Val Val Leu Thr Lys
            1155                1160                1165

Phe Val Glu Gly Ala Arg Glu Val Glu Met Asp Ala Val Gly Lys Asp
    1170                1175                1180

Gly Arg Val Ile Ser His Ala Ile Ser Glu His Val Glu Asp Ala Gly
1185                1190                1195                1200

Val His Ser Gly Asp Ala Thr Leu Met Leu Pro Thr Gln Thr Ile Ser
            1205                1210                1215

Gln Gly Ala Ile Glu Lys Val Lys Asp Ala Thr Arg Lys Ile Ala Lys
        1220                1225                1230

Ala Phe Ala Ile Ser Gly Pro Phe Asn Val Gln Phe Leu Val Lys Gly
        1235                1240                1245

Asn Asp Val Leu Val Ile Glu Cys Asn Leu Arg Ala Ser Arg Ser Phe
    1250                1255                1260

Pro Phe Val Ser Lys Thr Leu Gly Val Asp Phe Ile Asp Val Ala Thr
    1265                1270                1275                1280
```

```
Lys Val Met Ile Gly Glu Asn Val Asp Glu Lys His Leu Pro Thr Leu
            1285                1290                1295

Asp His Pro Ile Ile Pro Ala Asp Tyr Val Ala Ile Lys Ala Pro Met
        1300                1305                1310

Phe Ser Trp Pro Arg Leu Arg Asp Ala Asp Pro Ile Leu Arg Cys Glu
        1315                1320                1325

Met Ala Ser Thr Gly Glu Val Ala Cys Phe Gly Glu Gly Ile His Thr
        1330                1335                1340

Ala Phe Leu Lys Ala Met Leu Ser Thr Gly Phe Lys Ile Pro Gln Lys
1345                1350                1355                1360

Gly Ile Leu Ile Gly Ile Gln Gln Ser Phe Arg Pro Arg Phe Leu Gly
            1365                1370                1375

Val Ala Glu Gln Leu His Asn Glu Gly Phe Lys Leu Phe Ala Thr Glu
            1380                1385                1390

Ala Thr Ser Asp Trp Leu Asn Ala Asn Asn Val Pro Ala Thr Pro Val
        1395                1400                1405

Ala Trp Pro Ser Gln Glu Gly Gln Asn Pro Ser Leu Ser Ser Ile Arg
        1410                1415                1420

Lys Leu Ile Arg Asp Gly Ser Ile Asp Leu Val Ile Asn Leu Pro Asn
1425                1430                1435                1440

Asn Asn Thr Lys Phe Val His Asp Asn Tyr Val Ile Arg Arg Thr Ala
            1445                1450                1455

Val Asp Ser Gly Ile Pro Leu Leu Thr Asn Phe Gln Val Thr Lys Leu
            1460                1465                1470

Phe Ala Glu Ala Val Gln Lys Ser Arg Lys Val Asp Ser Lys Ser Leu
        1475                1480                1485

Phe His Tyr Arg Gln Tyr Ser Ala Gly Lys Ala Ala
        1490                1495                1500

<210> SEQ ID NO 21
<211> LENGTH: 1500
<212> TYPE: PRT
<213> ORGANISM: Homo sapiens

<400> SEQUENCE: 21

Met Thr Arg Ile Leu Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
    50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
    130                 135                 140

Ala Thr Lys Ser Leu Gly Gln Trp Leu Gln Glu Glu Lys Val Pro Ala
145                 150                 155                 160
```

```
Ile Tyr Gly Val Asp Thr Arg Met Leu Thr Lys Ile Ile Arg Asp Lys
            165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
            195                 200                 205

Val Lys Val Tyr Gly Lys Gly Asn Pro Thr Lys Val Val Ala Val Asp
        210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
            275                 280                 285

Pro Leu Phe Gly Ile Ser Thr Gly Asn Leu Ile Thr Gly Leu Ala Ala
        290                 295                 300

Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
            340                 345                 350

Phe Val Asn Val Asn Asp Gln Thr Asn Glu Gly Ile Met His Glu Ser
            355                 360                 365

Lys Pro Phe Phe Ala Val Gln Phe His Pro Glu Val Thr Pro Gly Pro
        370                 375                 380

Ile Asp Thr Glu Tyr Leu Phe Asp Ser Phe Ser Leu Ile Lys Lys
385                 390                 395                 400

Gly Lys Ala Thr Thr Ile Thr Ser Val Leu Pro Lys Pro Ala Leu Val
                405                 410                 415

Ala Ser Arg Val Glu Val Ser Lys Val Leu Ile Leu Gly Ser Gly Gly
            420                 425                 430

Leu Ser Ile Gly Gln Ala Gly Glu Phe Asp Tyr Ser Gly Ser Gln Ala
        435                 440                 445

Val Lys Ala Met Lys Glu Glu Asn Val Lys Thr Val Leu Met Asn Pro
450                 455                 460

Asn Ile Ala Ser Val Gln Thr Asn Glu Val Gly Leu Lys Gln Ala Asp
465                 470                 475                 480

Thr Val Tyr Phe Leu Pro Ile Thr Pro Gln Phe Val Thr Glu Val Ile
                485                 490                 495

Lys Ala Glu Gln Pro Asp Gly Leu Ile Leu Gly Met Gly Gly Gln Thr
            500                 505                 510

Ala Leu Asn Cys Gly Val Glu Leu Phe Lys Arg Gly Val Leu Lys Glu
            515                 520                 525

Tyr Gly Val Lys Val Leu Gly Thr Ser Val Glu Ser Ile Met Ala Thr
        530                 535                 540

Glu Asp Arg Gln Leu Phe Ser Asp Lys Leu Asn Glu Ile Asn Glu Lys
545                 550                 555                 560

Ile Ala Pro Ser Phe Ala Val Glu Ser Ile Glu Asp Ala Leu Lys Ala
                565                 570                 575
```

-continued

```
Ala Asp Thr Ile Gly Tyr Pro Val Met Ile Arg Ser Ala Tyr Ala Leu
            580                 585                 590
Gly Gly Leu Gly Ser Gly Ile Cys Pro Asn Arg Glu Thr Leu Met Asp
        595                 600                 605
Leu Ser Thr Lys Ala Phe Ala Met Thr Asn Gln Ile Leu Val Glu Lys
        610                 615                 620
Ser Val Thr Gly Trp Lys Glu Ile Glu Tyr Glu Val Val Arg Asp Ala
625                 630                 635                 640
Asp Asp Asn Cys Val Thr Val Cys Asn Met Glu Asn Val Asp Ala Met
                645                 650                 655
Gly Val His Thr Gly Asp Ser Val Val Val Ala Pro Ala Gln Thr Leu
            660                 665                 670
Ser Asn Ala Glu Phe Gln Met Leu Arg Arg Thr Ser Ile Asn Val Val
        675                 680                 685
Arg His Leu Gly Ile Val Gly Glu Cys Asn Ile Gln Phe Ala Leu His
        690                 695                 700
Pro Thr Ser Met Glu Tyr Cys Ile Ile Glu Val Asn Ala Arg Leu Ser
705                 710                 715                 720
Arg Ser Ser Ala Leu Ala Ser Lys Ala Thr Gly Tyr Pro Leu Ala Phe
                725                 730                 735
Ile Ala Ala Lys Ile Ala Leu Gly Ile Pro Leu Pro Glu Ile Lys Asn
            740                 745                 750
Val Val Ser Gly Lys Thr Ser Ala Cys Phe Glu Pro Ser Leu Asp Tyr
        755                 760                 765
Met Val Thr Lys Ile Pro Arg Trp Asp Leu Asp Arg Phe His Gly Thr
        770                 775                 780
Ser Ser Arg Ile Gly Ser Ser Met Lys Ser Val Gly Glu Val Met Ala
785                 790                 795                 800
Ile Gly Arg Thr Phe Glu Glu Ser Phe Gln Lys Ala Leu Arg Met Cys
                805                 810                 815
His Pro Ser Ile Glu Gly Phe Thr Pro Arg Leu Pro Met Asn Lys Glu
            820                 825                 830
Trp Pro Ser Asn Leu Asp Leu Arg Lys Glu Leu Ser Glu Pro Ser Ser
        835                 840                 845
Thr Arg Ile Tyr Ala Ile Ala Lys Ala Ile Asp Asp Asn Met Ser Leu
        850                 855                 860
Asp Glu Ile Glu Lys Leu Thr Tyr Ile Asp Lys Trp Phe Leu Tyr Lys
865                 870                 875                 880
Met Arg Asp Ile Leu Asn Met Glu Lys Thr Leu Lys Gly Leu Asn Ser
                885                 890                 895
Glu Ser Met Thr Glu Glu Thr Leu Lys Arg Ala Lys Glu Ile Gly Phe
            900                 905                 910
Ser Asp Lys Gln Ile Ser Lys Cys Leu Gly Leu Thr Glu Ala Gln Thr
        915                 920                 925
Arg Glu Leu Arg Leu Lys Lys Asn Ile His Pro Trp Val Lys Gln Ile
        930                 935                 940
Asp Thr Leu Ala Ala Glu Tyr Pro Ser Val Thr Asn Tyr Leu Tyr Val
945                 950                 955                 960
Thr Tyr Asn Gly Gln Glu His Asp Val Asn Phe Asp Asp His Gly Met
                965                 970                 975
Met Val Leu Gly Cys Gly Pro Tyr His Ile Gly Ser Ser Val Glu Phe
            980                 985                 990
Asp Trp Cys Ala Val Ser Ser Ile Arg Thr Leu Arg Gln Leu Gly Lys
```

-continued

```
                995                 1000                1005
Lys Thr Val Val Val Asn Cys Asn Pro Glu Thr Val Ser Thr Asp Phe
        1010                1015                1020

Asp Glu Cys Asp Lys Leu Tyr Phe Glu Glu Leu Ser Leu Glu Arg Ile
1025                1030                1035                1040

Leu Asp Ile Tyr His Gln Glu Ala Cys Gly Gly Cys Ile Ile Ser Val
                1045                1050                1055

Gly Gly Gln Ile Pro Asn Asn Leu Ala Val Pro Leu Tyr Lys Asn Gly
        1060                1065                1070

Val Lys Ile Met Gly Thr Ser Pro Leu Gln Ile Asp Arg Ala Glu Asp
        1075                1080                1085

Arg Ser Ile Phe Ser Ala Val Leu Asp Glu Leu Lys Val Ala Gln Ala
        1090                1095                1100

Pro Trp Lys Ala Val Asn Thr Leu Asn Glu Ala Leu Glu Phe Ala Lys
1105                1110                1115                1120

Ser Val Asp Tyr Pro Cys Leu Leu Arg Pro Ser Tyr Val Leu Ser Gly
                1125                1130                1135

Ser Ala Met Asn Val Val Phe Ser Glu Asp Glu Met Lys Lys Phe Leu
        1140                1145                1150

Glu Glu Ala Thr Arg Val Ser Gln Val His Pro Val Val Leu Thr Lys
        1155                1160                1165

Phe Val Glu Gly Ala Arg Glu Val Glu Met Asp Ala Val Gly Lys Asp
        1170                1175                1180

Gly Arg Val Ile Ser His Ala Ile Ser Glu His Val Glu Asp Ala Gly
1185                1190                1195                1200

Val His Ser Gly Asp Ala Thr Leu Met Leu Pro Thr Gln Thr Ile Ser
                1205                1210                1215

Gln Gly Ala Ile Glu Lys Val Lys Asp Ala Thr Arg Lys Ile Ala Lys
        1220                1225                1230

Ala Phe Ala Ile Ser Gly Pro Phe Asn Val Gln Phe Leu Val Lys Gly
        1235                1240                1245

Asn Asp Val Leu Val Ile Glu Cys Asn Leu Arg Ala Ser Arg Ser Phe
        1250                1255                1260

Pro Phe Val Ser Lys Thr Leu Gly Val Asp Phe Ile Asp Val Ala Thr
1265                1270                1275                1280

Lys Val Met Ile Gly Glu Asn Val Asp Glu Lys His Leu Pro Thr Leu
                1285                1290                1295

Asp His Pro Ile Ile Pro Ala Asp Tyr Val Ala Ile Lys Ala Pro Met
        1300                1305                1310

Phe Ser Trp Pro Arg Leu Arg Asp Ala Asp Pro Ile Leu Arg Cys Glu
        1315                1320                1325

Met Ala Ser Thr Gly Glu Val Ala Cys Phe Gly Glu Gly Ile His Thr
        1330                1335                1340

Ala Phe Leu Lys Ala Met Leu Ser Thr Gly Phe Lys Ile Pro Gln Lys
1345                1350                1355                1360

Gly Ile Leu Ile Gly Ile Gln Gln Ser Phe Arg Pro Arg Phe Leu Gly
                1365                1370                1375

Val Ala Glu Gln Leu His Asn Glu Gly Phe Lys Leu Phe Ala Thr Glu
        1380                1385                1390

Ala Thr Ser Asp Trp Leu Asn Ala Asn Asn Val Pro Ala Thr Pro Val
        1395                1400                1405

Ala Trp Pro Ser Gln Glu Gly Gln Asn Pro Ser Leu Ser Ser Ile Arg
        1410                1415                1420
```

-continued

```
Lys Leu Ile Arg Asp Gly Ser Ile Asp Leu Val Ile Asn Leu Pro Asn
1425                1430                1435                1440

Asn Asn Thr Lys Phe Val His Asp Asn Tyr Val Ile Arg Arg Thr Ala
            1445                1450                1455

Val Asp Ser Gly Ile Pro Leu Leu Thr Asn Phe Gln Val Thr Lys Leu
        1460                1465                1470

Phe Ala Glu Ala Val Gln Lys Ser Arg Lys Val Asp Ser Lys Ser Leu
    1475                1480                1485

Phe His Tyr Arg Gln Tyr Ser Ala Gly Lys Ala Ala
    1490                1495                1500

<210> SEQ ID NO 22
<211> LENGTH: 169
<212> TYPE: PRT
<213> ORGANISM: Homo sapiens

<400> SEQUENCE: 22

Pro Ser Glu Pro Gly Asp Pro Ala Arg Leu Leu Gln Pro Glu Arg Gly
1               5                   10                  15

Arg Phe Ser His His Pro Asp Asp Val Trp Leu Arg Arg Gly Val Gly
            20                  25                  30

Arg Ala Leu Pro Pro Arg Val Pro Ala Gly Arg Leu Arg Arg Gln Gly
        35                  40                  45

Leu His Arg Leu Glu Arg Gly Pro Ala Leu Leu Asp Arg Gly His
    50                  55                  60

Gly Gly Ser Asp His Pro Ala Gln Val Gly Gly Pro Cys Gly Gly
65              70                  75                  80

Ala Val Glu Ser Leu Pro Gly Gly His Val Arg Gly Val Ala Pro Gln
            85                  90                  95

Ile Pro Gly Glu Arg Glu Gly Asp Ala Ala His Gly Ile Pro Ile
        100                 105                 110

Val Gly Ile Ile Ala Gly Leu Val Leu Phe Gly Ala Val Ile Thr Gly
    115                 120                 125

Ala Val Val Ala Ala Val Arg Trp Arg Arg Lys Ser Ser Asp Arg Lys
130                 135                 140

Gly Gly Ser Tyr Ser Gln Ala Ala Ser Ser Asp Ser Ala Gln Gly Ser
145                 150                 155                 160

Asp Val Ser Leu Thr Ala Cys Lys Val
                165

<210> SEQ ID NO 23
<211> LENGTH: 287
<212> TYPE: PRT
<213> ORGANISM: Homo sapiens

<400> SEQUENCE: 23

Met Ala Val Met Ala Pro Arg Thr Leu Leu Leu Leu Leu Gly Ala
1               5                   10                  15

Leu Ala Leu Thr Gln Thr Trp Ala Gly Ser His Ser Met Arg Tyr Phe
            20                  25                  30

Thr Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65              70                  75                  80
```

```
Pro Glu Tyr Trp Asp Leu Gln Thr Arg Asn Val Lys Ala Gln Ser Gln
                85                  90                  95

Thr Asp Arg Ala Asn Leu Gly Thr Leu Arg Gly Tyr Tyr Asn Gln Ser
            100                 105                 110

Glu Ala Gly Ser His Thr Ile Gln Met Met Tyr Gly Cys Asp Val Gly
        115                 120                 125

Ser Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Ala Ala Arg Val
                165                 170                 175

Ala Glu Gln Leu Arg Ala Tyr Leu Glu Gly Thr Cys Val Glu Trp Leu
            180                 185                 190

Arg Met Val Pro Ser Gly Gln Glu Gln Arg Tyr Thr Cys His Val Gln
        195                 200                 205

His Glu Gly Leu Pro Lys Pro Leu Thr Leu Arg Trp Glu Pro Ser Ser
    210                 215                 220

Gln Pro Thr Ile Pro Ile Val Gly Ile Ile Ala Gly Leu Val Leu Phe
225                 230                 235                 240

Gly Ala Val Ile Thr Gly Ala Val Val Ala Ala Val Arg Trp Arg Arg
                245                 250                 255

Lys Ser Ser Asp Arg Lys Gly Gly Ser Tyr Ser Gln Ala Ala Ser Ser
            260                 265                 270

Asp Ser Ala Gln Gly Ser Asp Val Ser Leu Thr Ala Cys Lys Val
        275                 280                 285

<210> SEQ ID NO 24
<211> LENGTH: 275
<212> TYPE: PRT
<213> ORGANISM: Homo sapiens

<400> SEQUENCE: 24

Val Lys Ala Gln Ser Gln Thr His Arg Val Asp Leu Gly Thr Leu Arg
  1               5                  10                  15

Gly Tyr Tyr Asn Gln Ser Glu Ala Val Ser His Thr Val Gln Arg Met
                20                  25                  30

Tyr Gly Cys Asp Val Gly Ser Asp Gly Arg Phe Leu Arg Gly Tyr His
            35                  40                  45

Gln Val Ala Tyr Asp Gly Lys Asp Tyr Ile Ala Leu Lys Glu Asp Leu
    50                  55                  60

Arg Ser Trp Thr Ala Ala Asp Met Ala Ala Gln Thr Thr Lys His Lys
65                  70                  75                  80

Trp Glu Ala Ala His Val Ala Glu Gln Leu Arg Ala Tyr Leu Glu Gly
                85                  90                  95

Thr Cys Val Glu Trp Leu Arg Arg Tyr Leu Glu Asn Gly Lys Glu Thr
            100                 105                 110

Leu Gln Arg Thr Asp Ala Pro Lys Thr His Met Thr His His Ala Val
        115                 120                 125

Ser Asp His Glu Ala Thr Leu Arg Cys Trp Ala Leu Ser Phe Tyr Pro
    130                 135                 140

Ala Glu Ile Thr Leu Thr Trp Gln Arg Asp Gly Glu Asp Gln Thr Gln
145                 150                 155                 160

Asp Thr Glu Leu Val Glu Thr Arg Pro Ala Gly Asp Gly Thr Phe Gln
```

-continued

```
                165                 170                 175
Lys Trp Ala Ala Val Val Pro Ser Gly Glu Glu Gln Arg Tyr Thr
            180                 185                 190

Cys His Val Gln His Glu Gly Leu Pro Lys Pro Leu Thr Leu Arg Trp
            195                 200                 205

Glu Pro Ser Ser Gln Pro Thr Ile Pro Ile Val Gly Ile Ile Ala Gly
            210                 215                 220

Leu Val Leu Leu Gly Ala Val Ile Thr Gly Ala Val Val Ala Ala Val
225                 230                 235                 240

Met Trp Arg Arg Lys Ser Ser Asp Arg Lys Gly Gly Ser Tyr Ser Gln
            245                 250                 255

Ala Ala Ser Ser Asp Ser Ala Gln Gly Ser Asp Val Ser Leu Thr Ala
            260                 265                 270

Cys Lys Val
            275

<210> SEQ ID NO 25
<211> LENGTH: 365
<212> TYPE: PRT
<213> ORGANISM: Homo sapiens

<400> SEQUENCE: 25

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Tyr Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
        50                  55                  60

Ala Ser Gln Arg Met Glu Pro Arg Ala Pro Trp Ile Glu Gln Glu Gly
65                  70                  75                  80

Pro Glu Tyr Trp Asp Arg Asn Thr Arg Asn Val Lys Ala Gln Ser Gln
                85                  90                  95

Thr Asp Arg Val Asp Leu Gly Thr Leu Arg Gly Tyr Tyr Asn Gln Ser
            100                 105                 110

Glu Ala Gly Ser His Thr Ile Gln Met Met Tyr Gly Cys Asp Val Gly
            115                 120                 125

Ser Asp Gly Arg Phe Leu Arg Gly Tyr Arg Gln Asp Ala Tyr Asp Gly
        130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
        210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255
```

```
Thr Arg Pro Ala Gly Asp Gly Thr Phe Gln Lys Trp Val Ala Val
                260                 265                 270

Val Pro Ser Gly Gln Glu Gln Arg Tyr Thr Cys His Val Gln His Glu
275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
                340                 345                 350

Ala Gln Gly Ser Asp Val Ser Leu Thr Ala Cys Lys Val
                355                 360                 365

<210> SEQ ID NO 26
<211> LENGTH: 46
<212> TYPE: PRT
<213> ORGANISM: Homo sapiens

<400> SEQUENCE: 26

Asp Leu Lys Ala Leu Thr Pro Phe Trp Tyr Leu Thr Gly His Phe Leu
1               5                   10                  15

Pro Thr Asp Arg Lys Gly Gly Ser Tyr Ser Gln Ala Ala Ser Ser Asp
                20                  25                  30

Ser Ala Gln Gly Ser Asp Val Ser Leu Thr Ala Cys Lys Val
                35                  40                  45

<210> SEQ ID NO 27
<211> LENGTH: 326
<212> TYPE: PRT
<213> ORGANISM: Homo sapiens

<400> SEQUENCE: 27

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
                20                  25                  30

Thr Thr Ser Val Ser Arg Pro Gly Arg Gly Glu Pro Arg Phe Ile Ala
                35                  40                  45

Val Gly Tyr Val Asp Asp Thr Gln Phe Val Arg Phe Asp Ser Asp Ala
50                  55                  60

Ala Ser Gln Arg Met Glu Pro Arg Ala Pro Trp Ile Glu Gln Glu Gly
65                  70                  75                  80

Pro Glu Tyr Trp Asp Leu Gln Thr Arg Asn Val Lys Ala Gln Ser Gln
                85                  90                  95

Thr Asp Arg Ala Asn Leu Gly Thr Leu Arg Gly Tyr Tyr Asn Gln Ser
                100                 105                 110

Glu Ala Gly Ser His Thr Ile Gln Met Met Tyr Gly Cys Asp Val Gly
                115                 120                 125

Ser Asp Gly Arg Phe Leu Arg Gly Tyr Arg Gln Asp Ala Tyr Asp Gly
                130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Ala Ala Arg Val
                165                 170                 175
```

```
Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
            210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Asp Arg Lys Gly Gly Ser
            290                 295                 300

Tyr Ser Gln Ala Ala Ser Ser Asp Ser Ala Gln Gly Ser Asp Val Ser
305                 310                 315                 320

Leu Thr Ala Cys Lys Val
                325

<210> SEQ ID NO 28
<211> LENGTH: 365
<212> TYPE: PRT
<213> ORGANISM: Homo sapiens

<400> SEQUENCE: 28

Met Ala Val Met Gly Pro Arg Thr Leu Val Leu Leu Leu Ser Gly Ala
  1               5                  10                  15

Leu Ala Leu Thr Gln Thr Trp Ala Gly Ser His Ser Met Arg Tyr Phe
             20                  25                  30

Ser Thr Ser Val Ser Arg Pro Gly Arg Gly Glu Pro Arg Phe Ile Ala
             35                  40                  45

Val Gly Tyr Val Asp Asp Thr Gln Phe Val Arg Phe Asp Ser Asp Ala
         50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                 85                  90                  95

Thr Asp Arg Glu Asn Leu Arg Ile Ala Leu Arg Tyr Tyr Asn Gln Ser
            100                 105                 110

Glu Ala Gly Ser His Thr Leu Gln Met Met Phe Gly Cys Asp Val Gly
            115                 120                 125

Ser Asp Gly Arg Phe Leu Arg Gly Tyr His Gln Tyr Ala Tyr Asp Gly
            130                 135                 140

Lys Asp Tyr Ile Ala Leu Lys Glu Asp Leu Arg Ser Trp Thr Ala Ala
145                 150                 155                 160

Asp Met Ala Ala Gln Ile Thr Lys Arg Lys Trp Glu Ala Ala His Val
                165                 170                 175

Ala Glu Gln Gln Arg Ala Tyr Leu Glu Gly Thr Cys Val Asp Gly Leu
            180                 185                 190

Arg Arg Tyr Leu Glu Asn Gly Lys Glu Thr Leu Gln Arg Ala Asp Pro
            195                 200                 205

Pro Lys Thr His Met Thr His His Pro Ile Ser Asp His Glu Ala Thr
            210                 215                 220
```

```
Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Val Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Asn Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 29
<211> LENGTH: 365
<212> TYPE: PRT
<213> ORGANISM: Homo sapiens

<400> SEQUENCE: 29

Met Ala Val Met Ala Pro Arg Thr Leu Leu Leu Leu Leu Leu Gly Ala
1               5                   10                  15

Leu Ala Leu Thr Gln Thr Trp Ala Gly Ser His Ser Met Arg Tyr Phe
            20                  25                  30

Thr Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Leu Gln Thr Arg Asn Val Lys Ala Gln Ser Gln
                85                  90                  95

Thr Asp Arg Ala Asn Leu Gly Thr Leu Arg Gly Tyr Tyr Asn Gln Ser
            100                 105                 110

Glu Ala Gly Ser His Thr Ile Gln Met Met Tyr Gly Cys Asp Val Gly
        115                 120                 125

Ser Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Ala Ala Arg Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
```

```
                225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
            290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Arg Trp Arg Arg Lys Ser
            325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
            355                 360                 365

<210> SEQ ID NO 30
<211> LENGTH: 365
<212> TYPE: PRT
<213> ORGANISM: Homo sapiens

<400> SEQUENCE: 30

Met Ala Val Met Pro Pro Arg Thr Leu Leu Leu Leu Leu Ser Gly Ala
 1               5                  10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
            35                  40                  45

Val Gly Tyr Val Asp Asp Ser Gln Phe Val Gln Phe Asp Ser Asp Ala
    50                  55                  60

Ala Ser Gln Arg Met Glu Pro Arg Ala Pro Trp Ile Glu Gln Glu Glu
65                  70                  75                  80

Pro Glu Tyr Trp Asp Glu Glu Thr Arg Asn Val Lys Ala His Ser Gln
            85                  90                  95

Thr Asn Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
            115                 120                 125

Ser Asp Gly Arg Phe Leu Arg Gly Tyr Arg Gln Asp Ala Tyr Asp Gly
            130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Ala Arg Arg
            165                 170                 175

Ala Glu Gln Leu Arg Ala Tyr Leu Glu Gly Glu Cys Val Asp Gly Leu
            180                 185                 190

Arg Arg Tyr Leu Glu Asn Gly Lys Glu Thr Leu Gln Arg Thr Asp Pro
            195                 200                 205

Pro Lys Thr His Met Thr His His Pro Ile Ser Asp His Glu Ala Thr
            210                 215                 220

Leu Arg Cys Trp Ala Leu Ser Phe Tyr Pro Ala Glu Ile Thr Leu Thr
225                 230                 235                 240
```

```
Trp Gln Arg Asp Gly Glu Asp Gln Thr Gln Asp Thr Glu Leu Val Glu
                    245                 250                 255

Thr Arg Pro Ala Gly Asp Gly Thr Phe Gln Lys Trp Ala Ala Val Val
                260                 265                 270

Val Pro Ser Gly Lys Glu Lys Arg Tyr Thr Cys His Val Gln His Glu
            275                 280                 285

Gly Leu Pro Glu Pro Leu Thr Leu Arg Trp Glu Pro Ser Ser Gln Pro
        290                 295                 300

Thr Ile Pro Ile Val Gly Ile Ile Ala Gly Leu Val Leu Leu Gly Ala
305                 310                 315                 320

Val Ile Ala Gly Ala Val Ala Ala Val Met Trp Arg Lys Lys Ser
                325                 330                 335

Ser Val Arg Lys Gly Gly Ser Tyr Ser Gln Ala Ala Ser Ser Asp Ser
                340                 345                 350

Ala Gln Gly Ser Asp Val Ser Leu Thr Ala Cys Lys Val
                355                 360                 365

<210> SEQ ID NO 31
<211> LENGTH: 46
<212> TYPE: PRT
<213> ORGANISM: Homo sapiens

<400> SEQUENCE: 31

Asp Leu Lys Ala Leu Thr Pro Phe Trp Tyr Leu Thr Gly His Phe Leu
1               5                   10                  15

Pro Thr Asp Arg Lys Gly Gly Ser Tyr Ser Gln Ala Ala Ser Ser Asp
                20                  25                  30

Ser Ala Gln Gly Ser Asp Val Ser Leu Thr Ala Cys Lys Val
            35                  40                  45

<210> SEQ ID NO 32
<211> LENGTH: 365
<212> TYPE: PRT
<213> ORGANISM: Homo sapiens

<400> SEQUENCE: 32

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
                20                  25                  30

Ser Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Tyr Asn Gln Ser
                100                 105                 110

Glu Ala Gly Ser His Thr Leu Gln Met Met Phe Gly Cys Asp Val Gly
            115                 120                 125

Ser Asp Gly Arg Phe Leu Arg Gly Tyr His Gln Tyr Ala Tyr Asp Gly
        130                 135                 140

Lys Asp Tyr Ile Ala Leu Lys Glu Asp Leu Arg Ser Trp Thr Ala Ala
145                 150                 155                 160
```

```
Asp Met Ala Ala Gln Ile Thr Gln Arg Lys Trp Glu Ala Ala Arg Val
            165                 170                 175

Ala Glu Gln Leu Arg Ala Tyr Leu Glu Gly Thr Cys Val Asp Gly Leu
        180                 185                 190

Arg Arg Tyr Leu Glu Asn Gly Lys Glu Thr Leu Gln Arg Thr Asp Pro
            195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Val His Ile Val Gly Ile Ile Ala Gly Leu Val Leu Leu Gly Ala
305                 310                 315                 320

Val Ile Thr Gly Ala Val Val Ala Ala Val Met Trp Arg Arg Asn Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 33
<211> LENGTH: 365
<212> TYPE: PRT
<213> ORGANISM: Homo sapiens

<400> SEQUENCE: 33

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175
```

-continued

```
Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 34
<211> LENGTH: 365
<212> TYPE: PRT
<213> ORGANISM: Homo sapiens

<400> SEQUENCE: 34

Met Ala Val Met Ala Pro Arg Thr Leu Val Leu Leu Leu Ser Gly Ala
 1               5                  10                  15

Leu Ala Leu Thr Gln Thr Trp Ala Gly Ser His Ser Met Arg Tyr Phe
                20                  25                  30

Ser Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
        50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Asn Gln Ser
            100                 105                 110

Glu Ala Gly Ser His Thr Leu Gln Met Met Phe Gly Cys Asp Val Gly
        115                 120                 125

Ser Asp Gly Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Ile Thr Lys Arg Lys Trp Glu Ala Ala His Val
                165                 170                 175

Ala Glu Gln Gln Arg Ala Tyr Leu Glu Gly Thr Cys Val Asp Gly Leu
```

-continued

```
                180                 185                 190
Arg Arg Tyr Leu Glu Asn Gly Lys Glu Thr Leu Gln Arg Thr Asp Pro
            195                 200                 205
Pro Lys Thr His Met Thr His His Pro Ile Ser Asp His Glu Ala Thr
210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Gly Thr Phe Gln Lys Trp Ala Ala Val Val
            260                 265                 270
Val Pro Ser Gly Glu Glu Gln Arg Tyr Thr Cys His Val Gln His Glu
        275                 280                 285
Gly Leu Pro Lys Pro Leu Thr Leu Arg Trp Glu Pro Ser Ser Gln Pro
    290                 295                 300
Thr Val Pro Ile Val Gly Ile Ile Ala Gly Leu Val Leu Leu Gly Ala
305                 310                 315                 320
Val Ile Thr Gly Ala Val Val Ala Ala Val Met Trp Arg Arg Asn Ser
                325                 330                 335
Ser Asp Arg Lys Gly Gly Ser Tyr Ser Gln Ala Ala Ser Ser Asp Ser
            340                 345                 350
Ala Gln Gly Ser Asp Val Ser Leu Thr Ala Cys Lys Val
        355                 360                 365
```

<210> SEQ ID NO 35
<211> LENGTH: 432
<212> TYPE: PRT
<213> ORGANISM: Homo sapiens

<400> SEQUENCE: 35

```
Met Pro Ala Arg Pro Gly Arg Leu Leu Pro Leu Leu Ala Arg Pro Ala
1               5                   10                  15
Ala Leu Thr Ala Leu Leu Leu Leu Leu Gly His Gly Gly Gly Gly
            20                  25                  30
Arg Trp Gly Ala Arg Ala Gln Glu Ala Ala Ala Ala Ala Ala Asp Gly
        35                  40                  45
Pro Pro Ala Ala Asp Gly Glu Asp Gly Gln Asp Pro His Ser Lys His
    50                  55                  60
Leu Tyr Thr Ala Asp Met Phe Thr His Gly Ile Gln Ser Ala Ala His
65                  70                  75                  80
Phe Val Met Phe Phe Ala Pro Trp Cys Gly His Cys Gln Arg Leu Gln
                85                  90                  95
Pro Thr Trp Asn Asp Leu Gly Asp Lys Tyr Asn Ser Met Glu Asp Ala
            100                 105                 110
Lys Val Tyr Val Ala Lys Val Asp Cys Thr Ala His Ser Asp Val Cys
        115                 120                 125
Ser Ala Gln Gly Val Arg Gly Tyr Pro Thr Leu Lys Leu Phe Lys Pro
    130                 135                 140
Gly Gln Glu Ala Val Lys Tyr Gln Gly Pro Arg Asp Phe Gln Thr Leu
145                 150                 155                 160
Glu Asn Trp Met Leu Gln Thr Leu Asn Glu Glu Pro Val Thr Pro Glu
                165                 170                 175
Pro Glu Val Glu Pro Pro Ser Ala Pro Glu Leu Lys Gln Gly Leu Tyr
            180                 185                 190
```

-continued

```
Glu Leu Ser Ala Ser Asn Phe Glu Leu His Val Ala Gln Gly Asp His
            195                 200                 205

Phe Ile Lys Phe Phe Ala Pro Trp Cys Gly His Cys Lys Ala Leu Ala
        210                 215                 220

Pro Thr Trp Glu Gln Leu Ala Leu Gly Leu His Ser Glu Thr Val
225                 230                 235                 240

Lys Ile Gly Lys Val Asp Cys Thr Gln His Tyr Glu Leu Cys Ser Gly
                245                 250                 255

Asn Gln Val Arg Gly Tyr Pro Thr Leu Leu Trp Phe Arg Asp Gly Lys
            260                 265                 270

Lys Val Asp Gln Tyr Lys Gly Lys Arg Asp Leu Glu Ser Leu Arg Glu
        275                 280                 285

Tyr Val Glu Ser Gln Leu Gln Arg Thr Glu Thr Gly Ala Thr Glu Thr
    290                 295                 300

Val Thr Pro Ser Glu Ala Pro Val Leu Ala Ala Glu Pro Glu Ala Asp
305                 310                 315                 320

Lys Gly Thr Val Leu Ala Leu Thr Glu Asn Asn Phe Asp Asp Thr Ile
                325                 330                 335

Ala Glu Gly Ile Thr Phe Ile Lys Phe Tyr Ala Pro Trp Cys Gly His
            340                 345                 350

Cys Lys Thr Leu Ala Pro Thr Trp Glu Glu Leu Ser Lys Lys Glu Phe
        355                 360                 365

Pro Gly Leu Ala Gly Val Lys Ile Ala Glu Val Asp Cys Thr Ala Glu
    370                 375                 380

Arg Asn Ile Cys Ser Lys Tyr Ser Val Arg Gly Tyr Pro Thr Leu Leu
385                 390                 395                 400

Leu Phe Arg Gly Gly Lys Lys Val Ser Glu His Ser Gly Gly Arg Asp
                405                 410                 415

Leu Asp Ser Leu His Arg Phe Val Leu Ser Gln Ala Lys Asp Glu Leu
            420                 425                 430

<210> SEQ ID NO 36
<211> LENGTH: 389
<212> TYPE: PRT
<213> ORGANISM: Homo sapiens

<400> SEQUENCE: 36

Met Lys Gln Met Asn Ile Leu Phe Pro Asn Val Glu Thr Gln Cys Gly
1               5                   10                  15

Thr Ala Ser Ala Arg Phe Ser Arg Asp Cys Lys Gln Leu Met Thr Gln
            20                  25                  30

Ser Val Asp Ser Asn Arg Gly Asn Arg Asn Glu Lys Arg Cys Gly His
        35                  40                  45

Cys Gln Arg Leu Gln Pro Thr Trp Asn Asp Leu Gly Asp Lys Tyr Asn
    50                  55                  60

Ser Met Glu Asp Ala Lys Val Tyr Val Ala Lys Val Asp Cys Thr Ala
65                  70                  75                  80

His Ser Asp Val Cys Ser Ala Gln Gly Val Arg Gly Tyr Pro Thr Leu
                85                  90                  95

Lys Leu Phe Lys Pro Gly Gln Glu Ala Val Lys Tyr Gln Gly Pro Arg
            100                 105                 110

Asp Phe Gln Thr Leu Glu Asn Trp Met Leu Gln Thr Leu Asn Glu Glu
        115                 120                 125

Pro Val Thr Pro Glu Pro Glu Val Glu Pro Pro Ser Ala Pro Glu Leu
    130                 135                 140
```

-continued

Lys Gln Gly Leu Tyr Glu Leu Ser Ala Ser Asn Phe Glu Leu His Val
145                 150                 155                 160

Ala Gln Gly Asp His Phe Ile Lys Phe Phe Ala Pro Trp Cys Gly His
                165                 170                 175

Cys Lys Ala Leu Ala Pro Thr Trp Glu Gln Leu Ala Leu Gly Leu Glu
            180                 185                 190

His Ser Glu Thr Val Lys Ile Gly Lys Val Asp Cys Thr Gln His Tyr
        195                 200                 205

Glu Leu Cys Ser Gly Asn Gln Val Arg Gly Tyr Pro Thr Leu Leu Trp
    210                 215                 220

Phe Arg Asp Gly Lys Lys Val Asp Gln Tyr Lys Gly Lys Arg Asp Leu
225                 230                 235                 240

Glu Ser Leu Arg Glu Tyr Val Glu Ser Gln Leu Gln Arg Thr Glu Thr
                245                 250                 255

Gly Ala Thr Glu Thr Val Thr Pro Ser Glu Ala Pro Val Leu Ala Ala
            260                 265                 270

Glu Pro Glu Ala Asp Lys Gly Thr Val Leu Ala Leu Thr Glu Asn Asn
        275                 280                 285

Phe Asp Asp Thr Ile Ala Glu Gly Ile Thr Phe Ile Lys Phe Tyr Ala
    290                 295                 300

Pro Trp Cys Gly His Cys Lys Thr Leu Ala Pro Thr Trp Glu Glu Leu
305                 310                 315                 320

Ser Lys Lys Glu Phe Pro Gly Leu Ala Gly Val Lys Ile Ala Glu Val
                325                 330                 335

Asp Cys Thr Ala Glu Arg Asn Ile Cys Ser Lys Tyr Ser Val Arg Gly
            340                 345                 350

Tyr Pro Thr Leu Leu Leu Phe Arg Gly Gly Lys Lys Val Ser Glu His
        355                 360                 365

Ser Gly Gly Arg Asp Leu Asp Ser Leu His Arg Phe Val Leu Ser Gln
    370                 375                 380

Ala Lys Asp Glu Leu
385

<210> SEQ ID NO 37
<211> LENGTH: 432
<212> TYPE: PRT
<213> ORGANISM: Homo sapiens

<400> SEQUENCE: 37

Met Pro Ala Arg Pro Gly Arg Leu Leu Pro Leu Leu Ala Arg Pro Ala
1               5                   10                  15

Ala Leu Thr Ala Leu Leu Leu Leu Leu Gly His Gly Gly Gly Gly
            20                  25                  30

Arg Trp Gly Ala Arg Ala Gln Glu Ala Ala Ala Ala Ala Ala Asp Gly
        35                  40                  45

Pro Pro Ala Ala Asp Gly Glu Asp Gly Gln Asp Pro His Ser Lys His
    50                  55                  60

Leu Tyr Thr Ala Asp Met Phe Thr His Gly Ile Gln Ser Ala Ala His
65                  70                  75                  80

Phe Val Met Phe Phe Ala Pro Trp Cys Gly His Cys Gln Arg Leu Gln
                85                  90                  95

Pro Thr Trp Asn Asp Leu Gly Asp Lys Tyr Asn Ser Met Glu Asp Ala
            100                 105                 110

Lys Val Tyr Val Ala Lys Val Asp Cys Thr Ala His Ser Asp Val Cys

```
                115                 120                 125
Ser Ala Gln Gly Val Arg Gly Tyr Pro Thr Leu Lys Leu Phe Lys Pro
    130                 135                 140

Gly Gln Glu Ala Val Lys Tyr Gln Gly Pro Arg Asp Phe Gln Thr Leu
145                 150                 155                 160

Glu Asn Trp Met Leu Gln Thr Leu Asn Glu Glu Pro Val Thr Pro Glu
                165                 170                 175

Pro Glu Val Glu Pro Pro Ser Ala Pro Glu Leu Lys Gln Gly Leu Tyr
            180                 185                 190

Glu Leu Ser Ala Ser Asn Phe Glu Leu His Val Ala Gln Gly Asp His
            195                 200                 205

Phe Ile Lys Phe Phe Ala Pro Trp Cys Gly His Cys Lys Ala Leu Ala
    210                 215                 220

Pro Thr Trp Glu Gln Leu Ala Leu Gly Leu Glu His Ser Glu Thr Val
225                 230                 235                 240

Lys Ile Gly Lys Val Asp Cys Thr Gln His Tyr Glu Leu Cys Ser Gly
                245                 250                 255

Asn Gln Val Arg Gly Tyr Pro Thr Leu Leu Trp Phe Arg Asp Gly Lys
            260                 265                 270

Lys Val Asp Gln Tyr Lys Gly Lys Arg Asp Leu Glu Ser Leu Arg Glu
        275                 280                 285

Tyr Val Glu Ser Gln Leu Gln Arg Thr Glu Thr Gly Ala Thr Glu Thr
    290                 295                 300

Val Thr Pro Ser Glu Ala Pro Val Leu Ala Ala Glu Pro Glu Ala Asp
305                 310                 315                 320

Lys Gly Thr Val Leu Ala Leu Thr Glu Asn Asn Phe Asp Asp Thr Ile
                325                 330                 335

Ala Glu Gly Ile Thr Phe Ile Lys Phe Tyr Ala Pro Trp Cys Gly His
            340                 345                 350

Cys Lys Thr Leu Ala Pro Thr Trp Glu Glu Leu Ser Lys Lys Glu Phe
        355                 360                 365

Pro Gly Leu Ala Gly Val Lys Ile Ala Glu Val Asp Cys Thr Ala Glu
    370                 375                 380

Arg Asn Ile Cys Ser Lys Tyr Ser Val Arg Gly Tyr Pro Thr Leu Leu
385                 390                 395                 400

Leu Phe Arg Gly Gly Lys Lys Val Ser Glu His Ser Gly Gly Arg Asp
                405                 410                 415

Leu Asp Ser Leu His Arg Phe Val Leu Ser Gln Ala Lys Asp Glu Leu
            420                 425                 430

<210> SEQ ID NO 38
<211> LENGTH: 324
<212> TYPE: PRT
<213> ORGANISM: Homo sapiens

<400> SEQUENCE: 38

Met Glu Asp Ala Lys Val Tyr Val Ala Lys Val Asp Cys Thr Ala His
1               5                   10                  15

Ser Asp Val Cys Ser Ala Gln Gly Val Arg Gly Tyr Pro Thr Leu Lys
                20                  25                  30

Leu Phe Lys Pro Gly Gln Glu Ala Val Lys Tyr Gln Gly Pro Arg Asp
            35                  40                  45

Phe Gln Thr Leu Glu Asn Trp Met Leu Gln Thr Leu Asn Glu Glu Pro
        50                  55                  60
```

```
Val Thr Pro Glu Pro Glu Val Glu Pro Pro Ser Ala Pro Glu Leu Lys
 65                  70                  75                  80

Gln Gly Leu Tyr Glu Leu Ser Ala Ser Asn Phe Glu Leu His Val Ala
                 85                  90                  95

Gln Gly Asp His Phe Ile Lys Phe Phe Ala Pro Trp Cys Gly His Cys
            100                 105                 110

Lys Ala Leu Ala Pro Thr Trp Glu Gln Leu Ala Leu Gly Leu Glu His
        115                 120                 125

Ser Glu Thr Val Lys Ile Gly Lys Val Asp Cys Thr Gln His Tyr Glu
    130                 135                 140

Leu Cys Ser Gly Asn Gln Val Arg Gly Tyr Pro Thr Leu Leu Trp Phe
145                 150                 155                 160

Arg Asp Gly Lys Lys Val Asp Gln Tyr Lys Gly Lys Arg Asp Leu Glu
                165                 170                 175

Ser Leu Arg Glu Tyr Val Glu Ser Gln Leu Gln Arg Thr Glu Thr Gly
            180                 185                 190

Ala Thr Glu Thr Val Thr Pro Ser Glu Ala Pro Val Leu Ala Ala Glu
        195                 200                 205

Pro Glu Ala Asp Lys Gly Thr Val Leu Ala Leu Thr Glu Asn Asn Phe
    210                 215                 220

Asp Asp Thr Ile Ala Glu Gly Ile Thr Phe Ile Lys Phe Tyr Ala Pro
225                 230                 235                 240

Trp Cys Gly His Cys Lys Thr Leu Ala Pro Thr Trp Glu Glu Leu Ser
                245                 250                 255

Lys Lys Glu Phe Pro Gly Leu Ala Gly Val Lys Ile Ala Glu Val Asp
            260                 265                 270

Cys Thr Ala Glu Arg Asn Ile Cys Ser Lys Tyr Ser Val Arg Gly Tyr
        275                 280                 285

Pro Thr Leu Leu Leu Phe Arg Gly Gly Lys Lys Val Ser Glu His Ser
    290                 295                 300

Gly Gly Arg Asp Leu Asp Ser Leu His Arg Phe Val Leu Ser Gln Ala
305                 310                 315                 320

Lys Asp Glu Leu

<210> SEQ ID NO 39
<211> LENGTH: 324
<212> TYPE: PRT
<213> ORGANISM: Homo sapiens

<400> SEQUENCE: 39

Met Glu Asp Ala Lys Val Tyr Val Ala Lys Val Asp Cys Thr Ala His
 1               5                  10                  15

Ser Asp Val Cys Ser Ala Gln Gly Val Arg Gly Tyr Pro Thr Leu Lys
                 20                  25                  30

Leu Phe Lys Pro Gly Gln Glu Ala Val Lys Tyr Gln Gly Pro Arg Asp
            35                  40                  45

Phe Gln Thr Leu Glu Asn Trp Met Leu Gln Thr Leu Asn Glu Glu Pro
        50                  55                  60

Val Thr Pro Glu Pro Glu Val Glu Pro Pro Ser Ala Pro Glu Leu Lys
 65                  70                  75                  80

Gln Gly Leu Tyr Glu Leu Ser Ala Ser Asn Phe Glu Leu His Val Ala
                 85                  90                  95

Gln Gly Asp His Phe Ile Lys Phe Phe Ala Pro Trp Cys Gly His Cys
            100                 105                 110
```

-continued

```
Lys Ala Leu Ala Pro Thr Trp Glu Gln Leu Ala Leu Gly Leu Glu His
        115                 120                 125

Ser Glu Thr Val Lys Ile Gly Lys Val Asp Cys Thr Gln His Tyr Glu
    130                 135                 140

Leu Cys Ser Gly Asn Gln Val Arg Gly Tyr Pro Thr Leu Leu Trp Phe
145                 150                 155                 160

Arg Asp Gly Lys Lys Val Asp Gln Tyr Lys Gly Lys Arg Asp Leu Glu
                165                 170                 175

Ser Leu Arg Glu Tyr Val Glu Ser Gln Leu Gln Arg Thr Glu Thr Gly
            180                 185                 190

Ala Thr Glu Thr Val Thr Pro Ser Glu Ala Pro Val Leu Ala Ala Glu
        195                 200                 205

Pro Glu Ala Asp Lys Gly Thr Val Leu Ala Leu Thr Glu Asn Asn Phe
    210                 215                 220

Asp Asp Thr Ile Ala Glu Gly Ile Thr Phe Ile Lys Phe Tyr Ala Pro
225                 230                 235                 240

Trp Cys Gly His Cys Lys Thr Leu Ala Pro Thr Trp Glu Glu Leu Ser
                245                 250                 255

Lys Lys Glu Phe Pro Gly Leu Ala Gly Val Lys Ile Ala Glu Val Asp
            260                 265                 270

Cys Thr Ala Glu Arg Asn Ile Cys Ser Lys Tyr Ser Val Arg Gly Tyr
        275                 280                 285

Pro Thr Leu Leu Leu Phe Arg Gly Gly Lys Lys Val Ser Glu His Ser
    290                 295                 300

Gly Gly Arg Asp Leu Asp Ser Leu His Arg Phe Val Leu Ser Gln Ala
305                 310                 315                 320

Lys Asp Glu Leu

<210> SEQ ID NO 40
<211> LENGTH: 389
<212> TYPE: PRT
<213> ORGANISM: Homo sapiens

<400> SEQUENCE: 40

Met Lys Gln Met Asn Ile Leu Phe Pro Asn Val Glu Thr Gln Cys Gly
1               5                   10                  15

Thr Ala Ser Ala Arg Phe Ser Arg Asp Cys Lys Gln Leu Met Thr Gln
            20                  25                  30

Ser Val Asp Ser Asn Arg Gly Asn Arg Asn Glu Lys Arg Cys Gly His
        35                  40                  45

Cys Gln Arg Leu Gln Pro Thr Trp Asn Asp Leu Gly Asp Lys Tyr Asn
    50                  55                  60

Ser Met Glu Asp Ala Lys Val Tyr Val Ala Lys Val Asp Cys Thr Ala
65                  70                  75                  80

His Ser Asp Val Cys Ser Ala Gln Gly Val Arg Gly Tyr Pro Thr Leu
                85                  90                  95

Lys Leu Phe Lys Pro Gly Gln Glu Ala Val Lys Tyr Gln Gly Pro Arg
            100                 105                 110

Asp Phe Gln Thr Leu Glu Asn Trp Met Leu Gln Thr Leu Asn Glu Glu
        115                 120                 125

Pro Val Thr Pro Glu Pro Glu Val Glu Pro Ser Ala Pro Glu Leu
    130                 135                 140

Lys Gln Gly Leu Tyr Glu Leu Ser Ala Ser Asn Phe Glu Leu His Val
145                 150                 155                 160
```

-continued

Ala Gln Gly Asp His Phe Ile Lys Phe Phe Ala Pro Trp Cys Gly His
            165                 170                 175

Cys Lys Ala Leu Ala Pro Thr Trp Glu Gln Leu Ala Leu Gly Leu Glu
            180                 185                 190

His Ser Glu Thr Val Lys Ile Gly Lys Val Asp Cys Thr Gln His Tyr
            195                 200                 205

Glu Leu Cys Ser Gly Asn Gln Val Arg Gly Tyr Pro Thr Leu Leu Trp
            210                 215                 220

Phe Arg Asp Gly Lys Lys Val Asp Gln Tyr Lys Gly Lys Arg Asp Leu
225                 230                 235                 240

Glu Ser Leu Arg Glu Tyr Val Glu Ser Gln Leu Gln Arg Thr Glu Thr
            245                 250                 255

Gly Ala Thr Glu Thr Val Thr Pro Ser Glu Ala Pro Val Leu Ala Ala
            260                 265                 270

Glu Pro Glu Ala Asp Lys Gly Thr Val Leu Ala Leu Thr Glu Asn Asn
            275                 280                 285

Phe Asp Asp Thr Ile Ala Glu Gly Ile Thr Phe Ile Lys Phe Tyr Ala
290                 295                 300

Pro Trp Cys Gly His Cys Lys Thr Leu Ala Pro Thr Trp Glu Glu Leu
305                 310                 315                 320

Ser Lys Lys Glu Phe Pro Gly Leu Ala Gly Val Lys Ile Ala Glu Val
            325                 330                 335

Asp Cys Thr Ala Glu Arg Asn Ile Cys Ser Lys Tyr Ser Val Arg Gly
            340                 345                 350

Tyr Pro Thr Leu Leu Leu Phe Arg Gly Gly Lys Lys Val Ser Glu His
            355                 360                 365

Ser Gly Gly Arg Asp Leu Asp Ser Leu His Arg Phe Val Leu Ser Gln
            370                 375                 380

Ala Lys Asp Glu Leu
385

<210> SEQ ID NO 41
<211> LENGTH: 99
<212> TYPE: PRT
<213> ORGANISM: Homo sapiens

<400> SEQUENCE: 41

Met Ala Ser Ala Ser Ala Arg Gly Asn Gln Asp Lys Asp Ala His Phe
1               5                   10                  15

Pro Pro Pro Ser Lys Gln Ser Leu Leu Phe Cys Pro Lys Ser Lys Leu
            20                  25                  30

His Ile His Arg Ala Glu Ile Ser Lys Ile Met Arg Glu Cys Gln Glu
            35                  40                  45

Glu Ser Phe Trp Lys Arg Ala Leu Pro Phe Ser Leu Val Ser Met Leu
        50                  55                  60

Val Thr Gln Gly Leu Val Tyr Gln Gly Tyr Leu Ala Ala Asn Ser Arg
65                  70                  75                  80

Phe Gly Ser Leu Pro Lys Val Ala Arg Thr Ala Ser Leu Pro Val Arg
            85                  90                  95

Asn Ala Lys

<210> SEQ ID NO 42
<211> LENGTH: 91
<212> TYPE: PRT
<213> ORGANISM: Homo sapiens

```
<400> SEQUENCE: 42

Met Ala Ser Ala Ser Ala Arg Gly Asn Gln Asp Lys Asp Ala His Phe
1               5                   10                  15

Pro Pro Pro Ser Lys Gln Ser Leu Leu Phe Cys Pro Lys Ser Lys Leu
            20                  25                  30

His Ile His Arg Ala Glu Ile Ser Lys Ile Met Arg Glu Cys Gln Glu
            35                  40                  45

Glu Ser Phe Trp Lys Arg Ala Leu Pro Phe Ser Leu Val Ser Met Leu
        50                  55                  60

Val Thr Gln Gly Leu Val Tyr Gln Gly Tyr Leu Ala Ala Asn Ser Arg
65                  70                  75                  80

Phe Gly Ser Leu Pro Lys Val Ala Arg Lys Ser
                85                  90

<210> SEQ ID NO 43
<211> LENGTH: 2048
<212> TYPE: PRT
<213> ORGANISM: Homo sapiens

<400> SEQUENCE: 43

Met Leu Arg Val Ile Val Glu Ser Ala Ser Asn Ile Pro Lys Thr Lys
1               5                   10                  15

Phe Gly Lys Pro Asp Pro Ile Val Ser Val Ile Phe Lys Asp Glu Lys
            20                  25                  30

Lys Lys Thr Lys Lys Val Asp Asn Glu Leu Asn Pro Val Trp Asn Glu
            35                  40                  45

Ile Leu Glu Phe Asp Leu Arg Gly Ile Pro Leu Asp Phe Ser Ser Ser
        50                  55                  60

Leu Gly Ile Ile Val Lys Asp Phe Glu Thr Ile Gly Gln Asn Lys Leu
65                  70                  75                  80

Ile Gly Thr Ala Thr Val Ala Leu Lys Asp Leu Thr Gly Asp Gln Ser
                85                  90                  95

Arg Ser Leu Pro Tyr Lys Leu Ile Ser Leu Leu Asn Glu Lys Gly Gln
            100                 105                 110

Asp Thr Gly Ala Thr Ile Asp Leu Val Ile Gly Tyr Asp Pro Pro Ser
            115                 120                 125

Ala Pro His Pro Asn Asp Leu Ser Gly Pro Ser Val Pro Gly Met Gly
            130                 135                 140

Gly Asp Gly Glu Glu Asp Glu Gly Asp Glu Asp Arg Leu Asp Asn Ala
145                 150                 155                 160

Val Arg Gly Pro Gly Pro Lys Gly Pro Val Gly Thr Val Ser Glu Ala
            165                 170                 175

Gln Leu Ala Arg Arg Leu Thr Lys Val Lys Asn Ser Arg Arg Met Leu
            180                 185                 190

Ser Asn Lys Pro Gln Asp Phe Gln Ile Arg Val Arg Val Ile Glu Gly
            195                 200                 205

Arg Gln Leu Ser Gly Asn Asn Ile Arg Pro Val Val Lys Val His Val
            210                 215                 220

Cys Gly Gln Thr His Arg Thr Arg Ile Lys Arg Gly Asn Asn Pro Phe
225                 230                 235                 240

Phe Asp Glu Leu Phe Phe Tyr Asn Val Asn Met Thr Pro Ser Glu Leu
                245                 250                 255

Met Asp Glu Ile Ile Ser Ile Arg Val Tyr Asn Ser His Ser Leu Arg
            260                 265                 270
```

-continued

```
Ala Asp Cys Leu Met Gly Glu Phe Lys Ile Asp Val Gly Phe Val Tyr
        275                 280                 285

Asp Glu Pro Gly His Ala Val Met Arg Lys Trp Leu Leu Leu Asn Asp
        290                 295                 300

Pro Glu Asp Thr Ser Ser Gly Ser Lys Gly Tyr Met Lys Val Ser Met
305                 310                 315                 320

Phe Val Leu Gly Thr Gly Asp Glu Pro Pro Glu Arg Arg Asp Arg
                325                 330                 335

Asp Asn Asp Ser Asp Asp Val Glu Ser Asn Leu Leu Leu Pro Ala Gly
                340                 345                 350

Ile Ala Leu Arg Trp Val Thr Phe Leu Leu Lys Ile Tyr Arg Ala Glu
                355                 360                 365

Asp Ile Pro Gln Met Asp Asp Ala Phe Ser Gln Thr Val Lys Glu Ile
        370                 375                 380

Phe Gly Gly Asn Ala Asp Lys Lys Asn Leu Val Asp Pro Phe Val Glu
385                 390                 395                 400

Val Ser Phe Ala Gly Lys Lys Val Cys Thr Asn Ile Ile Glu Lys Asn
                405                 410                 415

Ala Asn Pro Glu Trp Asn Gln Val Val Asn Leu Gln Ile Lys Phe Pro
                420                 425                 430

Ser Val Cys Glu Lys Ile Lys Leu Thr Ile Tyr Asp Trp Asp Arg Leu
                435                 440                 445

Thr Lys Asn Asp Val Val Gly Thr Thr Tyr Leu His Leu Ser Lys Ile
        450                 455                 460

Ala Ala Ser Gly Gly Glu Val Glu Val Asn Thr Gly Glu Thr Glu Val
465                 470                 475                 480

Gly Phe Val Pro Thr Phe Gly Pro Cys Tyr Leu Asn Leu Tyr Gly Ser
                485                 490                 495

Pro Arg Glu Tyr Thr Gly Phe Pro Asp Pro Tyr Asp Glu Leu Asn Thr
                500                 505                 510

Gly Lys Gly Glu Gly Val Ala Tyr Arg Gly Arg Ile Leu Val Glu Leu
                515                 520                 525

Ala Thr Phe Leu Glu Lys Thr Pro Pro Asp Lys Lys Leu Glu Pro Ile
                530                 535                 540

Ser Asn Asp Asp Leu Leu Val Val Glu Lys Tyr Gln Arg Arg Lys
545                 550                 555                 560

Tyr Ser Leu Ser Ala Val Phe His Ser Ala Thr Met Leu Gln Asp Val
                565                 570                 575

Gly Glu Ala Ile Gln Phe Glu Val Ser Ile Gly Asn Tyr Gly Asn Lys
                580                 585                 590

Phe Asp Thr Thr Cys Lys Pro Leu Ala Ser Thr Gln Tyr Ser Arg
        595                 600                 605

Ala Val Phe Asp Gly Asn Tyr Tyr Tyr Leu Pro Trp Ala His Thr
        610                 615                 620

Lys Pro Val Val Thr Leu Thr Ser Tyr Trp Glu Asp Ile Ser His Arg
625                 630                 635                 640

Leu Asp Ala Val Asn Thr Leu Leu Ala Met Ala Glu Arg Leu Gln Thr
                645                 650                 655

Asn Ile Glu Ala Leu Lys Ser Gly Ile Gln Gly Lys Ile Pro Ala Asn
                660                 665                 670

Gln Leu Ala Glu Leu Trp Leu Lys Leu Ile Asp Glu Val Ile Glu Asp
                675                 680                 685

Thr Arg Tyr Thr Leu Pro Leu Thr Glu Gly Lys Ala Asn Val Thr Val
```

-continued

```
            690                 695                 700
Leu Asp Thr Gln Ile Arg Lys Leu Arg Ser Arg Ser Leu Ser Gln Ile
705                 710                 715                 720

His Glu Ala Ala Val Arg Met Arg Ser Glu Ala Thr Asp Val Lys Ser
                725                 730                 735

Thr Leu Ala Glu Ile Glu Asp Trp Leu Asp Lys Leu Met Gln Leu Thr
            740                 745                 750

Glu Glu Pro Gln Asn Ser Met Pro Asp Ile Ile Ile Trp Met Ile Arg
        755                 760                 765

Gly Glu Lys Arg Leu Ala Tyr Ala Arg Ile Pro Ala His Gln Val Leu
770                 775                 780

Tyr Ser Thr Ser Gly Glu Asn Ala Ser Gly Lys Tyr Cys Gly Lys Thr
785                 790                 795                 800

Gln Thr Ile Phe Leu Lys Tyr Pro Gln Glu Lys Asn Asn Gly Pro Lys
                805                 810                 815

Val Pro Val Glu Leu Arg Val Asn Ile Trp Leu Gly Leu Ser Ala Val
            820                 825                 830

Glu Lys Lys Phe Asn Ser Phe Ala Glu Gly Thr Phe Thr Val Phe Ala
        835                 840                 845

Glu Met Tyr Glu Asn Gln Ala Leu Met Phe Gly Lys Trp Gly Thr Ser
850                 855                 860

Gly Leu Val Gly Arg His Lys Phe Ser Asp Val Thr Gly Lys Ile Lys
865                 870                 875                 880

Leu Lys Arg Glu Phe Phe Leu Pro Pro Lys Gly Trp Glu Trp Glu Gly
                885                 890                 895

Glu Trp Ile Val Asp Pro Glu Arg Ser Leu Leu Thr Glu Ala Asp Ala
            900                 905                 910

Gly His Thr Glu Phe Thr Asp Glu Val Tyr Gln Asn Glu Ser Arg Tyr
        915                 920                 925

Pro Gly Gly Asp Trp Lys Pro Ala Glu Asp Thr Tyr Thr Asp Ala Asn
930                 935                 940

Gly Asp Lys Ala Ala Ser Pro Ser Glu Leu Thr Cys Pro Pro Gly Trp
945                 950                 955                 960

Glu Trp Glu Asp Ala Trp Ser Tyr Asp Ile Asn Arg Ala Val Asp
                965                 970                 975

Glu Lys Gly Trp Glu Tyr Gly Ile Thr Ile Pro Pro Asp His Lys Pro
            980                 985                 990

Lys Ser Trp Val Ala Ala Glu Lys Met Tyr His Thr His Arg Arg Arg
        995                 1000                1005

Arg Leu Val Arg Lys Arg Lys Lys Asp Leu Thr Gln Thr Ala Ser Ser
1010                1015                1020

Thr Ala Arg Ala Met Glu Glu Leu Gln Asp Gln Glu Gly Trp Glu Tyr
1025                1030                1035                1040

Ala Ser Leu Ile Gly Trp Lys Phe His Trp Lys Gln Arg Ser Ser Asp
                1045                1050                1055

Thr Phe Arg Arg Arg Trp Arg Lys Met Ala Pro Ser Glu Thr
            1060                1065                1070

His Gly Ala Ala Ala Ile Phe Lys Leu Glu Gly Ala Leu Gly Ala Asp
        1075                1080                1085

Thr Thr Glu Asp Gly Asp Glu Lys Ser Leu Glu Lys Gln Lys His Ser
1090                1095                1100

Ala Thr Thr Val Phe Gly Ala Asn Thr Pro Ile Val Ser Cys Asn Phe
1105                1110                1115                1120
```

-continued

```
Asp Arg Val Tyr Ile Tyr His Leu Arg Cys Tyr Val Tyr Gln Ala Arg
            1125                1130                1135

Asn Leu Leu Ala Leu Asp Lys Asp Ser Phe Ser Asp Pro Tyr Ala His
        1140                1145                1150

Ile Cys Phe Leu His Arg Ser Lys Thr Thr Glu Ile Ile His Ser Thr
        1155                1160                1165

Leu Asn Pro Thr Trp Asp Gln Thr Ile Ile Phe Asp Glu Val Glu Ile
    1170                1175                1180

Tyr Gly Glu Pro Gln Thr Val Leu Gln Asn Pro Pro Lys Val Ile Met
1185                1190                1195                1200

Glu Leu Phe Asp Asn Asp Gln Val Gly Lys Asp Glu Phe Leu Gly Arg
        1205                1210                1215

Ser Ile Phe Ser Pro Val Val Lys Leu Asn Ser Glu Met Asp Ile Thr
        1220                1225                1230

Pro Lys Leu Leu Trp His Pro Val Met Asn Gly Asp Lys Ala Cys Gly
        1235                1240                1245

Asp Val Leu Val Thr Ala Glu Leu Ile Leu Arg Gly Lys Asp Gly Ser
        1250                1255                1260

Asn Leu Pro Ile Leu Pro Pro Gln Arg Ala Pro Asn Leu Tyr Met Val
1265                1270                1275                1280

Pro Gln Gly Ile Arg Pro Val Val Gln Leu Thr Ala Ile Glu Ile Leu
        1285                1290                1295

Ala Trp Gly Leu Arg Asn Met Lys Asn Phe Gln Met Ala Ser Ile Thr
        1300                1305                1310

Ser Pro Ser Leu Val Val Glu Cys Gly Gly Glu Arg Val Glu Ser Val
        1315                1320                1325

Val Ile Lys Asn Leu Lys Lys Thr Pro Asn Phe Pro Ser Ser Val Leu
        1330                1335                1340

Phe Met Lys Val Phe Leu Pro Lys Glu Glu Leu Tyr Met Pro Pro Leu
1345                1350                1355                1360

Val Ile Lys Val Ile Asp His Arg Gln Phe Gly Arg Lys Pro Val Val
        1365                1370                1375

Gly Gln Cys Thr Ile Glu Arg Leu Asp Arg Phe Arg Cys Asp Pro Tyr
        1380                1385                1390

Ala Gly Lys Glu Asp Ile Val Pro Gln Leu Lys Ala Ser Leu Leu Ser
        1395                1400                1405

Ala Pro Pro Cys Arg Asp Ile Val Ile Glu Met Glu Asp Thr Lys Pro
        1410                1415                1420

Leu Leu Ala Ser Lys Leu Thr Glu Lys Glu Glu Ile Val Asp Trp
1425                1430                1435                1440

Trp Ser Lys Phe Tyr Ala Ser Ser Gly Glu His Glu Lys Cys Gly Gln
            1445                1450                1455

Tyr Ile Gln Lys Gly Tyr Ser Leu Lys Ile Tyr Asn Cys Glu Leu
            1460                1465                1470

Glu Asn Val Ala Glu Phe Glu Gly Leu Thr Asp Phe Ser Asp Thr Phe
        1475                1480                1485

Lys Leu Tyr Arg Gly Lys Ser Asp Glu Asn Glu Asp Pro Ser Val Val
        1490                1495                1500

Gly Glu Phe Lys Gly Ser Phe Arg Ile Tyr Pro Leu Pro Asp Asp Pro
1505                1510                1515                1520

Ser Val Pro Ala Pro Pro Arg Gln Phe Arg Glu Leu Pro Asp Ser Val
        1525                1530                1535
```

-continued

Pro Gln Glu Cys Thr Val Arg Ile Tyr Ile Val Arg Gly Leu Glu Leu
                1540                1545                1550

Gln Pro Gln Asp Asn Asn Gly Leu Cys Asp Pro Tyr Ile Lys Ile Thr
                1555                1560                1565

Leu Gly Lys Lys Val Ile Glu Asp Arg Asp His Tyr Ile Pro Asn Thr
                1570                1575                1580

Leu Asn Pro Val Phe Gly Arg Met Tyr Glu Leu Ser Cys Tyr Leu Pro
1585                1590                1595                1600

Gln Glu Lys Asp Leu Lys Ile Ser Val Tyr Asp Tyr Asp Thr Phe Thr
                1605                1610                1615

Arg Asp Glu Lys Val Gly Glu Thr Ile Ile Asp Leu Glu Asn Arg Phe
                1620                1625                1630

Leu Ser Arg Phe Gly Ser His Cys Gly Ile Pro Glu Glu Tyr Cys Val
                1635                1640                1645

Ser Gly Val Asn Thr Trp Arg Asp Gln Leu Arg Pro Thr Gln Leu Leu
                1650                1655                1660

Gln Asn Val Ala Arg Phe Lys Gly Phe Pro Gln Pro Ile Leu Ser Glu
1665                1670                1675                1680

Asp Gly Ser Arg Ile Arg Tyr Gly Gly Arg Asp Tyr Ser Leu Asp Glu
                1685                1690                1695

Phe Glu Ala Asn Lys Ile Leu His Gln His Leu Gly Ala Pro Glu Glu
                1700                1705                1710

Arg Leu Ala Leu His Ile Leu Arg Thr Gln Gly Leu Val Pro Glu His
                1715                1720                1725

Val Glu Thr Arg Thr Leu His Ser Thr Phe Gln Pro Asn Ile Ser Gln
                1730                1735                1740

Gly Lys Leu Gln Met Trp Val Asp Val Phe Pro Lys Ser Leu Gly Pro
1745                1750                1755                1760

Pro Gly Pro Pro Phe Asn Ile Thr Pro Arg Lys Ala Lys Lys Tyr Tyr
                1765                1770                1775

Leu Arg Val Ile Ile Trp Asn Thr Lys Asp Val Ile Leu Asp Glu Lys
                1780                1785                1790

Ser Ile Thr Gly Glu Glu Met Ser Asp Ile Tyr Val Lys Gly Trp Ile
                1795                1800                1805

Pro Gly Asn Glu Glu Asn Lys Gln Lys Thr Asp Val His Tyr Arg Ser
                1810                1815                1820

Leu Asp Gly Glu Gly Asn Phe Asn Trp Arg Phe Val Phe Pro Phe Asp
1825                1830                1835                1840

Tyr Leu Pro Ala Glu Gln Leu Cys Ile Val Ala Lys Lys Glu His Phe
                1845                1850                1855

Trp Ser Ile Asp Gln Thr Glu Phe Arg Ile Pro Pro Arg Leu Ile Ile
                1860                1865                1870

Gln Ile Trp Asp Asn Asp Lys Phe Ser Leu Asp Asp Tyr Leu Gly Phe
                1875                1880                1885

Leu Glu Leu Asp Leu Arg His Thr Ile Ile Pro Ala Lys Ser Pro Glu
                1890                1895                1900

Lys Cys Arg Leu Asp Met Ile Pro Asp Leu Lys Ala Met Asn Pro Leu
1905                1910                1915                1920

Lys Ala Lys Thr Ala Ser Leu Phe Glu Gln Lys Ser Met Lys Gly Trp
                1925                1930                1935

Trp Pro Cys Tyr Ala Glu Lys Asp Gly Ala Arg Val Met Ala Gly Lys
                1940                1945                1950

Val Glu Met Thr Leu Glu Ile Leu Asn Glu Lys Glu Ala Asp Glu Arg

-continued

```
                        1955                1960                1965

Pro Ala Gly Lys Gly Arg Asp Glu Pro Asn Met Asn Pro Lys Leu Asp
        1970                1975                1980

Leu Pro Asn Arg Pro Glu Thr Ser Phe Leu Trp Phe Thr Asn Pro Cys
1985                1990                1995                2000

Lys Thr Met Lys Phe Ile Val Trp Arg Arg Phe Lys Trp Val Ile Ile
            2005                2010                2015

Gly Leu Leu Phe Leu Leu Ile Leu Leu Phe Val Ala Val Leu Leu
            2020                2025                2030

Tyr Ser Leu Pro Asn Tyr Leu Ser Met Lys Ile Val Lys Pro Asn Val
            2035                2040                2045

<210> SEQ ID NO 44
<211> LENGTH: 2061
<212> TYPE: PRT
<213> ORGANISM: Homo sapiens

<400> SEQUENCE: 44

Met Leu Arg Val Ile Val Glu Ser Ala Ser Asn Ile Pro Lys Thr Lys
 1               5                  10                  15

Phe Gly Lys Pro Asp Pro Ile Val Ser Val Ile Phe Lys Asp Glu Lys
            20                  25                  30

Lys Lys Thr Lys Lys Val Asp Asn Glu Leu Asn Pro Val Trp Asn Glu
        35                  40                  45

Ile Leu Glu Phe Asp Leu Arg Gly Ile Pro Leu Asp Phe Ser Ser Ser
 50                  55                  60

Leu Gly Ile Ile Val Lys Asp Phe Glu Thr Ile Gly Gln Asn Lys Leu
65                  70                  75                  80

Ile Gly Thr Ala Thr Val Ala Leu Lys Asp Leu Thr Gly Asp Gln Ser
                85                  90                  95

Arg Ser Leu Pro Tyr Lys Leu Ile Ser Leu Leu Asn Glu Lys Gly Gln
            100                 105                 110

Asp Thr Gly Ala Thr Ile Asp Leu Val Ile Gly Tyr Asp Pro Pro Ser
        115                 120                 125

Ala Pro His Pro Asn Asp Leu Ser Gly Pro Ser Val Pro Gly Met Gly
    130                 135                 140

Gly Asp Gly Glu Glu Asp Glu Gly Asp Glu Asp Arg Leu Asp Asn Ala
145                 150                 155                 160

Val Arg Gly Pro Gly Pro Lys Gly Pro Val Gly Thr Val Ser Glu Ala
                165                 170                 175

Gln Leu Ala Arg Arg Leu Thr Lys Val Lys Asn Ser Arg Arg Met Leu
            180                 185                 190

Ser Asn Lys Pro Gln Asp Phe Gln Ile Arg Val Arg Val Ile Glu Gly
        195                 200                 205

Arg Gln Leu Ser Gly Asn Asn Ile Arg Pro Val Val Lys Val His Val
    210                 215                 220

Cys Gly Gln Thr His Arg Thr Arg Ile Lys Arg Gly Asn Asn Pro Phe
225                 230                 235                 240

Phe Asp Glu Leu Phe Phe Tyr Asn Val Asn Met Thr Pro Ser Glu Leu
                245                 250                 255

Met Asp Glu Ile Ile Ser Ile Arg Val Tyr Asn Ser His Ser Leu Arg
            260                 265                 270

Ala Asp Cys Leu Met Gly Glu Phe Lys Ile Asp Val Gly Phe Val Tyr
        275                 280                 285
```

-continued

```
Asp Glu Pro Gly His Ala Val Met Arg Lys Trp Leu Leu Asn Asp
    290                 295                 300
Pro Glu Asp Thr Ser Ser Gly Ser Lys Gly Tyr Met Lys Val Ser Met
305                 310                 315                 320
Phe Val Leu Gly Thr Gly Asp Glu Pro Pro Glu Arg Arg Asp Arg
                325                 330                 335
Asp Asn Asp Ser Asp Asp Val Glu Ser Asn Leu Leu Leu Pro Ala Gly
                340                 345                 350
Ile Ala Leu Arg Trp Val Thr Phe Leu Leu Lys Ile Tyr Arg Ala Glu
                355                 360                 365
Asp Ile Pro Gln Met Asp Asp Ala Phe Ser Gln Thr Val Lys Glu Ile
    370                 375                 380
Phe Gly Gly Asn Ala Asp Lys Lys Asn Leu Val Asp Pro Phe Val Glu
385                 390                 395                 400
Val Ser Phe Ala Gly Lys Lys Val Cys Thr Asn Ile Ile Glu Lys Asn
                405                 410                 415
Ala Asn Pro Glu Trp Asn Gln Val Val Asn Leu Gln Ile Lys Phe Pro
                420                 425                 430
Ser Val Cys Glu Lys Ile Lys Leu Thr Ile Tyr Asp Trp Asp Arg Leu
            435                 440                 445
Thr Lys Asn Asp Val Val Gly Thr Thr Tyr Leu His Leu Ser Lys Ile
    450                 455                 460
Ala Ala Ser Gly Gly Glu Val Glu Asp Phe Ser Ser Ser Gly Thr Gly
465                 470                 475                 480
Ala Ala Ser Tyr Thr Val Asn Thr Gly Glu Thr Val Gly Phe Val
                485                 490                 495
Pro Thr Phe Gly Pro Cys Tyr Leu Asn Leu Tyr Gly Ser Pro Arg Glu
                500                 505                 510
Tyr Thr Gly Phe Pro Asp Pro Tyr Asp Glu Leu Asn Thr Gly Lys Gly
            515                 520                 525
Glu Gly Val Ala Tyr Arg Gly Arg Ile Leu Val Glu Leu Ala Thr Phe
    530                 535                 540
Leu Glu Lys Thr Pro Pro Asp Lys Lys Leu Glu Pro Ile Ser Asn Asp
545                 550                 555                 560
Asp Leu Leu Val Val Glu Lys Tyr Gln Arg Arg Lys Tyr Ser Leu
                565                 570                 575
Ser Ala Val Phe His Ser Ala Thr Met Leu Gln Asp Val Gly Glu Ala
                580                 585                 590
Ile Gln Phe Glu Val Ser Ile Gly Asn Tyr Gly Asn Lys Phe Asp Thr
            595                 600                 605
Thr Cys Lys Pro Leu Ala Ser Thr Thr Gln Tyr Ser Arg Ala Val Phe
    610                 615                 620
Asp Gly Asn Tyr Tyr Tyr Leu Pro Trp Ala His Thr Lys Pro Val
625                 630                 635                 640
Val Thr Leu Thr Ser Tyr Trp Glu Asp Ile Ser His Arg Leu Asp Ala
                645                 650                 655
Val Asn Thr Leu Leu Ala Met Ala Glu Arg Leu Gln Thr Asn Ile Glu
                660                 665                 670
Ala Leu Lys Ser Gly Ile Gln Gly Lys Ile Pro Ala Asn Gln Leu Ala
            675                 680                 685
Glu Leu Trp Leu Lys Leu Ile Asp Glu Val Ile Glu Asp Thr Arg Tyr
    690                 695                 700
Thr Leu Pro Leu Thr Glu Gly Lys Ala Asn Val Thr Val Leu Asp Thr
```

-continued

```
                705                 710                 715                 720
Gln Ile Arg Lys Leu Arg Ser Arg Ser Leu Ser Gln Ile His Glu Ala
                    725                 730                 735
Ala Val Arg Met Arg Ser Glu Ala Thr Asp Val Lys Ser Thr Leu Ala
                740                 745                 750
Glu Ile Glu Asp Trp Leu Asp Lys Leu Met Gln Leu Thr Glu Glu Pro
                755                 760                 765
Gln Asn Ser Met Pro Asp Ile Ile Trp Met Ile Arg Gly Glu Lys
                770                 775                 780
Arg Leu Ala Tyr Ala Arg Ile Pro Ala His Gln Val Leu Tyr Ser Thr
785                 790                 795                 800
Ser Gly Glu Asn Ala Ser Gly Lys Tyr Cys Gly Lys Thr Gln Thr Ile
                    805                 810                 815
Phe Leu Lys Tyr Pro Gln Glu Lys Asn Asn Gly Pro Lys Val Pro Val
                820                 825                 830
Glu Leu Arg Val Asn Ile Trp Leu Gly Leu Ser Ala Val Glu Lys Lys
                835                 840                 845
Phe Asn Ser Phe Ala Glu Gly Thr Phe Thr Val Phe Ala Glu Met Tyr
850                 855                 860
Glu Asn Gln Ala Leu Met Phe Gly Lys Trp Gly Thr Ser Gly Leu Val
865                 870                 875                 880
Gly Arg His Lys Phe Ser Asp Val Thr Gly Lys Ile Lys Leu Lys Arg
                    885                 890                 895
Glu Phe Phe Leu Pro Pro Lys Gly Trp Glu Trp Glu Gly Glu Trp Ile
                    900                 905                 910
Val Asp Pro Glu Arg Ser Leu Leu Thr Glu Ala Asp Ala Gly His Thr
                915                 920                 925
Glu Phe Thr Asp Glu Val Tyr Gln Asn Glu Ser Arg Tyr Pro Gly Gly
                930                 935                 940
Asp Trp Lys Pro Ala Glu Asp Thr Tyr Thr Asp Ala Asn Gly Asp Lys
945                 950                 955                 960
Ala Ala Ser Pro Ser Glu Leu Thr Cys Pro Pro Gly Trp Glu Trp Glu
                    965                 970                 975
Asp Asp Ala Trp Ser Tyr Asp Ile Asn Arg Ala Val Asp Glu Lys Gly
                980                 985                 990
Trp Glu Tyr Gly Ile Thr Ile Pro Pro Asp His Lys Pro Lys Ser Trp
                    995                 1000                1005
Val Ala Ala Glu Lys Met Tyr His Thr His Arg Arg Arg Leu Val
                1010                1015                1020
Arg Lys Arg Lys Lys Asp Leu Thr Gln Thr Ala Ser Ser Thr Ala Arg
1025                1030                1035                1040
Ala Met Glu Glu Leu Gln Asp Gln Glu Gly Trp Glu Tyr Ala Ser Leu
                    1045                1050                1055
Ile Gly Trp Lys Phe His Trp Lys Gln Arg Ser Ser Asp Thr Phe Arg
                    1060                1065                1070
Arg Arg Arg Trp Arg Arg Lys Met Ala Pro Ser Glu Thr His Gly Ala
                1075                1080                1085
Ala Ala Ile Phe Lys Leu Glu Gly Ala Leu Gly Ala Asp Thr Thr Glu
                1090                1095                1100
Asp Gly Asp Glu Lys Ser Leu Glu Lys Gln Lys His Ser Ala Thr Thr
1105                1110                1115                1120
Val Phe Gly Ala Asn Thr Pro Ile Val Ser Cys Asn Phe Asp Arg Val
                    1125                1130                1135
```

```
Tyr Ile Tyr His Leu Arg Cys Tyr Val Tyr Gln Ala Arg Asn Leu Leu
        1140                1145                1150

Ala Leu Asp Lys Asp Ser Phe Ser Asp Pro Tyr Ala His Ile Cys Phe
        1155                1160                1165

Leu His Arg Ser Lys Thr Thr Glu Ile Ile His Ser Thr Leu Asn Pro
        1170                1175                1180

Thr Trp Asp Gln Thr Ile Ile Phe Asp Glu Val Glu Ile Tyr Gly Glu
1185                1190                1195                1200

Pro Gln Thr Val Leu Gln Asn Pro Pro Lys Val Ile Met Glu Leu Phe
        1205                1210                1215

Asp Asn Asp Gln Val Gly Lys Asp Glu Phe Leu Gly Arg Ser Ile Phe
        1220                1225                1230

Ser Pro Val Val Lys Leu Asn Ser Glu Met Asp Ile Thr Pro Lys Leu
        1235                1240                1245

Leu Trp His Pro Val Met Asn Gly Asp Lys Ala Cys Gly Asp Val Leu
        1250                1255                1260

Val Thr Ala Glu Leu Ile Leu Arg Gly Lys Asp Gly Ser Asn Leu Pro
1265                1270                1275                1280

Ile Leu Pro Pro Gln Arg Ala Pro Asn Leu Tyr Met Val Pro Gln Gly
        1285                1290                1295

Ile Arg Pro Val Val Gln Leu Thr Ala Ile Glu Ile Leu Ala Trp Gly
        1300                1305                1310

Leu Arg Asn Met Lys Asn Phe Gln Met Ala Ser Ile Thr Ser Pro Ser
        1315                1320                1325

Leu Val Val Glu Cys Gly Gly Glu Arg Val Glu Ser Val Val Ile Lys
        1330                1335                1340

Asn Leu Lys Lys Thr Pro Asn Phe Pro Ser Ser Val Leu Phe Met Lys
1345                1350                1355                1360

Val Phe Leu Pro Lys Glu Glu Leu Tyr Met Pro Pro Leu Val Ile Lys
        1365                1370                1375

Val Ile Asp His Arg Gln Phe Gly Arg Lys Pro Val Val Gly Gln Cys
        1380                1385                1390

Thr Ile Glu Arg Leu Asp Arg Phe Arg Cys Asp Pro Tyr Ala Gly Lys
        1395                1400                1405

Glu Asp Ile Val Pro Gln Leu Lys Ala Ser Leu Leu Ser Ala Pro Pro
        1410                1415                1420

Cys Arg Asp Ile Val Ile Glu Met Glu Asp Thr Lys Pro Leu Leu Ala
1425                1430                1435                1440

Ser Lys Leu Thr Glu Lys Glu Glu Ile Val Asp Trp Trp Ser Lys
        1445                1450                1455

Phe Tyr Ala Ser Ser Gly Glu His Glu Lys Cys Gly Gln Tyr Ile Gln
        1460                1465                1470

Lys Gly Tyr Ser Lys Leu Lys Ile Tyr Asn Cys Glu Leu Glu Asn Val
        1475                1480                1485

Ala Glu Phe Glu Gly Leu Thr Asp Phe Ser Asp Thr Phe Lys Leu Tyr
        1490                1495                1500

Arg Gly Lys Ser Asp Glu Asn Glu Asp Pro Ser Val Val Gly Glu Phe
1505                1510                1515                1520

Lys Gly Ser Phe Arg Ile Tyr Pro Leu Pro Asp Pro Ser Val Pro
        1525                1530                1535

Ala Pro Pro Arg Gln Phe Arg Glu Leu Pro Asp Ser Val Pro Gln Glu
        1540                1545                1550
```

-continued

```
Cys Thr Val Arg Ile Tyr Ile Val Arg Gly Leu Glu Leu Gln Pro Gln
            1555                1560                1565

Asp Asn Asn Gly Leu Cys Asp Pro Tyr Ile Lys Ile Thr Leu Gly Lys
            1570                1575                1580

Lys Val Ile Glu Asp Arg Asp His Tyr Ile Pro Asn Thr Leu Asn Pro
1585                1590                1595                1600

Val Phe Gly Arg Met Tyr Glu Leu Ser Cys Tyr Leu Pro Gln Glu Lys
            1605                1610                1615

Asp Leu Lys Ile Ser Val Tyr Asp Tyr Asp Thr Phe Thr Arg Asp Glu
            1620                1625                1630

Lys Val Gly Glu Thr Ile Ile Asp Leu Glu Asn Arg Phe Leu Ser Arg
            1635                1640                1645

Phe Gly Ser His Cys Gly Ile Pro Glu Glu Tyr Cys Val Ser Gly Val
            1650                1655                1660

Asn Thr Trp Arg Asp Gln Leu Arg Pro Thr Gln Leu Leu Gln Asn Val
1665                1670                1675                1680

Ala Arg Phe Lys Gly Phe Pro Gln Pro Ile Leu Ser Glu Asp Gly Ser
            1685                1690                1695

Arg Ile Arg Tyr Gly Gly Arg Asp Tyr Ser Leu Asp Glu Phe Glu Ala
            1700                1705                1710

Asn Lys Ile Leu His Gln His Leu Gly Ala Pro Glu Glu Arg Leu Ala
            1715                1720                1725

Leu His Ile Leu Arg Thr Gln Gly Leu Val Pro Glu His Val Glu Thr
            1730                1735                1740

Arg Thr Leu His Ser Thr Phe Gln Pro Asn Ile Ser Gln Gly Lys Leu
1745                1750                1755                1760

Gln Met Trp Val Asp Val Phe Pro Lys Ser Leu Gly Pro Pro Gly Pro
            1765                1770                1775

Pro Phe Asn Ile Thr Pro Arg Lys Ala Lys Lys Tyr Tyr Leu Arg Val
            1780                1785                1790

Ile Ile Trp Asn Thr Lys Asp Val Ile Leu Asp Glu Lys Ser Ile Thr
            1795                1800                1805

Gly Glu Glu Met Ser Asp Ile Tyr Val Lys Gly Trp Ile Pro Gly Asn
            1810                1815                1820

Glu Glu Asn Lys Gln Lys Thr Asp Val His Tyr Arg Ser Leu Asp Gly
1825                1830                1835                1840

Glu Gly Asn Phe Asn Trp Arg Phe Val Phe Pro Phe Asp Tyr Leu Pro
            1845                1850                1855

Ala Glu Gln Leu Cys Ile Val Ala Lys Lys Glu His Phe Trp Ser Ile
            1860                1865                1870

Asp Gln Thr Glu Phe Arg Ile Pro Pro Arg Leu Ile Ile Gln Ile Trp
            1875                1880                1885

Asp Asn Asp Lys Phe Ser Leu Asp Asp Tyr Leu Gly Phe Leu Glu Leu
            1890                1895                1900

Asp Leu Arg His Thr Ile Ile Pro Ala Lys Ser Pro Glu Lys Cys Arg
1905                1910                1915                1920

Leu Asp Met Ile Pro Asp Leu Lys Ala Met Asn Pro Leu Lys Ala Lys
            1925                1930                1935

Thr Ala Ser Leu Phe Glu Gln Lys Ser Met Lys Gly Trp Trp Pro Cys
            1940                1945                1950

Tyr Ala Glu Lys Asp Gly Ala Arg Val Met Ala Gly Lys Val Glu Met
            1955                1960                1965

Thr Leu Glu Ile Leu Asn Glu Lys Glu Ala Asp Glu Arg Pro Ala Gly
```

-continued

```
              1970                1975                1980
Lys Gly Arg Asp Glu Pro Asn Met Asn Pro Lys Leu Asp Leu Pro Asn
1985                1990                1995                2000

Arg Pro Glu Thr Ser Phe Leu Trp Phe Thr Asn Pro Cys Lys Thr Met
                2005                2010                2015

Lys Phe Ile Val Trp Arg Arg Phe Lys Trp Val Ile Ile Gly Leu Leu
                2020                2025                2030

Phe Leu Leu Ile Leu Leu Leu Phe Val Ala Val Leu Leu Tyr Ser Leu
                2035                2040                2045

Pro Asn Tyr Leu Ser Met Lys Ile Val Lys Pro Asn Val
    2050                2055                2060

<210> SEQ ID NO 45
<211> LENGTH: 2057
<212> TYPE: PRT
<213> ORGANISM: Homo sapiens

<400> SEQUENCE: 45

Met Leu Arg Val Ile Val Glu Ser Ala Ser Asn Ile Pro Lys Thr Lys
1               5                   10                  15

Phe Gly Lys Pro Asp Pro Ile Val Ser Val Ile Phe Lys Asp Glu Lys
                20                  25                  30

Lys Lys Thr Lys Lys Val Asp Asn Glu Leu Asn Pro Val Trp Asn Glu
            35                  40                  45

Ile Leu Glu Phe Asp Leu Arg Gly Ile Pro Leu Asp Phe Ser Ser Ser
50              55                  60

Leu Gly Ile Ile Val Lys Asp Phe Glu Thr Ile Gly Gln Asn Lys Leu
65                  70                  75                  80

Ile Gly Thr Ala Thr Val Ala Leu Lys Asp Leu Thr Gly Asp Gln Ser
                85                  90                  95

Arg Ser Leu Pro Tyr Lys Leu Ile Ser Leu Leu Asn Glu Lys Gly Gln
                100                 105                 110

Asp Thr Gly Ala Thr Ile Asp Leu Val Ile Gly Tyr Asp Pro Pro Ser
            115                 120                 125

Ala Pro His Pro Asn Asp Leu Ser Gly Pro Ser Val Pro Gly Met Gly
130             135                 140

Gly Asp Gly Glu Glu Asp Glu Gly Asp Glu Asp Arg Leu Asp Asn Ala
145                 150                 155                 160

Val Arg Gly Pro Gly Pro Lys Gly Pro Val Gly Thr Val Ser Glu Ala
                165                 170                 175

Gln Leu Ala Arg Arg Leu Thr Lys Val Lys Asn Ser Arg Arg Met Leu
                180                 185                 190

Ser Asn Lys Pro Gln Asp Phe Gln Ile Arg Val Arg Val Ile Glu Gly
            195                 200                 205

Arg Gln Leu Ser Gly Asn Asn Ile Arg Pro Val Val Lys Val His Val
210             215                 220

Cys Gly Gln Thr His Arg Thr Arg Ile Lys Arg Gly Asn Asn Pro Phe
225                 230                 235                 240

Phe Asp Glu Leu Phe Phe Tyr Asn Val Asn Met Thr Pro Ser Glu Leu
                245                 250                 255

Met Asp Glu Ile Ile Ser Ile Arg Val Tyr Asn Ser His Ser Leu Arg
                260                 265                 270

Ala Asp Cys Leu Met Gly Glu Phe Lys Ile Asp Val Gly Phe Val Tyr
            275                 280                 285
```

-continued

```
Asp Glu Pro Gly His Ala Val Met Arg Lys Trp Leu Leu Asn Asp
    290                 295                 300
Pro Glu Asp Thr Ser Ser Gly Ser Lys Gly Tyr Met Lys Val Ser Met
305                 310                 315                 320
Phe Val Leu Gly Thr Gly Asp Glu Pro Pro Glu Arg Arg Asp Arg
            325                 330                 335
Asp Asn Asp Ser Asp Asp Val Glu Ser Asn Leu Leu Pro Ala Gly
            340                 345                 350
Ile Ala Leu Arg Trp Val Thr Phe Leu Leu Lys Ile Tyr Arg Ala Glu
        355                 360                 365
Asp Ile Pro Gln Met Asp Asp Ala Phe Ser Gln Thr Val Lys Glu Ile
        370                 375                 380
Phe Gly Gly Asn Ala Asp Lys Lys Asn Leu Val Asp Pro Phe Val Glu
385                 390                 395                 400
Val Ser Phe Ala Gly Lys Lys Val Cys Thr Asn Ile Ile Glu Lys Asn
            405                 410                 415
Ala Asn Pro Glu Trp Asn Gln Val Val Asn Leu Gln Ile Lys Phe Pro
        420                 425                 430
Ser Val Cys Glu Lys Ile Lys Leu Thr Ile Tyr Asp Trp Asp Arg Leu
        435                 440                 445
Thr Lys Asn Asp Val Val Gly Thr Thr Tyr Leu His Leu Ser Lys Ile
450                 455                 460
Ala Ala Ser Gly Gly Glu Val Glu Asp Phe Ser Ser Ser Gly Thr Gly
465                 470                 475                 480
Ala Ala Ser Tyr Thr Val Asn Thr Gly Glu Thr Val Gly Phe Val
            485                 490                 495
Pro Thr Phe Gly Pro Cys Tyr Leu Asn Leu Tyr Gly Ser Pro Arg Glu
            500                 505                 510
Tyr Thr Gly Phe Pro Asp Pro Tyr Asp Glu Leu Asn Thr Gly Lys Gly
        515                 520                 525
Glu Gly Val Ala Tyr Arg Gly Arg Ile Leu Val Glu Leu Ala Thr Phe
        530                 535                 540
Leu Glu Lys Thr Pro Pro Asp Lys Lys Leu Glu Pro Ile Ser Asn Asp
545                 550                 555                 560
Asp Leu Leu Val Val Glu Lys Tyr Gln Arg Arg Lys Tyr Ser Leu
            565                 570                 575
Ser Ala Val Phe His Ser Ala Thr Met Leu Gln Asp Val Gly Glu Ala
            580                 585                 590
Ile Gln Phe Glu Val Ser Ile Gly Asn Tyr Gly Asn Lys Phe Asp Thr
        595                 600                 605
Thr Cys Lys Pro Leu Ala Ser Thr Thr Gln Tyr Ser Arg Ala Val Phe
    610                 615                 620
Asp Gly Asn Tyr Tyr Tyr Leu Pro Trp Ala His Thr Lys Pro Val
625                 630                 635                 640
Val Thr Leu Thr Ser Tyr Trp Glu Asp Ile Ser His Arg Leu Asp Ala
            645                 650                 655
Val Asn Thr Leu Leu Ala Met Ala Glu Arg Leu Gln Thr Asn Ile Glu
            660                 665                 670
Ala Leu Lys Ser Gly Ile Gln Gly Lys Ile Pro Ala Asn Gln Leu Ala
        675                 680                 685
Glu Leu Trp Leu Lys Leu Ile Asp Glu Val Ile Glu Asp Thr Arg Tyr
    690                 695                 700
Thr Leu Pro Leu Thr Glu Gly Lys Ala Asn Val Thr Val Leu Asp Thr
```

-continued

```
            705                 710                 715                 720
Gln Ile Arg Lys Leu Arg Ser Arg Ser Leu Ser Gln Ile His Glu Ala
                725                 730                 735
Ala Val Arg Met Arg Ser Glu Ala Thr Asp Val Lys Ser Thr Leu Ala
                740                 745                 750
Glu Ile Glu Asp Trp Leu Asp Lys Leu Met Gln Leu Thr Glu Glu Pro
                755                 760                 765
Gln Asn Ser Met Pro Asp Ile Ile Trp Met Ile Arg Gly Glu Lys
                770                 775                 780
Arg Leu Ala Tyr Ala Arg Ile Pro Ala His Gln Val Leu Tyr Ser Thr
785                 790                 795                 800
Ser Gly Glu Asn Ala Ser Gly Lys Tyr Cys Gly Lys Thr Gln Thr Ile
                805                 810                 815
Phe Leu Lys Tyr Pro Gln Glu Lys Asn Asn Gly Pro Lys Val Pro Val
                820                 825                 830
Glu Leu Arg Val Asn Ile Trp Leu Gly Leu Ser Ala Val Glu Lys Lys
                835                 840                 845
Phe Asn Ser Phe Ala Glu Gly Thr Phe Thr Val Phe Ala Glu Met Tyr
850                 855                 860
Glu Asn Gln Ala Leu Met Phe Gly Lys Trp Gly Thr Ser Gly Leu Val
865                 870                 875                 880
Gly Arg His Lys Phe Ser Asp Val Thr Gly Lys Ile Lys Leu Lys Arg
                885                 890                 895
Glu Phe Phe Leu Pro Pro Lys Gly Trp Glu Trp Glu Gly Glu Trp Ile
                900                 905                 910
Val Asp Pro Glu Arg Ser Leu Leu Thr Glu Ala Asp Ala Gly His Thr
                915                 920                 925
Glu Phe Thr Asp Glu Val Tyr Gln Asn Glu Ser Arg Tyr Pro Gly Gly
                930                 935                 940
Asp Trp Lys Pro Ala Glu Asp Thr Tyr Thr Asp Ala Asn Gly Asp Lys
945                 950                 955                 960
Ala Ala Ser Pro Ser Glu Leu Thr Cys Pro Pro Gly Trp Glu Trp Glu
                965                 970                 975
Asp Asp Ala Trp Ser Tyr Asp Ile Asn Arg Ala Val Asp Glu Lys Gly
                980                 985                 990
Trp Glu Tyr Gly Ile Thr Ile Pro Pro Asp His Lys Pro Lys Ser Trp
                995                1000                1005
Val Ala Ala Glu Lys Met Tyr His Thr His Arg Arg Arg Leu Val
                1010                1015                1020
Arg Lys Arg Lys Lys Asp Leu Thr Gln Thr Ala Ser Ser Thr Ala Arg
1025                1030                1035                1040
Ala Met Glu Glu Leu Gln Asp Gln Gly Trp Glu Tyr Ala Ser Leu
                1045                1050                1055
Ile Gly Trp Lys Phe His Trp Lys Gln Arg Ser Ser Asp Thr Phe Arg
                1060                1065                1070
Arg Arg Arg Trp Arg Arg Lys Met Ala Pro Ser Glu Thr His Gly Ala
                1075                1080                1085
Ala Ala Ile Phe Lys Leu Glu Gly Ala Leu Gly Ala Asp Thr Thr Glu
                1090                1095                1100
Asp Gly Asp Glu Lys Ser Leu Glu Lys Gln Lys His Ser Ala Thr Thr
1105                1110                1115                1120
Val Phe Gly Ala Asn Thr Pro Ile Val Ser Cys Asn Phe Asp Arg Val
                1125                1130                1135
```

```
Tyr Ile Tyr His Leu Arg Cys Tyr Val Tyr Gln Ala Arg Asn Leu Leu
            1140                1145                1150

Ala Leu Asp Lys Asp Ser Phe Ser Asp Pro Tyr Ala His Ile Cys Phe
        1155                1160                1165

Leu His Arg Ser Lys Thr Thr Glu Ile Ile His Ser Thr Leu Asn Pro
        1170                1175                1180

Thr Trp Asp Gln Thr Ile Ile Phe Asp Glu Val Glu Ile Tyr Gly Glu
1185                1190                1195                1200

Pro Gln Thr Val Leu Gln Asn Pro Pro Lys Val Ile Met Glu Leu Phe
            1205                1210                1215

Asp Asn Asp Gln Val Gly Lys Asp Glu Phe Leu Gly Arg Ser Ile Phe
        1220                1225                1230

Ser Pro Val Val Lys Leu Asn Ser Glu Met Asp Ile Thr Pro Lys Leu
            1235                1240                1245

Leu Trp His Pro Val Met Asn Gly Asp Lys Ala Cys Gly Asp Val Leu
            1250                1255                1260

Val Thr Ala Glu Leu Ile Leu Arg Gly Lys Asp Gly Ser Asn Leu Pro
1265                1270                1275                1280

Ile Leu Pro Pro Gln Arg Ala Pro Asn Leu Tyr Met Val Pro Gln Gly
            1285                1290                1295

Ile Arg Pro Val Val Gln Leu Thr Ala Ile Glu Ile Leu Ala Trp Gly
            1300                1305                1310

Leu Arg Asn Met Lys Asn Phe Gln Met Ala Ser Ile Thr Ser Pro Ser
            1315                1320                1325

Leu Val Val Glu Cys Gly Gly Glu Arg Val Glu Ser Val Val Ile Lys
            1330                1335                1340

Asn Leu Lys Lys Thr Pro Asn Phe Pro Ser Ser Val Leu Phe Met Lys
1345                1350                1355                1360

Val Phe Leu Pro Lys Glu Glu Leu Tyr Met Pro Pro Leu Val Ile Lys
            1365                1370                1375

Val Ile Asp His Arg Gln Phe Gly Arg Lys Pro Val Val Gly Gln Cys
            1380                1385                1390

Thr Ile Glu Arg Leu Asp Arg Phe Arg Cys Asp Pro Tyr Ala Gly Lys
            1395                1400                1405

Glu Asp Ile Val Pro Gln Leu Lys Ala Ser Leu Leu Ser Ala Pro Pro
            1410                1415                1420

Cys Arg Asp Ile Val Ile Glu Met Glu Asp Thr Lys Pro Leu Leu Ala
1425                1430                1435                1440

Ser Lys Glu Glu Glu Ile Val Asp Trp Trp Ser Lys Phe Tyr Ala Ser
            1445                1450                1455

Ser Gly Glu His Glu Lys Cys Gly Gln Tyr Ile Gln Lys Gly Tyr Ser
            1460                1465                1470

Lys Leu Lys Ile Tyr Asn Cys Glu Leu Glu Asn Val Ala Glu Phe Glu
            1475                1480                1485

Gly Leu Thr Asp Phe Ser Asp Thr Phe Lys Leu Tyr Arg Gly Lys Ser
            1490                1495                1500

Asp Glu Asn Glu Asp Pro Ser Val Val Gly Glu Phe Lys Gly Ser Phe
1505                1510                1515                1520

Arg Ile Tyr Pro Leu Pro Asp Asp Pro Ser Val Pro Ala Pro Pro Arg
            1525                1530                1535

Gln Phe Arg Glu Leu Pro Asp Ser Val Pro Gln Glu Cys Thr Val Arg
            1540                1545                1550
```

-continued

```
Ile Tyr Ile Val Arg Gly Leu Glu Leu Gln Pro Gln Asp Asn Asn Gly
        1555                1560                1565

Leu Cys Asp Pro Tyr Ile Lys Ile Thr Leu Gly Lys Lys Val Ile Glu
    1570                1575                1580

Asp Arg Asp His Tyr Ile Pro Asn Thr Leu Asn Pro Val Phe Gly Arg
1585                1590                1595                1600

Met Tyr Glu Leu Ser Cys Tyr Leu Pro Gln Glu Lys Asp Leu Lys Ile
                1605                1610                1615

Ser Val Tyr Asp Tyr Asp Thr Phe Thr Arg Asp Glu Lys Val Gly Glu
            1620                1625                1630

Thr Ile Ile Asp Leu Glu Asn Arg Phe Leu Ser Arg Phe Gly Ser His
        1635                1640                1645

Cys Gly Ile Pro Glu Glu Tyr Cys Val Ser Gly Val Asn Thr Trp Arg
    1650                1655                1660

Asp Gln Leu Arg Pro Thr Gln Leu Leu Gln Asn Val Ala Arg Phe Lys
1665                1670                1675                1680

Gly Phe Pro Gln Pro Ile Leu Ser Glu Asp Gly Ser Arg Ile Arg Tyr
                1685                1690                1695

Gly Gly Arg Asp Tyr Ser Leu Asp Glu Phe Glu Ala Asn Lys Ile Leu
            1700                1705                1710

His Gln His Leu Gly Ala Pro Glu Glu Arg Leu Ala Leu His Ile Leu
        1715                1720                1725

Arg Thr Gln Gly Leu Val Pro Glu His Val Glu Thr Arg Thr Leu His
    1730                1735                1740

Ser Thr Phe Gln Pro Asn Ile Ser Gln Gly Lys Leu Gln Met Trp Val
1745                1750                1755                1760

Asp Val Phe Pro Lys Ser Leu Gly Pro Pro Gly Pro Pro Phe Asn Ile
                1765                1770                1775

Thr Pro Arg Lys Ala Lys Lys Tyr Tyr Leu Arg Val Ile Ile Trp Asn
            1780                1785                1790

Thr Lys Asp Val Ile Leu Asp Glu Lys Ser Ile Thr Gly Glu Glu Met
        1795                1800                1805

Ser Asp Ile Tyr Val Lys Gly Trp Ile Pro Gly Asn Glu Glu Asn Lys
    1810                1815                1820

Gln Lys Thr Asp Val His Tyr Arg Ser Leu Asp Gly Glu Gly Asn Phe
1825                1830                1835                1840

Asn Trp Arg Phe Val Phe Pro Phe Asp Tyr Leu Pro Ala Glu Gln Leu
                1845                1850                1855

Cys Ile Val Ala Lys Lys Glu His Phe Trp Ser Ile Asp Gln Thr Glu
            1860                1865                1870

Phe Arg Ile Pro Pro Arg Leu Ile Ile Gln Ile Trp Asp Asn Asp Lys
        1875                1880                1885

Phe Ser Leu Asp Asp Tyr Leu Gly Phe Leu Glu Leu Asp Leu Arg His
    1890                1895                1900

Thr Ile Ile Pro Ala Lys Ser Pro Glu Lys Cys Arg Leu Asp Met Ile
1905                1910                1915                1920

Pro Asp Leu Lys Ala Met Asn Pro Leu Lys Ala Lys Thr Ala Ser Leu
                1925                1930                1935

Phe Glu Gln Lys Ser Met Lys Gly Trp Trp Pro Cys Tyr Ala Glu Lys
            1940                1945                1950

Asp Gly Ala Arg Val Met Ala Gly Lys Val Glu Met Thr Leu Glu Ile
        1955                1960                1965

Leu Asn Glu Lys Glu Ala Asp Glu Arg Pro Ala Gly Lys Gly Arg Asp
```

```
                1970                1975                1980
Glu Pro Asn Met Asn Pro Lys Leu Asp Leu Pro Asn Arg Pro Glu Thr
1985                1990                1995                2000

Ser Phe Leu Trp Phe Thr Asn Pro Cys Lys Thr Met Lys Phe Ile Val
                2005                2010                2015

Trp Arg Arg Phe Lys Trp Val Ile Ile Gly Leu Leu Phe Leu Leu Ile
                2020                2025                2030

Leu Leu Leu Phe Val Ala Val Leu Leu Tyr Ser Leu Pro Asn Tyr Leu
                2035                2040                2045

Ser Met Lys Ile Val Lys Pro Asn Val
                2050                2055

<210> SEQ ID NO 46
<211> LENGTH: 351
<212> TYPE: PRT
<213> ORGANISM: Homo sapiens

<400> SEQUENCE: 46

Met Ser Pro Asp Ser Lys Ala Ser His Asn Pro Ser Phe Pro Lys Met
1               5                   10                  15

Gly Val Glu Ser Asp Met Glu Asp Glu Thr Thr Ala Trp Met Asn Leu
                20                  25                  30

Lys Pro Thr Lys Ser Cys Thr Ser Thr Ser Gly Pro Leu Lys Ser Gly
                35                  40                  45

Leu Leu Phe Thr Ser Ser Gly Leu Arg Gly Trp Ser Leu Ser Thr Trp
50                  55                  60

Lys Gln Gly Leu Cys Thr Ala Pro Ser Ser Pro Thr Leu Tyr Tyr Leu
65                  70                  75                  80

Arg Val Ile Ile Trp Asn Thr Lys Asp Val Ile Leu Asp Glu Lys Ser
                85                  90                  95

Ile Thr Gly Glu Glu Met Ser Asp Ile Tyr Val Lys Gly Trp Ile Pro
                100                 105                 110

Gly Asn Glu Glu Asn Lys Gln Lys Thr Asp Val His Tyr Arg Ser Leu
                115                 120                 125

Asp Gly Glu Gly Asn Phe Asn Trp Arg Phe Val Phe Pro Phe Asp Tyr
                130                 135                 140

Leu Pro Ala Glu Gln Leu Cys Ile Val Ala Lys Lys Glu His Phe Trp
145                 150                 155                 160

Ser Ile Asp Gln Thr Glu Phe Arg Ile Pro Pro Arg Leu Ile Ile Gln
                165                 170                 175

Ile Trp Asp Asn Asp Lys Phe Ser Leu Asp Asp Tyr Leu Gly Phe Leu
                180                 185                 190

Glu Leu Asp Leu Arg His Thr Ile Ile Pro Ala Lys Ser Pro Glu Lys
                195                 200                 205

Cys Arg Leu Asp Met Ile Pro Asp Leu Lys Ala Met Asn Pro Leu Lys
210                 215                 220

Ala Lys Thr Ala Ser Leu Phe Glu Gln Lys Ser Met Lys Gly Trp Trp
225                 230                 235                 240

Pro Cys Tyr Ala Glu Lys Asp Gly Ala Arg Val Met Ala Gly Lys Val
                245                 250                 255

Glu Met Thr Leu Glu Ile Leu Asn Glu Lys Glu Ala Asp Glu Arg Pro
                260                 265                 270

Ala Gly Lys Gly Arg Asp Glu Pro Asn Met Asn Pro Lys Leu Asp Leu
                275                 280                 285
```

```
Pro Asn Arg Pro Glu Thr Ser Phe Leu Trp Phe Thr Asn Pro Cys Lys
    290                 295                 300

Thr Met Lys Phe Ile Val Trp Arg Arg Phe Lys Trp Val Ile Ile Gly
305                 310                 315                 320

Leu Leu Phe Leu Leu Ile Leu Leu Phe Val Ala Val Leu Leu Tyr
                    325                 330                 335

Ser Leu Pro Asn Tyr Leu Ser Met Lys Ile Val Lys Pro Asn Val
                340                 345                 350

<210> SEQ ID NO 47
<211> LENGTH: 764
<212> TYPE: PRT
<213> ORGANISM: Homo sapiens

<400> SEQUENCE: 47

Met Leu Leu Phe Val Leu Thr Cys Leu Leu Ala Val Phe Pro Ala Ile
  1               5                  10                  15

Ser Thr Lys Ser Pro Ile Phe Gly Pro Glu Glu Val Asn Ser Val Glu
                 20                  25                  30

Gly Asn Ser Val Ser Ile Thr Cys Tyr Tyr Pro Pro Thr Ser Val Asn
             35                  40                  45

Arg His Thr Arg Lys Tyr Trp Cys Arg Gln Gly Ala Arg Gly Gly Cys
         50                  55                  60

Ile Thr Leu Ile Ser Ser Glu Gly Tyr Val Ser Ser Lys Tyr Ala Gly
 65                  70                  75                  80

Arg Ala Asn Leu Thr Asn Phe Pro Glu Asn Gly Thr Phe Val Val Asn
                 85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
290                 295                 300

Asp Gly Ser Phe Ser Val Val Ile Thr Gly Leu Arg Lys Glu Asp Ala
305                 310                 315                 320
```

```
Gly Arg Tyr Leu Cys Gly Ala His Ser Asp Gly Gln Leu Gln Glu Gly
            325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Ser Ser Val Ala
            355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
            435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
            515                 520                 525

Leu Thr Leu Asn Leu Val Thr Arg Ala Asp Glu Gly Trp Tyr Trp Cys
            530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
            595                 600                 605

Lys Ala Val Ala Asp Thr Arg Asp Gln Ala Asp Gly Ser Arg Ala Ser
            610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
            645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
            675                 680                 685

Ser Arg Glu Phe Gly Ala Asn Asp Asn Met Gly Ala Ser Ser Ile Thr
            690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735
```

```
Glu Glu Ala Glu Met Ala Tyr Lys Asp Phe Leu Leu Gln Ser Ser Thr
                740                 745                 750

Val Ala Ala Glu Ala Gln Asp Gly Pro Gln Glu Ala
            755                 760

<210> SEQ ID NO 48
<211> LENGTH: 764
<212> TYPE: PRT
<213> ORGANISM: Homo sapiens

<400> SEQUENCE: 48

Met Leu Leu Phe Val Leu Thr Cys Leu Leu Ala Val Phe Pro Ala Ile
  1               5                  10                  15

Ser Thr Lys Ser Pro Ile Phe Gly Pro Glu Val Asn Ser Val Glu
                 20                  25                  30

Gly Asn Ser Val Ser Ile Thr Cys Tyr Tyr Pro Pro Thr Ser Val Asn
            35                  40                  45

Arg His Thr Arg Lys Tyr Trp Cys Arg Gln Gly Ala Arg Gly Gly Cys
         50                  55                  60

Ile Thr Leu Ile Ser Ser Glu Gly Tyr Val Ser Ser Lys Tyr Ala Gly
 65                  70                  75                  80

Arg Ala Asn Leu Thr Asn Phe Pro Glu Asn Gly Thr Phe Val Val Asn
                 85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350
```

-continued

```
Pro Arg Ser Pro Thr Val Val Lys Gly Val Ala Gly Gly Ser Val Ala
        355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
    610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
    755                 760
```

<210> SEQ ID NO 49
<211> LENGTH: 764
<212> TYPE: PRT
<213> ORGANISM: Homo sapiens

<400> SEQUENCE: 49

```
Met Leu Leu Phe Val Leu Thr Cys Leu Leu Ala Val Phe Pro Ala Ile
  1               5                  10                  15

Ser Thr Lys Ser Pro Ile Phe Gly Pro Glu Val Asn Ser Val Glu
             20                  25                  30

Gly Asn Ser Val Ser Ile Thr Cys Tyr Tyr Pro Pro Thr Ser Val Asn
             35                  40                  45

Arg His Thr Arg Lys Tyr Trp Cys Arg Gln Ala Arg Gly Gly Cys
     50                  55                  60

Ile Thr Leu Ile Ser Ser Glu Gly Tyr Val Ser Ser Lys Tyr Ala Gly
 65                  70                  75                  80

Arg Ala Asn Leu Thr Asn Phe Pro Glu Asn Gly Thr Phe Val Val Asn
                 85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
            115                 120                 125

Gln Gly Pro Gly Leu Leu Asn Asp Thr Lys Val Tyr Thr Val Asp Leu
        130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Gly Ser Val Ala
        355                 360                 365

Val Leu Cys Pro Tyr Asn Arg Lys Glu Ser Lys Ser Ile Lys Tyr Trp
    370                 375                 380
```

```
Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
            405                 410                 415

Glu Glu Pro Gly Asn Gly Thr Phe Thr Val Ile Leu Asn Gln Leu Thr
        420                 425                 430

Ser Arg Asp Ala Gly Phe Tyr Trp Cys Leu Thr Asn Gly Asp Thr Leu
    435                 440                 445

Trp Arg Thr Thr Val Glu Ile Lys Ile Ile Glu Gly Glu Pro Asn Leu
450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
    610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
        755                 760

<210> SEQ ID NO 50
<211> LENGTH: 764
<212> TYPE: PRT
<213> ORGANISM: Homo sapiens
```

<400> SEQUENCE: 50

```
Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Thr Ser Val Asn
        35                  40                  45

Arg His Thr Arg Lys Tyr Trp Cys Arg Gln Gly Ala Arg Gly Gly Cys
        50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
            115                 120                 125

Gln Gly Pro Gly Leu Leu Asn Asp Thr Lys Val Tyr Thr Val Asp Leu
130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Gly Ser Val Ala
        355                 360                 365

Val Leu Cys Pro Tyr Asn Arg Lys Glu Ser Lys Ser Ile Lys Tyr Trp
370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415
```

```
Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Gly Ser Arg Asp Val Ser Leu Ala
                565                 570                 575

Lys Ala Asp Ala Ala Pro Asp Glu Lys Val Leu Asp Ser Gly Phe Arg
                580                 585                 590

Glu Ile Glu Asn Lys Ala Ile Gln Asp Pro Arg Leu Phe Ala Glu Glu
            595                 600                 605

Lys Ala Val Ala Asp Thr Arg Asp Gln Ala Asp Gly Ser Arg Ala Ser
610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
            645                 650                 655

Ala Val Gly Val Ala Arg Ala Arg His Arg Lys Asn Val Asp Arg Val
                660                 665                 670

Ser Ile Arg Ser Tyr Arg Thr Asp Ile Ser Met Ser Asp Phe Glu Asn
    675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
        755                 760

<210> SEQ ID NO 51
<211> LENGTH: 362
<212> TYPE: PRT
<213> ORGANISM: Homo sapiens

<400> SEQUENCE: 51

Met Arg Val Thr Ala Pro Arg Thr Leu Leu Leu Leu Leu Trp Gly Ala
 1               5                  10                  15

Val Ala Leu Thr Glu Thr Trp Ala Gly Ser His Ser Met Arg Tyr Phe
```

-continued

```
                    20                  25                  30
His Thr Ser Val Ser Arg Pro Gly Arg Gly Glu Pro Arg Phe Ile Thr
             35                  40                  45
Val Gly Tyr Val Asp Asp Thr Leu Phe Val Arg Phe Asp Ser Asp Ala
 50                  55                  60
Ala Ser Pro Arg Glu Glu Pro Arg Ala Pro Trp Ile Glu Gln Glu Gly
 65                  70                  75                  80
Pro Glu Tyr Trp Asp Arg Glu Thr Gln Ile Cys Lys Ala Lys Ala Gln
                 85                  90                  95
Thr Asp Arg Glu Asn Leu Arg Ile Ala Leu Arg Tyr Tyr Asn Gln Ser
            100                 105                 110
Glu Ala Gly Ser His Thr Leu Gln Asn Met Tyr Gly Cys Asp Val Gly
            115                 120                 125
Pro Asp Gly Arg Leu Leu Arg Gly Tyr His Gln Asp Ala Tyr Asp Gly
            130                 135                 140
Lys Asp Tyr Ile Ala Leu Asn Glu Asp Leu Ser Ser Trp Thr Ala Ala
145                 150                 155                 160
Asp Thr Ala Ala Gln Ile Thr Gln Arg Lys Trp Glu Ala Ala Arg Val
                165                 170                 175
Ala Glu Gln Leu Arg Ala Tyr Leu Glu Gly Glu Cys Val Glu Trp Leu
            180                 185                 190
Arg Arg Tyr Leu Glu Asn Gly Lys Glu Thr Leu Gln Arg Ala Asp Pro
            195                 200                 205
Pro Lys Thr His Val Thr His His Pro Ile Ser Asp His Glu Ala Thr
            210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Arg Thr Phe Gln Lys Trp Ala Ala Val Val
            260                 265                 270
Val Pro Ser Gly Glu Glu Gln Arg Tyr Thr Cys His Val Gln His Glu
            275                 280                 285
Gly Leu Pro Lys Pro Leu Thr Leu Arg Trp Glu Pro Ser Ser Gln Ser
            290                 295                 300
Thr Val Pro Ile Val Gly Ile Val Ala Gly Leu Ala Val Leu Ala Val
305                 310                 315                 320
Val Val Ile Gly Ala Val Val Ala Ala Val Met Cys Arg Arg Lys Ser
                325                 330                 335
Ser Gly Gly Lys Gly Gly Ser Tyr Ser Gln Ala Ala Cys Ser Asp Ser
            340                 345                 350
Ala Gln Gly Ser Asp Val Ser Leu Thr Ala
            355                 360
```

<210> SEQ ID NO 52
<211> LENGTH: 366
<212> TYPE: PRT
<213> ORGANISM: Homo sapiens

<400> SEQUENCE: 52

```
Met Arg Val Met Glu Pro Arg Thr Leu Ile Leu Leu Leu Ser Gly Ala
  1               5                  10                  15
Leu Ala Leu Thr Glu Thr Trp Ala Cys Ser His Ser Met Arg Tyr Phe
             20                  25                  30
```

```
Tyr Thr Ala Val Ser Arg Pro Ser Arg Gly Glu Pro His Phe Ile Ala
        35                  40                  45

Val Gly Tyr Val Asp Asp Thr Gln Phe Val Arg Phe Asp Ser Asp Ala
 50                  55                  60

Ala Ser Pro Arg Gly Glu Pro Arg Gly Arg Trp Val Glu Gln Glu Gly
 65                  70                  75                  80

Pro Glu Tyr Trp Asp Arg Glu Thr Gln Lys Tyr Asn Arg Gln Ala Gln
                 85                  90                  95

Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Glu Trp Arg Ala Tyr Leu Glu Gly Cys Val Glu Trp Leu
            180                 185                 190

Arg Arg Tyr Leu Glu Asn Gly Lys Glu Lys Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Glu Pro Ser Ser Gln Pro
    290                 295                 300

Thr Ile Pro Ile Val Gly Ile Val Ala Gly Leu Ala Val Leu Ala Val
305                 310                 315                 320

Leu Ala Val Leu Gly Ala Val Val Ala Val Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Glu Ser Leu Ile Ala Ser Lys Ala
        355                 360                 365
```

<210> SEQ ID NO 53
<211> LENGTH: 362
<212> TYPE: PRT
<213> ORGANISM: Homo sapiens

<400> SEQUENCE: 53

```
Met Leu Val Met Ala Pro Arg Thr Val Leu Leu Leu Leu Ser Ala Ala
 1               5                  10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45
```

Val Gly Tyr Val Asp Asp Thr Gln Phe Val Arg Phe Asp Ser Asp Ala
            50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
115                 120                 125

Pro Asp Gly Arg Leu Leu Arg Gly His Asp Gln Tyr Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
            195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 54
<211> LENGTH: 362
<212> TYPE: PRT
<213> ORGANISM: Homo sapiens

<400> SEQUENCE: 54

Met Leu Val Met Ala Pro Arg Thr Val Leu Leu Leu Leu Ser Ala Ala
 1               5                  10                  15

Leu Ala Leu Thr Glu Thr Trp Ala Gly Ser His Ser Met Arg Tyr Phe
                20                  25                  30

Tyr Thr Ser Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala

```
                50                  55                  60
Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Ser Lys Thr Asn Thr Gln
                85                  90                  95

Thr Tyr Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asn Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Ser Gln Arg Lys Leu Glu Ala Ala Arg Val
                165                 170                 175

Ala Glu Gln Leu Arg Ala Tyr Leu Glu Gly Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Thr Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 55
<211> LENGTH: 362
<212> TYPE: PRT
<213> ORGANISM: Homo sapiens

<400> SEQUENCE: 55

Met Leu Val Met Ala Pro Arg Thr Val Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60
```

```
Ala Ser Pro Arg Glu Glu Pro Arg Ala Pro Trp Ile Glu Gln Glu Gly
 65                  70                  75                  80

Pro Glu Tyr Trp Asp Arg Asn Thr Gln Ile Tyr Lys Ala Gln Ala Gln
                 85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asn Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Ser Gln Arg Lys Leu Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Thr Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 56
<211> LENGTH: 362
<212> TYPE: PRT
<213> ORGANISM: Homo sapiens

<400> SEQUENCE: 56

Met Arg Val Thr Ala Pro Arg Thr Leu Leu Leu Leu Leu Trp Gly Ala
 1               5                  10                  15

Val Ala Leu Thr Glu Thr Trp Ala Gly Ser His Ser Met Arg Tyr Phe
                 20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
        50                  55                  60

Ala Ser Pro Arg Glu Glu Pro Arg Ala Pro Trp Ile Glu Gln Glu Gly
 65                  70                  75                  80
```

-continued

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
            115                 120                 125

Pro Asp Gly Arg Leu Leu Arg Gly Tyr His Gln Asp Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 57
<211> LENGTH: 362
<212> TYPE: PRT
<213> ORGANISM: Homo sapiens

<400> SEQUENCE: 57

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
            50                  55                  60

Thr Ser Pro Arg Lys Glu Pro Arg Ala Pro Trp Ile Glu Gln Glu Gly
65                  70                  75                  80

Pro Glu Tyr Trp Asp Arg Glu Thr Gln Ile Ser Lys Thr Asn Thr Gln

-continued

```
                    85                  90                  95
Thr Tyr Arg Glu Asp Leu Arg Thr Leu Leu Arg Tyr Tyr Asn Gln Ser
                100                 105                 110

Glu Ala Gly Ser His Thr Leu Gln Arg Met Phe Gly Cys Asp Val Gly
            115                 120                 125

Pro Asp Gly Arg Leu Leu Arg Gly Tyr His Gln Asp Ala Tyr Asp Gly
        130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360
```

<210> SEQ ID NO 58
<211> LENGTH: 363
<212> TYPE: PRT
<213> ORGANISM: Homo sapiens

<400> SEQUENCE: 58

```
Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Cys Lys Ala Lys Ala Gln
                85                  90                  95
```

```
Thr Asp Arg Val Gly Leu Arg Asn Leu Arg Gly Tyr Tyr Asn Gln Ser
            100                 105                 110

Glu Asp Gly Ser His Thr Trp Gln Thr Met Tyr Gly Cys Asp Met Gly
            115                 120                 125

Pro Asp Gly Arg Leu Leu Arg Gly Tyr Asn Gln Phe Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg His Leu Glu Asn Gly Lys Glu Thr Leu Gln Arg Ala Asp Pro
            195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Gln Glu Pro Cys Thr Leu Arg Trp Lys Pro Ser Ser Gln Ser
            290                 295                 300

Thr Ile Pro Ile Val Gly Ile Val Ala Gly Leu Ala Val Leu Val Val
305                 310                 315                 320

Thr Val Ala Val Val Ala Val Val Ala Val Met Cys Arg Arg Lys
                325                 330                 335

Ser Ser Gly Gly Lys Gly Gly Ser Tyr Ser Gln Ala Ala Ser Ser Asp
            340                 345                 350

Ser Ala Gln Gly Ser Asp Val Ser Leu Thr Ala
            355                 360

<210> SEQ ID NO 59
<211> LENGTH: 366
<212> TYPE: PRT
<213> ORGANISM: Homo sapiens

<400> SEQUENCE: 59

Met Arg Val Met Ala Pro Arg Thr Leu Leu Leu Leu Leu Ser Gly Ala
1               5                   10                  15

Leu Ala Leu Thr Glu Thr Trp Ala Cys Ser His Ser Met Arg Tyr Phe
            20                  25                  30

Tyr Thr Ala Val Ser Arg Pro Ser Arg Gly Glu Pro His Phe Ile Ala
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
            100                 105                 110
```

```
Glu Ala Gly Ser His Thr Leu Gln Arg Met Tyr Gly Cys Asp Leu Gly
            115                 120                 125

Pro Asp Gly Arg Leu Leu Arg Gly Tyr Asp Gln Ser Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Glu Pro Ser Ser Gln Pro
    290                 295                 300

Thr Ile Pro Ile Val Gly Ile Val Ala Gly Leu Ala Val Leu Ala Val
305                 310                 315                 320

Leu Ala Val Leu Gly Ala Val Val Ala Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Glu Ser Leu Ile Ala Cys Lys Ala
        355                 360                 365

<210> SEQ ID NO 60
<211> LENGTH: 362
<212> TYPE: PRT
<213> ORGANISM: Homo sapiens

<400> SEQUENCE: 60

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu His Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
```

-continued

```
            115                 120                 125
Pro Asp Gly Arg Leu Leu Arg Gly Tyr His Gln Asp Ala Tyr Asp Gly
        130                 135                 140
Lys Asp Tyr Ile Ala Leu Asn Glu Asp Leu Ser Ser Trp Thr Ala Ala
145                 150                 155                 160
Asp Thr Ala Ala Gln Ile Thr Gln Arg Lys Trp Glu Ala Ala Arg Val
                165                 170                 175
Ala Glu Gln Leu Arg Ala Tyr Leu Glu Gly Glu Cys Val Glu Trp Leu
            180                 185                 190
Arg Arg Tyr Leu Glu Asn Gly Lys Glu Thr Leu Gln Arg Ala Asp Pro
                195                 200                 205
Pro Lys Thr His Val Thr His His Pro Ile Ser Asp His Glu Ala Thr
        210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Arg Thr Phe Gln Lys Trp Ala Ala Val Val
            260                 265                 270
Val Pro Ser Gly Glu Glu Gln Arg Tyr Thr Cys His Val Gln His Glu
        275                 280                 285
Gly Leu Pro Lys Pro Leu Thr Leu Arg Trp Glu Pro Ser Ser Gln Ser
        290                 295                 300
Thr Val Pro Ile Val Gly Ile Val Ala Gly Leu Ala Val Leu Ala Val
305                 310                 315                 320
Val Val Ile Gly Ala Val Val Ala Ala Val Met Cys Arg Arg Lys Ser
                325                 330                 335
Ser Gly Gly Lys Gly Gly Ser Tyr Ser Gln Ala Ala Cys Ser Asp Ser
                340                 345                 350
Ala Gln Gly Ser Asp Val Ser Leu Thr Ala
        355                 360

<210> SEQ ID NO 61
<211> LENGTH: 362
<212> TYPE: PRT
<213> ORGANISM: Homo sapiens

<400> SEQUENCE: 61

Met Arg Val Thr Ala Pro Arg Thr Leu Leu Leu Leu Leu Trp Gly Ala
  1               5                  10                  15
Val Ala Leu Thr Glu Thr Trp Ala Gly Ser His Ser Met Arg Tyr Phe
                20                  25                  30
His Thr Ser Val Ser Arg Pro Gly Arg Gly Glu Pro Arg Phe Ile Thr
            35                  40                  45
Val Gly Tyr Val Asp Asp Thr Leu Phe Val Arg Phe Asp Ser Asp Ala
        50                  55                  60
Thr Ser Pro Arg Lys Glu Pro Arg Ala Pro Trp Ile Glu Gln Glu Gly
65                  70                  75                  80
Pro Glu Tyr Trp Asp Arg Glu Thr Gln Ile Ser Lys Thr Asn Thr Gln
                85                  90                  95
Thr Tyr Arg Glu Ser Leu Arg Asn Leu Arg Gly Tyr Tyr Asn Gln Ser
            100                 105                 110
Glu Ala Gly Ser His Thr Leu Gln Ser Met Tyr Gly Cys Asp Val Gly
        115                 120                 125
```

```
Pro Asp Gly Arg Leu Leu Arg Gly His Asp Gln Ser Ala Tyr Asp Gly
130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Val
            165                 170                 175

Ala Glu Gln Leu Arg Ala Tyr Leu Glu Gly Glu Cys Val Glu Trp Leu
                180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 62
<211> LENGTH: 362
<212> TYPE: PRT
<213> ORGANISM: Homo sapiens

<400> SEQUENCE: 62

Met Arg Val Thr Ala Pro Arg Thr Leu Leu Leu Leu Leu Trp Gly Ala
1               5                   10                  15

Val Ala Leu Thr Glu Thr Trp Ala Gly Ser His Ser Met Arg Tyr Phe
                20                  25                  30

Tyr Thr Ala Met Ser Arg Pro Gly Arg Gly Glu Pro Arg Phe Ile Thr
            35                  40                  45

Val Gly Tyr Val Asp Asp Thr Gln Phe Val Arg Phe Asp Ser Asp Ala
        50                  55                  60

Thr Ser Pro Arg Met Ala Pro Arg Ala Pro Trp Ile Glu Gln Glu Gly
65                  70                  75                  80

Pro Glu Tyr Trp Asp Arg Glu Thr Gln Ile Ser Lys Thr Asn Thr Gln
                85                  90                  95

Thr Tyr Arg Glu Asn Leu Arg Thr Ala Leu Arg Tyr Tyr Asn Gln Ser
            100                 105                 110

Glu Ala Gly Ser His Thr Trp Gln Thr Met Tyr Gly Cys Asp Leu Gly
        115                 120                 125

Pro Asp Gly Arg Leu Leu Arg Gly His Asn Gln Leu Ala Tyr Asp Gly
    130                 135                 140
```

```
Lys Asp Tyr Ile Ala Leu Asn Glu Asp Leu Ser Ser Trp Thr Ala Ala
145                 150                 155                 160

Asp Thr Ala Ala Gln Ile Thr Gln Leu Lys Trp Glu Ala Ala Arg Val
            165                 170                 175

Ala Glu Gln Leu Arg Ala Tyr Leu Glu Gly Glu Cys Val Glu Trp Leu
        180                 185                 190

Arg Arg Tyr Leu Glu Asn Gly Lys Glu Thr Leu Gln Arg Ala Asp Pro
    195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Arg Thr Phe Gln Lys Trp Ala Ala Val Val
        260                 265                 270

Val Pro Ser Gly Glu Glu Gln Arg Tyr Thr Cys His Val Gln His Glu
    275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
            325                 330                 335

Ser Gly Gly Lys Gly Gly Ser Tyr Ser Gln Ala Ala Cys Ser Asp Ser
        340                 345                 350

Ala Gln Gly Ser Asp Val Ser Leu Thr Ala
    355                 360

<210> SEQ ID NO 63
<211> LENGTH: 338
<212> TYPE: PRT
<213> ORGANISM: Homo sapiens

<400> SEQUENCE: 63

Gly Ser His Ser Met Arg Tyr Phe His Thr Ser Val Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Glu Thr
    50                  55                  60

Gln Ile Cys Lys Ala Lys Ala Gln Thr Asp Arg Glu Asp Leu Arg Thr
65                  70                  75                  80

Leu Leu Arg Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
```

-continued

```
            145                 150                 155                 160
Glu Gly Glu Cys Val Glu Trp Leu Arg Arg Tyr Leu Glu Asn Gly Lys
                165                 170                 175
Glu Thr Leu Gln Arg Ala Asp Pro Pro Lys Thr His Val Thr His His
            180                 185                 190
Pro Ile Ser Asp His Glu Ala Thr Leu Arg Cys Trp Ala Leu Gly Phe
            195                 200                 205
Tyr Pro Ala Glu Ile Thr Leu Thr Trp Gln Arg Asp Gly Glu Asp Gln
            210                 215                 220
Thr Gln Asp Thr Glu Leu Val Glu Thr Arg Pro Ala Gly Asp Arg Thr
225                 230                 235                 240
Phe Gln Lys Trp Ala Ala Val Val Val Pro Ser Gly Glu Glu Gln Arg
                245                 250                 255
Tyr Thr Cys His Val Gln His Glu Gly Leu Pro Lys Pro Leu Thr Leu
                260                 265                 270
Arg Trp Glu Pro Ser Ser Gln Ser Thr Val Pro Ile Val Gly Ile Val
            275                 280                 285
Ala Gly Leu Ala Val Leu Ala Val Val Val Ile Gly Ala Val Val Ala
            290                 295                 300
Ala Val Met Cys Arg Arg Lys Ser Ser Gly Gly Lys Gly Gly Ser Tyr
305                 310                 315                 320
Ser Gln Ala Ala Cys Ser Asp Ser Ala Gln Gly Ser Asp Val Ser Leu
                325                 330                 335
Thr Ala

<210> SEQ ID NO 64
<211> LENGTH: 362
<212> TYPE: PRT
<213> ORGANISM: Homo sapiens

<400> SEQUENCE: 64

Met Arg Val Thr Ala Pro Arg Thr Leu Leu Leu Leu Leu Trp Gly Ala
1               5                   10                  15
Val Ala Leu Thr Glu Thr Trp Ala Gly Ser His Ser Met Arg Tyr Phe
            20                  25                  30
His Thr Ser Val Ser Arg Pro Gly Arg Gly Glu Pro Arg Phe Ile Thr
        35                  40                  45
Val Gly Tyr Val Asp Asp Thr Leu Phe Val Arg Phe Asp Ser Asp Ala
    50                  55                  60
Thr Ser Pro Arg Lys Glu Pro Arg Ala Pro Trp Ile Glu Gln Glu Gly
65                  70                  75                  80
Pro Glu Tyr Trp Asp Arg Glu Thr Gln Ile Ser Lys Thr Asn Thr Gln
                85                  90                  95
Thr Tyr Arg Glu Ser Leu Arg Asn Leu Arg Gly Tyr Tyr Asn Gln Ser
            100                 105                 110
Glu Ala Gly Ser His Ile Ile Gln Arg Met Tyr Gly Cys Asp Leu Gly
        115                 120                 125
Pro Asp Gly Arg Leu Leu Arg Gly His Asn Gln Tyr Ala Tyr Asp Gly
    130                 135                 140
Lys Asp Tyr Ile Ala Leu Asn Glu Asp Leu Arg Ser Trp Thr Ala Ala
145                 150                 155                 160
Asp Thr Ala Ala Gln Ile Thr Gln Arg Lys Trp Glu Ala Ala Arg Val
                165                 170                 175
Ala Glu Gln Leu Arg Ala Tyr Leu Glu Gly Glu Cys Val Glu Trp Leu
```

-continued

```
                180                 185                 190
Arg Arg Tyr Leu Glu Asn Gly Lys Glu Thr Leu Gln Arg Ala Asp Pro
            195                 200                 205
Pro Lys Thr His Val Thr His His Pro Ile Ser Asp His Glu Ala Thr
210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Arg Thr Phe Gln Lys Trp Ala Ala Val Val
            260                 265                 270
Val Pro Ser Gly Glu Glu Gln Arg Tyr Thr Cys His Val Gln His Glu
        275                 280                 285
Gly Leu Pro Lys Pro Leu Thr Leu Arg Trp Glu Pro Ser Ser Gln Ser
    290                 295                 300
Thr Val Pro Ile Val Gly Ile Val Ala Gly Leu Ala Val Leu Ala Val
305                 310                 315                 320
Val Val Ile Gly Ala Val Val Ala Ala Val Met Cys Arg Arg Lys Ser
                325                 330                 335
Ser Gly Gly Lys Gly Gly Ser Tyr Ser Gln Ala Ala Cys Ser Asp Ser
            340                 345                 350
Ala Gln Gly Ser Asp Val Ser Leu Thr Ala
        355                 360

<210> SEQ ID NO 65
<211> LENGTH: 362
<212> TYPE: PRT
<213> ORGANISM: Homo sapiens

<400> SEQUENCE: 65

Met Arg Val Thr Ala Pro Arg Thr Leu Leu Leu Leu Leu Trp Gly Ala
1               5                   10                  15
Val Ala Leu Thr Glu Thr Trp Ala Gly Ser His Ser Met Arg Tyr Phe
                20                  25                  30
His Thr Ser Val Ser Arg Pro Gly Arg Gly Glu Pro Arg Phe Ile Thr
            35                  40                  45
Val Gly Tyr Val Asp Asp Thr Leu Phe Val Arg Phe Asp Ser Asp Ala
        50                  55                  60
Thr Ser Pro Arg Lys Glu Pro Arg Ala Pro Trp Ile Glu Gln Glu Gly
65                  70                  75                  80
Pro Glu Tyr Trp Asp Arg Glu Thr Gln Ile Ser Lys Thr Asn Thr Gln
                85                  90                  95
Thr Tyr Arg Glu Ser Leu Arg Asn Leu Arg Gly Tyr Tyr Asn Gln Ser
            100                 105                 110
Glu Ala Gly Ser His Thr Leu Gln Ser Met Tyr Gly Cys Asp Val Gly
        115                 120                 125
Pro Asp Gly Arg Leu Leu Arg Gly His Asn Gln Tyr Ala Tyr Asp Gly
    130                 135                 140
Lys Asp Tyr Ile Ala Leu Asn Glu Asp Leu Arg Ser Trp Thr Ala Ala
145                 150                 155                 160
Asp Thr Ala Ala Gln Ile Thr Gln Arg Lys Trp Glu Ala Ala Arg Val
                165                 170                 175
Ala Glu Gln Leu Arg Ala Tyr Leu Glu Gly Glu Cys Val Glu Trp Leu
            180                 185                 190
```

```
Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 66
<211> LENGTH: 372
<212> TYPE: PRT
<213> ORGANISM: Homo sapiens

<400> SEQUENCE: 66

Met Arg Val Met Ala Pro Gln Ala Leu Leu Leu Leu Leu Ser Gly Ala
  1               5                  10                  15

Leu Ala Leu Ile Glu Thr Trp Ala Gly Ser His Ser Met Arg Tyr Phe
                20                  25                  30

Tyr Thr Ala Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Asn Leu Arg Lys Leu Arg Gly Tyr Tyr Asn Gln Ser
            100                 105                 110

Glu Ala Gly Ser His Thr Ile Gln Arg Met Tyr Gly Cys Asp Leu Gly
        115                 120                 125

Pro Asp Gly Arg Leu Leu Arg Gly Tyr Asn Gln Phe Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Ser Gln Arg Lys Leu Glu Ala Ala Arg Glu
                165                 170                 175

Ala Glu Gln Leu Arg Ala Tyr Leu Glu Gly Glu Cys Val Glu Trp Leu
            180                 185                 190

Arg Gly Tyr Leu Glu Asn Gly Lys Glu Thr Leu Gln Arg Ala Glu Arg
        195                 200                 205
```

```
Pro Lys Thr His Val Thr His His Pro Val Ser Asp His Glu Ala Thr
    210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Gly Thr Phe Gln Lys Trp Ala Ala Val Val
            260                 265                 270
Val Pro Ser Gly Gln Glu Gln Arg Tyr Thr Cys His Val Gln His Glu
        275                 280                 285
Gly Leu Gln Glu Pro Cys Thr Leu Arg Trp Lys Pro Ser Ser Gln Pro
    290                 295                 300
Thr Ile Pro Asn Leu Gly Ile Val Ser Gly Pro Ala Val Leu Ala Val
305                 310                 315                 320
Leu Ala Val Leu Ala Val Leu Ala Val Leu Gly Ala Val Val Ala Ala
                325                 330                 335
Val Ile His Arg Arg Lys Ser Ser Gly Gly Lys Gly Gly Ser Cys Ser
            340                 345                 350
Gln Ala Ala Ser Ser Asn Ser Ala Gln Gly Ser Asp Glu Ser Leu Ile
        355                 360                 365
Ala Cys Lys Ala
    370

<210> SEQ ID NO 67
<211> LENGTH: 3775
<212> TYPE: DNA
<213> ORGANISM: Homo sapiens

<400> SEQUENCE: 67
cccgagccct gacgcccgcc ctggccgagc gtagctggcg gaccagagcc ggtagcgagg     60
ttgggagaga cggagcggac ctcagcgctg aagcagaagt ccccggagct gcggtctccc    120
cgccgcggct gagccatgcg gctccctgac ctgagaccct ggacctccct gctgctggtg    180
gacgcggctt tactgtggct gcttcagggc cctctgggga ctttgcttcc tcaagggctg    240
ccaggactat ggctggaggg accctgcgg ctgggagggc tgtgggggct gctaaagcta    300
agagggctgc tgggatttgt ggggacactg ctgctcccgc tctgtctggc cacccccctg    360
actgtctccc tgagagccct ggtcgcgggg gcctcacgtg ctcccccagc cagagtcgct    420 tcagccccctt ggagctggct gctggtgggg tacggggctg cggggctcag ctggtcactg    480
tgggctgttc tgagccctcc tggagcccag gagaaggagc aggaccaggt gaacaacaaa    540
gtcttgatgt ggaggctgct gaagctctcc aggccggacc tgcctctcct cgttgccgcc    600
ttcttcttcc ttgtccttgc tgttttgggt gagacattaa tccctcacta ttctggtcgt    660
gtgattgaca tcctggggagg tgattttgac ccccatgcct tgccagtgc catcttcttc    720 atgtgcctct tctcctttgg cagctcactg tctgcaggct gccgaggagg ctgcttcacc    780
tacaccatgt ctcgaatcaa cttgcggatc cgggagcagc ttttctcctc cctgctgcgc    840
caggacctcg gtttcttcca ggagactaag acagggagc tgaactcacg gctgagctcg    900
gataccaccc tgatgagtaa ctggcttcct ttaaatgcca atgtgctctt gcgaagcctg    960
gtgaaagtgg tggggctgta tggcttcatg ctcagcatat cgcctcgact caccctcctt   1020
tctctgctgc acatgccctt cacaatagca gcggagaagg tgtacaacac ccgccatcag   1080
gaagtgcttc gggagatcca ggatgcagtg gccagggcgg ggcaggtggt gcgggaagcc   1140
```

```
gttggagggc tgcagaccgt tcgcagtttt ggggccgagg agcatgaagt ctgtcgctat    1200
aaagaggccc ttgaacaatg tcggcagctg tattggcgga gagacctgga acgcgccttg    1260
tacctgctcg taaggagggt gctgcacttg ggggtgcaga tgctgatgct gagctgtggg    1320
ctgcagcaga tgcaggatgg ggagctcacc cagggcagcc tgctttcctt tatgatctac    1380
caggagagcg tggggagcta tgtgcagacc ctggtataca tatatgggga tatgctcagc    1440
aacgtgggag ctgcagagaa ggttttctcc tacatggacc gacagccaaa tctgccttca    1500
cctggcacgc ttgcccccac cactctgcag ggggttgtga aattccaaga cgtctccttt    1560
gcatatccca atcgccctga caggcctgtg ctcaaggggc tgacgtttac cctacgtcct    1620
ggtgaggtga cggcgctggt gggacccaat gggtctggga gagcacagt ggctgccctg     1680 ctgcagaatc tgtaccagcc cacaggggga caggtgctgc tggatgaaaa gcccatctca    1740
cagtatgaac actgctacct gcacagccag gtggtttcag ttgggcagga gcctgtgctg    1800
ttctccggtt ctgtgaggaa caacattgct tatgggctgc agagctgcga agatgataag    1860 gtgatgcgg ctgcccaggc tgcccacgca gatgacttca tccaggaaat ggagcatgga    1920
atatacacag atgtagggga aaggggagc cagctggctg cgggacagaa acaacgtctg     1980
gccattgccc gggcccttgt acgagacccg cgggtcctca tcctggatga ggctactagt    2040
gccctagatg tgcagtgcga gcaggccctg caggactgga attcccgtgg ggatcgcaca    2100
gtgctggtga ttgctcacag gctgcagaca gttcagcgcg cccaccagat cctggtgctc    2160 cagggggca agctgcagaa gcttgcccag ctctaggagg acaggacct ctattcccgc      2220 ctggtgcagc agcggctgat ggactgaggc cccagggata ctgggccctc ttctcagggg    2280
cgtctccagg acccagagct gttcctgctt tgagtttccc tagagctgtg cggccagata    2340
gctgttcctg agttgcaggc acgatggaga tttggacact gtgtgctttt ggtggggtag    2400
agaggtgggg tgggggggg tggggctgt ctgtgtccag gaaacttaat tccctggtga      2460
ctagagcttt gcctggtgat gaggagtatt ttgtggcata atacatatat tttaaaatat    2520
tttccttctt acatgaactg tatacattca tatagaaaat ttagacaata taaaaaagta    2580
caaagaagaa aagtaaaagt acccattgtt tcacttcctg gagataacca tagttgctat    2640
tttgctgcct gtcccatcag tcgtttatct gttgtttgag atagaaatta accaaaaatg    2700
acataaatat tcatgagatt gccttcctat atccctcctt gttcctacca gtgtctgcta    2760
ttttgaagaa gctagggtct ggagggacag agaacagttc cctgattaac agtattaata    2820
gtgacattgg taacagctac catttataga gttttaatgt gagtaggagc tatgctaagt    2880 gttttttcatg tattatcgtt tttaatcatt atctccaacc ctatgaggtt ggttattatc   2940 cccatttac agatgaggaa actgaagctc aaagaggctc aatgactttc ccaaggtggt     3000
cgtagtggtg gagttggagt ttgaacacag gcctgaccct agagtccaca ccctgaccca    3060
atcaattata ttgcatcttg ggtccataaa ccctaatcca taatcccatc aagaaaagct    3120
ctgctgctct tagctctaaa taattcagaa tctattctct tctctccagt cccgttgtta    3180
tagtcttcac tcatagacag cccatctgtc tcaccctctc ctgttgtatc cagctccacg    3240
acaaacttct gccttcccca acaccttgt gcctttgcat atggtgtttt cttgcccatt     3300
ttctgctcga ctcgcccctg attttcaagt tcaagactta actcagggtt caggtcttcc    3360
aggaggcctt acttatgtcg tcagtctggg gaactctcca tgtgcttcta tcactgtgcg    3420
gttacctctt tcacagccct tttaaagttc tatcttccct ttcccacctt ttttgacctt    3480
```

-continued

| | | |
|---|---|---|
| ccactagacc atgagcacct gggcggaaag ccatatatct tattaagctt tatatctgct | 3540 |
| acctggccga gggcctaatt catagtggag aataaatagt caattgaata aatgaataaa | 3600 |
| tatctccacc atcgtactaa tcttaatcct ccctgcccac tcccaccact gaaaatgcaa | 3660 |
| cattgtacac atcactggtt gttgggaggg acttaccttg gaaagttgct attctaggaa | 3720 |
| agagaaacct tcatattcct ggaaacagca ggtagtttcc agtgctggca atgaa | 3775 |

<210> SEQ ID NO 68
<211> LENGTH: 2506
<212> TYPE: DNA
<213> ORGANISM: Homo sapiens

<400> SEQUENCE: 68

| | |
|---|---|
| agagagccat gcggctccct gacctgagac cctggacctc cctgctgctg gtggacgcgg | 60 |
| ctttactgtg gctgcttcag ggccctctgg ggactttgct tcctcaaggg ctgccaggac | 120 |
| tatggctgga ggggaccctg cggctgggag ggctgtgggg gctgctaaag ctaagagggc | 180 |
| tgctgggatt tgtggggaca ctgctgctcc cgctctgtct ggccaccccc ctgactgtct | 240 |
| ccctgagagc cctggtcgcg ggggcctcac gtgctccccc agccagagtc gcttcagccc | 300 |
| cttggagctg gctgctggtg gggtacgggg ctgcggggct cagctggtca ctgtgggctg | 360 |
| ttctgagccc tcctggagcc aggagaagg agcaggacca ggtgaacaac aaagtcttga | 420 |
| tgtggaggct gctgaagctc tccaggccgg acctgcctct cctcgttgcc gccttcttct | 480 |
| tccttgtcct tgctgttttg ggtgagacat taatccctca ctattctggt cgtgtgattg | 540 |
| acatcctggg aggtgatttt gacccccatg cctttgccag tgccatcttc ttcatgtgcc | 600 |
| tcttctcctt tggcagctca ctgtctcag gctgccgagg aggctgcttc acctacacca | 660 |
| tgtctcgaat caacttgcgg atccgggagc agcttttctc ctccctgctg cgccaggacc | 720 |
| tcggtttctt ccaggagact aagacagggg agctgaactc acggctgagc tcggatacca | 780 |
| ccctgatgag taactggctt cctttaaatg ccaatgtgct cttgcgaagc ctggtgaaag | 840 |
| tggtggggct gtatggcttc atgctcagca tatcgcctcg actcaccctc ctttctctgc | 900 |
| tgcacatgcc cttcacaata gcagcggaga aggtgtacaa cacccgccat caggaagtgc | 960 |
| ttcgggagat ccaggatgca gtggccaggc cggggcaggt ggtgcgggaa gccgttggag | 1020 |
| ggctgcagac cgttcgcagt tttggggccg aggagcatga agtctgtcgc tataaagagg | 1080 |
| cccttgaaca atgtcggcag ctgtattggc ggagagacct ggaacgcgcc ttgtacctgc | 1140 |
| tcgtaaggag ggtgctgcac ttgggggtgc agatgctgat gctgagctgt gggctgcagc | 1200 |
| agatgcagga tggggagctc acccagggca gcctgctttc ctttatgatc taccaggaga | 1260 |
| gcgtggggag ctatgtgcag accctggtat acatatatgg ggatatgctc agcaacgtgg | 1320 |
| gagctgcaga aaggttttc tcctacatgg accgacagcc aaatctgcct tcacctggca | 1380 |
| cgcttgcccc caccactctg caggggggttg tgaaattcca agacgtctcc tttgcatatc | 1440 |
| ccaatcgccc tgacaggcct gtgctcaagg ggctgacgtt taccctacgt cctggtgagg | 1500 |
| tgacggcgct ggtgggaccc aatgggtctg gaaagagcac agtggctgcc ctgctgcaga | 1560 |
| atctgtacca gcccacaggg ggacaggtgc tgctggatga aaagcccatc tcacagtatg | 1620 |
| aacactgcta cctgcacagc caggtggttt cagttgggca ggagcctgtg ctgttctccg | 1680 |
| gttctgtgag gaacaacatt gcttatgggc tgcagagctg cgaagatgat aaggtgatgg | 1740 |
| cggctgccca ggctgcccac gcagatgact tcatccagga aatggagcat ggaatataca | 1800 |
| cagatgtagg ggagaaggga agccagctgg ctgcgggaca gaaacaacgt ctggccattg | 1860 |

```
cccgggccct tgtacgagac ccgcgggtcc tcatcctgga tgaggctact agtgccctag    1920
atgtgcagtg cgagcaggcc ctgcaggact ggaattcccg tggggatcgc acagtgctgg    1980
tgattgctca caggctgcag acagttcagc gcgcccacca gatcctggtg ctccaggagg    2040
gcaagctgca gaagcttgcc cagctctagg agggacagga cctctattcc cgcctggtgc    2100
agcagcggct gatggactga ggccccaggg atactgggcc ctcttctcag gggcgtctcc    2160
aggacccaga gctgttcctg cttggagttt ccctagagct gtgcggccag atagctgttc    2220
ctgagttgca ggcacgatgg agatttggac actgtgtgct tttggtgggg tagagaggtg    2280
gggtggggtg gggtgggggc tgtctgtgtc caggaaactt aattccctgg tgactagagc    2340
tttgcctggt gatgaggagt attttgtggc ataatacata tattttaaaa tattttcctt    2400
cttacatgaa ctgtatacat tcatatagaa aatttagaca atataaaaaa gtacaaagaa    2460
gaaaagtaaa agtacccatt gtttcaaaaa aaaaaaaaaa aaaaaa                   2506
```

<210> SEQ ID NO 69
<211> LENGTH: 2497
<212> TYPE: DNA
<213> ORGANISM: Homo sapiens

<400> SEQUENCE: 69

```
gaggttggga gagacggagc ggacctcagc gctgaagcag aagtccccgg agctgcggtc      60
tccccgccgc ggctgagcca tgcggctccc tgacctgaga ccctggacct ccctgctgct     120
ggtggacgcg gctttactgt ggctgcttca gggccctctg ggactttgc ttcctcaagg      180 gctgccagga ctatggctgg aggggaccct gcggctggga gggctgtggg gctgctaaa     240 gctaagaggg ctgctgggat tgtggggac actgctgctc ccgctctgtc tggccacccc    300
cctgactgtc tccctgagag ccctggtcgc ggggcctca cgtgctcccc cagccagagt    360
cgcttcagcc ccttggagct ggctgctggt ggggtacggg gctgcgggc tcagctggtc    420 actgtgggct gttctgagcc ctcctggagc ccaggagaag gagcaggacc aggtgaacaa     480
caaagtcttg atgtggaggc tgctgaagct ctccaggccg gacctgcctc tcctcgttgc    540
cgccttcttc ttccttgtcc ttgctgtttt gggtgagaca ttaatccctc actattctgg    600
tcgtgtcatt gacatcctgg gaggtgattt tgacccccat gcctttgcca gtgccatctt    660
cttcatgtgc ctcttctcct ttggcagctc actgtctgca ggctgccgag gaggctgctt     720
cacctacacc atgtctcgaa tcaacttgcg gatccgggag cagctttttct cctcctgct    780 gcgccaggac ctcggttcct tccaggagac taagacaggg gagctgaact cacggctgag    840
ctcggatacc accctgatga gtaactggct tccttaaaat gccaatgtgc tcttgcgaag    900
cctggtgaaa gtggtggggc tgtatggctt catgctcagc atatcgcctc gactcaccct    960
cctttctctg ctgcacatgc ccttcacaat agcagcggag aaggtgtaca acacccgcca   1020
tcaggaagtg cttcgggaga tccaggatgc agtggccagg gcggggcagg tggtgcggga   1080
agccgttgga gggctgcaga ccgttcgcag ttttggggcc gaggagcatg aagtctgtcg   1140
ctataaagag gcccttgaac aatgtcggca gctgtattgg cggagagacc tggaacgcgc   1200
cttgtacctg ctcataagga gggtgctgca cttgggtgtg cagatgctga tgctgagctg   1260
tgggctgcag cagatgcagg atgggagct cacccagggc agcctgcttt cctttatgat   1320
ctaccaggag agcgtgggga gctatgtgca gaccctggta tacatatatg gggatatgct   1380
cagcaacgtg ggagctgcag agaaggttt ctcctacatg gaccgacagc caaatctgcc   1440
```

```
ttcacctggc acgcttgccc ccaccactct gcaggggggtt gtgaaattcc aagacgtctc    1500
ctttgcatat cccaatcgcc ctgacaggcc tgtgctcaag gggctgacgt ttaccctacg    1560
tcctggtgag gtgacggcgc tggtgggacc caatgggtct gggaagagca cagtggctgc    1620
cctgctgcag aatctgtacc agcccacagg gggacaggtg ctgctggatg aaaagcccat    1680
ctcacagtat gaacactgct acctgcacag ccaggtggtt tcagttgggc aggagcctgt    1740
gctgttctcc ggttctgtga ggaacaacat tgcttatggg ctgcagagct gcgaagatga    1800
taaggtgatg gcggctgccc aggctgccca cgcagatgac ttcatccagg aaatggagca    1860
tggaatatac acagatgtag gggagaaggg aagccagctg gctgcgggac agaaacaacg    1920
tctggccatt gcccgggccc ttgtacgaga cccgcgggtc ctcatcctgg atgaggctac    1980
tagtgcccta gatgtgcagt gcgagcaggc caaaacccttt ggaagttca tgatattttg    2040 aatttcaatg gatatttcct gggaataatg agttcaaatg aacgaatatg tggaacaaag    2100
catcaccaac atttatttttt tcaggatgag gtgatggaca aaaccatcac agggaaattg    2160
aggcaaatag tacatgtaaa acaatacttc gggtgagtcc acctatccca aagtcgtatc    2220
aaagaagtgg ctgcagattg gagcccaaag ccttttggttc ctcagtttcc aaatggattc    2280
tcactaggtg ggatcatgag tttgcttttgg acaccccaaa ttctaactat ttcttttgtt    2340
tcttacatcc tttccctctt ccccagcccc ttcccctcat gttacacctc ttgctggttt    2400
gagacgtcaa tcaccactga gaaagaatta aaccagtatt ttgagctggc aaaattctta    2460
gcctagtaca attccttcaa ttaaactgta gctcaac                             2497
```

<210> SEQ ID NO 70
<211> LENGTH: 2553
<212> TYPE: DNA
<213> ORGANISM: Homo sapiens

<400> SEQUENCE: 70

```
cccgagccct gacgccgcc ctggccgagc gtagctggcg gaccagagcc ggtagcgagg      60
ttgggagaga cggagcggac ctcagcgctg aagcagaagt ccccggagct gcggtctccc    120
cgccgcggct gagccatgcg gctccctgac ctgagaccct ggacctccct gctgctggtg    180
gacgcggctt tactgtggct gcttcagggc cctctgggga ctttgcttcc tcaagggctg    240
ccaggactat ggctggaggg gaccctgcgg ctgggagggc tgtgggggct gctaaagcta    300
agagggctgc tgggatttgt ggggacactg ctgctcccgc tctgtctggc cacccccctg    360
actgtctccc tgagagccct ggtcgcgggg gcctcacgtg ctccccccagc cagagtcgct    420 tcagcccctt ggagctggct gctggtgggg tacggggctg cggggctcag ctggtcactg    480
tgggctgttc tgagccctcc tggagcccag gagaaggagc aggaccaggt gaacaacaaa    540
gtcttgatgt ggaggctgct gaagctctcc aggccggacc tgcctctcct cgttgccgcc    600
ttcttcttcc ttgtccttgc tgttttgggt gagacattaa tccctcacta ttctggtcgt    660
gtgattgaca tcctgggagg tgattttgac ccccatgcct tgccagtgc catcttcttc     720 atgtgcctct tctcctttgg cagctcactg tctgcaggct gccgaggagg ctgcttcacc    780
tacaccatgt ctcgaatcaa cttgcggatc cgggagcagc ttttctcctc cctgctgcgc    840
caggacctcg gtttcttcca ggagactaag acagggagc tgaactcacg gctgagctcg    900
gataccaccc tgatgagtaa ctggcttcct ttaaatgcca atgtgctctt gcgaagcctg    960
gtgaaagtgg tggggctgta tggcttcatg ctcagcatat cgcctcgact cacccctcctt   1020 tctctgctgc acatgccctt cacaatagca gcggagaagg tgtacaacac ccgccatcag    1080
```

```
gaagtgcttc gggagatcca ggatgcagtg gccagggcgg ggcaggtggt gcgggaagcc    1140
gttggagggc tgcagaccgt tcgcagtttt ggggccgagg agcatgaagt ctgtcgctat    1200
aaagaggccc ttgaacaatg tcggcagctg tattggcgga gagacctgga acgcgccttg    1260
tacctgctcg taaggagggt gctgcacttg ggggtgcaga tgctgatgct gagctgtggg    1320
ctgcagcaga tgcaggatgg ggagctcacc cagggcagcc tgctttcctt tatgatctac    1380
caggagagcg tggggagcta tgtgcagacc ctggtataca tatatgggga tatgctcagc    1440
aacgtgggag ctgcagagaa ggttttctcc tacatggacc gacagccaaa tctgccttca    1500
cctggcacgc ttgcccccac cactctgcag ggggttgtga aattccaaga cgtctccttt    1560
gcatatccca atcgccctga caggcctgtg ctcaaggggc tgacgtttac cctacgtcct    1620
ggtgaggtga cggcgctggt gggacccaat gggtctggga agagcacagt ggctgccctg    1680
ctgcagaatc tgtaccagcc cacaggggga caggtgctgc tggatgaaaa gcccatctca    1740
cagtatgaac actgctacct gcacagccag gtggtttcag ttgggcagga gcctgtgctg    1800
ttctccggtt ctgtgaggaa caacattgct tatgggctgc agagctgcga agatgataag    1860
gtgatggcgg ctgcccaggc tgcccacgca gatgacttca tccaggaaat ggagcatgga    1920
atatacacag atgtagggga gaaggggagc cagctggctg cgggacagaa caacgtctg     1980 gccattgccc gggcccttgt acgagacccg cgggtcctca tcctggatga ggctactagt    2040
gccctagatg tgcagtgcga gcaggccaaa acccttttgga agttcatgat attttgaatt    2100
tcaatggata tttcctggga ataatgagtt caaatgaacg aatatgtgga acaaagcatc    2160
accaacattt attttttcag gatgaggtga tggacaaaac catcacaggg aaattgaggc    2220
aaatagtaca tgtaaaacaa tacttcgggt gagtccacct atcccaaagt cgtatcaaag    2280
aagtggctgc agattggagc ccaaagcctt tggttcctca gtttccaaat ggattctcac    2340
taggtgggat catgagtttg ctttggacac cccaaattct aactatttct tttgtttctt    2400
acatcctttc cctcttcccc agccccttcc cctcatgtta cacctcttgc tggtttgaga    2460
cgtcaatcac cactgagaaa gaattaaacc agtattttga gctggcaaaa ttcttagcct    2520
agtacaattc cttcaattaa actgtagctc aac                                 2553

<210> SEQ ID NO 71
<211> LENGTH: 1183
<212> TYPE: DNA
<213> ORGANISM: Homo sapiens
<220> FEATURE:
<221> NAME/KEY: misc_feature
<222> LOCATION: (1)...(1183)
<223> OTHER INFORMATION: n = A,T,C or G

<400> SEQUENCE: 71
cgcccaagaa gaaaatggcc ataagtggag tccctgtgct aggattttc atcatagctg       60 tgctgatgag cgctcaggaa tcatgggcta tcaaagaaga acatgtgatc atccaggccg     120
agttctatct gaatcctgac caatcaggcg agtttatgtt tgactttgat ggtgatgaga    180 tttccatgt ggatatggca aagaaggaga cggtctggcg gcttgaagaa tttggacgat      240
ttgccagctt tgaggctcaa ggtgcattgg ccaacatagc tgtggacaaa gccaacttgg    300
aaatcatgac aaagcgctcc aactatactc cgatcaccaa tgtacctcca gaggtaactg    360
tgctcacgaa cagccctgtg gaactgagag agcccaacgt cctcatctgt ttcatcgaca    420
agttcacccc accagtggtc aatgtcacgt ggcttcgaaa tggaaaacct gtcaccacag    480
```

| | |
|---|---|
| gagtgtcaga gacagtcttc ctgcccaggg aagaccacct tttccgcaag ttccactatc | 540 |
| tccccttcct gccctcaact gaggacgttt acgactgcag ggtggagcac tggggcttgg | 600 |
| atgagcctct tctcaagcac tgggagtttg atgctccaag ccctctccca gagactacag | 660 |
| agaacgtggt gtgtgccctg gcctgactg tgggtctggt gggcatcatt attgggacca | 720 |
| tcttcatcat caagggagtg cgcaaaagca atgcagcaga acgcagggg cctctgtaag | 780 |
| gcacatggag gtgatgatgt tcttagaga aagatcact gaagaaactt ctgctttaat | 840 |
| gactttacaa agctggcaat attacaatcc ttgacctcag tgaaagcagt catcttcagc | 900 |
| gttttccagc cctatagcca ccccaagtgt ggttatgcct cctcgattgc tccgtactct | 960 |
| aacatctagc tggcttccct gtctattgcc ttttcctgta tctatttcc tctatttcct | 1020 |
| atcattttat tatcaccatg caatgcctct ggaataaaac atacaggagt ctgtctctgc | 1080 |
| tatggaatgc cccatggggc atctcttgtg tacttattgt ttaaggtttc ctcaaactgn | 1140 |
| gattcttctg aacacaataa actattttga tgatcttggg tgg | 1183 |

<210> SEQ ID NO 72
<211> LENGTH: 1253
<212> TYPE: DNA
<213> ORGANISM: Homo sapiens

<400> SEQUENCE: 72

| | |
|---|---|
| cacattctct tttcttttat tcttgtctgt tctgcctcac tcccgagctc tactgactcc | 60 |
| caacagagcg cccaagaaga aaatggccat aagtggagtc cctgtgctag gattttcat | 120 |
| catagctgtg ctgatgagcg ctcaggaatc atgggctatc aaagaagaac atgtgatcat | 180 |
| ccaggccgag ttctatctga atcctgacca atcaggcgag tttatgtttg actttgatgg | 240 |
| tgatgagatt ttccatgtgg atatggcaaa gaaggagacg gtctggcggc ttgaagaatt | 300 |
| tggacgattt gccagctttg aggctcaagg tgcattggcc aacatagctg tggacaaagc | 360 |
| caacctggaa atcatgacaa agcgctccaa ctatactccg atcaccaatg tacctccaga | 420 |
| ggtaactgtg ctcacgaaca gccctgtgga actgagagag cccaacgtcc tcatctgttt | 480 |
| catcgacaag ttcaccccac cagtggtcaa tgtcacgtgg cttcgaaatg gaaaacctgt | 540 |
| caccacagga gtgtcagaga cagtcttcct gcccagggaa gaccaccttt ccgcaagtt | 600 |
| ccactatctc cccttcctgc cctcaactga ggacgtttac gactgcaggg tggagcactg | 660 |
| gggcttggat gagcctcttc tcaagcactg ggagtttgat gctccaagcc ctctcccaga | 720 |
| gactacagag aacgtggtgt gtgccctggg cctgactgtg gtctggtgg gcatcattat | 780 |
| tgggaccatc ttcatcatca agggagtgcg caaaagcaat gcagcagaac gcagggggcc | 840 |
| tctgtaaggc acatggaggt gatggtgttt cttagagaga agatcactga agaaacttct | 900 |
| gctttaatga ctttacaaag ctggcaatat tacaatcctt gacctcagtg aaagcagtca | 960 |
| tcttcagcgt tttccagccc tatagccacc ccaagtgtgg ttatgcctcc tcgattgctc | 1020 |
| cgtactctaa catctagctg gcttccctgt ctattgcctt ttcctgtatc tatttcctc | 1080 |
| tatttcctat cattttatta tcaccatgca atgcctctgg aataaaacat acaggagtct | 1140 |
| gtctctgcta tggaatgccc catggggcat ctcttgtgta cttattgttt aaggtttcct | 1200 |
| caaactgtga ttttctgaa cacaataaac tattttgatg atcttgggtg gaa | 1253 |

<210> SEQ ID NO 73
<211> LENGTH: 1200
<212> TYPE: DNA
<213> ORGANISM: Homo sapiens

<400> SEQUENCE: 73

```
cacattctct tttcttttat tcttgtctgt tctgcctcac tcccgagctc tactgactcc    60
caacagagcg cccaagaaga aaatggccat aagtggagtc cctgtgctag gattttcat    120
catagctgtg ctgatgagcg ctcaggaatc atgggctatc aaagaagaac atgtgatcat   180
ccaggccgag ttctatctga atcctgacca atcaggcgag tttatgtttg actttgatgg   240
tgatgagatt ttccatgtgg atatggcaaa gaaggagacg gtctggcggc ttgaagaatt   300
tggacgattt gccagctttg aggctcaagg tgcattggcc aacatagctg tggacaaagc   360
caacctggaa atcatgacaa agcgctccaa ctatactccg atcaccaatg tacctccaga   420
ggtaactgtg ctcacgaaca gccctgtgga actgagagag cccaacgtcc tcatctgttt   480
catcgacaag ttcaccccac cagtggtcaa tgtcacgtgg cttcgaaatg gaaaacctgt   540
caccacagga gtgtcagaga cagtcttcct gcccagggaa gaccacctt tccgcaagtt   600
ccactatctc cccttcctgc cctcaactga ggacgtttac gactgcaggg tggagcactg   660
gggcttggat gagcctcttc tcaagcactg ggagtttgat gctccaagcc ctctcccaga   720
gactacagag aacgtggtgt gtgccctggg cctgactgtg ggtctggtgg gcatcattat   780
tgggaccatc ttcatcatca agggagtgat ggtgttcctt agagagaaga tcactgaaga   840
aacttctgct ttaatgactt tacaaagctg gcaatattac aatccttgac ctcagtgaaa   900
gcagtcatct tcagcgtttt ccagccctat agccaccca agtgtggtta tgcctcctcg   960
attgctccgt actctaacat ctagctgct tccctgtcta ttgccttttc ctgtatctat  1020
tttcctctat ttcctatcat tttattatca ccatgcaatg cctctggaat aaaacataca  1080
ggagtctgtc tctgctatgg aatgccccat ggggcatctc ttgtgtactt attgtttaag  1140
gtttcctcaa actgtgattt ttctgaacac aataaactat tttgatgatc ttgggtggaa  1200
```

<210> SEQ ID NO 74
<211> LENGTH: 1331
<212> TYPE: DNA
<213> ORGANISM: Homo sapiens

<400> SEQUENCE: 74

```
cacattctct tttcttttat tcttgtctgt tctgcctcac tcccgagctc tactgactcc    60
caacagagcg cccaagaaga aaatggccat aagtggagtc cctgtgctag gattttcat    120
catagctgtg ctgatgagcg ctcaggaatc atgggctatc aaagagcaac attggtgctg   180
ttgtaaagat gtactgtaga aaagtattct tcacccagca tgaccccac agaaggtgtc   240
agaagaaacat gtgatcatcc aggccgagtt ctatctgaat cctgaccaat caggcgagtt   300
tatgtttgac tttgatggtg atgagatttt ccatgtggat atggcaaaga aggagacggt   360
ctggcggctt gaagaatttg gacgatttgc cagctttgag gctcaaggtg cattggccaa   420
catagctgtg gacaaagcca acctggaaat catgacaaag cgctccaact atactccgat   480
caccaatgta cctccagagg taactgtgct cacgaacagc cctgtggaac tgagagagcc   540
caacgtcctc atctgtttca tcgacaagtt caccccacca gtggtcaatg tcacgtggct   600
tcgaaatgga aaacctgtca ccacaggagt gtcagacaa tcttcctgc ccagggaaga   660
ccacctttc cgcaagttcc actatctccc cttcctgccc tcaactgagg acgtttacga   720
ctgcaggtg gagcactggg gcttggatga gcctcttctc aagcactggg agtttgatgc   780
tccaagccct ctcccagaga ctacagagaa cgtggtgtgt gccctgggcc tgactgtggg   840
```

| | |
|---|---:|
| tctggtgggc atcattattg ggaccatctt catcatcaag ggagtgcgca aaagcaatgc | 900 |
| agcagaacgc aggggggcctc tgtaaggcac atggaggtga tggtgtttct tagagagaag | 960 |
| atcactgaag aaacttctgc tttaatgact ttacaaagct ggcaatatta caatccttga | 1020 |
| cctcagtgaa agcagtcatc ttcagcgttt tccagcccta tagccacccc aagtgtggtt | 1080 |
| atgcctcctc gattgctccg tactctaaca tctagctggc ttccctgtct attgcctttt | 1140 |
| cctgtatcta ttttcctcta tttcctatca ttttattatc accatgcaat gcctctggaa | 1200 |
| taaaacatac aggagtctgt ctctgctatg gaatgcccca tggggcatct cttgtgtact | 1260 |
| tattgtttaa ggtttcctca aactgtgatt tttctgaaca caataaacta ttttgatgat | 1320 |
| cttgggtgga a | 1331 |

<210> SEQ ID NO 75
<211> LENGTH: 3140
<212> TYPE: DNA
<213> ORGANISM: Homo sapiens

<400> SEQUENCE: 75

| | |
|---|---:|
| ggccaggaac gcacgctgcc tggccgtatc gccgccccca ccgccgccgc cgccgggact | 60 |
| agaagtgagc cgcccgggtc ccaaacgcca gccagccagt cagtgggtcc cgcagtcgcc | 120 |
| cgcaaccggg gcgaatcatg gcggccgcca aggtggcttt aaccaagaga gcagatccag | 180 |
| ctgagcttag aacaatattt ttgaagtatg caagcattga gaaaaacggt gaattttcca | 240 |
| tgtcccccaa tgactttgtc actcgatact tgaacatttt tggagaaagc cagcctaatc | 300 |
| caaagactgt ggaacttta agtggagtgg tggatcagac caaagatgga ttaatatctt | 360 |
| ttcaagaatt tgttgccttt gaatctgtcc tgtgtgcccc tgatgctttg tttatggtag | 420 |
| cctttcagct gtttgacaaa gctggcaaag gagaagtaac ttttgaggat gttaagcaag | 480 |
| ttttttggaca gaccacaatt catcaacata ttccatttaa ctgggattca gaatttgtgc | 540 |
| aactacattt tggaaaagaa agaaaaagac acctgacata tgcggaattt actcagtttt | 600 |
| tattggaaat acaactggag cacgcaaagc aagcctttgt gcaacgggac aatgctagga | 660 |
| ctgggagagt cacagccatc gacttccgag acatcatggt caccatccgc ccccatgtct | 720 |
| tgactccttt tgtagaagaa tgtctagtag ctgctgctgg aggtaccaca tcccatcaag | 780 |
| ttagtttctc ctatttttaat ggatttaatt cgctccttaa caacatggaa ctcattagaa | 840 |
| agatctatag cactctggct ggcaccagga aagatgttga agtgactaag gaggagtttg | 900 |
| ttctggcagc tcagaaattt ggtcaggtta cacccatgga agttgacatc ttgtttcagt | 960 |
| tagcagattt atatgagcca aggggacgta tgaccttagc agacattgaa cggattgctc | 1020 |
| ctctggaaga gggaactctg cccttaact tggctgaggc ccagaggcag aaggcctcag | 1080 |
| gtgattcagc tcgaccagtt cttctacaag ttgcagagtc ggcctacagg tttggtctgg | 1140 |
| gttctgttgc tggagctgtt ggagccactg ctgtgtatcc tatcgatctt gtaaaaactc | 1200 |
| gaatgcagaa ccaacgatca actggctctt tgtgggagag actcatgtat aaaaacagct | 1260 |
| ttgactgttt taagaaagtg ctacgctatg aaggcttctt tggactgtat agaggtctgt | 1320 |
| tgccacagtt attgggagtt gccccagaga aggccataaa acttacagtg aacgattttg | 1380 |
| tgagggataa atttatgcac aaagatggtt cggtcccact tgcagcagaa attcttgctg | 1440 |
| gaggctgcgc tggaggctcc caggtgattt tcacaaatcc tttagaaatc gtcaagatcc | 1500 |
| gtttgcaagt ggcaggagaa atcaccactg gtcctcgagt cagtgctctg tctgtcgtgc | 1560 |
| gggacctggg gttttttggg atctacaagg gtgccaaagc atgctttctg cgggacattc | 1620 |

```
ctttctcggc catctacttt ccgtgctatg ctcatgtgaa ggcttccttt gcaaatgaag    1680
atgggcaggt tagcccagga agcctgctct tagctggtgc catagctggt atgcctgcag    1740
catctttagt gacccctgct gatgttatca agacgagatt acaggtggct gcccgggctg    1800
gccaaaccac ttacagcgga gtgatagact gctttagaaa gatactgcgt gaagaaggac    1860
caaaagctct gtggaaggga gctggtgctc gtgtatttcg atcctcaccc cagtttggtg    1920
taactttgct gacttacgaa ttgctacagc gatggttcta cattgatttt ggaggagtaa    1980
aacccatggg atcagagcca gttcctaaat ccaggatcaa cctgcctgcc cgaatcctg     2040
atcacgttgg gggctacaaa ctggcagttg ctacatttgc agggattgaa aacaaatttg    2100
gactttacct acctctcttc aagccatcag tatctacctc aaaggctatt ggtggaggcc    2160
cataggaaga tcagccctgg atagtgctg tcttttgtg ggtactgcag taaagaacat      2220
ccctcctggg aatgaagcaa tgcttcatcc cttttacgtc catctcttgt ttaaattcaa    2280
gtccaggctt ttttatcatg tgaaatcatt cattttctgg gtgttttctt aaccagatca    2340
ttgtgaaatt attcataatt attatttggc cctctgccca gaaacctttg tttgcatctg    2400
aaaattgatg ggatttggtc aacactaaca tgatttgggg aaaggagcaa gtcagaatag    2460
aaattagtac tcccctcctt gaactaggat tgtagtccca agaggctac tgtaaggcaa     2520
tcatggtgct cagagcagtg tttcgtgtgt gttttaaact ggtaggaaac taggtgcata    2580
tttataaaaa taaaaacac tgggagaaat gaaaaatat atatcaaata tattcagcct      2640
ggcttcaaat tgtaagcatg cacaaattct gtctctggat tatattatga agcttttatg    2700
tgaaacatgt ttctttgtaa tgaaaaccac attggagatg tttagtaatc atattgttac    2760
tggtaccaag actactaggg aaatgccttt gtacttaggg aagtactttt ggcatttta     2820
ctgtacagac agaaaaaact gagatgtagc ccctctcctg gaagtgctaa ttttgaaaaa    2880
ctgctcatat gatgtacatg tactgattac tgcctatttt aataaacact cttgaaaaat    2940
gcatgttgcc ctgttgctgc ctgccctatt ctcctcatct ccccatcatt ggtacccact    3000
tgctttttaaa atccactta tcttgaataa tgtaagacaa atatgttctg acataagtat    3060
ttaattcatg ttgccttgca taatggtcag aggcgcatga atttgtgaag gtggaaataa    3120
actatttgta aagtgattga                                                3140
```

<210> SEQ ID NO 76
<211> LENGTH: 3150
<212> TYPE: DNA
<213> ORGANISM: Homo sapiens

<400> SEQUENCE: 76

```
ggccaggaac gcacgctgcc tggccgtatc gccgcccca ccgacgccgc cgccgggact     60
agaagtgagc cgcccgggtc ccaaacgcca gccagccagt cagtgggtcc cgcagtcgcc    120
cgcaaccggg gcgaatcatg gcggccgcca aggtggcttt aaccaagaga gcagatccag    180
ctgagcttag aacaatattt ttgaagtatg caagcattga gaaaaacggt gaatttttca    240
tgtcccccaa tgactttgtc actcgatact tgaacatttt tggagaaagc cagcctaatc    300
caaagactgt ggaactttta agtggagtgg tggatcagac caaagatgga ttaatatctt    360
ttcaagaatt tgttgccttt gaatctgtcc tgtgtgcccc tgatgctttg tttatggtag    420
cctttcagct gtttgacaaa gctggcaaag gagaagtaac ttttgaggat gttaagcaag    480
ttttttggaca gaccacaatt catcaacata ttccatttaa ctgggattca gaatttgtgc    540
```

```
aactacattt tggaaaagaa agaaaaagac acctgacata tgcggaattt actcagtttt    600
tattggaaat acaactggag cacgcaaagc aagcctttgt gcaacgggac aatgctagga    660
ctggagagt cacagccatc gacttccgag acatcatggt caccatccgc ccccatgtct     720
tgactccttt tgtagaagaa tgtctagtag ctgctgctgg aggtaccaca tcccatcaag    780
ttagtttctc ctattttaat ggatttaatt cgctccttaa caacatgaa ctcattagaa     840
agatctatag cactctggct ggcaccagga aagatgttga agtgactaag gaggagtttg    900
ttctggcagc tcagaaattt ggtcaggtta cacccatgga agttgacatc ttgtttcagt    960
tagcagattt atatgagcca aggggacgta tgaccttagc agacattgaa cggattgctc   1020
ctctggaaga gggaactctg ccctttaact ggctgaggc ccagaggcag aaggcctcag    1080
gtgattcagc tcgaccagtt cttctacaag ttgcagagtc ggcctacagg tttggtctgg   1140
gttctgttgc tggagctgtt ggagccactg ctgtgtatcc tatcgatctt gtaaaaactc   1200
gaatgcagaa ccaacgatca actggctctt tgtgggaga actcatgtat aaaaacagct    1260
ttgactgttt taagaaagtg ctacgctatg aaggcttctt tggactgtat agaggtctgt   1320
tgccacagtt attgggagtt gccccagaga aggcctaaaa acttacagtg aacgattttg   1380
tgagggataa atttatgcac aaagatggtt cggtcccact gcagcagaa attcttgctg    1440
gaggctgcgc tggaggctcc caggtgattt tcacaaatcc tttagaaatc gtcaagatcc   1500
gtttgcaagt ggcaggagaa atcaccactg gtcctcgagt cagtgctctg tctgtcgtgc   1560
gggacctggg gttttttggg atctacaagg gtgccaaagc atgctttctg cgggacattc   1620
cttttctcggc catctacttt ccgtgctatg ctcatgtgaa ggcttccttt gcaaatgaag   1680
atgggcaggt tagcccagga agcctgctct tagctggtgc catagctggt atgcctgcag   1740
catctttagt gaccctgct gatgttatca agacgagatt acaggtggct gcccgggctg    1800
gccaaaccac ttacagcgga gtgatagact gctttagaaa gatactgcgt gaagaaggac   1860
caaaagctct gtggaaggga gctggtgctc gtgtatttcg atcctcaccc cagtttggtg   1920
taactttgct gacttacgaa ttgctacagc gatggttcta cattgatttt ggaggagtaa   1980
aacccatggg atcagagcca gttcctaaat ccaggatcaa cctgcctgcc ccgaatcctg   2040
atcacgttgg gggctacaaa ctggcagttg ctacatttgc agggattgaa acaaatttg    2100
gactttacct acctctcttc aagccatcag tatctacctc aaaggctatt ggtggaggcc   2160
cataggaaga tcagccctgg gatagtgctg tcttttttgtg ggtactgcag taaagaacat  2220
ccctcctggg aatgaagcaa tgcttcatcc cttttacgtc catctcttgt ttaaattcaa   2280
gtccaggctt ttttatcatg tgaaatcatt cattttctgg gtgttttctt aaccagatca   2340
ttgtgaaatt attcataatt attatttggc cctctgccca gaaacctttg tttgcatctg   2400
aaaattgatg ggatttggtc aacactaaca tgatttgggg aaaggagcaa gtcagaatag   2460
aaattagtac tccctccctt gaactaggat tgtagtccca aagaggctac tgtaaggcaa   2520
tcatggtgct cagagcagtg tttcgtgtgt gttttaaact ggtaggaaac taggtgcata   2580
tttataaaaa taaaaacac tgggagaaat gaaaaatat atatcaaata tattcagcct    2640
ggcttcaaat tgtaagcatg cacaaattct gtctctggat tatattatga agcttttatg   2700
tgaaacatgt ttctttgtaa tgaaaccac attggagatg tttagtaatc atattgttac    2760
tggtaccaag actactaggg aaatgccttt gtactttagg gaagtacttt tggcattta    2820
ctgtacagac agaaaaaact gagatgtagc ccctctcctg gaagtgctaa ttttgaaaaa   2880
ctgctcatat gatgtacatg tactgattac tgcctatttt aataaacact cttgaaaaat   2940
```

| | |
|---|---:|
| gcatgttgcc ctgttgctgc ctgccctatt ctcctcatct ccccatcatt ggtacccact | 3000 |
| tgcttttaaa atccacttta tcttgaataa tgtaagacaa atatgttctg acataagtat | 3060 |
| ttaattcatg ttgccttgca taatggtcag aggcgcatga atttgtgaag gtggaaataa | 3120 |
| actatttgta aagtgaaaaa aaaaaaaaaa | 3150 |

```
<210> SEQ ID NO 77
<211> LENGTH: 2727
<212> TYPE: DNA
<213> ORGANISM: Homo sapiens

<400> SEQUENCE: 77
```

| | |
|---|---:|
| cgcgcgggcg agcggttgtg cttgtgcttg tggcgcgtgg tgcgggtttc ggcggcggct | 60 |
| gaggaagaag cgcgggcggc gccttcggga ggcgagcagg cagcagttgg ccgtgccgta | 120 |
| gcagcgtccc gcgcgcggcg ggcagcggcc caggaggcgc gtggcggcgc tcggcctcgc | 180 |
| ggcggcggcg cactgcggcg tgtgcagaga gcgcctgcga cccgagaggg agccccgcct | 240 |
| gctgccctgt ttgcactcgg cctgtagtgc ctgcttaggg cccgcggccc ccgccgccgc | 300 |
| caacagctcg ggggacggcg gggcggcggg cgacggcacc gtggtggact gtcccgtgtg | 360 |
| caagcaacag tgcttctcca aagacatcgt ggagaattat ttcatgcgtg atagtggcag | 420 |
| caaggctgcc accgacgccc aggatgcgaa ccagtgctgc actagctgtg aggataatgc | 480 |
| cccagccacc agctactgtg tggagtgctc ggagcctctg tgtgagacct gtgtagaggc | 540 |
| gcaccagcgg gtgaagtaca ccaaggacca tactgtgcgc tctactgggc cagccaagtc | 600 |
| tcgggatggt gaacgtactg tctattgcaa cgtacacaag catgaacccc ttgtgctgtt | 660 |
| ttgtgagagc tgtgatactc tcacctgccg agactgccac ctcaatgccc acaaggacca | 720 |
| ccagtaccag ttcttagagg atgcagtgag gaaccagcgc aagctcctgg cctcactggt | 780 |
| gaagcgcctt ggggacaaac atgcaacatt gcagaagagc accaaggagg ttcgcagctc | 840 |
| aatccgccag gtgtctgacg tacagaagcg tgtgcaagtg gatgtcaaga tggccatcct | 900 |
| gcagatcatg aaggagctga ataagcgggg ccgtgtgctg gtcaatgatg cccagaaggt | 960 |
| gactgagggg cagcaggagc gcctggagcg gcagcactgg accatgacca agatccagaa | 1020 |
| gcaccaggag cacattctgc gctttgcctc ttgggctctg gagagtgaca acaacacagc | 1080 |
| cctttttgctt tctaagaagt tgatctactt ccagctgcac cgggccctca agatgattgt | 1140 |
| ggatccgtg gagccacatg gcgagatgaa gtttcagtgg gacctcaatg cctgaccaa | 1200 |
| gagtgccgag gcctttggca agattgtggc agagcgtcct ggcactaact caacaggccc | 1260 |
| tgcacccatg gcccctccaa gagcccccagg gcccctgagc aagcagggct ctggcagcag | 1320 |
| ccagcccatg gaggtgcagg aaggctatgg ctttgggtca ggagatgatc cctactcaag | 1380 |
| tgcagagccc catgtgtcag gtgtgaaacg gtcccgctca ggtgagggcg aggtgagcgg | 1440 |
| ccttatgcgc aaggtgccac gagtgagcct tgaacgcctg gacctggacc tcacagctga | 1500 |
| cagccagcca cccgtcttca aggtcttccc aggcagtacc actgaggact acaaccttat | 1560 |
| tgttattgaa cgtggcgctg ccgctgcagc taccggccag ccagggactg cgcctgcagg | 1620 |
| aaccccctggt gccccacccc tggctggcat ggccattgtc aaggaggagg agacggaggc | 1680 |
| tgccattgga gcccctccta ctgccactga gggccctgag accaaacctg tgcttatggc | 1740 |
| tcttgcggag ggtcctggtg ctgagggtcc ccgcctggcc tcacctagtg gcagcaccag | 1800 |
| ctcagggctg gaggtggtgg ctcctgaggg tacctcagcc ccaggtggtg gcccgggaac | 1860 |

-continued

```
cctggatgac agtgccacca tttgccgtgt ctgccagaag ccaggcgatc tggttatgtg    1920
caaccagtgt gagttttgtt tccacctgga ctgtcacctg ccggccctgc aggatgtacc    1980
aggggaggag tggagctgct cactctgcca tgtgctccct gacctgaagg aggaggatgg    2040
cagcctcagc ctggatggtg cagacagcac tggcgtggtg gccaagctct caccagccaa    2100
ccagcggaaa tgtgagcgtg tactgctggc cctattctgt cacgaaccct gccgcccccct   2160 gcatcagctg gctaccgact ccaccttctc cctggaccag cccggtggca ccctggatct    2220
gaccctgatc cgtgcccgcc tccaggagaa gttgtcacct ccctacagct ccccacagga    2280
gtttgcccag gatgtgggcc gcatgttcaa gcaattcaac aagttaactg aggacaaggc    2340
agacgtgcag tccatcatcg gcctgcagcg cttcttcgag acgcgcatga acgaggcctt    2400
cggtgacacc aagttctctg ctgtgctggt ggagcccccg ccgatgagcc tgcctggtgc    2460
tggcctgagt tcccaggagc tgtctggtgg ccctggtgat ggccctgag gctggagccc    2520 ccatggccag cccagcctgg ctctgttctc tgtcctgtca ccccatcccc actccctgg    2580 tggcctgact cccactccct ggtggcccca tccccagtt cctcacgata tggtttttac    2640
ttctgtggat ttaataaaaa cttcaccagt tcctcaggcg ttggctggtt ggggggactgt   2700 ggtcctgggg cctggtttat tgactgt                                         2727
```

<210> SEQ ID NO 78
<211> LENGTH: 3146
<212> TYPE: DNA
<213> ORGANISM: Homo sapiens

<400> SEQUENCE: 78

```
cggcggcgaa gagacgcggg ttgaggaaga gggacggatt gcccatgcgc ttgggcgcac      60
agcggcccgc ttctgtgtgg tctggaggtg gagctgagag gggaatcaca ctctataaag     120
gttcgcatac cccactggcg gattcaattg cggcagtgac gtcacagagg ccccgccccg     180
cccccacaag agccccaccg acgtgggggtt ggcggtggtg gaaggactag gagttggcgc    240
gtgcgtactg gcggcctctc ccgcaccgac cggcctgggc cccgccccg ggcgtgaggc      300 gcccaatgcg cgtgcgcggc ggcgtcggcg ccagttattt ctgtcccgcc cccgcggcctc    360 ggctctttct gcgagcgggc gcgcgggcga gcggttgtgc ttgtgcttgt ggcgcgtggt    420
gcgggtttcg gcggcggctg aggaagaagc gcgggcggcc ccttcgggag gcgagcaggc    480
agcagttggc cgtgccgtag cagcgtcccg cgcgcggcgg gcagcggccc aggaggcgcg    540
tggcggcgct cggcctcgcg gcggcggcgg cggcagcggc ccagcagttg gcggcgagcg    600
cgtctgcgcc tgcgcggcgg gccccgcgcc cctcctcccc cctgggcgc ccccggcggc     660 gtgtgaatgg cggcctccgc ggcggcagcc tcggcagcag cggcctcggc cgcctctggc    720
agcccgggcc cggcgagggg ctccgctggc ggcgaaaagc gctccaccgc cccttcggcc    780
gcagcctcgg cctctgcctc agccgcggcg tcgtcgcccg cgggggggcgg cgccgaggcg    840 ctggagctgc tggagcactg cggcgtgtgc agagagcgcc tgcgacccga gagggagccc    900
cgcctgctgc cctgtttgca ctcggcctgt agtgcctgct tagggcccgc ggcccccgcc    960
gccgccaaca gctcggggga cggcggggcg gcgggcgacg gcaccgggcc agccaagtct   1020
cgggatggtg aacgtactgt ctattgcaac gtacacaagc atgaacccct tgtgctgttt   1080
tgtgagagct gtgatactct cacctgccga gactgccagc tcaatgccca caaggaccac   1140
cagtaccagt tcttagagga tgcagtgagg aaccagcgca agctcctggc ctcactggtg   1200
aagcgccttg gggacaaaca tgcaacattg cagaagagca ccaaggaggt tcgcagctca   1260
```

| | |
|---|---|
| atccgccagg tgtctgacgt acagaagcgt gtgcaagtgg atgtcaagat ggccatcctg | 1320 |
| cagatcatga aggagctgaa taagcggggc cgtgtgctgg tcaatgatgc ccagaaggtg | 1380 |
| actgaggggc agcaggagcg cctggagcgg cagcactgga ccatgaccaa gatccagaag | 1440 |
| caccaggagc acattctgcg cttttgcctct tgggctctgg agagtgacaa caacacagcc | 1500 |
| cttttgcttt ctaagaagtt gatctacttc cagctgcacc gggccctcaa gatgattgtg | 1560 |
| gatcccgtgg agccacatgg cgagatgaag tttcagtggg acctcaatgc ctggaccaag | 1620 |
| agtgccgagg cctttggcaa gattgtggca gagcgtcctg cactaactc aacaggccct | 1680 |
| gcacccatgg cccctccaag agccccaggg cccctgagca agcagggctc tggcagcagc | 1740 |
| cagcccatgg aggtgcagga aggctatggc tttgggtcag gagatgatcc ctactcaagt | 1800 |
| gcagagcccc atgtgtcagg tgtgaaacgg tcccgctcag gtgagggcga ggtgagcggc | 1860 |
| cttatgcgca aggtgccacg agtgagcctt gaacgcctgg acctggacct cacagctgac | 1920 |
| agccagccac ccgtcttcaa ggtcttccca ggcagtacca ctgaggacta aaccttatt | 1980 |
| gttattgaac gtggcgctgc cgctgcagct accggccagc cagggactgc gcctgcagga | 2040 |
| accccctggtg ccccaccccct ggctggcatg gccattgtca aggaggagga gacggaggct | 2100 |
| gccattggag cccctcctac tgccactgag ggccctgaga ccaaacctgt gcttatggct | 2160 |
| cttgcggagg gtcctggtgc tgagggtccc cgcctggcct cacctagtgg cagcaccagc | 2220 |
| tcagggctgg aggtggtggc tcctgagggt acctcagccc caggtggtgg cccgggaacc | 2280 |
| ctggatgaca gtgccaccat ttgccgtgtc tgccagaagc caggcgatct ggttatgtgc | 2340 |
| aaccagtgtg agttttgttt ccacctggac tgtcacctgc cggccctgca ggatgtacca | 2400 |
| ggggaggagt ggagctgctc actctgccat gtgctccctg acctgaagga ggaggatggc | 2460 |
| agcctcagcc tggatggtgc agacagcact ggcgtggtgg ccaagctctc accagccaac | 2520 |
| cagcggaaat gtgagcgtgt actgctggcc ctattctgtc acgaaccctg ccgcccctg | 2580 |
| catcagctgg ctaccgactc caccttctcc ctggaccagc ccgtggcac cctggatctg | 2640 |
| accctgatcc gtgcccgcct ccaggagaag ttgtcacctc cctacagctc cccacaggag | 2700 |
| tttgcccagg atgtgggccg catgttcaag caattcaaca agttaactga ggacaaggca | 2760 |
| gacgtgcagt ccatcatcgg cctgcagcgc ttcttcgaga cgcgcatgaa cgaggccttc | 2820 |
| ggtgacacca gttctctgc tgtgctggtg agccccccgc cgatgagcct gcctggtgct | 2880 |
| ggcctgagtt cccaggagct gtctggtggc cctggtgatg gccccctgagg ctggagcccc | 2940 |
| catggccagc ccagcctggc tctgttctct gtcctgtcac cccatcccca ctccctggt | 3000 |
| ggcctgactc ccactccctg gtggccccat ccccagttc ctcacgatat ggttttact | 3060 |
| tctgtggatt taataaaaac ttcaccagtt cctcaggcgt tggctggttg ggggactgtg | 3120 |
| gtcctggggc ctggtttatt gactgt | 3146 |

<210> SEQ ID NO 79
<211> LENGTH: 2989
<212> TYPE: DNA
<213> ORGANISM: Homo sapiens

<400> SEQUENCE: 79

| | |
|---|---|
| ggcgcgcggg cgagcggttg tgcttgtgct tgtggcgcgt ggtgcgggtt tcggcggcgg | 60 |
| ctgaggaaga agcgcgggcg gcgccttcgg gaggcgagca ggcagcagtt ggccgtgccg | 120 |
| tagcagcgtc ccgcgcgcgg cgggcagcgg cccaggaggc gcgtggcggc gctcggcctc | 180 |

-continued

```
gcggcggcgg cggcggcagc ggcccagcag ttggcggcga gcgcgtctgc gcctgcgcgg    240
cgggccccgc gcccctcctc ccccctgggc gccccggc ggcgtgtgaa tggcggcctc    300
cgcggcggca gcctcggcag cagcggcctc ggccgcctct ggcagccgg gcccgggcga    360 gggctccgct ggcggcgaaa agcgctccac cgccccttcg gccgcagcct cggcctctgc    420
ctcagccgcg cgtcgtcgc ccgcgggggg cggcgccgag gcgctggagc tgctggagca    480
ctgcggcgtg tgcagagagc gcctgcgacc cgagagggag ccccgcctgc tgccctgttt    540
gcactcggcc tgtagtgcct gcttagggcc cgcggccccc gccgccgcca acagctcggg    600
ggacggcggg gcggcgggcg acggcaccgt ggtggactgt cccgtgtgca agcaacagtg    660
cttctccaaa gacatcgtgg agaattattt catgcgtgat agtggcagca aggctgccac    720
cgacgcccag gatgcgaacc agtgctgcac tagctgtgag gataatgccc cagccaccag    780
ctactgtgtg gagtgctcgg agcctctgtg tgagacctgt gtagaggcgc accagcgggt    840
gaagtacacc aaggaccata ctgtgcgctc tactgggcca gccaagtctc gggatggtga    900
acgtactgtc tattgcaacg tacacaagca tgaacccctt gtgctgtttt gtgagagctg    960
tgatactctc acctgccgag actgccagct caatgcccac aaggaccacc agtaccagtt    1020
cttagaggat gcagtgagga accagcgcaa gctcctggcc tcactggtga agcgccttgg    1080
ggacaaacat gcaacattgc agaagagcac caaggaggtt cgcagctcaa tccgccaggt    1140
gtctgacgta cagaagcgtg tgcaagtgga tgtcaagatg gccatcctgc agatcatgaa    1200
ggagctgaat aagcggggcc gtgtgctggt caatgatgcc cagaaggtga ctgaggggca    1260
gcaggagcgc ctggagcggc agcactggac catgaccaag atccagaagc accaggagca    1320
cattctgcgc tttgcctctt gggctctgga gagtgacaac aacacagccc ttttgctttc    1380
taagaagttg atctacttcc agctgcaccg ggccctcaag atgattgtgg atcccgtgga    1440
gccacatggc gagatgaagt ttcagtggga cctcaatgcc tggaccaaga gtgccgaggc    1500
ctttggcaag attgtggcag agcgtcctgg cactaactca acaggccctg cacccatggc    1560
ccctccaaga gccccaggc ccctgagcaa gcagggctct ggcagcagcc agcccatgga    1620
ggtgcaggaa ggctatggct ttgggtcagg agatgatccc tactcaagtg cagagcccca    1680
tgtgtcaggt gtgaaacggt cccgctcagt gagggcgag gtgagcggcc ttatgcgcaa    1740
ggtgccacga gtgagccttg aacgcctgga cctggacctc acagctgaca gccagccacc    1800
cgtcttcaag gtcttcccag gcagtaccac tgaggactac aaccttattg ttattgaacg    1860
tggcgctgcc gctgcagcta ccggccagcc agggactgcg cctgcaggaa cccctggtgc    1920
cccacccctg gctggcatgg ccattgtcaa ggaggaggag acggaggctg ccattggagc    1980
ccctcctact gccactgagg gccctgagac caaacctgtg cttatggctc ttgcggaggg    2040
tcctggtgct gagggtcccc gcctggcctc acctagtggc agcaccagct cagggctgga    2100
ggtggtggct cctgagggta cctcagcccc aggtggtggc ccgggaaccc tggatgacag    2160
tgccaccatt tgccgtgtct gccagaagcc aggcgatctg gttatgtgca accagtgtga    2220
gttttgtttc cacctggact gtcacctgcc ggccctgcag gatgtaccag gggaggagtg    2280
gagctgctca ctctgccatg tgctccctga cctgaaggag gaggatggca gcctcagcct    2340
ggatggtgca gacagcactg gcgtggtggc caagctctca ccagccaacc agcggaaatg    2400
tgagcgtgta ctgctggccc tattctgtca cgaaccctgc cgcccctgc atcagctggc    2460 taccgactcc accttctccc tggaccagcc cggtggcacc ctggatctga ccctgatccg    2520
tgcccgcctc caggagaagt tgtcacctcc ctacagctcc ccacaggagt ttgcccagga    2580
```

-continued

| | |
|---|---|
| tgtgggccgc atgttcaagc aattcaacaa gttaactgag gacaaggcag acgtgcagtc | 2640 |
| catcatcggc ctgcagcgct tcttcgagac gcgcatgaac gaggccttcg gtgacaccaa | 2700 |
| gttctctgct gtgctggtgg agccccgcc gatgagcctg cctggtgctg gcctgagttc | 2760 |
| ccaggagctg tctggtggcc ctggtgatgg cccctgaggc tggagccccc atggccagcc | 2820 |
| cagcctggct ctgttctctg tcctgtcacc ccatccccac tccctggtg gcctgactcc | 2880 |
| cactccctgg tggccccatc ccccagttcc tcacgatatg gttttactt ctgtggattt | 2940 |
| aataaaaact tcaccagtta aaaaaaaaa aaaaaaaaa aaaaaaaaa | 2989 |

<210> SEQ ID NO 80
<211> LENGTH: 3392
<212> TYPE: DNA
<213> ORGANISM: Homo sapiens

<400> SEQUENCE: 80

| | |
|---|---|
| cggcggcgaa gagacgcggg ttgaggaaga gggacggatt gcccatgcgc ttgggcgcac | 60 |
| agcggcccgc ttctgtgtgg tctggaggtg gagctgagag gggaatcaca ctctataaag | 120 |
| gttcgcatac cccactggcg gattcaattg cggcagtgac gtcacagagg ccccgccccg | 180 |
| cccccacaag agccccaccg acgtgggggtt ggcggtggtg gaaggactag gagttggcgc | 240 |
| gtgcgtactg gcggcctctc ccgcaccgac cggcctgggc cccgccccg ggcgtgaggc | 300 |
| gcccaatgcg cgtgcgcggc ggcgtcggcg ccagttattt ctgtcccgcc cccggcctc | 360 |
| ggctcttttct gcgagcgggc gcgcgggcga gcggttgtgt ttgtgcttgt ggcgcgtggt | 420 |
| gcgggtttcg gcggcggctg aggaagaagc gcgggcggcg ccttcgggag gcgagcaggc | 480 |
| agcagttggc cgtgccgtag cagcgtcccg cgcgcggcgg gcagcggccc aggaggcgcg | 540 |
| tggcggcgct cggcctcgcg gcggcggcg cggcagcggc ccagcagttg gcggcgagcg | 600 |
| cgtctgcgcg tgcgcggcgg gccccgcgcc cctcctcccc cctgggcgc cccggcggc | 660 |
| gtgtgaatgg cggcctccgc ggcggcagcc tcggcagcag cggcctcggc cgcctctggc | 720 |
| agcccgggcc cgggcgaggg ctccgctggc ggcgaaaagc gctccaccgc cccttcggcc | 780 |
| gcagcctcgg cctctgcctc agcgcggcg tcgtcgcccg cggggggcgg cgccgaggcg | 840 |
| ctggagctgc tggagcactg cggcgtgtgc agagagcgcc tgcgaccgga gggagccc | 900 |
| cgcctgctgc cctgtttgca ctcggcctgt agtgcctgct tagggcccgc ggccccgcc | 960 |
| gccgccaaca gctcggggga cggcggggcg gcgggcgacg gcaccgtggt ggactgtccc | 1020 |
| gtgtgcaagc aacagtgctt ctccaaagac atcgtggaga attatttcat gcgtgatagt | 1080 |
| ggcagcaagg ctgccaccga cgcccaggat gcgaaccagt gctgcactag ctgtgaggat | 1140 |
| aatgccccag ccaccagcta ctgtgtggag tgctcggagc ctctgtgtga gacctgtgta | 1200 |
| gaggcgcacc agcgggtgaa gtacaccaag gaccatactg tgcgctctac tgggccagcc | 1260 |
| aagtctcggg atggtgaacg tactgtctat tgcaacgtac acaagcatga ccccttgtg | 1320 |
| ctgttttgtg agagctgtga tactctcacc tgccgagact gccagctcaa tgcccacaag | 1380 |
| gaccaccagt accagttctt agaggatgca gtgaggaacc agcgcaagct cctggcctca | 1440 |
| ctggtgaagc gccttgggga caaacatgca acattgcaga gagcaccaa ggaggttcgc | 1500 |
| agctcaatcc gccaggtgtc tgacgtacag aagcgtgtgc aagtggatgt caagatggcc | 1560 |
| atcctgcaga tcatgaagga gctgaataag cggggccgtg tgctggtcaa tgatgcccag | 1620 |
| aaggtgactg aggggcagca ggagcgcctg gagcggcagc actggaccat gaccaagatc | 1680 |

-continued

| | |
|---|---:|
| cagaagcacc aggagcacat tctgcgcttt gcctcttggg ctctggagag tgacaacaac | 1740 |
| acagcccttt tgctttctaa gaagttgatc tacttccagc tgcaccgggc cctcaagatg | 1800 |
| attgtggatc ccgtggagcc acatggcgag atgaagtttc agtgggacct caatgcctgg | 1860 |
| accaagagtg ccgaggcctt tggcaagatt gtggcagagc gtcctggcac taactcaaca | 1920 |
| ggccctgcac ccatggcccc tccaagagcc cagggcccc tgagcaagca gggctctggc | 1980 |
| agcagccagc ccatggaggt gcaggaaggc tatggctttg ggtcaggaga tgatccctac | 2040 |
| tcaagtgcag agccccatgt gtcaggtgtg aaacggtccc gctcaggtga gggcgaggtg | 2100 |
| agcggcctta tgcgcaaggt gccacgagtg agccttgaac gcctggacct ggacctcaca | 2160 |
| gctgacagcc agccacccgt cttcaaggtc ttcccaggca gtaccactga ggactacaac | 2220 |
| cttattgtta ttgaacgtgg cgctgccgct gcagctaccg ccagccagg gactgcgcct | 2280 |
| gcaggaaccc ctggtgcccc accctggct ggcatggcca ttgtcaagga ggaggagacg | 2340 |
| gaggctgcca ttggagcccc tcctactgcc actgagggcc ctgagaccaa acctgtgctt | 2400 |
| atggctcttg cggagggtcc tggtgctgag gtccccgcc tggcctcacc tagtggcagc | 2460 |
| accagctcag gctggaggt ggtggctcct gagggtacct cagccccagg tggtggcccg | 2520 |
| ggaaccctgg atgacagtgc caccatttgc cgtgtctgcc agaagccagg cgatctggtt | 2580 |
| atgtgcaacc agtgtgagtt tgtttccac ctggactgtc acctgccggc cctgcaggat | 2640 |
| gtaccagggg aggagtggag ctgctcactc tgccatgtgc tccctgacct gaaggaggag | 2700 |
| gatggcagcc tcagcctgga tggtgcagac agcactggcg tggtggccaa gctctcacca | 2760 |
| gccaaccagc ggaaatgtga gcgtgtactg ctggccctat tctgtcacga accctgccgc | 2820 |
| cccctgcatc agctggctac cgactccacc ttctccctgg accagcccgg tgcaccctg | 2880 |
| gatctgaccc tgatccgtgc ccgcctccag agaagttgt cacctcccta cagctcccca | 2940 |
| caggagtttg cccaggatgt gggccgcatg ttcaagcaat tcaacaagtt aactgaggac | 3000 |
| aaggcagacg tgcagtccat catcggcctg cagcgcttct tcgagacgcg catgaacgag | 3060 |
| gccttcggtg acaccaagtt ctctgctgtg ctggtggagc cccgccgat gagcctgcct | 3120 |
| ggtgctggcc tgagttccca ggagctgtct ggtggccctg gtgatggccc ctgaggctgg | 3180 |
| agccccatg ccagcccag cctggctctg ttctctgtcc tgtcacccca tccccactcc | 3240 |
| cctggtggcc tgactcccac tccctggtgg ccccatcccc cagttcctca cgatatggtt | 3300 |
| tttacttctg tggatttaat aaaaacttca ccagttcctc aggcgttggc tggttggggg | 3360 |
| actgtggtcc tggggcctgg tttattgact gt | 3392 |

<210> SEQ ID NO 81
<211> LENGTH: 9090
<212> TYPE: DNA
<213> ORGANISM: Homo sapiens

<400> SEQUENCE: 81

| | |
|---|---:|
| cgagcccagt cgagccgcgc tcacctcggg ctcccgctcc gtctccacct ccgcctttgc | 60 |
| cctggcggcg cgaccccgtc ccggcgcggc ccccagcagt cgcgcgccgt tagcctcgcg | 120 |
| cccgccgcgc agtccgggcc cggcgcgatg ggggccgccg ccggccggag ccccacctg | 180 |
| gggcccgcgc ccgcccgccg cccgcagcgc tctctgctcc tgctgcagct gctgctgctc | 240 |
| gtcgctgccc cggggtccac gcaggccag gccgcccgt tccccgagct gtgcagttat | 300 |
| acatgggaag ctgttgatac caaaaataat gtactttata aaatcaacat ctgtggaagt | 360 |
| gtggatattg tccagtgcgg gccatcaagt gctgtttgta tgcacgactt gaagacacgc | 420 |

```
acttatcatt cagtgggtga ctctgttttg agaagtgcaa ccagatctct cctggaattc      480
aacacaacag tgagctgtga ccagcaaggc acaaatcaca gagtccagag cagcattgcc      540
ttcctgtgtg ggaaaaccct gggaactcct gaatttgtaa ctgcaacaga atgtgtgcac      600
tactttgagt ggaggaccac tgcagcctgc aagaaagaca tatttaaagc aaataaggag      660
gtgccatgct atgtgtttga tgaagagttg aggaagcatg atctcaatcc tctgatcaag      720
cttagtggtg cctacttggt ggatgactcc gatccggaca cttctctatt catcaatgtt      780
tgtagagaca tagacacact acgagaccca ggttcacagc tgcgggcctg tcccccggc      840 actgccgcct gcctggtaag aggacaccag gcgtttgatg ttggccagcc ccgggacgga      900
ctgaagctgg tgcgcaagga caggcttgtc ctgagttacg tgagggaaga ggcaggaaag      960 ctagacttttt gtgatggtca cagccctgcg gtgactatta catttgtttg cccgtcggag     1020
cggagagagg gcaccattcc caaactcaca gctaaatcca actgccgcta tgaaattgag     1080
tggattactg agtatgcctg ccacagagat tacctggaaa gtaaaacttg ttctctgagc     1140
ggcgagcagc aggatgtctc catagacctc acaccacttg cccagagcgg aggttcatcc     1200
tatatttcag atggaaaaga atatttgttt tatttgaatg tctgtggaga aactgaaata     1260
cagttctgta taaaaaaaca agctgcagtt tgccaagtga aaaagagcga tacctctcaa     1320
gtcaaagcag caggaagata ccacaatcag accctccgat attcggatgg agacctcacc     1380
ttgatatatt ttggaggtga tgaatgcagc tcagggtttc agcggatgag cgtcataaac     1440
tttgagtgca ataaaaccgc aggtaacgat gggaaaggaa ctcctgtatt cacagggag      1500 gttgactgca cctacttctt cacatgggac acggaatacg cctgtgttaa ggagaaggaa     1560
gacctcctct gcggtgccac cgacgggaag aagcgctatg acctgtccgc gctggtccgc     1620
catgcagaac cagagcagaa ttgggaagct gtggatggca gtcagacgga aacagagaag     1680
aagcattttt tcattaatat ttgtcacaga gtgctgcagg aaggcaaggc acgagggtgt     1740
cccgaggacg cggcagtgtg tgcagtggat aaaaatggaa gtaaaaatct gggaaaattt     1800
atttcctctc ccatgaaaga gaaaggaaac attcaactct cttattcaga tggtgatgat     1860
tgtggtcatg gcaagaaaat taaaactaat atcacacttg tatgcaagcc aggtgatctg     1920
gaaagtgcac cagtgttgag aacttctggg gaaggcggtt gctttttatga gtttgagtgg     1980 cgcacagctg cggcctgtgt gctgtctaag acagaagggg agaactgcac ggtctttgac     2040
tcccaggcag ggttttcttt tgacttatca cctctcacaa agaaaaatgg tgcctataaa     2100
gttgagacaa agaagtatga cttttatata aatgtgtgtg gcccggtgtc tgtgagcccc     2160
tgtcagccca actcaggagc ctgccaggtg gcaaaaagtg atgagaagac ttggaacttg     2220
ggtctgagta atgcgaagct ttcatattat gatgggatga tccaactgaa ctacagaggc     2280
ggcacaccct ataacaatga agacacaca ccgagagcta cgctcatcac ctttctctgt     2340
gatcgagacg cgggagtggg cttccctgaa tatcaggaag aggataactc cacctacaac     2400
ttccggtggt acaccagcta tgcctgcccg gaggagcccc tggaatgcgt agtgaccgac     2460
ccctccacgc tggagcagta cgacctctcc agtctggcaa atctgaagg tggccttgga      2520 ggaaactggt atgccatgga caactcaggg gaacatgtca cgtggaggaa atactacatt     2580
aacgtgtgtc ggcctctgaa tccagtgccg ggctgcaacc gatatgcatc ggcttgccag     2640
atgaagtatg aaaaagatca gggctccttc actgaagtgg tttccatcag taacttggga     2700
atggcaaaga ccggcccggt ggttgaggac agcggcagcc tccttctgga atacgtgaat     2760
```

```
gggtcggcct gcaccaccag cgatggcaga cagaccacat ataccacgag gatccatctc    2820
gtctgctcca ggggcaggct gaacagccac cccatctttt ctctcaactg ggagtgtgtg    2880
gtcagtttcc tgtggaacac agaggctgcc tgtcccattc agacaacgac ggatacagac    2940
caggcttgct ctataaggga tcccaacagt ggatttgtgt ttaatcttaa tccgctaaac    3000
agttcgcaag gatataacgt ctctggcatt gggaagattt ttatgtttaa tgtctgcggc    3060
acaatgcctg tctgtgggac catcctggga aaacctgctt ctggctgtga ggcagaaacc    3120
caaactgaag agctcaagaa ttggaagcca gcaaggccag tcggaattga gaaaagcctc    3180
cagctgtcca cagagggctt catcactctg acctacaaag ggcctctctc tgccaaaggt    3240
accgctgatg cttttatcgt ccgctttgtt tgcaatgatg atgtttactc agggcccctc    3300
aaattcctgc atcaagatat cgactctggg caagggatcc gaaacactta ctttgagttt    3360
gaaaccgcgt tggcctgtgt tccttctcca gtggactgcc aagtcaccga cctggctgga    3420
aatgagtacg acctgactgg cctaagcaca gtcaggaaac cttggacggc tgttgacacc    3480
tctgtcgatg ggagaaagag gactttctat ttgagcgttt gcaatcctct cccttacatt    3540
cctggatgcc agggcagcgc agtggggtct tgcttagtgt cagaaggcaa tagctggaat    3600
ctgggtgtgg tgcagatgag tccccaagcc gcggcgaatg gatctttgag catcatgtat    3660
gtcaacggtg acaagtgtgg gaaccagcgc ttctccacca ggatcacgtt tgagtgtgct    3720
cagatatcgg gctcaccagc atttcagctt caggatggtt gtgagtacgt gtttatctgg    3780
agaactgtga aagcctgtcc cgttgtcaga gtggaagggg acaactgtga ggtgaaagac    3840
ccaaggcatg gcaacttgta tgacctgaag cccctgggcc tcaacgacac catcgtgagc    3900
gctggcgaat acacttatta cttccgggtc tgtgggaagc tttcctcaga cgtctgcccc    3960
acaagtgaca agtccaaggt ggtctcctca tgtcaggaaa agcgggaacc gcagggattt    4020
cacaaagtgg caggtctcct gactcagaag ctaacttatg aaaatggctt gttaaaaatg    4080
aacttcacgg gggggacac ttgccataag gtttatcagc gctccacagc catcttcttc    4140
tactgtgacc gcggcaccca gcggccagta tttctaaagg agacttcaga ttgttcctac    4200
ttgtttgagt ggcgaacgca gtatgcctgc ccaccttcg atctgactga atgttcattc    4260
aaagatgggg ctggcaactc cttcgacctc tcgtccctgt caaggtacag tgacaactgg    4320
gaagccatca ctgggacggg ggacccggag cactacctca tcaatgtctg caagtctctg    4380
gccccgcagg ctggcactga gccgtgccct ccagaagcag ccgcgtgtct gctgggtggc    4440
tccaagcccg tgaacctcgg cagggtaagg gacggacctc agtggagaga tggcataatt    4500
gtcctgaaat acgttgatgg cgacttatgt ccagatggga ttcggaaaaa gtcaaccacc    4560
atccgattca cctgcagcga gagccaagtg aactccaggc ccatgttcat cagcgccgtg    4620
gaggactgtg agtacacctt tgcctggccc acagccacag cctgtcccat gaagagcaac    4680
gagcatgatg actgccaggt caccaaccca agcacaggac acctgtttga tctgagctcc    4740
ttaagtggca gggcgggatt cacagctgct tacagcgaga aggggttggt ttacatgagc    4800
atctgtgggg agaatgaaaa actgccctcc tggcgtgggg cctgctttgg acagaccagg    4860
attagcgtgg gcaaggccaa caagaggctg agatacgtgg accaggtcct gcagctggtg    4920
tacaaggatg ggtcccttg tccctccaaa tccggcctga ctataagag tgtgatcagt    4980
ttcgtgtgca ggcctgaggc cgggccaacc aataggccca tgctcatctc cctggacaag    5040
cagacatgca ctctcttctt ctcctggcac acgccgctgg cctgcgagca agcgaccgaa    5100
tgttccgtga ggaatggaag ctctattgtt gacttgtctc cccttattca tcgcactggt    5160
```

```
ggttatgagg cttatgatga gagtgaggat gatgcctccg ataccaaccc tgatttctac    5220
atcaatattt gtcagccact aaatcccatg cacgcagtgc cctgtcctgc cggagccgct    5280
gtgtgcaaag ttcctattga tggtcccccc atagatatcg gccgggtagc aggaccacca    5340
atactcaatc caatagcaaa tgagatttac ttgaattttg aaagcagtac tccttgctta    5400
gcggacaagc atttcaacta cacctcgctc atcgcgtttc actgtaagag aggtgtgagc    5460
atgggaacgc ctaagctgtt aaggaccagc gagtgcgact ttgtgttcga atgggagact    5520
cctgtcgtct gtcctgatga agtgaggatg gatggctgta ccctgacaga tgagcagctc    5580
ctctacagct tcaacttgtc cagccttttcc acgagcacct ttaaggtgac tcgcgactcg    5640
cgcacctaca gcgttggggt gtgcacccttt gcagtcgggc cagaacaagg aggctgtaag    5700
gacggaggag tctgtctgct ctcaggcacc aagggggcat cctttggacg gctgcaatca    5760
atgaaactgg attacaggca ccaggatgaa gcggtcgttt aagttacgt gaatggtgat    5820 cgttgccctc cagaaaccga tgacggcgtc ccctgtgtct tcccctttcat attcaatggg    5880 aagagctacg aggagtgcat catagagagc agggcgaagc tgtggtgtag cacaactgcg    5940
gactacgaca gagaccacga gtggggcttc tgcagacact caaacagcta ccggacatcc    6000
agcatcatat ttaagtgtga tgaagatgag gacattggga ggccacaagt cttcagtgaa    6060
gtgcgtgggt gtgatgtgac atttgagtgg aaaacaaaag ttgtctgccc tccaaagaag    6120
ttggagtgca aattcgtcca gaaacacaaa acctacgacc tgcggctgct ctcctctctc    6180
accgggtcct ggtccctggt ccacaacgga gtctcgtact atataaatct gtgccagaaa    6240
atatataaag ggcccctggg ctgctctgaa agggccagca tttgcagaag gaccacaact    6300
ggtgacgtcc aggtcctggg actcgttcac acgcagaagc tgggtgtcat aggtgacaaa    6360
gttgttgtca cgtactccaa aggttatccg tgtggtggaa ataagaccgc atcctccgtg    6420
atagaattga cctgtacaaa gacggtgggc agacctgcat tcaagaggtt tgatatcgac    6480
agctgcactt actacttcag ctgggactcc cgggctgcct gcgccgtgaa gcctcaggag    6540
gtgcagatgg tgaatgggac catcaccaac cctataaatg gcaagagctt cagcctcgga    6600
gatatttatt ttaagctgtt cagagcctct ggggacatga ggaccaatgg ggacaactac    6660
ctgtatgaga tccaactttc ctccatcaca agctccagaa acccggcgtg ctctggagcc    6720
aacatatgcc aggtgaagcc caacgatcag cacttcagtc ggaaagttgg aacctctgac    6780
aagaccaagt actaccttca agacggcgat ctcgatgtcg tgtttgcctc ttcctctaag    6840
tgcggaaagg ataagaccaa gtctgtttct tccaccatct tcttccactg tgaccctctg    6900
gtggaggacg ggatccccga gttcagtcac gagactgccg actgccagta cctcttctct    6960
tggtacacct cagccgtgtg tcctctgggg gtgggctttg acagcgagaa tcccggggac    7020
gacgggcaga tgcacaaggg gctgtcagaa cggagccagg cagtcggcgc ggtgctcagc    7080
ctgctgctgg tggcgctcac ctgctgcctg ctggccctgt tgctctacaa gaaggagagg    7140
agggaaacag tgataagtaa gctgaccact tgctgtagga aagttccaa cgtgtcctac    7200 aaatactcaa aggtgaataa ggaagaagag acagatgaga atgaaacaga gtggctgatg    7260
gaagagatcc agctgcctcc tccacggcag ggaaaggaag gcaggagaa cggccatatt    7320 accaccaagt cagtgaaagc cctcagctcc ctgcatgggg atgaccagga cagtgaggat    7380
gaggttctga ccatcccaga ggtgaaagtt cactcgggca ggggagctgg ggcagagagc    7440
tcccacccag tgagaaacgc acagagcaat gcccttcagg agcgtgagga cgataggtg    7500
```

```
gggctggtca ggggtgagaa ggcgaggaaa gggaagtcca gctctgcaca gcagaagaca    7560
gtgagctcca ccaagctggt gtccttccat gacgacagcg acgaggacct cttacacatc    7620
tgactccgca gtgcctgcag gggagcacgg agccgcggga cagccaagca cctccaacca    7680
aataagactt ccactcgatg atgcttctat aattttgcct ttaacagaaa ctttcaaaag    7740
ggaagagttt ttgtgatggg ggagagggtg aaggaggtca ggccccactc cttcctgatt    7800
gtttacagtc attggaataa ggcatggctc agatcggcca cagggcggta ccttgtgccc    7860
agggttttgc cccaagtcct catttaaaag cataaggccg gacgcatctc aaaacagagg    7920
gctgcattcg aagaaaccct tgctgcttta gtcccgatag ggtatttgac cccgatatat    7980
tttagcattt taattctctc cccctattta ttgactttga caattactca ggtttgagaa    8040
aaaggaaaaa aaaacagcca ccgtttcttc ctgccagcag gggtgtgatg taccagtttg    8100
tccatcttga gatggtgagg ctgtcagtgt atggggcagc ttccggcggg atgttgaact    8160
ggtcattaat gtgtccctg agttggagct cattctgtct cttttctctt ttgctttctg    8220
tttcttaagg gcacacacac gtgcgtgcga gcacacacac acatacgtgc acagggtccc    8280
cgagtgccta ggttttggag agtttgcctg ttctatgcct ttagtcagga atggctgcac    8340 cttttttgcat gatatcttca agcctgggcg tacagagcac atttgtcagt attttttgccg   8400 gctggtgaat tcaaacaacc tgcccaaaga ttgatttgtg tgtttgtgtg tgtgtgtgtg    8460
tgtgtgtgtg tgtgtgagtg gagttgaggt gtcagagaaa atgaatttt tccagatttg     8520 gggtataggt ctcatctctt caggttctca tgataccacc tttactgtgc ttatttttt     8580 aagaaaaaag tgttgatcaa ccattcgacc tataagaagc cttaatttgc acagtgtgtg    8640
acttacagaa actgcatgaa aaatcatggg ccagagcctc ggccctagca ttgcacttgg    8700
cctcatgctg gagggaggct gggcgggtac agcgcggagg aggagggagg ccaggcgggc    8760
atggcgtgga ggaggaggga ggccgggcgg tcacagcatg gaggaggagg gaggcgctgc    8820
tggtgttctt attctggcgg cagcgccttt cctgccatgt ttagtgaatg acttttctcg    8880
cattgtagaa ttgtatatag actctggtgt tctattgctg agaagcaaac cgccctgcag    8940
catccctcag cctgtaccgg tttggctggc ttgtttgatt tcaacatgag tgtatttttt    9000
aaaattgatt tttctcttca ttttttttttc aatcaacttt actgtaatat aaagtattca   9060
acaatttcaa taaagataaa attattaaaa                                     9090
```

<210> SEQ ID NO 82
<211> LENGTH: 9091
<212> TYPE: DNA
<213> ORGANISM: Homo sapiens

<400> SEQUENCE: 82

```
cgagcccagt cgagccgcgc tcacctcggg ctcccgctcc gtctccacct ccgcctttgc      60
cctggcggcg cgaccccgtc ccgggcgcgg ccccccagcag tcgcgcgccg ttagcctcgc    120
gcccgccgcg cagtccgggc cccgcccgat ggggccgcc gccggccgga gccccacct      180 ggggcccgcg cccgcccgcc gcccgcagcg ctctctgctc ctgctgcagc tgctgctgct    240
cgtcgctgcc ccggggtcca cgcaggccca ggccgccccg ttccccgagc tgtgcagtta    300
tacatgggaa gctgttgata ccaaaaataa tgtactttat aaaatcaaca tctgtggaag    360
tgtggatatt gtccagtgcg ggccatcaag tgctgtttgt atgcacgact tgaagacacg    420
cacttatcat tcagtgggtg actctgtttt gagaagtgca accagatctc tcctggaatt    480
caacacaaca gtgagctgtg accagcaagg cacaaatcac agagtccaga gcagcattgc    540
```

-continued

| | |
|---|---|
| cttcctgtgt gggaaaaccc tgggaactcc tgaatttgta actgcaacag aatgtgtgca | 600 |
| ctactttgag tggaggacca ctgcagcctg caagaaagac atatttaaag caaataagga | 660 |
| ggtgccatgc tatgtgtttg atgaagagtt gaggaagcat gatctcaatc ctctgatcaa | 720 |
| gcttagtggt gcctacttgg tggatgactc cgatccggac acttctctat tcatcaatgt | 780 |
| ttgtagagac atagacacac tacgagaccc aggttcacag ctgcgggcct gtcccccggg | 840 |
| cactgccgcc tgcctggtaa gaggacacca ggcgtttgat gttggccagc cccgggacgg | 900 |
| actgaagctg gtgcgcaagg acaggcttgt cctgagttac gtgagggaag aggcaggaaa | 960 |
| gctagacttt tgtgatggtc acagccctgc ggtgactatt acatttgttt gcccgtcgga | 1020 |
| gcggagagag ggcaccattc ccaaactcac agctaaatcc aactgccgct atgaaattga | 1080 |
| gtggattact gagtatgcct gccacagaga ttacctggaa agtaaaactt gttctctgag | 1140 |
| cggcgagcag caggatgtct ccatagacct cacaccactt gcccagagcg gaggttcatc | 1200 |
| ctatatttca gatggaaaag aatatttgtt ttatttgaat gtctgtggag aaactgaaat | 1260 |
| acagttctgt aataaaaaac aagctgcagt ttgccaagtg aaaaagagcg atacctctca | 1320 |
| agtcaaagca gcaggaagat accacaatca gaccctccga tattcggatg agacctcac | 1380 |
| cttgatatat tttggaggtg atgaatgcag ctcagggttt cagcggatga gcgtcataaa | 1440 |
| cttttgagtgc aataaaaccg caggtaacga tgggaaagga actcctgtat tcacagggga | 1500 |
| ggttgactgc acctacttct tcacatggga cacggaatac gcctgtgtta aggagaagga | 1560 |
| agacctcctc tgcggtgcca ccgacgggaa gaagcgctat gacctgtccg cgctggtccg | 1620 |
| ccatgcagaa ccagagcaga attgggaagc tgtggatggc agtcagacgg aaacagagaa | 1680 |
| gaagcatttt tcattaata tttgtcacag agtgctgcag gaaggcaagg cacgagggtg | 1740 |
| tcccgaggac gcggcagtgt gtgcagtgga taaaaatgga agtaaaaatc tgggaaaatt | 1800 |
| tatttcctct cccatgaaag agaaaggaaa cattcaactc tcttattcag atggtgatga | 1860 |
| ttgtggtcat ggcaagaaaa ttaaaactaa tatcacactt gtatgcaagc caggtgatct | 1920 |
| ggaaagtgca ccagtgttga gaacttctgg ggaaggcggt tgcttttatg agtttgagtg | 1980 |
| gcacacagct gcggcctgtg tgctgtctaa gacagaaggg gagaactgca cggtctttga | 2040 |
| ctcccaggca gggttttctt ttgacttatc acctctcaca aagaaaaatg gtgcctataa | 2100 |
| agttgagaca agaagtatg acttttatat aaatgtgtgt ggcccggtgt ctgtgagccc | 2160 |
| ctgtcagcca gactcaggag cctgccaggt ggcaaaaagt gatgagaaga cttggaactt | 2220 |
| gggtctgagt aatgcgaagc tttcatatta tgatgggatg atccaactga actacagagg | 2280 |
| cggcacaccc tataacaatg aaagacacac accgagagct acgctcatca cctttctctg | 2340 |
| tgatcgagac gcgggagtgg gcttccctga atatcaggaa gaggataact ccacctacaa | 2400 |
| cttccggtgg tacaccagct atgcctgccc ggaggagccc ctggaatgcg tagtgaccga | 2460 |
| cccctccacg ctggagcagt acgacctctc cagtctggca aaatctgaag gtggccttgg | 2520 |
| aggaaactgg tatgccatgg acaactcagg ggaacatgtc acgtggagga aatactacat | 2580 |
| taacgtgtgt cggcctctga atccagtgcc gggctgcaac cgatatgcat cggcttgcca | 2640 |
| gatgaagtat gaaaaagatc agggctcctt cactgaagtg gtttccatca gtaacttggg | 2700 |
| aatggcaaag accggcccgg tggttgagga cagcggcagc ctccttctgg aatacgtgaa | 2760 |
| tgggtcggcc tgcaccacca gcgatggcag acagaccaca tataccacga ggatccatct | 2820 |
| cgtctgctcc aggggcaggc tgaacagcca ccccatcttt tctctcaact gggagtgtgt | 2880 |

```
ggtcagtttc ctgtggaaca cagaggctgc ctgtcccatt cagacaacga cggatacaga    2940
ccaggcttgc tctataaggg atcccaacag tggatttgtg tttaatctta atccgctaaa    3000
cagttcgcaa ggatataacg tctctggcat tgggaagatt tttatgttta atgtctgcgg    3060
cacaatgcct gtctgtggga ccatcctggg aaaacctgct tctggctgtg aggcagaaac    3120
ccaaactgaa gagctcaaga attggaagcc agcaaggcca gtcggaattg agaaaagcct    3180
ccagctgtcc acagagggct tcatcactct gacctacaaa gggcctctct ctgccaaagg    3240
taccgctgat gcttttatcg tccgctttgt ttgcaatgat gatgtttact cagggcccct    3300
caaattcctg catcaagata tcgactctgg gcaagggatc cgaaacactt actttgagtt    3360
tgaaaccgcg ttggcctgtg ttccttctcc agtggactgc caagtcaccg acctggctgg    3420
aaatgagtac gacctgactg gcctaagcac agtcaggaaa ccttggacgg ctgttgacac    3480
ctctgtcgat gggagaaaga ggactttcta tttgagcgtt tgcaatcctc tcccttacat    3540
tcctggatgc cagggcagcg cagtgggggtc ttgcttagtg tcagaaggca atagctggaa    3600
tctgggtgtg gtgcagatga gtccccaagc cgcggcgaat ggatctttga gcatcatgta    3660
tgtcaacggt gacaagtgtg ggaaccagcg cttctccacc aggatcacgt ttgagtgtgc    3720
tcagatatcg ggctcaccag catttcagct tcaggatggt tgtgagtacg tgtttatctg    3780
gagaactgtg gaagcctgtc ccgttgtcag agtggaaggg gacaactgtg aggtgaaaga    3840
cccaaggcat ggcaacttgt atgacctgaa gccccctgggc ctcaacgaca ccatcgtgag    3900
cgctggcgaa tacacttatt acttccgggt ctgtgggaag cttctcctcag acgtctgccc    3960 cacaagtgac aagtccaagg tggtctcctc atgtcaggaa aagcgggaac cgcagggatt    4020
tcacaaagtg gcaggtctcc tgactcagaa gctaacttat gaaaatggct tgttaaaaat    4080
gaacttcacg gggggggaca cttgccataa ggtttatcag cgctccacag ccatcttctt    4140
ctactgtgac cgcggcaccc agcggccagt atttctaaag gagacttcag attgttccta    4200
cttgtttgag tggcgaacgc agtatgcctg cccaccttc gatctgactg aatgttcatt    4260
caaagatggg gctggcaact ccttcgacct ctcgtccctg tcaaggtaca gtgacaactg    4320
ggaagccatc actgggacgg gggacccgga gcactacctc atcaatgtct gcaagtctct    4380
ggccccgcag gctggcactg agccgtgccc tccagaagca gccgcgtgtc tgctgggtgg    4440
ctccaagccc gtgaacctcg gcagggtaag ggacggacct cagtggagag atggcataat    4500
tgtcctgaaa tacgttgatg gcgacttatg tccagatggg attcggaaaa agtcaaccac    4560
catccgattc acctgcagcg agagccaagt gaactccagg cccatgttca tcagcgccgt    4620
ggaggactgt gagtacacct ttgcctggcc cacagccaca gcctgtccca tgaagagcaa    4680
cgagcatgat gactgccagg tcaccaaccc aagcacagga cacctgtttg atctgagctc    4740
cttaagtggc agggcgggat tcacagctgc ttacagcgag aaggggttgg tttacatgag    4800
catctgtggg gagaatgaaa actgccctcc tggcgtgggg gcctgctttg gacagaccag    4860
gattagcgtg ggcaaggcca acaagaggct gagatacgtg gaccaggtcc tgcagctggt    4920
gtacaaggat gggtcccctt gtccctccaa atccggcctg agctataaga gtgtgatcag    4980
tttcgtgtgc aggcctgagg ccgggccaac caataggccc atgctcatct ccctggacaa    5040
gcagacatgc actctcttct tctcctggca cacgccgctg gcctgcgagc aagcgaccga    5100
atgttccgtg aggaatggaa gctctattgt tgacttgtct ccccttattc atcgcactgg    5160
tggttatgag gcttatgatg agagtgagga tgatgcctcc gataccaacc ctgatttcta    5220
catcaatatt tgtcagccac taaatcccat gcacggagtg ccctgtcctg ccggagccgc    5280
```

```
tgtgtgcaaa gttcctattg atggtccccc catagatatc ggccgggtag caggaccacc    5340
aatactcaat ccaatagcaa atgagattta cttgaatttt gaaagcagta ctccttgctt    5400
agcggacaag catttcaact acacctcgct catcgcgttt cactgtaaga gaggtgtgag    5460
catgggaacg cctaagctgt taaggaccag cgagtgcgac tttgtgttcg aatgggagac    5520
tcctgtcgtc tgtcctgatg aagtgaggat ggatggctgt accctgacag atgagcagct    5580
cctctacagc ttcaacttgt ccagcctttc cacgagcacc tttaaggtga ctcgcgactc    5640
gcgcacctac agcgttgggg tgtgcacctt tgcagtcggg ccagaacaag gaggctgtaa    5700
ggacggagga gtctgtctgc tctcaggcac caaggggca tcctttggac ggctgcaatc     5760
aatgaaactg gattacaggc accaggatga agcggtcgtt ttaagttacg tgaatggtga    5820
tcgttgccct ccagaaaccg atgacggcgt cccctgtgtc ttccccttca tattcaatgg    5880
gaagagctac gaggagtgca tcatagagag cagggcgaag ctgtggtgta gcacaactgc    5940
ggactacgac agagaccacg agtggggctt ctgcagacac tcaaacagct accggacatc    6000
cagcatcata tttaagtgtg atgaagatga ggacattggg aggccacaag tcttcagtga    6060
agtgcgtggg tgtgatgtga catttgagtg gaaaacaaaa gttgtctgcc ctccaaagaa    6120
gttggagtgc aaattcgtcc agaaacacaa aacctacgac ctgcggctgc tctcctctct    6180
caccgggtcc tggtccctgg tccacaacgg agtctcgtac tatataaatc tgtgccagaa    6240
aatatataaa gggcccctgg gctgctctga aagggccagc atttgcagaa ggaccacaac    6300
tggtgacgtc caggtcctgg gactcgttca cacgcagaag ctgggtgtca taggtgacaa    6360
agttgttgtc acgtactcca aaggttatcc gtgtggtgga aataagaccg catcctccgt    6420
gatagaattg acctgtacaa agacggtggg cagacctgca ttcaagaggt ttgatatcga    6480
cagctgcact tactacttca gctgggactc ccgggctgcc tgcgccgtga agcctcagga    6540
ggtgcagatg gtgaatggga ccatcaccaa ccctataaat ggcaagagct tcagcctcgg    6600
agatatttat tttaagctgt tcagagcctc tggggacatg aggaccaatg gggacaacta    6660
cctgtatgag atccaacttt cctccatcac aagctccaga aacccggcgt gctctggagc    6720
caacatatgc caggtgaagc ccaacgatca gcacttcagt cggaaagttg gaacctctga    6780
caagaccaag tactaccttc aagacggcga tctcgatgtc gtgtttgcct cttcctctaa    6840
gtgcggaaag gataagacca agtctgtttc ttccaccatc ttcttccact gtgaccctct    6900
ggtggaggac gggatccccg agttcagtca cgagactgcc gactgccagt acctcttctc    6960
ttggtacacc tcagccgtgt gtcctctggg ggtgggcttt gacagcgaga atcccgggga    7020
cgacgggcag atgcacaagg ggctgtcaga acggagccag gcagtcggcg cggtgctcag    7080
cctgctgctg gtggcgctca cctgctgcct gctggccctg ttgctctaca agaaggagag    7140
gagggaaaca gtgataagta agctgaccac ttgctgtagg agaagttcca acgtgtccta    7200
caaatactca aaggtgaata aggaagaaga gacagatgag aatgaaacag agtggctgat    7260
ggaagagatc cagctgcctc ctccacggca gggaaaggaa gggcaggaga acggccatat    7320
taccaccaag tcagtgaaag ccctcagctc cctgcatggg gatgaccagg acagtgagga    7380
tgaggttctg accatcccag aggtgaaagt tcactcgggc aggggagctg ggcagagag    7440 ctcccaccca gtgagaaacg cacagagcaa tgcccttcag gagcgtgagg acgatagggt    7500 gggctggtc aggggtgaga aggcgaggaa agggaagtcc agctctgcac agcagaagac     7560
agtgagctcc accaagctgg tgtccttcca tgacgacagc gacgaggacc tcttacacat    7620
```

| | |
|---|---|
| ctgactccgc agtgcctgca ggggagcacg gagccgcggg acagccaagc acctccaacc | 7680 |
| aaataagact tccactcgat gatgcttcta taattttgcc tttaacagaa actttcaaaa | 7740 |
| gggaagagtt tttgtgatgg gggagagggt gaaggaggtc aggccccact ccttcctgat | 7800 |
| tgtttacagt cattggaata aggcatggct cagatcggcc acagggcggt accttgtgcc | 7860 |
| cagggttttg ccccaagtcc tcatttaaaa gcataaggcc ggacgcatct caaaacagag | 7920 |
| ggctgcattc gaagaaaccc ttgctgcttt agtcccgata gggtatttga ccccgatata | 7980 |
| ttttagcatt ttaattctct ccccctattt attgactttg acaattactc aggtttgaga | 8040 |
| aaaggaaaa aaaacagcc accgtttctt cctgccagca ggggtgtgat gtaccagttt | 8100 |
| gtccatcttg agatggtgag gctgtcagtg tatgggcag cttccggcgg gatgttgaac | 8160 |
| tggtcattaa tgtgtccct gagttggagc tcattctgtc tcttttctct tttgctttct | 8220 |
| gtttcttaag ggcacacaca cgtgcgtgcg agcacacaca cacatacgtg cacagggtcc | 8280 |
| ccgagtgcct aggttttgga gagtttgcct gttctatgcc tttagtcagg aatggctgca | 8340 |
| cctttttgca tgatatcttc aagcctgggc gtacagagca catttgtcag tattttttgcc | 8400 |
| ggctggtgaa ttcaaacaac ctgcccaaag attgatttgt gtgtttgtgt gtgtgtgtgt | 8460 |
| gtgtgtgtgt gtgtgtgtga gtggagttga ggtgtcagag aaaatgaatt ttttccagat | 8520 |
| ttggggtata ggtctcatct cttcaggttc tcatgatacc accttactg tgcttatttt | 8580 |
| tttaagaaaa aagtgttgat caaccattcg acctataaga agccttaatt tgcacagtgt | 8640 |
| gtgacttaca gaaactgcat gaaaaatcat gggccagagc ctcggcccta gcattgcact | 8700 |
| tggcctcatg ctggagggag gctgggcggg tacagcgcgg aggaggaggg aggccaggcg | 8760 |
| ggcatggcgt ggaggaggag ggaggccggg cggtcacagc atggaggagg agggaggcgc | 8820 |
| tgctggtgtt cttattctgg cggcagcgcc tttcctgcca tgtttagtga atgacttttc | 8880 |
| tcgcattgta gaattgtata tagactctgg tgttctattg ctgagaagca aaccgccctg | 8940 |
| cagcatccct cagcctgtac cggtttggct ggcttgtttg atttcaacat gagtgtattt | 9000 |
| tttaaaattg atttttctct tcattttttt ttcaatcaac tttactgtaa tataaagtat | 9060 |
| tcaacaattt caataaaaga taaattatta a | 9091 |

<210> SEQ ID NO 83
<211> LENGTH: 5696
<212> TYPE: DNA
<213> ORGANISM: Homo sapiens

<400> SEQUENCE: 83

| | |
|---|---|
| gctctttaa aatagttgct ttcttaggaa atgtagttgc tttcttaacc tcatcaaatt | 60 |
| catgaagatt tagccgaggc ccatgctacc cattatcttc taaatggcct tcagaaatga | 120 |
| tggagaaact gacacgttat gagtatttcc tgccctacat ggattttgaa cttgaattcc | 180 |
| cagcctcgct tgcatctaga cacagccaca aatcatcaaa atgacgagga ttttgacagc | 240 |
| tttcaaagtg gtgaggacac tgaagactgg ttttggcttt accaatgtga ctgcacacca | 300 |
| aaatggaaa ttttcaagac ctggcatcag gctcctttct gtcaaggcac agacagcaca | 360 |
| cattgtcctg gaagatggaa ctaagatgaa aggttactcc tttggccatc catcctctgt | 420 |
| tgctggtgaa gtggtttta atactggcct gggagggtac ccagaagcta ttactgaccc | 480 |
| tgcctacaaa ggacagattc tcacaatggc caaccctatt attgggaatg gtggagctcc | 540 |
| tgatactact gctctggatg aactgggact tagcaaatat ttggagtcta atggaatcaa | 600 |
| ggtttcaggt ttgctggtgc tggattatag taaagactac aaccactggc tggctaccaa | 660 |

| | |
|---|---|
| gagtttaggg caatggctac aggaagaaaa ggttcctgca atttatggag tggacacaag | 720 |
| aatgctgact aaaataattc gggataaggg taccatgctt gggaagattg aatttgaagg | 780 |
| tcagcctgtg gattttgtgg atccaaataa acagaatttg attgctgagg tttcaaccaa | 840 |
| ggatgtcaaa gtgtacggca aggaaaccc cacaaaagtg gtagctgtag actgtgggat | 900 |
| taaaaacaat gtaatccgcc tgctagtaaa gcgaggagc gaagtgcact tagttccctg | 960 |
| gaaccatgat ttcaccaaga tggagtatga tgggattttg atcgcgggag gaccggggaa | 1020 |
| cccagctctt gcagaaccac taattcgaaa tgtcagaaag attttggaga gtgatcgcaa | 1080 |
| ggagccattg tttggaatca gtacaggaaa cttaataaca ggattggctg ctggtgccaa | 1140 |
| aacctacaag atgtccatgg ccaacagagg gcagaatcag cctgttttga atatcacaaa | 1200 |
| caaacaggct ttcattactg ctcagaatca tggctatgcc ttggacaaca ccctccctgc | 1260 |
| tggctggaaa ccacttttg tgaatgtcaa cgatcaaaca aatgagggga ttatgcatga | 1320 |
| gagcaaaccc ttcttcgctg tgcagttcca cccagaggtc accccggggc aatagacac | 1380 |
| tgagtacctg tttgattcct ttttctcact gataaagaaa ggaaaagcta ccaccattac | 1440 |
| atcagtctta ccgaagccag cactagttgc atctcgggtt gaggtttcca aagtccttat | 1500 |
| tctaggatca ggaggtctgt ccattggtca ggctggagaa tttgattact caggatctca | 1560 |
| agctgtaaaa gccatgaagg aagaaaatgt caaaactgtt ctgatgaacc caaacattgc | 1620 |
| atcagtccag accaatgagg tgggcttaaa gcaagcggat actgtctact ttcttcccat | 1680 |
| cacccctcag tttgtcacag aggtcatcaa ggcagaacag ccagatgggt taattctggg | 1740 |
| catgggtggc cagacagctc tgaactgtgg agtggaacta ttcaagagag gtgtgctcaa | 1800 |
| ggaatatggt gtgaaagtcc tgggaacttc agttgagtcc attatggcta cggaagacag | 1860 |
| gcagctgttt tcagataaac taaatgagat caatgaaaag attgctccaa gttttgcagt | 1920 |
| ggaatcgatt gaggatgcac tgaaggcagc agacaccatt ggctacccag tgatgatccg | 1980 |
| ttccgcctat gcactgggtg ggttaggctc aggcatctgt cccaacagag agactttgat | 2040 |
| ggacctcagc acaaaggcct tgctatgac caaccaaatt ctggtggaga agtcagtgac | 2100 |
| aggttggaaa gaaatagaat atgaagtggt tcgagatgct gatgacaatt gtgtcactgt | 2160 |
| ctgtaacatg gaaaatgttg atgccatggg tgttcacaca ggtgactcag ttgttgtggc | 2220 |
| tcctgcccag acactctcca atgccgagtt tcagatgttg agacgtactt caatcaatgt | 2280 |
| tgttcgccac ttgggcattg tgggtgaatg caacattcag tttgcccttc atcctacctc | 2340 |
| aatggaatac tgcatcattg aagtgaatgc cagactgtcc cgaagctctg ctctggcctc | 2400 |
| aaaagccact ggctacccat tggcattcat tgctgcaaag attgccctag gaatcccact | 2460 |
| tccagaaatt aagaacgtcg tatccgggaa gacatcagcc tgttttgaac ctagcctgga | 2520 |
| ttacatggtc accaagattc cccgctggga tcttgaccgt tttcatggaa catctagccg | 2580 |
| aattggtagc tctatgaaaa gtgtaggaga ggtcatggct attggtcgta cctttgagga | 2640 |
| gagtttccag aaagctttac ggatgtgcca cccatctata gaaggtttca ctccccgtct | 2700 |
| cccaatgaac aaagaatggc catctaattt agatcttaga aaagagttgt ctgaaccaag | 2760 |
| cagcacgcgt atctatgcca ttgccaaggc cattgatgac aacatgtccc ttgatgagat | 2820 |
| tgagaagctc acatacattg acaagtggtt tttgtataag atgcgtgata ttttaaacat | 2880 |
| ggaaaagaca ctgaaaggcc tcaacagtga gtccatgaca gaagaaaccc tgaaaagggc | 2940 |
| aaaggagatt gggttctcag ataagcagat ttcaaaatgc cttgggctca ctgaggccca | 3000 |

```
gacaagggag ctgaggttaa agaaaaacat ccacccttgg gttaaacaga ttgatacact    3060
ggctgcagaa tacccatcag taacaaacta tctctatgtt acctacaatg gtcaggagca    3120
tgatgtcaat tttgatgacc atggaatgat ggtgctaggc tgtggtccat atcacattgg    3180
cagcagtgtg gaatttgatt ggtgtgctgt ctctagtatc cgcacactgc gtcaacttgg    3240
caagaagacg gtggtggtga attgcaatcc tgagactgtg agcacagact ttgatgagtg    3300
tgacaaactg tactttgaag agttgtcctt ggagagaatc ctagacatct accatcagga    3360
ggcatgtggt ggctgcatca tatcagttgg aggccagatt ccaaacaacc tggcagttcc    3420
tctatacaag aatggtgtca agatcatggg cacaagcccc ctgcagatcg acagggctga    3480
ggatcgctcc atcttctcag ctgtcttgga tgagctgaag gtggctcagg caccttggaa    3540
agctgttaat actttgaatg aagcactgga atttgcaaag tctgtggact accctgctt    3600 gttgaggcct tcctatgttt tgagtgggtc tgctatgaat gtggtattct ctgaggatga    3660
gatgaaaaaa ttcctagaag aggcgactag agtttctcag gagcacccag tggtgctgac    3720
aaaatttgtt gaaggggccc gagaagtaga aatggacgct gttggcaaag atggaagggt    3780
tatctctcat gccatctctg aacatgttga agatgcaggt gtccactcgg agatgccac    3840 tctgatgctg cccacacaaa ccatcagcca agggccatt gaaaaggtga aggatgctac    3900
ccggaagatt gcaaaggctt ttgccatctc tggtccattc aacgtccaat tcttgtcaa    3960 aggaaatgat gtcttggtga ttgagtgtaa cttgagagct ctcgatcct tcccctttgt    4020 ttccaagact cttggggttg acttcattga tgtggccacc aaggtgatga ttggagagaa    4080
tgttgatgag aaacatcttc caacattgga ccatcccata attcctgctg actatgttgc    4140
aattaaggct cccatgtttt cctggccccg gttgagggat gctgacccca ttctgagatg    4200
tgagatggct tccactggag aggtggcttg ctttggtgaa ggtattcata cagccttcct    4260
aaaggcaatg ctttccacag gatttaagat accccagaaa ggcatcctga taggcatcca    4320
gcaatcattc cggccaagat tccttggtgt ggctgaacaa ttacacaatg aaggtttcaa    4380
gctgtttgcc acggaagcca catcagactg gctcaacgcc aacaatgtcc ctgccacccc    4440
agtggcatgg ccgtctcaag aaggacagaa tcccagcctc tcttccatca gaaaattgat    4500
tagagatggc agcattgacc tagtgattaa ccttcccaac aacaacacta aatttgtcca    4560
tgataattat gtgattcgga ggacagctgt tgatagtgga atccctctcc tcactaattt    4620
tcaggtgacc aaacttttg ctgaagctgt gcagaaatct cgcaaggtgg actccaagag    4680
tcttttccac tacaggcagt acagtgctgg aaaagcagca tagagatgca gacacccag    4740 ccccattatt aaatcaacct gagccacatg ttatctaaag gaactgattc acaactttct    4800
cagagatgaa tattgataac taaacttcat ttcagtttac tttgttatgc cttaatattc    4860
tgtgtctttt gcaattaaat tgtcagtcac ttcttcaaaa ccttacagtc cttcctaagt    4920
tactcttcat gaggatactc tattttaaa acactatctg caaactcagg acactttaac    4980
agggcagaat actctaaaaa cttgataaaa ttaaatatag atttaattta tgaaccttcc    5040
atcatgatgt ttgtgtattg cttctttttg gatcctcatt ctcacccatt tggctaatcc    5100
aggaatattg ttatcccttc ccattatatt gaagttgaga aatgtgacag aggcatttag    5160
agtatggact tttctttct tttctttttt cttttttct ttttgagatg gagtcacact    5220
ctccaggctg gagtgcagtg gcacaatctc ggctcactgc aatttccgtc tcccaagttc    5280
aagcgattct cctgctttag actatggatt tctttaagga atactggttt gcagttttgt    5340
tttctggact atatcagcag atggtagaca gtgtttatgt agatgtgttg ttgttttat    5400
```

```
cattggattt taacttggcc cgagtgaaat aatcagattt ttgtcattca cactctcccc    5460
cagttttgga ataacttgga agtaaggttc attcccttaa gacgatggat tctgttgaac    5520
tatggggtcc cacactgcac tattaattcc acccactgta agggcaagga caccattcct    5580
tctacatata agaaaaaagt ctctccccaa gggcagcctt tgttactttt aaatattttc    5640
tgttattaca agtgctctaa ttgtgaactt ttaaataaaa tactattaag aggtaa         5696
```

<210> SEQ ID NO 84
<211> LENGTH: 4503
<212> TYPE: DNA
<213> ORGANISM: Homo sapiens

<400> SEQUENCE: 84

```
atgacgagga ttttgacagc tttcaaagtg gtgaggacac tgaagactgg ttttggcttt      60
accaatgtga ctgcacacca aaaatggaaa ttttcaagac ctggcatcag gctccttcct     120
gtcaaggcac agacagcaca cattgtcctg gaagatggaa ctaagatgaa aggttactcc     180
tttggccatc catcctctgt tgctggtgaa gtggttttta atactggcct gggagggtac     240
ccagaagcta ttactgaccc tgcctacaaa ggacagattc tcacaatggc caaccctatt     300
attgggaatg gtggagctcc tgatactact gctctggatg aactgggact tagcaaatat     360
ttggagtcta atggaatcaa ggtttcaggt ttgctggtgc tggattatag taagactac      420 aaccactggc tggctaccaa gagtttaggg caatggctac aggaagaaaa ggttcctgca     480
atttatggag tggacacaag aatgctgact aaaataattc gggataaggg taccatgctt     540
gggaagattg aatttgaagg tcagcctgtg gattttgtgg atccaaataa acagaatttg     600
attgctgagg tttcaaccaa ggatgtcaaa gtgtacggca aaggaaaccc cacaaaagtg     660
gtagctgtag actgtgggat taaaaacaat gtaatccgcc tgctagtaaa gcgaggagct     720
gaagtgcact agttccctg gaaccatgat ttcaccaaga tggagtatga tgggattttg     780
atcgcgggag gaccggggaa cccagctctt gcagaaccac taattcgaa tgtcagaaag      840 attttggaga gtgatcgcaa ggagccattg tttggaatca gtacaggaaa cttaataaca     900
ggattggctg ctggtgccaa aacctacaag atgtccatgg ccaacagagg gcagaatcag     960
cctgttttga atatcacaaa caaacaggct ttcattactg ctcagaatca tggctatgcc    1020
ttggacaaca ccctccctgc tggctggaaa ccacttttg tgaatgtcaa cgatcaaaca    1080
aatgagggga ttatgcatga gagcaaaccc ttcttcgctg tgcagttcca cccagaggtc    1140
accccggggc caatagacac tgagtacctg tttgattcct ttttctcact gataaagaaa    1200
ggaaaagcta ccaccattac atcagtctta ccgaagccag cactagttgc atctcgggtt    1260
gaggtttcca aagtccttat tctaggatca ggaggtctgt ccattggtca ggctggagaa    1320
tttgattact caggatctca agctgtaaaa gccatgaagg aagaaaatgt caaaactgtt    1380
ctgatgaacc caaacattgc atcagtccag accaatgagg tgggcttaaa gcaagcggat    1440
actgtctact tcttcccat caccccctcag tttgtcacag aggtcatcaa ggcagaacag    1500
ccagatgggt taattctggg catgggtggc cagacagctc tgaactgtgg agtggaacta    1560
ttcaagagag gtgtgctcaa ggaatatggt gtgaaagtcc tgggaacttc agttgagtcc    1620
attatggcta cggaagacag gcagctgttt tcagataaac taaatgagat caatgaaaag    1680
attgctccaa gttttgcagt ggaatcgatt gaggatgcac tgaaggcagc agacaccatt    1740
ggctacccag tgatgatccg ttccgcctat gcactgggtg ggttaggctc aggcatctgt    1800
```

```
cccaacagag agactttgat ggacctcagc acaaaggcct ttgctatgac caaccaaatt    1860
ctggtggaga agtcagtgac aggttggaaa gaaatagaat atgaagtggt tcgagatgct    1920
gatgacaatt gtgtcactgt ctgtaacatg gaaaatgttg atgccatggg tgttcacaca    1980
ggtgactcag ttgttgtggc tcctgcccag acactctcca atgccgagtt tcagatgttg    2040
agacgtactt caatcaatgt tgttcgccac ttgggcattg tgggtgaatg caacattcag    2100
tttgcccttc atcctacctc aatggaatac tgcatcattg aagtgaatgc cagactgtcc    2160
cgaagctctg ctctggcctc aaaagccact ggctacccat tggcattcat tgctgcaaag    2220
attgccctag aatcccact tccagaaatt aagaacgtcg tatccgggaa gacatcagcc    2280
tgttttgaac ctagcctgga ttacatggtc accaagattc cccgctggga tcttgaccgt    2340
tttcatggaa catctagccg aattggtagc tctatgaaaa gtgtaggaga ggtcatggct    2400
attggtcgta cctttgagga gagtttccag aaagctttac ggatgtgcca cccatctata    2460
gaaggtttca ctccccgtct cccaatgaac aaagaatggc catctaattt agatcttaga    2520
aaagagttgt ctgaaccaag cagcacgcgt atctatgcca ttgccaaggc cattgatgac    2580
aacatgtccc ttgatgagat tgagaagctc acatacattg acaagtggtt tttgtataag    2640
atgcgtgata tttaaacat ggaaaagaca ctgaaaggcc tcaacagtga gtccatgaca    2700
gaagaaaccc tgaaaaggc aaaggagatt gggttctcag ataagcagat ttcaaaatgc    2760
cttgggctca ctgaggccca gacaagggag ctgaggttaa agaaaaacat ccaccttgg    2820 gttaaacaga ttgatacact ggctgcagaa tacccatcag taacaaacta tctctatgtt    2880
acctacaatg gtcaggagca tgatgtcaat tttgatgacc atggaatgat ggtgctaggc    2940
tgtggtccat atcacattgg cagcagtgtg gaatttgatt ggtgtgctgt ctctagtatc    3000
cgcacactgc gtcaacttgg caagaagacg gtggtggtga attgcaatcc tgagactgtg    3060
agcacagact ttgatgagtg tgacaaactg tactttgaag agttgtcctt ggagagaatc    3120
ctagacatct accatcagga ggcatgtggt ggctgcatca tatcagttgg aggccagatt    3180
ccaaacaacc tggcagttcc tctatacaag aatggtgtca agatcatggg cacaagcccc    3240
ctgcagatcg acagggctga ggatcgctcc atcttctcag ctgtcttgga tgagctgaag    3300
gtggctcagg caccttggaa agctgttaat actttgaatg aagcactgga atttgcaaag    3360
tctgtggact accctgctt gttgaggcct tcctatgttt tgagtgggtc tgctatgaat    3420
gtggtattct ctgaggatga gatgaaaaaa ttcctagaag aggcgactag agtttctcag    3480
gagcacccag tggtgctgac aaaatttgtt gaaggggccc gagaagtaga aatggacgct    3540
gttggcaaag atggaagggt tatctctcat gccatctctg aacatgttga agatgcaggt    3600
gtccactcgg gagatgccac tctgatgctg cccacacaaa ccatcagcca aggggccatt    3660
gaaaaggtga aggatgctac ccggaagatt gcaaaggctt ttgccatctc tggtccattc    3720
aacgtccaat tcttgtcaa aggaaatgat gtcttggtga ttgagtgtaa cttgagagct    3780
tctcgatcct tcccctttgt ttccaagact cttggggttg acttcattga tgtggccacc    3840
aaggtgatga ttggagagaa tgttgatgag aaacatcttc caacattgga ccatcccata    3900
attcctgctg actatgttgc aattaaggct cccatgtttt cctggccccg gttgagggat    3960
gctgacccca ttctgagatg tgagatggct tccactggag aggtggcttg ctttggtgaa    4020
ggtattcata cagccttcct aaaggcaatg ctttccacag gatttaagat accccagaaa    4080
ggcatcctga taggcatcca gcaatcattc cggccaagat tccttggtgt ggctgaacaa    4140
ttacacaatg aaggtttcaa gctgtttgcc acggaagcca catcagactg gctcaacgcc    4200
```

| | | | | |
|---|---|---|---|---|
| aacaatgtcc | ctgccacccc | agtggcatgg | ccgtctcaag | aaggacagaa tcccagcctc | 4260 |
| tcttccatca | gaaaattgat | tagagatggc | agcattgacc | tagtgattaa ccttcccaac | 4320 |
| aacaacacta | aatttgtcca | tgataattat | gtgattcgga | ggacagctgt tgatagtgga | 4380 |
| atccctctcc | tcactaattt | tcaggtgacc | aaacttttg | ctgaagctgt gcagaaatct | 4440 |
| cgcaaggtgg | actccaagag | tcttttccac | tacaggcagt | acagtgctgg aaaagcagca | 4500 |
| tag | | | | | 4503 |

<210> SEQ ID NO 85
<211> LENGTH: 5887
<212> TYPE: DNA
<213> ORGANISM: Homo sapiens

<400> SEQUENCE: 85

| | | | | | |
|---|---|---|---|---|---|
| agatcgctgt | gcagtcagcc | ttaaacactg | actgcacccc | tcccagattt cttttacatt | 60 |
| aactaaaaag | tcttatcaca | caatctcata | aaatttatgt | aatttcattt aattttagcc | 120 |
| acaaatcatc | aaaatgacga | ggattttgac | agctttcaaa | gtggtgagga cactgaagac | 180 |
| tggttttggc | tttaccaatg | tgactgcaca | ccaaaaatgg | aaattttcaa gacctggcat | 240 |
| caggctcctt | tctgtcaagg | cacagacagc | acacattgtc | ctggaagatg gaactaagat | 300 |
| gaaaggttac | tcctttggcc | atccatcctc | tgttgctggt | gaagtggttt ttaatactgg | 360 |
| cctgggaggg | tacccagaag | ctattactga | ccctgcctac | aaaggacaga ttctcacaat | 420 |
| ggccaaccct | attattggga | atggtggagc | tcctgatact | actgctctgg atgaactggg | 480 |
| acttagcaaa | tatttggagt | ctaatggaat | caaggtttca | ggtttgctgg tgctggatta | 540 |
| tagtaaagac | tacaaccact | ggctggctac | caagagttta | gggcaatggc tacaggaaga | 600 |
| aaaggttcct | gcaatttatg | gagtggacac | aagaatgctg | actaaaataa ttcgggataa | 660 |
| gggtaccatg | cttgggaaga | ttgaatttga | aggtcagcct | gtggattttg tggatccaaa | 720 |
| taaacagaat | ttgattgctg | aggtttcaac | caaggatgtc | aaagtgtacg gcaaaggaaa | 780 |
| ccccacaaaa | gtggtagctg | tagactgtgg | gattaaaaac | aatgtaatcc gcctgctagt | 840 |
| aaagcgagga | gctgaagtgc | acttagttcc | ctggaaccat | gatttcacca agatggagta | 900 |
| tgatgggatt | ttgatcgcgg | gaggaccggg | gaacccagct | cttgcagaac cactaattca | 960 |
| gaatgtcaga | aagattttgg | agagtgatcg | caaggagcca | ttgtttggaa tcagtacagg | 1020 |
| aaacttaata | acaggattgg | ctgctggtgc | caaaacctac | aagatgtcca tggccaacag | 1080 |
| agggcagaat | cagcctgttt | tgaatatcac | aaacaaacag | ctttcatta ctgctcagaa | 1140 |
| tcatggctat | gccttggaca | caccctccc | tgctggctgg | aaaccacttt ttgtgaatgt | 1200 |
| caacgatcaa | acaaatgagg | ggattatgca | tgagagcaaa | ccttcttcg ctgtgcagtt | 1260 |
| ccacccagag | gtcaccccgg | ggccaataga | cactgagtac | ctgtttgatt cctttttctc | 1320 |
| actgataaag | aaaggaaaag | ctaccaccat | tacatcagtc | ttaccgaagc cagcactagt | 1380 |
| tgcatctcgg | gttgaggttt | ccaaagtcct | tattctagga | tcaggaggtc tgtccattgg | 1440 |
| tcaggctgga | gaatttgatt | actcaggatc | tcaagctgta | aaagccatga aggaagaaaa | 1500 |
| tgtcaaaact | gttctgatga | acccaaacat | tgcatcagtc | cagaccaatg aggtgggctt | 1560 |
| aaagcaagcg | gatactgtct | actttcttcc | catcacccct | cagtttgtca cagaggtcat | 1620 |
| caaggcagaa | cagccagatg | ggttaattct | gggcatgggt | ggccagacag ctctgaactg | 1680 |
| tggagtggaa | ctattcaaga | gaggtgtgct | caaggaatat | ggtgtgaaag tcctgggaac | 1740 |

-continued

```
ttcagttgag tccattatgg ctacggaaga caggcagctg ttttcagata aactaaatga    1800
gatcaatgaa aagattgctc caagttttgc agtggaatcg attgaggatg cactgaaggc    1860
agcagacacc attggctacc cagtgatgat ccgttccgcc tatgcactgg gtgggttagg    1920
ctcaggcatc tgtcccaaca gagagacttt gatggacctc agcacaaagg cctttgctat    1980
gaccaaccaa attctggtgg agaagtcagt gacaggttgg aaagaaatag aatatgaagt    2040
ggttcgagat gctgatgaca attgtgtcac tgtctgtaac atggaaaatg ttgatgccat    2100
gggtgttcac acaggtgact cagttgttgt ggctcctgcc cagacactct ccaatgccga    2160
gtttcagatg ttgagacgta cttcaatcaa tgttgttcgc cacttgggca ttgtgggtga    2220
atgcaacatt cagtttgccc ttcatcctac ctcaatggaa tactgcatca ttgaagtgaa    2280
tgccagactg tcccgaagct ctgctctggc tcaaaagcc actggctacc cattggcatt     2340
cattgctgca aagattgccc taggaatccc acttccagaa attaagaacg tcgtatccgg    2400
gaagacatca gcctgttttg aacctagcct ggattacatg gtcaccaaga ttccccgctg    2460
ggatcttgac cgttttcatg gaacatctag ccgaattggt agctctatga aaagtgtagg    2520
agaggtcatg gctattggtc gtacctttga ggagagtttc cagaaagctt tacggatgtg    2580
ccacccatct atagaaggtt tcactccccg tctcccaatg aacaaagaat ggccatctaa    2640
tttagatctt agaaaagagt tgtctgaacc aagcagcacg cgtatctatg ccattgccaa    2700
ggccattgat gacaacatgt cccttgatga gattgagaag ctcacataca ttgacaagtg    2760
gttttttgtat aagatgcgtg atattttaaa catggaaaag acactgaaag cctcaacag    2820
tgagtccatg acagaagaaa ccctgaaaag ggcaaaggag attgggttct cagataagca    2880
gatttcaaaa tgccttgggc tcactgaggc ccagacaagg gagctgaggt taaagaaaaa    2940
catccaccct tgggttaaac agattgatac actggctgca gaatacccat cagtaacaaa    3000
ctatctctat gttacctaca atggtcagga gcatgatgtc aattttgatg accatggaat    3060
gatggtgcta ggctgtggtc catatcacat tggcagcagt gtggaatttg attggtgtgc    3120
tgtctctagt atccgcacac tgcgtcaact tggcaagaag acggtggtgg tgaattgcaa    3180
tcctgagact gtgagcacag actttgatga gtgtgacaaa ctgtactttg aagagttgtc    3240
cttggagaga atcctagaca tctaccatca ggaggcatgt ggtggctgca tcatatcagt    3300
tggaggccag attccaaaca acctggcagt tcctctatac aagaatggtg tcaagatcat    3360
gggcacaagc cccctgcaga tcgacagggc tgaggatcgc tccatcttct cagctgtctt    3420
ggatgagctg aaggtggctc aggcacccttg gaaagctgtt aatactttga atgaagcact    3480
ggaatttgca aagtctgtgg actacccctg cttgttgagg ccttcctatg ttttgagtgg    3540
gtctgctatg aatgtggtat tctctgagga tgagatgaaa aaattcctag aagaggcgac    3600
tagagttttct caggagcacc cagtggtgct gacaaaattt gttgaagggg cccgagaagt    3660
agaaatggac gctgttggca aagatggaag ggttatctct catgccatct ctgaacatgt    3720
tgaagatgca ggtgtccact cgggagatgc cactctgatg ctgcccacac aaaccatcag    3780
ccaaggggcc attgaaaagg tgaaggatgc tacccggaag attgcaaagg cttttgccat    3840
ctctggtcca ttcaacgtcc aatttcttgt caaaggaaat gatgtcttgg tgattgagtg    3900
taacttgaga gcttctcgat ccttcccctt tgtttccaag actcttgggg ttgacttcat    3960
tgatgtggcc accaaggtga tgattggaga gaatgttgat gagaaacatc ttccaacatt    4020
ggaccatccc ataattcctg ctgactatgt tgcaattaag gctcccatgt tttcctggcc    4080
ccggttgagg gatgctgacc ccattctgag atgtgagatg gcttccactg gagaggtggc    4140
```

```
ttgctttggt gaaggtattc atacagcctt cctaaaggca atgctttcca caggatttaa    4200 gatacccag aaaggcatcc tgataggcat ccagcaatca ttccggccaa gattccttgg    4260
tgtggctgaa caattacaca atgaaggttt caagctgttt gccacggaag ccacatcaga   4320
ctggctcaac gccaacaatg tccctgccac cccagtggca tggccgtctc aagaaggaca   4380
gaatcccagc ctctcttcca tcagaaaatt gattagagat ggcagcattg acctagtgat   4440
taaccttccc aacaacaaca ctaaatttgt ccatgataat tatgtgattc ggaggacagc   4500
tgttgatagt ggaatccctc tcctcactaa ttttcaggtg accaaacttt ttgctgaagc   4560
tgtgcagaaa tctcgcaagg tggactccaa gagtcttttc cactacaggc agtacagtgc   4620
tggaaaagca gcatagagat gcagacaccc cagccccatt attaaatcaa cctgagccac   4680
atgttatcta aaggaactga ttcacaactt tctcagagat gaatattgat aactaaactt   4740
catttcagtt tactttgtta tgccttaata ttctgtgtct tttgcaatta aattgtcagt   4800
cacttcttca aaaccttaca gtccttccta agttactctt catgagattt catccattta   4860
ctaatactgt attttggtg gactaggctt gcctatgtgc ttatgtgtag ctttttactt     4920
tttatggtgc tgattaatgg tgatcaaggt aggaaaagtt gctgttctat tttctgaact   4980
ctttctatac tttaagatac tctatttta aaacactatc tgcaaactca ggacacttta    5040
acagggcaga atactctaaa aacttgataa aattaaatat agatttaatt tatgaacctt   5100
ccatcatgat gtttgtgtat tgcttctttt tggatcctca ttctcaccca tttggctaat   5160
ccaggaatat tgttatccct tcccattata ttgaagttga gaaatgtgac agaggcattt   5220
agagtatgga cttttctttt cttttctctt ttctttttt cttttgaga tggagtcaca     5280 ctctccaggc tggagtgcag tggcacaatc tcggctcact gcaatttccg tctcccaagt   5340
tcaagcgatt ctcctgcttt agactatgga tttctttaag gaatactggt ttgcagtttt   5400
gttttctgga ctatatcagc agatggtaga cagtgtttat gtagatgtgt tgttgttttt    5460
atcattggat tttaacttgg cccgagtgaa ataatcagat ttttgtcatt cacactctcc   5520
cccagttttg gaataacttg gaagtaaggt tcattccctt aagacgatgg attctgttga   5580
actatggggt cccacactgc actattaatt ccacccactg taagggcaag gacaccattc   5640
cttctacata taagaaaaaa gtctctcccc aagggcagcc tttgttactt ttaaatattt   5700
tctgttatta caagtgctct aattgtgaac ttttaaataa aatactatta agaggtaatg   5760
cagttgaatc tggttttatt ttatgttgct gtacaaaaat cagtttactt ctatgataaa   5820
atagggtttt gggccaggat tgcattgctt atttattttt tccatgcaaa cccatatagg   5880
gatgaga                                                            5887
```

<210> SEQ ID NO 86
<211> LENGTH: 5887
<212> TYPE: DNA
<213> ORGANISM: Homo sapiens

<400> SEQUENCE: 86

```
agatcgctgt gcagtcagcc ttaaacactg actgcacccc tcccagattt cttttacatt     60
aactaaaaag tcttatcaca caatctcata aaatttatgt aatttcattt aattttagcc    120
acaaatcatc aaaatgacga ggattttgac agctttcaaa gtggtgagga cactgaagac    180
tggttttggc tttaccaatg tgactgcaca ccaaaaatgg aaattttcaa gacctggcat    240
caggctcctt tctgtcaagg cacagacagc acacattgtc ctggaagatg gaactaagat    300
```

-continued

```
gaaaggttac tcctttggcc atccatcctc tgttgctggt gaagtggttt ttaatactgg      360
cctgggaggg tacccagaag ctattactga ccctgcctac aaaggacaga ttctcacaat      420
ggccaaccct attattggga atggtggagc tcctgatact actgctctgg atgaactggg      480
acttagcaaa tatttggagt ctaatggaat caaggtttca ggtttgctgg tgctggatta      540
tagtaaagac tacaaccact ggctggctac caagagttta gggcaatggc tacaggaaga      600
aaaggttcct gcaatttatg gagtggacac aagaatgctg actaaaataa ttcgggataa      660
gggtaccatg cttgggaaga ttgaatttga aggtcagcct gtggattttg tggatccaaa      720
taaacagaat ttgattgctg aggtttcaac caaggatgtc aaagtgtacg gcaaaggaaa      780
ccccacaaaa gtggtagctg tagactgtgg gattaaaaac aatgtaatcc gcctgctagt      840
aaagcgagga gctgaagtgc acttagttcc ctggaaccat gatttcacca agatggagta      900
tgatgggatt ttgatcgcgg gaggaccggg gaacccagct cttgcagaac cactaattca      960
gaatgtcaga aagattttgg agagtgatcg caaggagcca ttgtttggaa tcagtacagg     1020
aaacttaata acaggattgg ctgctggtgc caaaacctac aagatgtcca tggccaacag     1080
agggcagaat cagcctgttt tgaatatcac aaacaaacag gctttcatta ctgctcagaa     1140
tcatggctat gccttggaca cacccctccc tgctggctgg aaaccacttt tgtgaatgt      1200 caacgatcaa acaaatgagg ggattatgca tgagagcaaa cccttcttcg ctgtgcagtt     1260
ccacccagag gtcaccccgg ggccaataga cactgagtac ctgtttgatt ccttttctc      1320 actgataaag aaaggaaaag ctaccaccat tacatcagtc ttaccgaagc cagcactagt     1380
tgcatctcgg gttgaggttt ccaaagtcct tattctagga tcaggaggtc tgtccattgg     1440
tcaggctgga gaatttgatt actcaggatc tcaagctgta aaagccatga aggaagaaaa     1500
tgtcaaaact gttctgatga acccaaacat tgcatcagtc cagaccaatg aggtgggctt     1560
aaagcaagcg gatactgtct actttcttcc catcacccct cagtttgtca cagaggtcat     1620
caaggcagaa cagccagatg ggttaattct gggcatgggt ggccagacag ctctgaactg     1680
tggagtggaa ctattcaaga gaggtgtgct caaggaatat ggtgtgaaag tcctgggaac     1740
ttcagttgag tccattatgg ctacggaaga caggcagctg ttttcagata aactaaatga     1800
gatcaatgaa aagattgctc caagttttgc agtggaatcg attgaggatg cactgaaggc     1860
agcagacacc attggctacc cagtgatgat ccgttccgcc tatgcactgg gtgggttagg     1920
ctcaggcatc tgtcccaaca gagagacttt gatggacctc agcacaaagg cctttgctat     1980
gaccaaccaa attctggtgg agaagtcagt gacaggttgg aaagaaatag aatatgaagt     2040
ggttcgagat gctgatgaca attgtgtcac tgtctgtaac atggaaaatg ttgatgccat     2100
gggtgttcac acaggtgact cagttgttgt ggctcctgcc cagacactct ccaatgccga     2160
gtttcagatg ttgagacgta cttcaatcaa tgttgttcgc cacttgggca ttgtgggtga     2220
atgcaacatt cagtttgccc ttcatcctac ctcaatggaa tactgcatca ttgaagtgaa     2280
tgccagactg tcccgaagct ctgctctggc ctcaaaagcc actggctacc cattggcatt     2340
cattgctgca aagattgccc taggaatccc acttccagaa attaagaacg tcgtatccgg     2400
gaagacatca gcctgttttg aacctagcct ggattacatg gtcaccaaga ttccccgctg     2460
ggatcttgac cgttttcatg aacatctag ccgaattggt agctctatga aaagtgtagg     2520
agaggtcatg gctattggtc gtaccttga ggagagtttc cagaaagctt tacggatgtg     2580
ccacccatct atagaaggtt tcactccccg tctcccaatg aacaaagaat ggccatctaa     2640
tttagatctt agaaaagagt tgtctgaacc aagcagcacg cgtatctatg ccattgccaa     2700
```

```
ggccattgat gacaacatgt cccttgatga gattgagaag ctcacataca ttgacaagtg   2760
gtttttgtat aagatgcgtg atattttaaa catggaaaag acactgaaag gcctcaacag   2820
tgagtccatg acagaagaaa ccctgaaaag ggcaaaggag attgggttct cagataagca   2880
gatttcaaaa tgccttgggc tcactgaggc ccagacaagg gagctgaggt taaagaaaaa   2940
catccaccct tgggttaaac agattgatac actggctgca gaatacccat cagtaacaaa   3000
ctatctctat gttacctaca atggtcagga gcatgatgtc aattttgatg accatggaat   3060
gatggtgcta ggctgtggtc catatcacat tggcagcagt gtggaatttg attggtgtgc   3120
tgtctctagt atccgcacac tgcgtcaact tggcaagaag acggtggtgg tgaattgcaa   3180
tcctgagact gtgagcacag actttgatga gtgtgacaaa ctgtactttg aagagttgtc   3240
cttggagaga atcctagaca tctaccatca ggaggcatgt ggtggctgca tcatatcagt   3300
tggaggccag attccaaaca acctggcagt tcctctatac aagaatggtg tcaagatcat   3360
gggcacaagc cccctgcaga tcgacagggc tgaggatcgc tccatcttct cagctgtctt   3420
ggatgagctg aaggtggctc aggcaccttg gaaagctgtt aatactttga atgaagcact   3480
ggaatttgca aagtctgtgg actacccctg cttgttgagg ccttcctatg ttttgagtgg   3540
gtctgctatg aatgtggtat tctctgagga tgagatgaaa aaattcctag aagaggcgac   3600
tagagtttct caggtacacc cagtggtgct gacaaaattt gttgaagggg cccgagaagt   3660
agaaatggac gctgttggca agatggaagg gttatctct catgccatct ctgaacatgt   3720
tgaagatgca ggtgtccact cgggagatgc cactctgatg ctgcccacac aaaccatcag   3780
ccaaggggcc attgaaaagg tgaaggatgc taccggaag attgcaaagg cttttgccat   3840
ctctggtcca ttcaacgtcc aatttcttgt caaaggaaat gatgtcttgg tgattgagtg   3900
taacttgaga gcttctcgat ccttcccctt tgtttccaag actcttgggg ttgacttcat   3960
tgatgtggcc accaaggtga tgattggaga gaatgttgat gagaaacatc ttccaacatt   4020
ggaccatccc ataattcctg ctgactatgt tgcaattaag gctcccatgt ttcctggcc   4080 ccggttgagg gatgctgacc ccattctgag atgtgagatg gcttccactg gagaggtggc   4140
ttgctttggt gaaggtattc atacagcctt cctaaaggca atgctttcca caggatttaa   4200
gataccccag aaaggcatcc tgataggcat ccagcaatca ttccggccaa gattccttgg   4260
tgtggctgaa caattacaca atgaaggttt caagctgttt gccacggaag ccacatcaga   4320
ctggctcaac gccaacaatg tccctgccac cccagtggca tggccgtctc aagaaggaca   4380
gaatcccagc ctctcttcca tcagaaaatt gattagagat ggcagcattg acctagtgat   4440
taaccttccc aacaacaaca ctaaatttgt ccatgataat tatgtgattc ggaggacagc   4500
tgttgatagt ggaatccctc tcctcactaa ttttcaggtg accaaacttt tgctgaagc   4560 tgtgcagaaa tctcgcaagg tggactccaa gagtcttttc cactacaggc agtacagtgc   4620
tggaaaagca gcatagagat gcagacaccc cagccccatt attaaatcaa cctgagccac   4680
atgttatcta aaggaactga ttcacaactt tctcagagat gaatattgat aactaaactt   4740
catttcagtt tactttgtta tgccttaata ttctgtgtct tttgcaatta aattgtcagt   4800
cacttcttca aaaccttaca gtccttccta agttactctt catgagattt catccattta   4860
ctaatactgt atttttggtg gactaggctt gcctatgtgc ttatgtgtag ctttttactt   4920
tttatggtgc tgattaatgg tgatcaaggt aggaaaagtt gctgttctat tttctgaact   4980
ctttctatac tttaagatac tctatttta aaacactatc tgcaaactca ggacacttta   5040
```

-continued

```
acagggcaga atactctaaa aacttgataa aattaaatat agatttaatt tatgaacctt      5100
ccatcatgat gtttgtgtat tgcttctttt tggatcctca ttctcaccca tttggctaat      5160
ccaggaatat tgttatccct tcccattata ttgaagttga gaaatgtgac agaggcattt      5220
agagtatgga cttttctttt cttttctctt ttcttttttt cttttgaga tggagtcaca       5280 ctctccaggc tggagtgcag tggcacaatc tcggctcact gcaatttccg tctcccaagt      5340
tcaagcgatt ctcctgcttt agactatgga tttctttaag gaatactggt ttgcagtttt      5400
gttttctgga ctatatcagc agatggtaga cagtgtttat gtagatgtgt tgttgttttt      5460
atcattggat tttaacttgg cccgagtgaa ataatcagat ttttgtcatt cacactctcc      5520
cccagttttg gaataacttg gaagtaaggt tcattccctt aagacgatgg attctgttga      5580
actatggggt cccacactgc actattaatt ccacccactg taagggcaag gacaccattc      5640
cttctacata taagaaaaaa gtctctcccc aagggcagcc tttgttactt ttaaatattt      5700
tctgttatta caagtgctct aattgtgaac ttttaaataa aatactatta agaggtaatg      5760
cagttgaatc tggttttatt ttatgttgct gtacaaaaat cagtttactt ctatgataaa      5820
atagggtttt gggccaggat tgcattgctt atttattttt tccatgcaaa cccatatagg      5880
gatgaga                                                                5887

<210> SEQ ID NO 87
<211> LENGTH: 1236
<212> TYPE: DNA
<213> ORGANISM: Homo sapiens

<400> SEQUENCE: 87
cgcttggcac agaagcagag gggtcagggc gaagtcccag ggccccaggc gtggctctca        60
gggtctcagg ccccgaaggc ggtgtatgga ttggggagtc ccagccttgg ggattcccca       120
actccgcagt ttcttttctc cctctcccaa cctatgtagg gtccttcttc ctggatactc       180
acgacgcgga cccagttctc actcccattg ggtgtcgggt ttccagagaa gccaatcagt       240
gtcgtcgcgg tcgcggttct aaagtccgca cgcacccacc gggactcaga ttctccccag       300
acgccgagga tggccgtcat ggcgccccga accctcctcc tgctactctt gggggccctg       360
gccctgaccc agacctgggc gggctcccac tccatgaggt atttcaccac atccgtgtcc       420
cggcccggcc gcggggagcc ccgcttcatc gccgtgggct acgtggacga cacgcagttc       480
gtgcggtttg acagcgacgc cgcgagccag aggatggagc gcggggcacc gtggatagag       540
caggaggggc cggagtattg ggacctgcag acacggaatg tgaaggccca gtcacagact       600
gaccgagcga acctggggac cctgcgcggc tactacaacc agagcgaggc cggttctcac       660
accatccaga tgatgtatgg ctgcgacgtg gggtcggacg gcgcgttcct ccgcgggtac       720
cggcaggacg cctacgacgg caaggattac atcgccttga acgaggacct gcgctcttgg       780
accgcggcgg acatggcggc tcagatcacc cagcgcaagt gggaggcggc ccgtgtggcg       840
gagcagttga gagcctacct ggagggcacg tgcgtggagt ggctccgcag atacctggag       900
aacgggaagg agacgctgca gcgcacggca tccccatcgt gggcatcatt gctggcctgg       960
ttctctttgg agctgtgatc actggagctg tggtcgctgc tgtgaggtgg aggaggaaga      1020
gctcagatag aaaaggaggg agctactctc aggctgcaag cagtgacagt gcccagggct      1080
ctgatgtgtc tctcacagct tgtaaagtgt gagacagctg ccttgtgtgg gactgagagg      1140
caagagttgt tcctgccctt cccttttgtga cttgaagaac cctgactttg tttctgcaaa      1200
ggcacctgca tgtgtctgtg ttcgtgtagg cataat                               1236
```

<210> SEQ ID NO 88
<211> LENGTH: 1586
<212> TYPE: DNA
<213> ORGANISM: Homo sapiens

<400> SEQUENCE: 88

| | | | | | |
|---|---|---|---|---|---|
| cgcttggcac | agaagcagag | gggtcagggc | gaagtcccag | ggccccaggc | gtggctctca | 60 |
| gggtctcagg | ccccgaaggc | ggtgtatgga | ttggggagtc | ccagccttgg | ggattcccca | 120 |
| actccgcagt | ttcttttctc | cctctcccaa | cctatgtagg | gtccttcttc | ctggatactc | 180 |
| acgacgcgga | cccagttctc | actcccattg | ggtgtcgggt | ttccagagaa | gccaatcagt | 240 |
| gtcgtcgcgg | tcgcggttct | aaagtccgca | cgcacccacc | gggactcaga | ttctccccag | 300 |
| acgccgagga | tggccgtcat | ggcgccccga | accctcctcc | tgctactctt | ggggggccctg | 360 |
| gccctgaccc | agacctgggc | gggctcccac | tccatgaggt | atttcaccac | atccgtgtcc | 420 |
| cggcccggcc | gcggggagcc | ccgcttcatc | gccgtgggct | acgtggacga | cacgcagttc | 480 |
| gtgcggtttg | acagcgacgc | cgcgagccag | aggatggagc | cgcgggcacc | gtggatagag | 540 |
| caggaggggc | cggagtattg | ggacctgcag | acacggaatg | tgaaggccca | gtcacagact | 600 |
| gaccgagcga | acctggggac | cctgcgcggc | tactacaacc | agagcgaggc | cggttctcac | 660 |
| accatccaga | tgatgtatgg | ctgcgacgtg | gggtcggacg | ggcgcttcct | ccgcgggtac | 720 |
| cggcaggacg | cctacgacgg | caaggattac | atcgccttga | acgaggacct | gcgctcttgg | 780 |
| accgcggcg | acatggcggc | tcagatcacc | cagcgcaagt | gggaggcggc | ccgtgtggcg | 840 |
| gagcagttga | gagcctacct | ggagggcacg | tgcgtggagt | ggctccgcat | ggtgccttct | 900 |
| ggacaggagc | agagatacac | ctgccatgtg | cagcatgagg | gtttgcccaa | gcccctcacc | 960 |
| ctgagatggg | agccgtcttc | ccagccacc | atccccatcg | tgggcatcat | tgctggcctg | 1020 |
| gttctctttg | gagctgtgat | cactggagct | gtggtcgctg | ctgtgaggtg | gaggaggaag | 1080 |
| agctcagata | gaaaaggagg | gagctactct | caggctgcaa | gcagtgacag | tgcccagggc | 1140 |
| tctgatgtgt | ctctcacagc | ttgtaaagtg | tgagacagct | gccttgtgtg | ggactgagag | 1200 |
| gcaagagttg | ttcctgccct | tccctttgtg | acttgaagaa | ccctgacttt | gtttctgcaa | 1260 |
| aggcacctgc | atgtgtctgt | gttcgtgtag | gcataatgtg | aggaggtggg | gagaccaccc | 1320 |
| caccccatg | tccaccatga | ccctcttccc | acgctgacct | gtgctccctc | cccaatcatc | 1380 |
| tttcctgttc | cagagaggtg | gggctgaggt | gtctccatct | ctgtctcaac | ttcatggtgc | 1440 |
| actgagctgt | aacttcttcc | ttccctatta | aaattagaac | ctgagtataa | atttactttc | 1500 |
| tcaaattctt | gccatgagag | gttgatgagt | taattaaagg | agaagattcc | taaaatttga | 1560 |
| gagacaaaat | aaatggaaca | catgag | | | | 1586 |

<210> SEQ ID NO 89
<211> LENGTH: 1128
<212> TYPE: DNA
<213> ORGANISM: Homo sapiens

<400> SEQUENCE: 89

| | | | | | |
|---|---|---|---|---|---|
| gtgaaggccc | agtcacagac | tcaccgagtg | gacctgggga | ccctgcgcgg | ctactacaac | 60 |
| cagagcgagg | ccgtgtctca | caccgtccag | aggatgtatg | gctgcgacgt | ggggtcggac | 120 |
| gggcgcttcc | tccgcgggta | ccaccaggta | gcctacgacg | gcaaggatta | catcgccctg | 180 |
| aaagaggacc | tgcgctcttg | gaccgcggcg | gacatggcag | ctcagaccac | caagcacaag | 240 |

```
tgggaggcgg cccatgtggc ggagcagttg agagcctacc tggagggcac gtgcgtggag    300
tggctccgca gatacctgga gaacgggaag gagacgctgc agcgcacgga cgcccccaaa    360
acgcatatga cccaccacgc tgtctctgac catgaagcca ccctgaggtg ctgggccctg    420
agcttctacc ctgcggagat cacactgacc tggcagcggg atggggagga ccagacccag    480
gacacggagc tcgtggagac caggcctgca ggagatggaa ccttccagaa gtgggcggct    540
gtggtggtgc cttctggaga ggagcagaga tacacctgcc atgtgcagca tgagggtctg    600
cccaagcccc tcaccctgag atgggagccg tcttcccagc ccaccatccc catcgtgggc    660
atcattgctg gcctggttct ccttggagct gtgatcactg gagctgtggt cgctgctgtg    720
atgtggagga ggaagagctc agatagaaaa ggagggagct actctcaggc tgcaagcagt    780
gacagtgccc agggctctga tgtgtctctc acagcttgta aagtgtgaga cagctgcctt    840
gtgtgggact gagaggcaag agttgttcct gcccttccct ttgtgacttg aagaaccctg    900
actttgtttc tgcaaaggca cctgcatgtg tctgtgttcg tgtaggcata atgtgaggag    960
gtggggagac caccccaccc ccatgtccac catgaccctc ttcccacgct gacctgtgct   1020
ccctccccaa tcatctttcc tgttccagag aggtggggct gaggtgtctc catctctgtc   1080
tcaacttcat ggtgcactga gctgtaactt cttccttccc tattaaaa              1128
```

```
<210> SEQ ID NO 90
<211> LENGTH: 2930
<212> TYPE: DNA
<213> ORGANISM: Homo sapiens

<400> SEQUENCE: 90
```

```
atggccgtca tggcgccccg aaccctcgtc ctgctactct cgggggccct ggccctgacc     60
cagacctggg cggtgagtg cggggtcggg agggaaacgg cctctgtggg gagaagcaag    120
gggcccgccc ggcgggggcg caggaccccgg gaagccgcgc ctggaggagg gtcgggcggg    180
tctcagccac tcctcgcccc caggctccca ctccatgagg tatttctaca cctccgtgtc    240
ccggcccggc cgcggggagc cccgcttcat cgccgtgggc tacgtggacg acacgcagtt    300
cgtgcggttc gacagcgacg ccgcgagcca gaggatggag ccgcgggcgc cgtggataga    360
gcaggagggg ccggagtatt gggaccggaa cacacggaat gtgaaggccc agtcacagac    420
tgaccgagtg gacctgggga ccctgcgcgg ctactacaac cagagcgagg ccggtgagtg    480
accccggccc ggggcgcagg tcacgacccc tcatccccca cggacgggcc aggtcgccca    540
cagtctccgg gtccgagatc cgccccgaag ccgcgggacc ccgagaccct gccccggga    600 gaggcccagg cgcctttacc cggtttcatt ttcagtttag gccaaaaatc ccccccgggtt    660 ggtcggggcg gggcggggct cggggggaccg ggctgacctc ggggtccggg ccaggttctc    720
acaccatcca gatgatgtat ggctgcgacg tggggtcgga cgggcgcttc ctccgcgggt    780
accggcagga cgcctacgac ggcaaggatt acatcgccct gaagaggac ctgcgctctt    840 ggaccgcggc ggacatggca gctcagacca ccaagcacaa gtgggaggcg gcccatgtgg    900
cggagcagtg gagagcctac ctggagggca cgtgcgtgga gtggctccgc agatacctgg    960
agaacgggaa ggagacgctg cagcgcacgg gtaccagggg ccacggggcg cctccctgat   1020
cgcctgtaga tctcccgggc tggcctccca caaggagggg agacaattgg gaccaacact   1080
agaatatcgc cctccctctg tcctgaggg agaggaatcc tcctgggttt ccagatcctg   1140
taccagagag tgactctgag gttccgcct gctctctgac acaattaagg gataaaatct   1200
ctgaaggaat gacgggaaga cgatccctcg aatactgatg agtggttccc tttgacacac   1260
```

| | |
|---|---|
| acaggcagca gccttgggcc cgtgactttt cctctcaggc cttgttctct gcttcacact | 1320 |
| caatgtgtgt gggggtctga gtccagcact tctgagtccc tcagcctcca ctcaggtcag | 1380 |
| gaccagaagt cgctgttccc tcttcaggga ctagaatttt ccacggaata ggagattatc | 1440 |
| ccaggtgcct gtgtccaggc tggtgtctgg gttctgtgct cccttcccca tcccaggtgt | 1500 |
| cctgtccatt ctcaagatag ccacatgtgt gctggaggag tgtcccatga cagatgcaaa | 1560 |
| atgcctgaat gatctgactc ttcctgagag acgcccccaa aacgcatatg actcaccacg | 1620 |
| ctgtctctga ccatgaagcc accctgaggt gctgggccct gagcttctac cctgcggaga | 1680 |
| tcacactgac ctggcagcgg gatggggagg accagaccca ggacacggag ctcgtggaga | 1740 |
| ccaggcctgc aggggatgga accttccaga agtgggtggc tgtggtggtg ccttctggac | 1800 |
| aggagcagag atacacctgc catgtgcagc atgagggttt gcccaagccc ctcaccctga | 1860 |
| gatggggtaa ggagggagac gggggtgtca tgtcttttag ggaaagcagg agcctctctg | 1920 |
| acctttagca gggtcagggc ccctcacctt ccctcttttt cccagagccg tcttcccagc | 1980 |
| ccaccatccc catcgtgggc atcattgctg gcctggttct cttttggagct gtgatcactg | 2040 |
| gagctgtggt cgctgctgtg atgtggagga ggaagagctc aggtggggaa ggggtgaagg | 2100 |
| gtgggtctga gatttcttgt ctcactgagg gttccaagac ccaggtagaa gtgtgccctg | 2160 |
| cctcgttact gggaagcacc acccacaatt atgggcctac ccagcctggg ccctgtgtgc | 2220 |
| cagcacttac tcttttgtaa agcacctgtt aaaatgaagg acagatttat caccttgatt | 2280 |
| acagcggtga tgggacctga tcccagcagt cacaagtcac aggggaaggt ccctgaggac | 2340 |
| cttcaggagg gcggttggtc caggaccccac acctgctttc ttcatgtttc ctgatcccgc | 2400 |
| cctgggtctg cagtcacaca tttctggaaa cttctctgag gtccaagact ggaggttcc | 2460 |
| tctaggacct taaggccctg actccttttct ggtatctcac aggacatttt cttcccacag | 2520 |
| atagaaaagg agggagctac tctcaggctg caagtaagta tgaaggaggc tgatgcctga | 2580 |
| ggtccttggg atattgtgtt tgggagccca tgggggagct cacccacccc acaattcctc | 2640 |
| ctctagccac atcttctgtg ggatctgacc aggttctgtt tttgttctac cccaggcagt | 2700 |
| gacagtgccc agggctctga tgtgtctctc acagcttgta aaggtgagag cctggagggc | 2760 |
| ctgatgtgtg ttgggtgttg gcggaacag tggacacagc tgtgctatgg ggtttctttc | 2820 |
| cattggatgt attgagcatg cgatgggctg tttaaagtgt gacccctcac tgtgacagat | 2880 |
| acgaatttgt tcatgaatat tttttttctat agtgtgagac agctgccttg | 2930 |

<210> SEQ ID NO 91
<211> LENGTH: 2235
<212> TYPE: DNA
<213> ORGANISM: Homo sapiens

<400> SEQUENCE: 91

| | |
|---|---|
| cgcttggcac agaagcagag gggtcagggc gaagtcccag ggccccaggc gtggctctca | 60 |
| gggtctcagg ccccgaaggc ggtgtatgga ttggggagtc ccagccttgg ggattcccca | 120 |
| actccgcagt ttcttttctc cctctcccaa cctatgtagg gtccttcttc ctggatactc | 180 |
| acgacgcgga cccagttctc actcccattg ggtgtcgggt ttccagagaa gccaatcagt | 240 |
| gtcgtcgcgg tcgcggttct aaagtccgca cgcacccacc gggactcaga ttctccccag | 300 |
| acgccgagga tggccgtcat ggcgcccga accctcctcc tgctactctt ggggccctg | 360 |
| gccctgaccc agacctgggc gggctcccac tccatgaggt atttcaccac atccgtgtcc | 420 |

-continued

```
cggcccggcc gcggggagcc ccgcttcatc gccgtgggct acgtggacga cacgcagttc      480
gtgcggtttg acagcgacgc cgcgagccag aggatggagc cgcgggcacc gtggatagag      540
caggaggggc cggagtattg ggacctgcag acacggaatg tgaaggccca gtcacagact      600
gaccgagcga acctggggac cctgcgcggc tactacaacc agagcgaggc cggttctcac      660
accatccaga tgatgtatgg ctgcgacgtg gggtcggacg gcgcttcct ccgcgggtac       720 cggcaggacg cctacgacgg caaggattac atcgccttga cgaggaccct gcgctcttgg      780 accgcgcgg acatggcggc tcagatcacc cagcgcaagt gggaggcggc ccgtgtggcg       840
gagcagttga gagcctacct ggagggcacg tgcgtggagt ggctccgcag atacctggag      900
aacgggaagg agacgctgca gcgcacggac gcccccaaaa cgcatatgac tcaccacgct      960
gtctctgacc atgaagccac cctgaggtgc tgggccctga gcttctaccc tgcggagatc     1020
acactgacct ggcagcggga tggggaggac cagacccagg acacggagct cgtggagacc     1080
aggcctgcag gggatggaac cttcagaag tgggcggctg tggtggtgcc ttctggacag      1140
gagcagagat acacctgcca tgtgcagcat gagggtttgc ccaagcccct caccctgaga     1200
tgggagccgt cttcccagcc caccatcccc atcgtgggca tcattgctgg cctggttctc     1260
tttggagctg tgatcactgg agctgtggtc gctgctgtga ggtggaggag aagagctca     1320 ggtggggaag gatgaaggg tgggtctgag atttcttgtc tcactgaggg ttccaagacc      1380
caggtagaag tgtgccctgc ctcgttactg ggaagcacca cccacaatta tgggcctacc     1440
cagcctgggc cctgtgtgcc agcacttact cttttgtaaa gcacctgtta aaatgaagga     1500
cagatttatc accttgatta cagcggtgat gggacctgat cccagcagtc acaagtcaca     1560
ggggaaggtc cctgaggacc ttcaggaggg cggttggtcc aggacccaca cctgcttttct    1620 tcatgtttcc tgatcccgcc ctgggtctgc agtcacacat ttctggaaac ttctctgagg     1680
tccaagactt ggaggttcct ctaggacctt aaggccctga ctcctttctg gtatctcaca     1740 ggacatttc ttcccacaga tagaaaagga gggagctact ctcaggctgc aagcagtgac      1800
agtgcccagg gctctgatgt gtctctcaca gcttgtaaag tgtgagacag ctgccttgtg     1860
tgggactgag aggcaagagt tgttcctgcc cttcccttg tgacttgaag aaccctgact      1920
ttgtttctgc aaaggcacct gcatgtgtct gtgttcgtgt aggcataatg tgaggaggtg     1980
gggagaccac cccacccca tgtccaccat gaccctcttc ccacgctgac ctgtgctccc      2040
tccccaatca tctttcctgt tccagagagg tggggctgag gtgtctccat ctctgtctca     2100
acttcatggt gcactgagct gtaacttctt ccttccctat taaaattaga acctgagtat     2160
aaatttactt tctcaaattc ttgccatgag aggttgatga gttaattaaa ggagaagatt     2220
cctaaaattt gagag                                                      2235
```

<210> SEQ ID NO 92
<211> LENGTH: 1701
<212> TYPE: DNA
<213> ORGANISM: Homo sapiens

<400> SEQUENCE: 92

```
cgcttggcac agaagcagag gggtcagggc gaagtcccag gccccaggc gtggctctca       60 gggtctcagg ccccgaaggc ggtgtatgga ttggggagtc ccagccttgg ggattcccca     120
actccgcagt ttcttttctc cctctcccaa cctatgtagg gtccttcttc ctggatactc     180
acgacgcgga cccagttctc actcccattg ggtgtcgggt ttccagagaa gccaatcagt     240
gtcgtcgcgg tcgcggttct aaagtccgca cgcacccacc gggactcaga ttctccccag     300
```

| | |
|---|---|
| acgccgagga tggccgtcat ggcgccccga accctcctcc tgctactctt gggggccctg | 360 |
| gccctgaccc agacctgggc gggctcccac tccatgaggt atttcaccac atccgtgtcc | 420 |
| cggcccggcc gcggggagcc ccgcttcatc gccgtgggct acgtggacga cacgcagttc | 480 |
| gtgcggtttg acagcgacgc cgcgagccag aggatggagc cgcgggcacc gtggatagag | 540 |
| caggaggggc cggagtattg ggacctgcag acacggaatg tgaaggccca gtcacagact | 600 |
| gaccgagcga acctggggac cctgcgcggc tactacaacc agagcgaggc cggttctcac | 660 |
| accatccaga tgatgtatgg ctgcgacgtg gggtcggacg ggcgcttcct ccgcgggtac | 720 |
| cggcaggacg cctacgacgg caaggattac atcgccttga cgaggaccct gcgctcttgg | 780 |
| accgcggcgg acatggcggc tcagatcacc cagcgcaagt gggaggcggc ccgtgtggcg | 840 |
| gagcagttga gagcctacct ggagggcacg tgcgtggagt ggctccgcag ataccctgga | 900 |
| aacgggaagg agacgctgca gcgcacggac gcccccaaaa cgcatatgac tcaccacgct | 960 |
| gtctctgacc atgaagccac cctgaggtgc tgggccctga gcttctaccc tgcggagatc | 1020 |
| acactgacct ggcagcggga tggggaggac cagacccagg acacggagct cgtggagacc | 1080 |
| aggcctgcag gggatggaac cttccagaag tgggcggctg tggtggtgcc ttctggacag | 1140 |
| gagcagagat acacctgcca tgtgcagcat gagggtttgc ccaagcccct caccctgaga | 1200 |
| tgggatagaa aggagggag ctactctcag gctgcaagca gtgacagtgc ccagggctct | 1260 |
| gatgtgtctc tcacagcttg taaagtgtga cacagctgcc ttgtgtggga ctgagaggca | 1320 |
| agagttgttc ctgcccttcc ctttgtgact tgaagaaccc tgactttgtt tctgcaaagg | 1380 |
| cacctgcatg tgtctgtgtt cgtgtaggca taatgtgagg aggtggggag accaccccac | 1440 |
| ccccatgtcc accatgaccc tcttcccacg ctgacctgtg ctccctcccc aatcatcttt | 1500 |
| cctgttccag agaggtgggg ctgaggtgtc tccatctctg tctcaacttc atggtgcact | 1560 |
| gagctgtaac ttcttccttc cctattaaaa ttagaacctg agtataaatt tactttctca | 1620 |
| aattcttgcc atgagaggtt gatgagttaa ttaaaggaga agattcctaa aatttgagag | 1680 |
| acaaaataaa tggaacacat g | 1701 |

<210> SEQ ID NO 93
<211> LENGTH: 3974
<212> TYPE: DNA
<213> ORGANISM: Homo sapiens

<400> SEQUENCE: 93

| | |
|---|---|
| ggccccgaag cggtgtatgg attggggagt cccagccttg ggattcccaa ttccgcagtt | 60 |
| tcttttctcc ctgtcccaac ctatgtaggg tccttctcct ggatactcac gacgcggacc | 120 |
| cagttctcac tcccattggg tgtcgggttt cgagagaagc caatcaatgt cgtcgcggtc | 180 |
| gctgttctaa agtccgcacg cacccaccgg gactcagatt ctccccagac gccgaggatg | 240 |
| gccgtcatgg ggccccgaac cctcgtcctg ctactctcgg gggccctggc cctgacccag | 300 |
| acctgggcag gtgagtgcgg ggtcgggagg gaaatcggcc ctctgcgggg agaagcaagg | 360 |
| ggcccgcctg gcggggcgc aagacccggg aagccgcgcc gggaggaggg tcgggcgggt | 420 |
| ctcagccact cctcgtcccc aggctcccac tccatgaggt attctccac atccgtgtcc | 480 |
| cggcccggcc gcggggagcc ccgcttcatc gccgtggct acgtggacga cacgcagttc | 540 |
| gtgcggttcg acagcgacgc cgcgagccag aggatggagc cgcgggcgcc gtggatagag | 600 |
| caggaggggc cggagtattg ggacgaggag acagggaaag tgaaggccca ctcacagact | 660 |

-continued

| | |
|---|---|
| gaccgagaga acctgcggat cgcgctccgc tactacaacc agagcgaggc cggtgagtga | 720 |
| ccccggcccg gggcgcaggt cacgaccctc atccccacg gagggccggg gcgcccacag | 780 |
| gctccgggc ctagatccac cccgaagccg cgggaccccg agaccctttgc cctgggagag | 840 |
| gcccaggcgc cttaacccgg tttcattttc agtttaggcc aaaaatcccc ccggggttggt | 900 |
| cggggccggg cggggctcgg gggactgggc tgaccgcggg gtcggggcca ggttctcaca | 960 |
| ccctccagat gatgtttggc tgcgacgtgg ggtcggacgg gcgcttcctc cgcgggtacc | 1020 |
| accagtacgc ctacgacggc aaggattaca tcgccctgaa agaggacctg cgctcttgga | 1080 |
| ccgcggcgga catggcggct cagatcacca agcgcaagtg ggaggcggcc catgtggcgg | 1140 |
| agcagcagag agcctacctg gagggcacgt gcgtggacgg gctccgcaga tacctggaga | 1200 |
| acgggaagga gacgctgcag cgcgcgggta ccaggggcca cggggcgcct acctgatcgc | 1260 |
| ctgtaggtct cccgggctgg ccctcccaca aggaggggag acaattggga ccaacactag | 1320 |
| aatatcgccc tccctctggt cttgagggag aggaatcctc ctgggtttcc agatcctgta | 1380 |
| ccagagagtg actctgaggt tccgccctgc tctctgacac aattaaggga taaaatctct | 1440 |
| gacggaatga cggaaagacg atccctcgaa tactgatgac tggttccctt tgacaccggc | 1500 |
| agcagccttg ggaccgtgac ttttcctctc aggccttgtt ctctgcttaa aacttaaatg | 1560 |
| tgtgtggggt ctgagtccag aacttctgag tctccagcct ccactcaggt caggaccaga | 1620 |
| agtcgctgtt ccctcctcag ggaatagaag attatcccag ggcctgtgtc caagctggtg | 1680 |
| tctgggttct gtactctctt ccccgtcccg ggtgtcctgt ccattctcca gatgccaca | 1740 |
| tgcatgctgg tggagtgtcc catgacaggt gcaaaacccg tcagacccc ccaagacaca | 1800 |
| tatgacccac caccccatct ctgaccatga ggccactctg agatgctggg ccctgggctt | 1860 |
| ctaccctgcg gagatcacac tgacctggca gcgggatggg gaggaccaga cccaggacac | 1920 |
| ggagcttgtg gagaccaggc ctgcagggga tggaaccttc cagaagtggg cagctgtggt | 1980 |
| ggtaccttct ggagaggagc agagatacac ctgccatgtg cagcatgagg gtctgcccaa | 2040 |
| gccctcacc ctgagatggg gtaaggaggg agatgggggt gtcatgtctc ttagggaaag | 2100 |
| caggagcctc tctggagacc tttagcaggg tcagggcccc tcaccttccc ctctttttccc | 2160 |
| agagccatct tcccagccca ccgtccccat cgtgggcatc attgctggcc tggttctcct | 2220 |
| tggagctgtg atcactggag ctgtggtcgc tgctgtgatg tggaggagga acagctcagg | 2280 |
| tggagaaggg gtgaagggtg gggtctgaga tttcttgtct cactgagggt tccaagcccc | 2340 |
| agctagaaat gtcccctgtc tcattactgg gaaggaccat ccacaatcat gggccgaccc | 2400 |
| agcctgggcc ctgtgtgcca gcacttactc ttttgtaaag cacctgtgac aatgaaggac | 2460 |
| agatttatca ccctgattat ggcggtgatg ggacctgatc ccagcagtca caagtcacag | 2520 |
| gggaaggtcc ctgacgacag atctctggag ggcgattggt ccagggccca catctgcttt | 2580 |
| cttcatgttt cctgatcctg ccctgggtct gcagtcacac atttctggaa acttctctgg | 2640 |
| ggtccaagac taggaggttc ctctaggacc ttaaggccct ggctcacttt ctggtatctc | 2700 |
| acaggacatt ttcttcccac agatagaaaa ggagggagct actctcaggc tgcaagtaag | 2760 |
| tatgaaggag gctgatgcct gaggtccttg ggatattgtg tttgggagcc catgggggag | 2820 |
| ctcaaccacc ccacaattcc tcctctagcc acatcttctg tgggatcga ccaggttctg | 2880 |
| tttttgttct accccaggca gtgacagtgc ccagggctct gatgtgtctc tcacagcttg | 2940 |
| taaaggtgag agcttggagg gcctgatgtg tgttgggtgt tgggcggaac cgtgacaca | 3000 |
| gctgtgctat ggggtttctt tgcattggat gtattgagca tgcgatgggc tgtttaaagt | 3060 |

-continued

| | |
|---|---|
| gtgacccctc actgtgacag atatgaagtt gttcatgaat ttttttttcta tagtgtgaga | 3120 |
| cagctgcctg tgtgggactg agaggcaaga gttgtcctgc ccttccctt gtgacttgaa | 3180 |
| gaaccctgac tttgtttctg caaaggcacc tgcatgtgtc tgtgttcatg taggcataat | 3240 |
| gtgaggaggt ggggagaacc accccacccc caatgtccac catgaccctc ttcccaacgc | 3300 |
| tgaacctgtg ctccctcccc aatcatcttt cctgttgcag agaggtgggg ctgagttgtc | 3360 |
| tccatctctg tctgaacttc atggtgcact gagctgtaac ttctccttcc ctattaaaat | 3420 |
| tagaacctga gtataaattt ctttctcaaa ttcttgccat gagaggttga tgagttaatt | 3480 |
| aaaggagaag attcctaaaa tttgagagac aaaataaatg gaacacatga gaaccttcca | 3540 |
| gagtccacgt gttgcttatg ctgatttgtt gcaggggagg agactagatg gggctgtgcc | 3600 |
| agttttctgt tcggccacca tgggctttat gtggtcactg cttgggtggg tcatccttgc | 3660 |
| tgctccactg cccgaggccc ttcagtagaa ccttgtccca ccaagacccg tgattacagg | 3720 |
| gagttggatg tcacctaggg tggtccctgc atacaaatct ccttgtggta gcaagagaca | 3780 |
| aattttaga cctgtccagg tcttgccttc ctcccagggc ttttttcctca ttgtattttc | 3840 |
| gatttttcct acaatctttt taaaggaacc agattgtgac atttgcagag aggagggtc | 3900 |
| catagtttct catcatgatt aactttctgt tggactcctc ttctgctctc ctactctctc | 3960 |
| ctgcttagtg tagt | 3974 |

<210> SEQ ID NO 94
<211> LENGTH: 1826
<212> TYPE: DNA
<213> ORGANISM: Homo sapiens

<400> SEQUENCE: 94

| | |
|---|---|
| cgcttggcac agaagcagag gggtcagggc gaagtcccag ggccccaggc gtggctctca | 60 |
| gggtctcagg ccccgaaggc ggtgtatgga ttggggagtc ccagccttgg ggattcccca | 120 |
| actccgcagt ttcttttctc cctctcccaa cctatgtagg gtccttcttc ctggatactc | 180 |
| acgacgcgga cccagttctc actcccattg ggtgtcgggt ttccagagaa gccaatcagt | 240 |
| gtcgtcgcgg tcgcggttct aaagtccgca cgcacccacc gggactcaga ttctccccag | 300 |
| acgccgagga tggccgtcat ggcgcccga accctcctcc tgctactctt ggggccctg | 360 |
| gccctgaccc agacctgggc gggctcccac tccatgaggt atttcaccac atccgtgtcc | 420 |
| cggcccggcc gcggggagcc ccgcttcatc gccgtgggct acgtggacga cacgcagttc | 480 |
| gtgcggtttg acagcgacgc cgcgagccag aggatggagc gcgggcacc gtggatagag | 540 |
| caggaggggc cggagtattg ggaccctgcag acacggaatg tgaaggccca gtcacagact | 600 |
| gaccgagcga acctggggac cctgcgcggc tactacaacc agagcgaggc cggttctcac | 660 |
| accatccaga tgatgtatgg ctgcgacgtg gggtcggacg gcgcttcct ccgcgggtac | 720 |
| cggcaggacg cctacgacgg caaggattac atcgccttga acgaggacct gcgctcttgg | 780 |
| accgcggcgg acatggcggc tcagatcacc cagcgcaagt gggaggcggc ccgtgtggcg | 840 |
| gagcagttga gagcctacct ggagggcacg tgcgtggagt ggctccgcag ataccttggag | 900 |
| aacgggaagg agacgctgca gcgcacggac gcccccaaaa cgcatatgac tcaccacgct | 960 |
| gtctctgacc atgaagccac cctgaggtgc tgggccctga gcttctaccc tgcggagatc | 1020 |
| acactgacct ggcagcggga tggggaggac cagacccagg acacggagct cgtggagacc | 1080 |
| aggcctgcag gggatggaac cttccagaag tgggcggctg tggtggtgcc ttctggacag | 1140 |

| | |
|---|---|
| gagcagagat acacctgcca tgtgcagcat gagggtttgc ccaagcccct caccctgaga | 1200 |
| tgggagccgt cttcccagcc caccatcccc atcgtgggca tcattgctgg cctggttctc | 1260 |
| tttggagctg tgatcactgg agctgtggtc gctgctgtga ggtggaggag gaagagctca | 1320 |
| gatagaaaag gagggagcta ctctcaggct gcaagcagtg acagtgccca gggctctgat | 1380 |
| gtgtctctca cagcttgtaa agtgtgagac agctgccttg tgtgggactg agaggcaaga | 1440 |
| gttgttcctg cccttccctt tgtgacttga agaaccctga ctttgtttct gcaaaggcac | 1500 |
| ctgcatgtgt ctgtgttcgt gtaggcataa tgtgaggagg tggggagacc accccacccc | 1560 |
| catgtccacc atgaccctct tcccacgctg acctgtgctc cctccccaat catctttcct | 1620 |
| gttccagaga ggtggggctg aggtgtctcc atctctgtct caacttcatg gtgcactgag | 1680 |
| ctgtaacttc ttccttccct attaaaatta gaacctgagt ataaatttac tttctcaaat | 1740 |
| tcttgccatg agaggttgat gagttaatta aaggagaaga ttcctaaaat ttgagagaca | 1800 |
| aaataaatgg aacacatgag aacctt | 1826 |

<210> SEQ ID NO 95
<211> LENGTH: 1098
<212> TYPE: DNA
<213> ORGANISM: Homo sapiens

<400> SEQUENCE: 95

| | |
|---|---|
| atggccgtca tgccgccccg aaccctcctc ctgctactct cgggggccct ggccctgacc | 60 |
| cagacctggg caggctccca ctccatgagg tatttcttca catccgtgtc ccggcccggc | 120 |
| cgcggggagc cccgcttcat cgcagtgggc tacgtggacg actcgcagtt cgtgcagttc | 180 |
| gacagcgacg ccgcgagcca gaggatggag ccgcgggcgc cgtggataga gcaggaggag | 240 |
| ccggagtatt gggacgagga gacacggaat gtgaaggccc actcacagac taaccgagcg | 300 |
| aacctgggga ccctgcgcgg ctactacaac cagagcgagg acggttctca ccaccatcca | 360 |
| ataatgtatg gctgcgacgt ggggtcggac gggcgcttcc tccgcgggta ccggcaggac | 420 |
| gcctacgacg gcaaggatta catcgccctg aacgaggacc tgcgctcttg gaccgcggcg | 480 |
| gacatggcgg ctcagatcac caagcgcaag tgggaggcgg cccgtcgggc ggagcagctg | 540 |
| agagcctacc tggagggcga gtgcgtggac gggctccgca gatacctgga aacgggaag | 600 |
| gagacgctgc agcgcacgga cccccccaag acacatatga cccaccaccc catctctgac | 660 |
| catgaggcca ctctgaggtg ctgggccctg agcttctacc ctgcggagat cacactgacc | 720 |
| tggcagcggg atggggagga ccagacccag gacacggagc tcgtggagac caggcctgca | 780 |
| ggggatggaa ccttccagaa gtgggcggct gtggtggtac cttctggaaa ggagaagaga | 840 |
| tacacctgcc atgtgcagca tgagggtctg cccgagcccc tcaccctgag atgggagcca | 900 |
| tcttcccagc ccaccatccc cattgtgggc atcattgctg gcctggttct ccttggagct | 960 |
| gtgatcgctg gagctgtggt cgctgccgtg atgtggagga gaagagctc agttagaaaa | 1020 |
| ggagggagct actctcaggc tgcaagcagt gacagtgccc agggctctga tgtgtctctc | 1080 |
| acagcttgta aagtgtga | 1098 |

<210> SEQ ID NO 96
<211> LENGTH: 1848
<212> TYPE: DNA
<213> ORGANISM: Homo sapiens

<400> SEQUENCE: 96

| | |
|---|---|
| cgcttggcac agaagcagag gggtcagggc gaagtcccag ggccccaggc gtggctctca | 60 |

```
gggtctcagg ccccgaaggc ggtgtatgga ttggggagtc ccagccttgg ggattcccca       120
actccgcagt ttcttttctc cctctcccaa cctatgtagg gtccttcttc ctggatactc       180
acgacgcgga cccagttctc actcccattg ggtgtcgggt ttccagagaa gccaatcagt       240
gtcgtcgcgg tcgcggttct aaagtccgca cgcacccacc gggactcaga ttctccccag       300
acgccgagga tggccgtcat ggcgccccga accctcctcc tgctactctt ggggccctg        360 gccctgaccc agacctgggc gggctcccac tccatgaggt atttcaccac atccgtgtcc       420
cggcccggcc gcggggagcc ccgcttcatc gccgtgggc acgtggacga cacgcagttc        480
gtgcggtttg acagcgacgc cgcgagccag aggatggagc cgcgggcacc gtggatagag       540
caggaggggc cggagtattg ggacctgcag acacggaatg tgaaggccca gtcacagact       600
gaccgagcga acctggggac cctgcgcggc tactacaacc agagcgaggc cggttctcac       660
accatccaga tgatgtatgg ctgcgacgtg gggtcgacg ggcgcttcct ccgcgggtac        720
cggcaggacg cctacgacgg caaggattac atcgccttga cgaggacct gcgctcttgg       780 accgcggcgg acatggcggc tcagatcacc cagcgcaagt gggaggcggc ccgtgtggcg       840
gagcagttga gagcctacct ggagggcacg tgcgtggagt ggctccgcag ataccctggag       900 aacgggaagg agacgctgca gcgcacggac gcccccaaaa cgcatatgac tcaccacgct       960
gtctctgacc atgaagccac cctgaggtgc tgggccctga gcttctaccc tgcggagatc      1020
acactgacct ggcagcggga tggggaggac cagacccagg acacggagct cgtggagacc      1080
aggcctgcag gggatggaac cttccagaag tgggcggctg tggtggtgcc ttctggacag      1140
gagcagagat acacctgcca tgtgcagcat gagggtttgc ccaagcccct caccctgaga      1200
tgggagccgt cttcccagcc caccatcccc atcgtgggca tcattgctgg cctggttctc      1260
tttggagctg tgatcactgg agctgtggtc gctgctgtga ggtggaggag gaagagctca      1320
gtcacacatt tctggaaact tctctgaggt ccaagacttg gaggttcctc taggacctta      1380
aggccctgac tccttctctg tatctcacag gacattttct tcccacagat agaaaaggag      1440
ggagctactc tcaggctgca agcagtgaca gtgcccaggg ctctgatgtg tctctcacag      1500
cttgtaaagt gtgagacagc tgccttgtgt gggactgaga ggcaagagtt gttcctgccc      1560 ttcccttgt gacttgaaga accctgactt tgtttctgca aaggcacctg catgtgtctg       1620
tgttcgtgta ggcataatgt gaggaggtgg ggagaccacc ccaccccat gtccaccatg       1680 accctcttcc cacgctgacc tgtgctccct ccccaatcat ctttcctgtt ccagagaggt      1740
ggggctgagg tgtctccatc tctgtctcaa cttcatggtg cactgagctg taacttcttc      1800
cttccctatt aaaattagaa cctgagtata aatttacttt ctcaaatt                    1848
```

<210> SEQ ID NO 97
<211> LENGTH: 1098
<212> TYPE: DNA
<213> ORGANISM: Homo sapiens

<400> SEQUENCE: 97

```
atggccgtca tggcgccccg aaccctcgtc ctgctactct cggggcccct ggccctgacc        60
cagacctggg caggctccca ctccatgagg tatttctcca catccgtgtc ccggcccggc       120
cgcggggagc ccgcttcat cgccgtgggc tacgtggaca cacgcagtt cgtgcggttc        180 gacagcgacg ccgcgagcca gaggatggag ccgcgggcgc gtggataga gcaggagggg       240 ccggagtatt gggacgagga gacagggaaa gtgaaggccc actcacagac tgaccgagag       300
```

```
aacctgcgga tcgcgctccg ctactacaac cagagcgagg ccggttctca caccctccag      360
atgatgtttg gctgcgacgt ggggtcggac gggcgcttcc tccgcgggta ccaccagtac      420
gcctacgacg gcaaggatta catcgccctg aaagaggacc tgcgctcttg gaccgcggcg      480
gacatggcgg ctcagatcac ccagcgcaag tgggaggcgg cccgtgtggc ggagcagttg      540
agagcctacc tggagggcac gtgcgtggac gggctccgca gatacctgga gaacgggaag      600
gagacgctgc agcgcacgga ccccccaag acacatatga cccaccaccc catctctgac       660
catgaggcca ctctgagatg ctgggccctg gcttctacc ctgcggagat cacactgacc        720
tggcagcggg atggggagga ccagacccag gacacgagc ttgtggagac caggcctgca        780
ggggatggaa ccttccagaa gtgggcagct gtggtggtac cttctggaga ggagcagaga      840
tacacctgcc atgtgcagca tgagggtctg cccaagcccc tcaccctgag atgggagcca      900
tcttcccagc ccaccgtcca catcgtgggc atcattgctg gcctggttct ccttggagct      960
gtgatcactg gagctgtggt cgctgctgtg atgtggagga ggaacagctc agatagaaaa     1020
ggagggagct actctcaggc tgcaagcagt gacagtgccc agggctctga tgtgtctctc     1080
acagcttgta aagtgtga                                                   1098

<210> SEQ ID NO 98
<211> LENGTH: 1098
<212> TYPE: DNA
<213> ORGANISM: Homo sapiens

<400> SEQUENCE: 98
atggccgtca tggcgccccg aaccctcgtc ctgctactct cggggctct ggccctgacc        60
cagacctggg cgggctctca ctccatgagg tatttcttca catccgtgtc ccggcccggc      120
cgcggggagc ccgcttcat cgcagtgggc tacgtggacg acacgcagtt cgtgcggttc       180
acagcgacg ccgcgagcca gaggatggag ccgcgggcgc cgtggataga gcaggagggt        240
ccggagtatt gggacgggga gacacggaaa gtgaaggccc actcacagac tcaccgagtg      300
gacctgggga ccctgcgcgg ctactacaac cagagcgagg ccggttctca caccgtccag      360
aggatgtatg gctgcgacgt ggggtcggac tggcgcttcc tccgcgggta ccaccagtac      420
gcctacgacg gcaaggatta catcgccctg aaagaggacc tgcgctcttg gaccgcggcg      480
gacatggcag ctcagaccac caagcacaag tgggaggcgg cccatgtggc ggagcagttg      540
agagcctacc tggagggcac gtgcgtggag tggctccgca gatacctgga gaacgggaag      600
gagacgctgc agcgcacgga cgcccccaaa acgcatatga ctcaccacgc tgtctctgac      660
catgaagcca ccctgaggtg ctgggccctg agcttctacc ctgcggagat cacactgacc      720
tggcagcggg atggggagga ccagacccag gacacgagc tcgtggagac caggcctgca       780
ggggatggaa ccttccagaa gtgggcggct gtggtggtgc cttctggaca ggagcagaga      840
tacacctgcc atgtgcagca tgagggttg cccaagcccc tcaccctgag atgggagccg        900
tcttcccagc ccaccatccc catcgtgggc atcattgctg gcctggttct ctttggagct      960
gtgatcactg gagctgtggt cgctgctgtg atgtggagga ggaagagctc agatagaaaa     1020
ggagggagct actctcaggc tgcaagcagt gacagtgccc agggctctga tgtgtctctc     1080
acagcttgta aagtgtga                                                   1098

<210> SEQ ID NO 99
<211> LENGTH: 1098
<212> TYPE: DNA
<213> ORGANISM: Homo sapiens
```

<400> SEQUENCE: 99

```
atggccgtca tggcgccccg aaccctcgtc ctgctactct cggggccct  ggccctgacc     60
cagacctggg caggctccca ctccatgagg tatttctcca catccgtgtc ccggcccggc    120
cgcggggagc cccgcttcat cgccgtgggc tacgtggacg acacgcagtt cgtgcggttc    180
gacagcgacg ccgcgagcca gaggatggag ccgcgggcgc cgtggataga gcaggagggg    240
ccggagtatt gggacgagga gacagggaaa gtgaaggccc actcacagac tgaccgagag    300
aacctgcgga tcgcgctccg ctactacaac cagagcgagg ccggttctca caccctccag    360
atgatgtttg gctgcgacgt ggggtcggac gggcgcttcc tccgcgggta ccaccagtac    420
gcctacgacg gcaaggatta catcgccctg aaagaggacc tgcgctcttg gaccgcggcg    480
gacatggcgg ctcagatcac caagcgcaag tgggaggcgg cccatgtggc ggagcagcag    540
agagcctacc tggagggcac gtgcgtggac gggctccgca gatacctgga gaacgggaag    600
gagacgctgc agcgcacgga ccccccccaag acacatatga cccaccaccc catctctgac    660
catgaggcca ctctgagatg ctgggccctg gcttctacc ctgcggagat cacactgacc     720
tggcagcggg atggggagga ccagacccag gacacgagc ttgtggagac caggcctgca     780
ggggatggaa ccttccagaa gtgggcagct gtggtggtac cttctggaga ggagcagaga    840
tacacctgcc atgtgcagca tgagggtctg cccaagcccc tcaccctgag atgggagcca    900
tcttcccagc ccaccgtccc catcgtgggc atcattgctg gcctggttct ccttggagct    960
gtgatcactg agctgtggt  cgctgctgtg atgtggagga ggaacagctc agatagaaaa   1020
ggagggagct actctcaggc tgcaagcagt gacagtgccc agggctctga tgtgtctctc   1080
acagcttgta aagtgtga                                                 1098
```

<210> SEQ ID NO 100
<211> LENGTH: 2950
<212> TYPE: DNA
<213> ORGANISM: Homo sapiens

<400> SEQUENCE: 100

```
cggcgagagc gcgcccagcc ccgccgcgat gcccgcgcgc ccaggacgcc tcctcccgct     60
gctggcccgg ccggcggccc tgactgcgct gctgctgctg ctgctgggcc atggcggcgg    120
cgggcgctgg ggcgcccggg cccaggaggc ggcggcggcg gcggcggacg gccccccgc    180
ggcagacggc gaggacggac aggacccgca cagcaagcac ctgtacacgg ccgacatgtt    240
cacgcacggg atccagagcg ccgcgcactt cgtcatgttc ttcgcgccct ggtgtggaca    300
ctgccagcgc ctgcagccga cttggaatga cctgggagac aaatacaaca gcatggaaga    360
tgccaaagtc tatgtggcta agtggactg  cacggcccac tccgacgtgt gctccgccca    420
gggggtgcga ggatacccca ccttaaagct tttcaagcca ggccaagaag ctgtgaagta    480
ccagggtcct cgggacttcc agacactgga aaactggatg ctgcagacac tgaacgagga    540
gccagtgaca ccagagccgg aagtggaacc gcccagtgcc cccgagctca gcaagggct    600
gtatgagctc tcagcaagca actttgagct gcacgttgca caaggcgacc actttatcaa    660
gttcttcgct ccgtggtgtg gtcactgcaa agccctggct ccaacctggg agcagctggc    720
tctgggcctt gaacattccg aaactgtcaa gattggcaag gttgattgta cacagcacta    780
tgaactctgc tccggaaacc aggttcgtgg ctatcccact cttctctggt tccgagatgg    840
gaaaaaggtg gatcagtaca agggaaagcg ggatttggag tcactgaggg agtacgtgga    900
```

-continued

```
gtcgcagctg cagcgcacag agactggagc gacggagacc gtcacgccct cagaggcccc      960
ggtgctggca gctgagcccg aggctgacaa gggcactgtg ttggcactca ctgaaaataa     1020
cttcgatgac accattgcag aaggaataac cttcatcaag ttttatgctc catggtgtgg     1080
tcattgtaag actctggctc ctacttggga ggaactctct aaaaaggaat ccctggtct      1140 ggcgggggtc aagatcgccg aagtagactg cactgctgaa cggaatatct gcagcaagta     1200
ttcggtacga ggctacccca cgttattgct tttccgagga gggaagaaag tcagtgagca     1260
cagtggaggc agagaccttg actcgttaca ccgctttgtc ctgagccaag cgaaagacga     1320
actttaggaa cacagttgga ggtcacctct cctgcccagc tcccgcaccc tgcgtttagg     1380
agttcagtcc cacagaggcc actgggttcc cagtggtggc tgttcagaaa cagaacata     1440 ctaagcgtga ggtatcttct ttgtgtgtgt gttttccaag ccaacacact ctacagattc     1500
tttattaagt taagtttctc taagtaaatg tgtaactcat ggtcactgtg taaacatttt     1560
cagtggcgat atatcccctt tgaccttctc ttgatgaaat ttacatggtt cctttgaga     1620 ctaaaatagc gttagggaa atgaaattgc tggactattt gtggctcctg agttgagtga     1680
ttttggtgaa agaaagcaca tccaaagcat agtttacctg cccacgagtt ctggaaaggt     1740
ggccttgtgg cagtattgac gttcctctga tcttaaggtc acagttgact caatactgtg     1800
ttggtccgta gcatggagca gattgaaatg caaaaaccca cacctctgga agataccttc     1860
acggccgctg ctggagcttc tgttgctgtg aatacttctc tcagtgtgag aggttagccg     1920
tgatgaaagc agcgttactt ctgaccgtgc ctgagtaaga gaatgctgat gccataactt     1980
tatgtgtcga tacttgtcaa atcagttact gttcagggga tccttctgtt tctcacgggg     2040
tgaaacatgt ctttagttcc tcatgttaac acgaagccag agcccacatg aactgttgga     2100
tgtcttcctt agaaagggta ggcatggaaa attccacgag gctcattctc agtatctcat     2160
taactcattg aaagattcca gttgtatttg tcacctgggg tgacaagacc agacaggctt     2220
tcccaggcct gggtatccag ggaggctctg cagccctgct gaagggccct aactagagtt     2280
ctagagtttc tgattctgtt tctcagtagt cctttagag gcttgctata cttggtctgc     2340
ttcaaggagg tcgaccttct aatgtatgaa gaatgggatg catttgatct caagaccaaa     2400
gacagatgtc agtgggctgc tctggccctg gtgtgcacgg ctgtggcagc tgttgatgcc     2460
agtgtcctct aactcatgct gtccttgtga ttaaacacct ctatctccct tgggaataag     2520
cacatacagg cttaagctct aagatagata ggtgtttgtc cttttaccat cgagctactt     2580
cccataataa ccactttgca tccaacactc ttcacccacc tcccatacgc aagggatgt     2640 ggatacttgg cccaaagtaa ctggtggtag gaatcttaga aacaagacca cttatactgt     2700
ctgtctgagg cagaagataa cagcagcatc tcgaccagcc tctgccttaa aggaaatctt     2760
tattaatcac gtatggttca cagataattc ttttttttaaa aaaacccaac ctcctagaga     2820
agcacaactg tcaagagtct tgtacacaca acttcagctt tgcatcacga gtcttgtatt     2880
ccaagaaaat caaagtggta caatttgttt gtttacacta tgatactttc taaataaact     2940
ctttttttt                                                             2950
```

<210> SEQ ID NO 101
<211> LENGTH: 3047
<212> TYPE: DNA
<213> ORGANISM: Homo sapiens

<400> SEQUENCE: 101

```
gggacagaga cccctgtggg ttgtgaggcc gccccggggcg gtggcagcaa gaagagggac      60
```

-continued

```
tccctgggga ctgcgggctc agcgcacctc attatcaagg atcttggaga aattcattca    120
aggcttttgg atcacagacc agttattcaa ggtgaaactc gttattttgt aaaagaattt    180
gaagaaaaac gtggtcttcg agaaatgcga gttcttgaaa atttgaagaa catgatccat    240
gaaacaaatg aacatactct tcccaaatgt agagacacaa tgcgggacag cctcagccag    300
gttctccaga gattgcaagc agctaatgac tcagtctgta gactccaaca gagggaacag    360
gaacgaaaaa aggtgtggac actgccagcg gctgcagccg acttggaatg acctgggaga    420
caaatacaac agcatggaag atgccaaagt ctatgtggct aaagtggact gcacggccca    480
ctccgacgtg tgctccgccc aggggtgcg aggatacccc accttaaagc ttttcaagcc     540
aggccaagaa gctgtgaagt accagggtcc tcgggacttc cagacactgg aaaactggat    600
gctgcagaca ctgaacgagg agccagtgac accagagccg aagtggaac cgcccagtgc     660
ccccgagctc aagcaagggc tgtatgagct ctcagcaagc aactttgagc tgcacgttgc    720
acaaggcgac cactttatca agttcttcgc tccgtggtgt ggtcactgca aagccctggc    780
tccaacctgg gagcagctgg ctctgggcct tgaacattcc gaaactgtca agattggcaa    840
ggttgattgt acacagcact atgaactctg ctccggaaac caggttcgtg gctatcccac    900
tcttctctgg ttccgagatg ggaaaaaggt ggatcagtac aagggaaagc gggatttgga    960
gtcactgagg gagtacgtgg agtcgcagct gcagcgcaca gagactggag cgacggagac   1020
cgtcacgccc tcagaggccc cggtgctggc agctgagccc gaggctgaca agggcactgt   1080
gttggcactc actgaaaata acttcgatga caccattgca gaaggaataa ccttcatcaa   1140
gtttttatgct ccatggtgtg gtcattgtaa actctggct cctacttggg aggaactctc   1200
taaaaaggaa ttccctggtc tggcgggggt caagatcgcc gaagtagact gcactgctga   1260
acggaatatc tgcagcaagt attcggtacg aggctacccc acgttattgc ttttccgagg   1320
agggaagaaa gtcagtgagc acagtggagg cagagacctt gactcgttac accgctttgt   1380
cctgagccaa gcgaaagacg aactttagga acacagttgg aggtcacctc tcctgcccag   1440
ctcccgcacc ctgcgtttag gagttcagtc ccacagaggc cactgggttc ccagtggtgg   1500
ctgttcagaa agcagaacat actaagcgtg aggtatcttc tttgtgtgtg tgttttccaa   1560
gccaacacac tctacagatt ctttattaag ttaagtttct ctaagtaaat gtgtaactca   1620
tggtcactgt gtaaacattt tcagtggcga tatatcccct ttgaccttct cttgatgaaa   1680
tttacatggt ttcctttgag actaaaatag cgttgaggga aatgaaattg ctggactatt   1740
tgtggctcct gagttgagtg attttggtga agaaagcac atccaaagca tagtttacct   1800
gcccacgagt tctggaaagg tggccttgtg gcagtattga cgttcctctg atcttaaggt   1860
cacagttgac tcaatactgt gttggtccgt agcatggagc agattgaaat gcaaaaaccc   1920
acacctctgg aagataccttt cacggccgct gctggagctt ctgttgctgt gaatacttct   1980
ctcagtgtga gaggttagcc gtgatgaaag cagcgttact tctgaccgtg cctgagtaag   2040
agaatgctga tgccataact ttatgtgtcg atacttgtca aatcagttac tgttcagggg   2100
atccttctgt ttctcacggg gtgaaacatg tctttagttc ctcatgttaa cacgaagcca   2160
gagcccacat gaactgttgg atgtcttcct tagaaagggt aggcatggaa aattccacga   2220
ggctcattct cagtatctca ttaactcatt gaaagattcc agttgtattt gtcacctggg   2280
gtgacaagac cagacaggct ttcccaggcc tgggtatcca gggaggctct gcagccctgc   2340
tgaagggccc taactagagt tctagagttt ctgattctgt ttctcagtag tcctttttaga   2400
```

```
ggcttgctat acttggtctg cttcaaggag gtcgacccttc taatgtatga agaatgggat    2460
gcatttgatc tcaagaccaa agacagatgt cagtgggctg ctctggccct ggtgtgcacg    2520
gctgtggcag ctgttgatgc cagtgtcctc taactcatgc tgtccttgtg attaaacacc    2580
tctatctccc ttgggaataa gcacatacag gcttaagctc taagatagat aggtgtttgt    2640
ccttttacca tcgagctact tcccataata accactttgc atccaacact cttcacccac    2700
ctcccatacg caaggggatg tggatacttg gcccaaagta actggtggta ggaatcttag    2760
aaacaagacc acttatactg tctgtctgag gcagaagata acagcagcat ctcgaccagc    2820
ctctgcctta aaggaaatct ttattaatca cgtatggttc acagataatt cttttttaa     2880 aaaaacccaa cctcctagag aagcacaact gtcaagagtc ttgtacacac aacttcagct    2940
ttgcatcacg agtcttgtat tccaagaaaa tcaaagtggt acaatttgtt tgtttacact    3000
atgatacttt ctaaataaac tctttttttt taaaaaaaaa aaaaaa                  3047
```

<210> SEQ ID NO 102
<211> LENGTH: 2925
<212> TYPE: DNA
<213> ORGANISM: Homo sapiens

<400> SEQUENCE: 102

```
gaattcaacc gcctcttgca cctcggcacc gagggagggg aaggtggggt cgtcgccctt      60
tcgggcagcc gggagtccaa atgtcacccc gcggtccctg cccagcgccc caaacttcct     120
gtgccggccg gacgcgcggc ctgcccgtgg gccacgtgca ctcaccgagg cggccttgct     180
gctgccgcgg ccaccggggt cggctgggac agactgcggg cacgtcccct tccagaggct    240
ttaactgaaa aatagaaccc aggaaggtgt ggacactgcc agcggctgca gccgacttgg    300
aatgacctgg gagacaaata caacagcatg gaagatgcca aagtctatgt ggctaaagtg    360
gactgcacgg cccactccga cgtgtgctcc gcccaggggg tgcgaggata ccccaccttca   420 aagcttttca gccaggcca agaagctgtg aagtaccagg gtcctcggga cttccagaca    480
ctggaaaact ggatgctgca gacactgaac gaggagccag tgacaccaga gccgaagtg    540 gaaccgccca gtgcccccga gctcaagcaa gggctgtatg agctctcagc aagcaacttt    600
gagctgcacg ttgcacaagg cgaccacttt atcaagttct tcgctccgtg gtgtggtcac    660
tgcaaagccc tggctccaac ctgggagcag ctggctctgg gccttgaaca ttccgaaact    720
gtcaagattg gcaaggttga ttgtacacag cactatgaac tctgctccgg aaaccaggtt    780
cgtggctatc ccactcttct ctggttccga gatgggaaaa aggtggatca gtacaaggga    840
aagcgggatt tggagtcact gaggagtac gtggagtcgc agctgcagcg cacagagact    900
ggagcgacgg agaccgtcac gccctcagag gccccgtgc tggcagctga gcccgaggct    960
gacaagggca ctgtgttggc actcactgaa aataacttcg atgacaccat tgcagaagga   1020
ataaccttca tcaagtttta tgctccatgg tgtggtcatt gtaagactct ggctcctact   1080
tgggaggaac tctctaaaaaa ggaattccct ggtctggcgg gggtcaagat cgccgaagta   1140
gactgcactg ctgaacggaa tatctgcagc aagtattcgg tacgaggcta ccccacgtta   1200
ttgcttttcc gaggagggaa gaaagtcagt gagcacagtg gaggcagaga ccttgactcg   1260
ttacaccgct ttgtcctgag ccaagcgaaa gacgaacttt aggaacacag ttggaggtca   1320
cctctcctgc ccagctcccg caccctgcgt ttaggagttc agtcccacag aggccactgg   1380
gttcccagtg gtggctgttc agaaaagcaga acatactaag cgtgaggtat cttcttgtg    1440 tgtgtgtttt ccaagccaac acactctaca gattctttat taagttaagt ttctctaagt   1500
```

| | |
|---|---|
| aaatgtgtaa ctcatggtca ctgtgtaaac attttcagtg gcgatatatc ccctttgacc | 1560 |
| ttctcttgat gaaatttaca tggtttcctt tgagactaaa atagcgttga gggaaatgaa | 1620 |
| attgctggac tatttgtggc tcctgagttg agtgattttg gtgaaagaaa gcacatccaa | 1680 |
| agcatagttt acctgcccac gagttctgga aaggtggcct tgtggcagta ttgacgttcc | 1740 |
| tctgatctta aggtcacagt tgactcaata ctgtgttggt ccgtagcatg gagcagattg | 1800 |
| aaatgcaaaa acccacacct ctggaagata ccttcacggc cgctgctgga gcttctgttg | 1860 |
| ctgtgaatac ttctctcagt gtgagaggtt agccgtgatg aaagcagcgt tacttctgac | 1920 |
| cgtgcctgag taagagaatg ctgatgccat aactttatgt gtcgatactt gtcaaatcag | 1980 |
| ttactgttca ggggatcctt ctgtttctca cggggtgaaa catgtcttta gttcctcatg | 2040 |
| ttaacacgaa gccagagccc acatgaactg ttggatgtct tccttagaaa gggtaggcat | 2100 |
| ggaaaattcc acgaggctca ttctcagtat ctcattaact cattgaaaga ttccagttgt | 2160 |
| atttgtcacc tggggtgaca agaccagaca ggctttccca ggcctgggta tccagggagg | 2220 |
| ctctgcagcc ctgctgaagg gccctaacta gagttctaga gtttctgatt ctgtttctca | 2280 |
| gtagtccttt tagaggcttg ctatacttgg tctgcttcaa ggaggtcgac cttctaatgt | 2340 |
| atgaagaatg ggatgcattt gatctcaaga ccaaagacag atgtcagtgg gctgctctgg | 2400 |
| ccctggtgtg cacggctgtg gcagctgttg atgccagtgt cctctaactc atgctgtcct | 2460 |
| tgtgattaaa cacctctatc tcccttggga ataagcacat acaggcttaa gctctaagat | 2520 |
| agataggtgt ttgtcctttt accatcgagc tacttcccat aataaccact ttgcatccaa | 2580 |
| cactcttcac ccacctccca tacgcaaggg gatgtggata cttggcccaa agtaactggt | 2640 |
| ggtaggaatc ttagaaacaa gaccacttat actgtctgtc tgaggcagaa gataacagca | 2700 |
| gcatctcgac cagcctctgc cttaaaggaa atctttatta atcacgtatg gttcacagat | 2760 |
| aattcttttt ttaaaaaaac ccaacctcct agagaagcac aactgtcaag agtcttgtac | 2820 |
| acacaacttc agctttgcat cacgagtctt gtattccaag aaaatcaaag tggtacaatt | 2880 |
| tgtttgttta cactatgata ctttctaaat aaactctttt ttttt | 2925 |

<210> SEQ ID NO 103
<211> LENGTH: 3081
<212> TYPE: DNA
<213> ORGANISM: Homo sapiens

<400> SEQUENCE: 103

| | |
|---|---|
| cggcgagagc gcgcccagcc ccgccgcgat gcccgcgcgc ccaggacgcc tcctcccgct | 60 |
| gctggcccgg ccggcggccc tgactgcgct gctgctgctg ctgctgggcc atggcggcgg | 120 |
| cgggcgctgg ggcgcccggg cccaggaggc ggcggcggcg gcgcggacg ggccccccgc | 180 |
| ggcagacggc gaggacggac aggacccgca cagcaagcac ctgtacacgg ccgacatgtt | 240 |
| cacgcacggg atccagagcg ccgcgcactt cgtcatgttc ttcgcgccct gagatgggat | 300 |
| cttgctctgt tacccagcct gaaaccagtg gtacgcagcc gcagctcact gtagcctcta | 360 |
| actcctgggc tcaagtgatt ctcctgcctc agcctctgaa gtagctgtga ctacaggcgc | 420 |
| aggtgtggac actgccagcg gctgcagccg acttggaatg acctgggaga caaatacaac | 480 |
| agcatggaag atgccaaagt ctatgtggct aaagtggact gcacggccca ctccgacgtg | 540 |
| tgctccgccc aggggtgcg aggatacccc accttaaagc ttttcaagcc aggccaagaa | 600 |
| gctgtgaagt accagggtcc tcgggacttc cagacactgg aaaactggat gctgcagaca | 660 |

```
ctgaacgagg agccagtgac accagagccg gaagtggaac cgcccagtgc ccccgagctc    720
aagcaagggc tgtatgagct ctcagcaagc aactttgagc tgcacgttgc acaaggcgac    780
cactttatca agttcttcgc tccgtggtgt ggtcactgca aagccctggc tccaacctgg    840
gagcagctgg ctctgggcct tgaacattcc gaaactgtca agattggcaa ggttgattgt    900
acacagcact atgaactctg ctccggaaac caggttcgtg gctatcccac tcttctctgg    960
ttccgagatg ggaaaaaggt ggatcagtac aagggaaagc gggatttgga gtcactgagg   1020
gagtacgtgg agtcgcagct gcagcgcaca gagactggag cgacggagac cgtcacgccc   1080
tcagaggccc cggtgctggc agctgagccc gaggctgaca agggcactgt gttggcactc   1140
actgaaaata acttcgatga caccattgca gaaggaataa ccttcatcaa gttttatgct   1200
ccatggtgtg gtcattgtaa gactctggct cctactgggg aggaactctc taaaaaggaa   1260
ttccctggtc tggcggggt caagatcgcc gaagtagact gcactgctga acggaatatc   1320
tgcagcaagt attcggtacg aggctacccc acgttattgc ttttccgagg agggaagaaa   1380
gtcagtgagc acagtggagg cagagacctt gactcgttac accgctttgt cctgagccaa   1440
gcgaaagacg aactttagga acacagttgg aggtcacctc tcctgcccag ctcccgcacc   1500
ctgcgtttag gagttcagtc ccacagaggc cactgggttc ccagtggtgg ctgttcagaa   1560
agcagaacat actaagcgtg aggtatcttc tttgtgtgtg tgttttccaa gccaacacac   1620
tctacagatt ctttattaag ttaagtttct ctaagtaaat gtgtaactca tggtcactgt   1680
gtaaacattt tcagtggcga tatatcccct ttgaccttct cttgatgaaa tttacatggt   1740
ttcctttgag actaaaatag cgttgaggga aatgaaattg ctggactatt tgtggctcct   1800
gagttgagtg attttggtga agaaagcac atccaaagca tagtttacct gcccacgagt   1860
tctgaaaagg tggccttgtg gcagtattga cgttcctctg atcttaaggt cacagttgac   1920
tcaatactgt gttggtccgt agcatggagc agattgaaat gcaaaaaccc acacctctgg   1980
aagataccct cacggccgct gctggagctt ctgttgctgt gaatacttct ctcagtgtga   2040
gaggttagcc gtgatgaaag cagcgttact tctgaccgtg cctgagtaag agaatgctga   2100
tgccataact ttatgtgtcg atacttgtca aatcagttac tgttcagggg atccttctgt   2160
ttctcacggg gtgaaacatg tctttagttc ctcatgttaa cacgaagcca gagcccacat   2220
gaactgttgg atgtcttcct tagaaagggt aggcatggaa aattccacga ggctcattct   2280
cagtatctca ttaactcatt gaaagattcc agttgtattt gtcacctggg gtgacaagac   2340
cagacaggct ttcccaggcc tgggtatcca gggaggctct gcagccctgc tgaagggccc   2400 taactgagt tctagagttt ctgattctgt ttctcagtag tcctttttaga ggcttgctat   2460 acttggtctg cttcaaggag gtcgaccttc taatgtatga agaatgggat gcatttgatc   2520
tcaagaccaa agacagatgt cagtgggctg ctctggccct ggtgtgcacg gctgtggcag   2580
ctgttgatgc cagtgtcctc taactcatgc tgtccttgtg attaaacacc tctatctccc   2640
ttgggaataa gcacatacag gcttaagctc taagatagat aggtgtttgt ccttttacca   2700
tcgagctact tccataata accactttgc atccaacact cttcacccac ctcccatacg   2760
caaggggatg tggatacttg gcccaaagta actggtggta ggaatcttag aaacaagacc   2820
acttatactg tctgtctgag gcagaagata acagcagcat ctcgaccagc ctctgcctta   2880
aaggaaatct ttattaatca cgtatggttc acagataatt cttttttaa aaaaacccaa    2940 cctcctagag aagcacaact gtcaagagtc ttgtacacac aacttcagct ttgcatcacg   3000
agtcttgtat tccaagaaaa tcaaagtggt acaatttgtt tgtttacact atgatacttt   3060
```
ctaaataaac tcttttttt t 3081

<210> SEQ ID NO 104
<211> LENGTH: 3081
<212> TYPE: DNA
<213> ORGANISM: Homo sapiens

<400> SEQUENCE: 104

| | | | | | |
|---|---|---|---|---|---|
| aggcgcagcg | tggccgcggg | tgggcggaac | tggtcgggat | gagtggcgga | gggacagaga | 60 |
| cccctgtggg | ttgtgaggcc | gccccgggcg | gtggcagcaa | gaagagggac | tccctgggga | 120 |
| ctgcgggctc | agcgcacctc | attatcaagg | atcttggaga | aattcattca | aggcttttgg | 180 |
| atcacagacc | agttattcaa | ggtgaaactc | gttattttgt | aaaagaattt | gaagaaaaac | 240 |
| gtggtcttcg | agaaatgcga | gttcttgaaa | atttgaagaa | catgatccat | gaaacaaatg | 300 |
| aacatactct | tcccaaatgt | agagacacaa | tgcgggacag | cctcagccag | gttctccaga | 360 |
| gattgcaagc | agctaatgac | tcagtctgta | gactccaaca | gagggaacag | gaacgaaaaa | 420 |
| aggtgtggac | actgccagcg | gctgcagccg | acttggaatg | acctgggaga | caaatacaac | 480 |
| agcatggaag | atgccaaagt | ctatgtggct | aaagtggact | gcacggccca | ctccgacgtg | 540 |
| tgctccgccc | agggggtgcg | aggataccc | accttaaagc | ttttcaagcc | aggccaagaa | 600 |
| gctgtgaagt | accagggtcc | tcgggacttc | cagacactgg | aaaactggat | gctgcagaca | 660 |
| ctgaacgagg | agccagtgac | accagagccg | aagtggaac | cgcccagtgc | ccccgagctc | 720 |
| aagcaagggc | tgtatgagct | ctcagcaagc | aactttgagc | tgcacgttgc | acaaggcgac | 780 |
| cactttatca | agttcttcgc | tccgtggtgt | ggtcactgca | aagccctggc | tccaacctgg | 840 |
| gagcagctgg | ctctgggcct | tgaacattcc | gaaactgtca | agattggcaa | ggttgattgt | 900 |
| acacagcact | atgaactctg | ctccggaaac | caggttcgtg | gctatcccac | tcttctctgg | 960 |
| ttccgagatg | gaaaaaggt | ggatcagtac | aagggaaagc | gggatttgga | gtcactgagg | 1020 |
| gagtacgtgg | agtcgcagct | gcagcgcaca | gagactggag | cgacggagac | cgtcacgccc | 1080 |
| tcagaggccc | cggtgctggc | agctgagccc | gaggctgaca | agggcactgt | gttggcactc | 1140 |
| actgaaaata | acttcgatga | caccattgca | gaaggaataa | ccttcatcaa | gttttatgct | 1200 |
| ccatggtgtg | gtcattgtaa | gactctggct | cctacttggg | aggaactctc | taaaaggaa | 1260 |
| ttccctggtc | tggcggggt | caagatcgcc | gaagtagact | gcactgctga | acggaatatc | 1320 |
| tgcagcaagt | attcggtacg | aggctacccc | acgttattgc | ttttccgagg | agggaagaaa | 1380 |
| gtcagtgagc | acagtggagg | cagagacctt | gactcgttac | accgctttgt | cctgagccaa | 1440 |
| gcgaaagacg | aactttagga | acacagttgg | aggtcacctc | tcctgcccag | ctcccgcacc | 1500 |
| ctgcgtttag | gagttcagtc | ccacagaggc | cactgggttc | ccagtggtgg | ctgttcagaa | 1560 |
| agcagaacat | actaagcgtg | aggtatcttc | tttgtgtgtg | tgttttccaa | gccaacacac | 1620 |
| tctacagatt | ctttattaag | ttaagtttct | ctaagtaaat | gtgtaactca | tggtcactgt | 1680 |
| gtaaacattt | tcagtggcga | tatatcccct | ttgaccttct | cttgatgaaa | tttacatggt | 1740 |
| ttcctttgag | actaaaatag | cgttgaggga | aatgaaattg | ctggactatt | tgtggctcct | 1800 |
| gagttgagtg | attttggtga | aagaaagcac | atccaaagca | tagtttacct | gcccacgagt | 1860 |
| tctggaaagg | tggccttgtg | gcagtattga | cgttcctctg | atcttaaggt | cacagttgac | 1920 |
| tcaatactgt | gttggtccgt | agcatggagc | agattgaaat | gcaaaaccc | acacctctgg | 1980 |
| aagataccctt | cacggccgct | gctggagctt | ctgttgctgt | gaatacttct | ctcagtgtga | 2040 |

```
gaggttagcc gtgatgaaag cagcgttact tctgaccgtg cctgagtaag agaatgctga    2100
tgccataact ttatgtgtcg atacttgtca aatcagttac tgttcagggg atccttctgt    2160
ttctcacggg gtgaaacatg tctttagttc ctcatgttaa cacgaagcca gagcccacat    2220
gaactgttgg atgtcttcct tagaaagggt aggcatggaa aattccacga ggctcattct    2280
cagtatctca ttaactcatt gaaagattcc agttgtattt gtcacctggg gtgacaagac    2340
cagacaggct ttcccaggcc tgggtatcca gggaggctct gcagccctgc tgaagggccc    2400
taactagagt tctagagttt ctgattctgt ttctcagtag ccttttaga ggcttgctat     2460 acttggtctg cttcaaggag gtcgaccttc taatgtatga agaatgggat gcatttgatc    2520
tcaagaccaa agacagatgt cagtgggctg ctctggccct ggtgtgcacg gctgtggcag    2580
ctgttgatgc cagtgtcctc taactcatgc tgtccttgtg attaaacacc tctatctccc    2640
ttgggaataa gcacatacag gcttaagctc taagatagat aggtgtttgt ccttttacca    2700
tcgagctact tcccataata accactttgc atccaacact cttcacccac ctcccatacg    2760
caaggggatg tggatacttg gcccaaagta actggtggta ggaatcttag aaacaagacc    2820
acttatactg tctgtctgag gcagaagata acagcagcat ctcgaccagc ctctgcctta    2880
aaggaaatct ttattaatca cgtatggttc acagataatt ctttttttaa aaaacccaa     2940 cctcctagag aagcacaact gtcaagagtc ttgtacacac aacttcagct ttgcatcacg    3000
agtcttgtat tccaagaaaa tcaaagtggt acaatttgtt tgtttacact atgatacttt    3060
ctaaataaac tcttttttt t                                               3081

<210> SEQ ID NO 105
<211> LENGTH: 1881
<212> TYPE: DNA
<213> ORGANISM: Homo sapiens

<400> SEQUENCE: 105
acaaagggcc ggaaggaagc cggggagaca ggtgggtac tcgggaagct ggagcgggcc       60
ggcggtgcag tcacggggga gcgaggcctg ctgggcttgg caacgaggga ctcggcctcg    120
gaggcgaccc agaccacaca gacactgggt caaggagtaa gcagaggata aacaactgga    180
aggagagcaa gcacaaagtc atcatggctt cagcgtctgc tcgtggaaac caagataaag    240
atgcccattt tccaccacca agcaagcaga gcctgttgtt ttgtccaaaa tcaaaactgc    300
acatccacag agcagagatc tcaaagatta tgcgagaatg tcaggaagaa agtttctgga    360
agagagctct gccttttttct cttgtaagca tgcttgtcac ccaggggacta gtctaccaag    420 gttatttggc agctaattct agatttggat cattgcccaa agttgcacgt aagtcataga    480
aataaaaaag caagccaagt gtggtggctc acatctgtaa tcccagcact ttgggaggct    540
gaggtgggta gattgcttga gtccaggagt tcgagaccag cctgggcagc atggtgaaac    600
cttgtatcta tttttttaaa aagtaataaa taaataaaaa ctttgaaaaa aagacattac    660
tagcaactgg agatacgaat gtccagccta actaaactgc ctgtattgac ttttggaaaa    720
atcagcccct atttctgcc actctgcatt tcttagttca ctcaacactt tctgatatac     780
agcttagcag ttgggacttc ttcttagacc atccttaaag catggactaa gagggactgg    840
caggatatat aatgagatta tcaatagcag agcctctgca tgatagatca tttatggatt    900
tttattttct tcttttgccc tggccagtct tttcaaaatg ttttctacga tggatataaa    960
aaatgagtaa ttttttaagaa tcaggggatt tctaataata gagtaaccac aaacttgggg   1020
tttcatcttc cttcacctgg tatcaataga tcttttatgt acaaaaagga cacatttag    1080
```

-continued

| | |
|---|---:|
| ttgatagtct gaaaccacat tcattcctag caggaggaac agattcgaga tctcttccat | 1140 |
| aggagggtcc ctctcctttg tgacctctct cctataggca agatggactg aagctctcca | 1200 |
| ctactccaag gccataagga agattagggg catttctacc cagtgatttg gaagctacct | 1260 |
| atagccacaa cccagccacc ttccctgcc cccgtggcct caaccgtttg cttgacaggt | 1320 |
| gggccctctc tggccatctg tctccaggac agcactgtgg cttgctctgt cctgcccctt | 1380 |
| ccaccaccag tgcaaagttg agatggggaa gtctccagtt cccaatcctg ttcttttaa | 1440 |
| atagagactt cattctcaga gtcttcattc attgatttag cgtggtcctt ttaattttaa | 1500 |
| aattaccagc gttgatttt aaagctctag aaaataacta atggagaaga ttctcaacta | 1560 |
| atctctccca acctgctttt acagttgctg gtctcttggg atttggcctt ggaaaggtat | 1620 |
| catacatagg agtatgccag agtaaattcc attttttga agatcagctc cgtgggctg | 1680 |
| gttttggtcc acagcataac aggcactgcc tccttacctg tgaggaatgc aaaataaagc | 1740 |
| atggattaag tgagaaggga gactctcagc cttcagcttc ctaaattctg tgtctgtgac | 1800 |
| tttcgaagtt ttttaaacct ctgaatttgt acacatttaa aatttcaagt gtactttaaa | 1860 |
| ataaaatact tctaatggaa c | 1881 |

<210> SEQ ID NO 106
<211> LENGTH: 6790
<212> TYPE: DNA
<213> ORGANISM: Homo sapiens

<400> SEQUENCE: 106

| | |
|---|---:|
| cttctctccc agggcggtgc gacccggagc tccagcgccc gagtctccac ttcgtttgct | 60 |
| gaaacttgct ttctaccagc taagaaccat gctgcgagtg attgtggaat ctgccagcaa | 120 |
| tatccctaaa acgaaatttg gcaagccgga tcctattgtt tctgtcattt ttaaggatga | 180 |
| gaaaagaaa acaaagaaag ttgataatga attgaaccct gtctggaatg agattttgga | 240 |
| gtttgacttg aggggtatac cactggactt ttcatcttcc cttgggatta ttgtgaaaga | 300 |
| ttttgagaca attggacaaa ataaattaat tggcacggcg actgtagccc tgaaggacct | 360 |
| gactggtgac cagagcagat ccctgccgta caagctgatc tccctgctaa atgaaaaagg | 420 |
| gcaagatact ggggccacca ttgacttggt gatcggctat gatccgcctt ctgctccaca | 480 |
| tccaaatgac ctgagcgggc ccagcgtgcc aggcatggga ggagatgggg aagaagatga | 540 |
| aggtgatgaa gacaggttgg acaatgcagt caggggccct gggcccaagg ggccagttgg | 600 |
| gacggtgtcg gaagctcagc ttgctcggag gctcaccaaa gtaaagaaca gccggcggat | 660 |
| gctgtcaaat aagccacagg acttccagat ccgcgtccga gtgattgagg gccgacagtt | 720 |
| aagtggtaac aacataaggc ctgtggtcaa agttcacgtc tgtggccaga cacaccgaac | 780 |
| aagaatcaag agaggaaaca acccttttt tgatgagttg ttttctaca atgtcaacat | 840 |
| gacccttct gaattgatgg atgagatcat cagcatccgg gtttataatt ctcactctct | 900 |
| gcgggcagat tgtctgatgg gggaatttaa gattgatgtt ggatttgttt atgatgaacc | 960 |
| tggccatgct gtcatgagaa agtggcttct tctcaatgac ccggaagata ccagttcagg | 1020 |
| ttctaaaggt tatatgaaag tcagcatgtt tgtcctggga accggagatg agcctcctcc | 1080 |
| tgagagacga gatcgtgata atgacagtga tgatgtggag agtaatttgt tactccctgc | 1140 |
| tggcattgcc ctccggtggg tgaccttctt gctgaaaatc taccgagctg aggacatccc | 1200 |
| ccagatggat gatgccttct cacagacagt aaaggaaata tttggaggca atgcagataa | 1260 |

-continued

```
gaaaaatctc gtggatcctt ttgtagaagt ttcctttgct ggaaaaaagg tttgtacaaa    1320
cataattgag aaaaatgcaa acccagagtg gaatcaggtc gtcaatcttc agatcaagtt    1380
tccttcagtg tgtgaaaaaa taaaactaac aatatatgac tgggaccgtc ttactaaaaa    1440
tgatgtagtt ggaacaacat atctacacct ctctaaaatt gctgcctctg gtggggaagt    1500
ggaagtaaac acaggagaaa cagaggtagg ctttgttcca acgtttggac cttgttacct    1560
gaatctttat ggaagcccca gggagtacac gggattccca gaccccctatg atgagctgaa   1620 tactggaaag ggggaaggag ttgcctacag aggcaggatc ttggttgaat tagccacttt   1680
tcttgagaag acaccaccag ataaaaagct tgagcccatt tcaaatgatg acctgctggt    1740
tgttgagaaa taccagcgaa ggcggaagta cagcctgtct gccgtgtttc attcagccac    1800
catgttgcaa gatgttggtg aggccattca gtttgaagtc agcattggga actatggcaa    1860
caagtttgac accacctgta agcctttggc atcaacaact cagtacagcc gtgctgtatt    1920
tgatggcaac tactattatt acttgccttg ggcccacacc aagccagttg ttaccctgac    1980
ttcatactgg gaggatatta gtcatcgcct ggatgcggtg aacactctcc tagctatggc    2040
agaacggctc aaacaaata tagaagctct aaaatcaggg atacaaggta aaattcctgc     2100
aaaccagctg gctgaattgt ggctgaagct gatagatgaa gttatagaag acacgagata    2160
cacgttgcct ctcacagaag gaaaagccaa cgtcacagtt ctcgatactc agatccgaaa    2220
gctgcggtcc aggtctctct cccaaataca tgaggcggct gtgaggatga ggtcggaagc    2280
cacagatgtg aagtccacac tggcagaaat tgaggactgg cttgataaat taatgcagct    2340
gactgaagag ccacagaaca gcatgcctga catcatcatc tggatgatcc ggggagagaa    2400
gagactggcc tatgcacgaa ttcccgcaca tcaggtcttg tactccacca gtggtgagaa    2460
tgcatctgga aaatactgtg ggaaaaccca aaccatcttt ctgaagtatc cacaggagaa    2520
aaacaacggg ccaaaggtgc ctgtggagtt gcgagtgaac atctggctag gcttaagtgc    2580
tgtggagaag aagtttaaca gcttcgcaga aggaactttc accgtctttg ctgaaatgta    2640
tgaaaatcaa gctctcatgt ttggaaaatg gggtacttct ggattagtag gacgtcataa    2700
gttttctgat gtcacaggaa aaataaaact caagagggaa ttttttctgc ctccaaaagg    2760 ctggaatgg gaaggagagt ggatagttga tcctgaaaga agcttgctga ctgaggcaga    2820
tgcaggtcac acggagttca ctgatgaagt ctatcagaac gagagccgct accccggggg    2880
cgactggaag ccggccgagg acacctacac ggatgcgaac ggcgataaag cagcatcacc    2940
cagcgagttg acttgtcctc caggttggga atgggaagat gatgcatggt cttatgacat    3000
aaatcgagcg gtggatgaga aaggctggga atatggaatc accattcctc ctgatcataa    3060
gcccaaatcc tgggttgcag cagagaaaat gtaccacact catagacggc gaaggctggt    3120
ccgaaaacgc aagaaagatt taacacagac tgcttcaagc accgcaaggg ccatggagga    3180
attgcaagac caagagggct gggaatatgc ttctctaatt ggctggaaat ttcactggaa    3240
acaacgtagt tcagatacct tccgccgcag acgctggagg agaaaaatgg ctccttcaga    3300
aacacatggt gcagctgcca tctttaaact tgaaggtgcc cttggggcag acactaccga    3360
agatggggat gagaagagcc tggagaaaca gaagcacagt gccaccactg tgttcggagc    3420 aaacacccccc attgtttcct gcaattttga cagagtctac atctaccatc tgcgctgcta    3480
tgtctatcaa gccagaaacc tcttggcttt agataaggat agcttttcag atccatatgc    3540
tcatatctgt ttcctccatc ggagcaaaac cactgagatc atccattcaa ccctgaatcc    3600
cacgtgggac caaacaatta tattcgatga agttgaaatc tatgggggaac cccaaacagt    3660
```

```
tctacagaat ccacccaaag ttatcatgga actttttgac aatgaccaag tgggcaaaga    3720
tgaatttta ggacgaagca ttttctctcc tgtggtgaaa ctgaactcag aaatggacat    3780
cacacccaaa cttctctggc acccagtaat gaatggagac aaagcctgcg gggatgttct    3840
tgtaactgca gagctgattc tgaggggcaa ggatggctcc aaccttccca ttcttccccc    3900
tcaaagggcg ccaaatctat acatggtccc ccagggatc aggcctgtgg tccagctcac     3960
tgccattgag attctagctt ggggcttaag aaatatgaaa aacttccaga tggcttctat    4020
cacatccccc agtcttgttg tggagtgtgg aggagaaagg gtggaatcgg tggtgatcaa    4080
aaaccttaag aagacaccca actttccaag ttctgttctc ttcatgaaag tgttcttgcc    4140
caaggaggaa ttgtacatgc ccccactggt gatcaaggtc atcgaccaca ggcagtttgg    4200
gcggaagcct gtcgtcggcc agtgcaccat cgagcgcctg daccgctttc gctgtgaccc    4260
ttatgcaggg aaagaggaca tcgtcccaca gctcaaagcc tcccttctgt ctgccccacc    4320
atgccgggac atcgttatcg aaatggaaga caccaaacca ttactggctt ctaagctgac    4380
agaaaaggag gaagaaatcg tggactggtg gagtaaattt tatgcttcct caggggaaca    4440
tgaaaaatgc ggacagtata ttcagaaagg ctattccaag ctcaagatat ataattgtga    4500
actagaaaat gtagcagaat ttgagggcct gacagacttc tcagatacgt tcaagttgta    4560
ccgaggcaag tcggatgaaa atgaagatcc ttctgtggtt ggagagttta agggctcctt    4620
tcggatctac cctctgccgg atgacccag cgtgccagcc cctcccagac agtttcggga    4680
attacctgac agcgtcccac aggaatgcac ggttaggatt tacattgttc gaggcttaga    4740
gctccagccc caggacaaca atggcctgtg tgacccttac ataaaaataa cactgggcaa    4800
aaaagtcatt gaagaccgag atcactacat tcccaacact ctcaacccag tctttggcag    4860
gatgtacgaa ctgagctgct acttacctca agaaaaagac ctgaaaattt ctgtctatga    4920
ttatgacacc tttacccggg atgaaaaagt aggagaaaca attattgatc tggaaaaccg    4980
attcctttcc cgctttgggt cccactgcgg cataccagag gagtactgtg tttctggagt    5040
caatacctgg cgagatcaac tgagaccaac acagctgctt caaaatgtcg ccagattcaa    5100
aggcttccca caacccatcc tttccgaaga tgggagtaga atcagatatg gaggacgaga    5160
ctacagcttg gatgaatttg aagccaacaa aatcctgcac cagcacctcg ggcccctga    5220
agagcggctt gctcttcaca tcctcaggac tcaggggctg gtccctgagc acgtggaaac    5280
aaggactttg cacagcacct tccagcccaa catttcccag ggaaaacttc agatgtgggt    5340
ggatgttttc cccaagagtt tggggccacc aggccctcct ttcaacatca caccccggaa    5400
agccaagaaa tactacctgc gtgtgatcat ctggaacacc aaggacgtta tcttggacga    5460
gaaaagcatc acaggagagg aaatgagtga catctacgtc aaaggctgga ttcctggcaa    5520
tgaagaaaac aaacagaaaa cagatgtcca ttacagatct ttggatggtg aagggaattt    5580
taactggcga tttgtttttcc cgtttgacta ccttccagcc gaacaactct gtatcgttgc    5640
gaaaaaagag catttctgga gtattgacca aacggaattt cgaatcccac ccaggctgat    5700
cattcagata tgggacaatg acaagttttc tctggatgac tacttgggtt tcctagaact    5760
tgacttgcgt cacacgatca ttcctgcaaa atcaccagag aaatgcaggt tggacatgat    5820
tccggacctc aaagccatga accccttaa agccaagaca gcctcctct ttgagcagaa     5880
gtccatgaaa ggatggtggc catgctacgc agagaaagat ggcgcccgcg taatggctgg    5940
gaaagtggag atgacattgg aaatcctcaa cgagaaggag gccgacgaga ggccagccgg    6000
```

| | | |
|---|---|---|
| gaaggggcgg gacgaaccca acatgaaccc caagctggac ttaccaaatc gaccagaaac | 6060 |
| ctccttcctc tggttcacca acccatgcaa gaccatgaag ttcatcgtgt ggcgccgctt | 6120 |
| taagtgggtc atcatcggct tgctgttcct gcttatcctg ctgctcttcg tggccgtgct | 6180 |
| cctctactct ttgccgaact atttgtcaat gaagattgta agccaaatg tgtaacaaag | 6240 |
| gcaaaggctt catttcaaga gtcatccagc aatgagagaa tcctgcctct gtagaccaac | 6300 |
| atccagtgtg attttgtgtc tgagaccaca ccccagtagc aggttacgcc atgtcaccga | 6360 |
| gccccattga ttcccagagg gtcttagtcc tggaaagtca ggccaacaag caacgtttgc | 6420 |
| atcatgttat ctcttaagta ttaaaagttt tattttctaa agtttaaatc atgttttca | 6480 |
| aaatattttt caaggtggct ggttccattt aaaaatcatc ttttatatg tgtcttcggt | 6540 |
| tctagacttc agcttttgga aattgctaaa tagaattcaa aaatctctgc atcctgaggt | 6600 |
| gatatacttc atatttgtaa tcaactgaaa gagctgtgca ttataaaatc agttagaata | 6660 |
| gttagaacaa ttcttattta tgcccacaac cattgctata ttttgtatgg atgtcataaa | 6720 |
| agtctattta acctctgtaa tgaaactaaa taaaaatgtt tcacctttaa aaaaaaaaa | 6780 |
| aaaaaaaaaa | 6790 |

<210> SEQ ID NO 107
<211> LENGTH: 6719
<212> TYPE: DNA
<213> ORGANISM: Homo sapiens

<400> SEQUENCE: 107

| | | |
|---|---|---|
| atgctgcgag tgattgtgga atctgccagc aatatcccta aaacgaaatt tggcaagccg | 60 |
| gatcctattg tttctgtcat ttttaaggat gagaaaaaga aaacaaagaa agttgataat | 120 |
| gaattgaacc ctgtctggaa tgagattttg gagtttgact tgagggggtat accactggac | 180 |
| ttttcatctt cccttgggat tattgtgaaa gattttgaga caattggaca aaataaatta | 240 |
| attggcacgg cgactgtagc cctgaaggac ctgactggtg accagagcag atccctgccg | 300 |
| tacaagctga tctccctgct aaatgaaaaa gggcaagata ctggggccac cattgacttg | 360 |
| gtgatcggct atgatccgcc ttctgctcca catccaaatg acctgagcgg gcccagcgtg | 420 |
| ccaggcatgg gaggagatgg ggaagaagat gaaggtgatg aagacaggtt ggacaatgca | 480 |
| gtcaggggcc ctgggcccaa ggggccagtt gggacggtgt cggaagctca gcttgctcgg | 540 |
| aggctcacca agtaaagaa cagccggcgg atgctgtcaa ataagccaca ggacttccag | 600 |
| atccgcgtcc gagtgattga gggccgacag ttaagtggta caacataag gcctgtggtc | 660 |
| aaagttcacg tctgtggcca gacacaccga acaagaatca agagaggaaa caacccttt | 720 |
| tttgatgagt tgttttcta caatgtcaac atgaccccctt ctgaattgat ggatgagatc | 780 |
| atcagcatcc gggtttataa ttcccactct ctgcgggcag attgtctgat ggggaattt | 840 |
| aagattgatg ttggatttgt ttatgatgaa cctggccatg ctgtcatgag aaagtggctt | 900 |
| cttctcaatg acccggaaga taccagttca ggttctaaag ttatatgaa agtcagcatg | 960 |
| tttgtccctg gaaccggaga tgagcctcct cctgagagac gagatcgtga taatgacagt | 1020 |
| gatgatgtgg agagtaattt gttactccct gctggcattg ccctccggtg ggtgaccttc | 1080 |
| ttgctgaaaa tctaccgagc tgaggacatc ccccagatgg atgatgcctt ctcacagaca | 1140 |
| gtaaaggaaa tatttggagg caatgcagat aagaaaaatc tcgtggatcc ttttgtagaa | 1200 |
| gtttcctttg ctgaaaaaaa ggtttgtaca aacataattg agaaaaatgc aaacccagag | 1260 |
| tggaatcagg tcgtcaatct tcagatcaag tttccttcag tgtgtgaaaa aataaaacta | 1320 |

```
acaatatatg actgggaccg tcttactaaa aatgatgtag ttggaacaac atatctacac   1380
ctctctaaaa ttgctgcctc tggtggggaa gtggaagatt tctcatcttc gggaactggg   1440
gctgcatcat atacagtaaa cacaggagaa acagaggtag gctttgttcc aacgtttgga   1500
ccttgttacc tgaatcttta tggaagcccc agagagtaca cgggattccc agacccctat   1560
gatgagctga atactggaaa gggggaagga gttgcctaca gaggcaggat cttggttgaa   1620
ttagccactt ttcttgagaa gacaccacca gataaaaagc ttgagcccat ttcaaatgat   1680
gacctgctgg ttgttgagaa ataccagcga aggcggaagt acagcctgtc tgccgtgttt   1740
cattcagcca ccatgttgca agatgttggt gaggccattc agtttgaagt cagcattggg   1800
aactatggca caagtttgaa caccacctgt aagcctttgg catcaacaac tcagtacagc   1860
cgtgctgtat ttgatggcaa ctactattat tacttgcctt gggcccacac caagccagtt   1920
gttaccctga cttcatactg gaggatatt agtcatcgcc tggatgcggt gaacactctc    1980
ctagctatgg cagaacggct gcaaacaaat atagaagctc taaaatcagg gatacaaggt   2040
aaaattcctg caaaccagct ggctgaattg tggctgaagc tgatagatga agttatagaa   2100
gacacgagat acacgttgcc tctcacagaa ggaaaagcca acgtcacagt tctcgatact   2160
cagatccgaa agctgcggtc caggtctctc tcccaaatac atgaggcggc tgtgaggatg   2220
aggtcggaag ccacagatgt gaagtccaca ctggcagaaa ttgaggactg gcttgataaa   2280
ttaatgcagc tgactgaaga gccacagaac agcatgcctg acatcatcat ctggatgatc   2340
cggggagaga agagactggc ctatgcacga attcccgcac atcaggtctt gtactccacc   2400
agtggtgaga atgcatctgg aaaatactgt gggaaaaccc aaaccatctt tctgaagtat   2460
ccacaggaga aaaacaacgg gccaaaggtg cctgtggagt tgcgagtgaa catctggcta   2520
ggcttaagtg ctgtggagaa gaagtttaac agcttcgcag aaggaacttt caccgtcttt   2580
gcggaaatgt atgaaaatca agctctcatg tttggaaaat ggggtacttc tggattagta   2640
ggacgtcata agttttctga tgtcacagga aaaataaaac tcaagaggga atttttttctg  2700
cctccaaaag ctgggaatgg gaaggagag tggatagttg atcctgaaag aagcttgctg    2760
actgaggcag atgcaggtca cacggagttc actgatgaag tctatcagaa cgagagccgc   2820
taccccgggg gcgactggaa gccggccgag gacacctaca cggatgcgaa cggcgataaa   2880
gcagcatcac ccagcgagtt gacttgtcct ccaggttggg aatgggaaga tgatgcatgg   2940
tcttatgaca taaatcgagc ggtggatgag aaaggctggg aatatggaat caccattcct   3000
cctgatcata agcccaaatc ctgggttgca gcagagaaaa tgtaccacac tcatagacgg   3060
cgaaggctgg tccgaaaacg caagaaagat ttaacacaga ctgcttcaag caccgcaagg   3120
gccatggagg aattgcaaga ccaagagggc tgggaatatg cttctctaat tggctggaaa   3180
tttcactgga acaacgtag ttcagatacc ttccgccgca gacgctggag gagaaaaatg    3240
gctccttcag aaacacatgg tgcagctgcc atctttaaac ttgaaggtgc ccttggggca   3300
gacactaccg aagatgggga tgagaagagc ctggagaaac agaagcacag tgccaccact   3360
gtgttcggag caaacacccc cattgtttcc tgcaattttg acagagtcta catctaccat   3420
ctgcgctgct atgtctatca agccagaaac ctcttggctt tagataagga tagcttttca   3480
gatccatatg ctcatatctg tttcctccat cggagcaaaa ccactgagat catccattca   3540
accctgaatc ccacgtggga ccaaacaatt atattcgatg aagttgaaat ctatggggaa   3600
ccccaaacag ttctacagaa tccacccaaa gttatcatgg aacttttga caatgaccaa   3660
```

```
gtgggcaaag atgaattttt aggacgaagc attttctctc ctgtggtgaa actgaactca  3720
gaaatggaca tcacacccaa acttctctgg cacccagtaa tgaatggaga caaagcctgc  3780
ggggatgttc ttgtaactgc agagctgatt ctgaggggca aggatggctc caaccttccc  3840
attcttcccc ctcaaagggc gccaaatctg tacatggtcc cccaggggat caggcctgtg  3900
gtccagctca ctgccattga gattctagct tggggcttaa gaaatatgaa aaacttccag  3960
atggcttcta tcacatcccc cagtcttgtt gtggagtgtg gaggagaaag ggtggaatcg  4020
gtggtgatca aaaaccttaa gaagacaccc aactttccaa gttctgttct cttcatgaaa  4080
gtgttcttgc ccaaggagga attgtacatg cccccactgg tgatcaaggt catcgaccac  4140
aggcagtttg gcggaagcc tgtcgtcggc cagtgcacca tcgagcgcct ggaccgcttt  4200
cgctgtgacc cttatgcagg gaaagaggac atcgtcccac agctcaaagc ctcccttctg  4260
tctgccccac catgccggga catcgttatc gaaatggaag acaccaaacc attactggct  4320
tctaagctga cagaaaagga ggaagaaatc gtggactggt ggagtaaatt ttatgcttcc  4380
tcagggaac atgaaaaatg cggacagtat attcagaaag ctattccaa gctcaagata  4440
tataattgcg aactagaaaa tgtagcagaa tttgagggcc tgacagactt ctcagatacg  4500
ttcaagttgt accgaggcaa gtcggatgaa aatgaagatc cttctgtggt tggagagttt  4560
aagggctcct ttcggatcta ccctctgccg gatgaccca gcgtgccagc ccctcccaga  4620
cagtttcggg aattacctga cagcgtccca caggaatgca cggttaggat ttacattgtt  4680
cgaggcttag agctccagcc ccaggacaac aatggcctgt gtgaccctta cataaaaata  4740
acactgggca aaaaagtcat tgaagaccga gatcactaca ttcccaacac tctcaaccca  4800
gtctttggca ggatgtacga actgagctgc tacttacctc aagaaaaaga cctgaaaatt  4860
tctgtctatg attatgacac ctttacccgg gatgaaaaag taggagaaac aattattgat  4920
ctggaaaacc gattcctttc ccgctttggg tcccactgcg gcataccaga ggagtactgt  4980
gtttctggag tcaatacctg gcgagatcaa ctgagaccaa cacagctgct tcaaaatgtc  5040
gccagattca aaggcttccc acaacccatc ctttccgaag atgggagtag aatcagatat  5100
ggaggacgag actacagctt ggatgaattt gaagccaaca aaatcctgca ccagcacctc  5160
ggggcccctg aagagcggct tgctcttcac atcctcagga ctcagggct ggtccctgag  5220
cacgtggaaa caaggacttt gcacagcacc ttccagccca catttcccca gggaaaactt  5280
cagatgtggg tggatgtttt ccccaagagt ttggggccac caggccctcc tttcaacatc  5340
acaccccgga aagccaagaa atactacctg cgtgtgatca tctggaacac caaggacgtt  5400
atcttggacg agaaaagcat cacaggagag gaaatgagtg acatctacgt caaaggctgg  5460
attcctggca tgaagaaaaa caaacagaaa acagatgtcc attacagatc tttggatggt  5520
gaagggaatt ttaactggcg atttgttttc ccgtttgact accttccagc cgaacaactc  5580
tgtatcgttg cgaaaaaaga gcatttctgg agtattgacc aaacggaatt tcgaatccca  5640
cccaggctga tcattcagat atgggacaat gacaagtttt ctctggatga ctacttgggt  5700
ttcctagaac ttgacttgcg tcacacgatc attcctgcaa aatcaccaga gaatgcagg  5760
ttggacatga ttccggacct caaagccatg aaccccctta agccaagac agcctccctc  5820
tttgagcaga agtccatgaa aggatggtgg ccatgctacg cagagaaaga tggcgcccgc  5880
gtaatggctg ggaaagtgga gatgacattg gaaatcctca acgagaagga ggccgacgag  5940
aggccagccg ggaaggggcg ggacgaaccc aacatgaacc ccaagctgga cttaccaaat  6000
cgaccagaaa cctccttcct ctggttcacc aacccatgca agaccatgaa gttcatcgtg  6060
```

```
tggcgccgct ttaagtgggt catcatcggc ttgctgttcc tgcttatcct gctgctcttc    6120
gtggccgtgc tcctctactc tttgccgaac tatttgtcaa tgaagattgt aaagccaaat    6180
gtgtaacaaa ggcaaaggct tcatttcaag agtcatccag caatgagaga atcctgcctc    6240
tgtagaccaa catccagtgt gattttgtgt ctgagaccac accccagtag caggttacgc    6300
catgtcaccg agcccattg attcccagag ggtcttagtc ctggaaagtc aggccaacaa    6360
gcaacgtttg catcatgtta tctcttaagt attaaaagtt ttattttcta aagtttaaat    6420 catgttttc aaaatattt tcaaggtggc tggttccatt taaaaatcat cttttatat    6480 gtgtcttcgg ttctagactt cagcttttgg aaattgctaa atagaattca aaaatctctg    6540
catcctgagg tgatatactt catatttgta atcaactgaa agagctgtgc attataaaat    6600
cagttagaat agttagaaca attcttattt atgcccacaa ccattgctat attttgtatg    6660
gatgtcataa aagtctattt aacctctgta atgaaactaa ataaaatgt ttcaccttt     6719

<210> SEQ ID NO 108
<211> LENGTH: 6818
<212> TYPE: DNA
<213> ORGANISM: Homo sapiens

<400> SEQUENCE: 108 atcctcccctt cactgggaga gaacttctct cccagggcgg tgcgacccgg agctccagcg      60
cccgagtctc cacttcgttt gctgaaactt gctttctacc agctaagaac catgctgcga     120
gtgattgtgg aatctgccag caatatccct aaaacgaaat ttggcaagcc ggatcctatt     180
gtttctgtca ttttttaagga tgagaaaaag aaaacaaaga aagttgataa tgaattgaac     240
cctgtctgga atgagatttt ggagtttgac ttgaggggta taccactgga cttttcatct     300
tcccttggga ttattgtgaa agattttgag acaattggac aaaataaatt aattggcacg     360
gcgactgtag ccctgaagga cctgactggt gaccagagca gatccctgcc gtacaagctg     420
atctccctgc taaatgaaaa agggcaagat actggggcca ccattgactt ggtgatcggc     480
tatgatccgc cttctgctcc acatccaaat gacctgagcg ggcccagcgt gccaggcatg     540
ggaggagatg gggaagaaga tgaaggtgat gaagacaggt tggacaatgc agtcaggggc     600
cctgggccca aggggccagt tgggacggtg tcggaagctc agcttgctcg gaggctcacc     660
aaagtaaaga acagccggcg gatgctgtca aataagccac aggacttcca gatccgcgtc     720
cgagtgattg agggccgaca gttaagtggt aacaacataa ggcctgtggt caaagttcac     780
gtctgtggcc agacacaccg aacaagaatc aagagaggaa acaacccttt ttttgatgag     840 ttgttttct acaatgtcaa catgaccccct tctgaattga tggatgagat catcagcatc     900
cgggtttata attctcactc tctgcgggca gattgtctga tggggaatt taagattgat     960 gttggatttg tttatgatga acctggccat gctgtcatga gaaagtggct tcttctcaat    1020
gacccggaag ataccagttc aggttctaaa ggttatatga aagtcagcat gtttgtcctg    1080
ggaaccggag atgagcctcc tcctgagaga cgagatcgtg ataatgacag tgatgatgtg    1140
gagagtaatt tgttactccc tgctggcatt gccctccggt gggtgacctt cttgctgaaa    1200
atctaccgag ctgaggacat cccccagatg gatgatgcct tctcacagac agtaaaggaa    1260
atatttggag gcaatgcaga taagaaaaat ctcgtggatc cttttgtaga agtttccttt    1320
gctggaaaaa aggtttgtac aaacataatt gagaaaatg caaacccaga gtggaatcag    1380
gtcgtcaatc ttcagatcaa gtttcctca gtgtgtgaaa aataaaaact aacaatatat     1440
```

```
gactgggacc gtcttactaa aaatgatgta gttggaacaa catatctaca cctctctaaa    1500
attgctgcct ctggtgggga agtggaagat ttctcatctt cgggaactgg ggctgcatca    1560
tatacagtaa acacaggaga aacagaggta ggctttgttc caacgtttgg accttgttac    1620
ctgaatcttt atggaagccc cagagagtac acgggattcc cagaccccta tgatgagctg    1680
aatactggaa aggggaagg agttgcctac agaggcagga tcttggttga attagccact    1740
tttcttgaga agacaccacc agataaaaag cttgagccca tttcaaatga tgacctgctg    1800
gttgttgaga ataccagcg aaggcggaag tacagcctgt ctgccgtgtt tcattcagcc    1860
accatgttgc aagatgttgg tgaggccatt cagtttgaag tcagcattgg gaactatggc    1920
aacaagtttg acaccacctg taagccttg gcatcaacaa ctcagtacag ccgtgctgta    1980
tttgatggca actactatta ttacttgcct tgggcccaca ccaagccagt tgttaccctg    2040
acttcatact gggaggatat tagtcatcgc ctggatgcgg tgaacactct cctagctatg    2100
gcagaacggc tgcaaacaaa tatagaagct ctaaaatcag ggatacaagg taaaattcct    2160
gcaaaccagc tggctgaatt gtggctgaag ctgatagatg aagttataga agacacgaga    2220
tacacgttgc ctctcacaga aggaaaagcc aacgtcacag ttctcgatac tcagatccga    2280
aagctgcggt ccaggtctct ctcccaaata catgaggcgg ctgtgaggat gaggtcggaa    2340
gccacagatg tgaagtccac actggcagaa attgaggact ggcttgataa attaatgcag    2400
ctgactgaag agccacagaa cagcatgcct gacatcatca tctggatgat ccggggagag    2460
aagagactgg cctatgcacg aattcccgca catcaggtct tgtactccac cagtggtgag    2520
aatgcatctg gaaaatactg tgggaaaacc caaaccatct ttctgaagta tccacaggag    2580
aaaaacaacg ggccaaaggt gcctgtggag ttgcgagtga acatctggct aggcttaagt    2640
gctgtggaga agaagtttaa cagcttcgca gaaggaactt tcaccgtctt tgctgaaatg    2700
tatgaaaatc aagctctcat gtttggaaaa tggggtactt ctggattagt aggacgtcat    2760
aagttttctg atgtcacagg aaaaataaaa ctcaagaggg aattttttct gcctccaaaa    2820
ggctgggaat gggaaggaga gtggatagtt gatcctgaaa gaagcttgct gactgaggca    2880
gatgcaggtc acacggagtt cactgatgaa gtctatcaga acgagagccg ctaccccggg    2940
ggcgactgga agccggccga ggacacctac acggatgcga acggcgataa agcagcatca    3000
cccagcgagt tgacttgtcc tccaggttgg gaatgggaag atgatgcatg gtcttatgac    3060
ataaatcgag cggtggatga gaaaggctgg gaatatggaa tcaccattcc tcctgatcat    3120
aagcccaaat cctgggttgc agcagagaaa atgtaccaca ctcatagacg gcgaaggctg    3180
gtccgaaaac gcaagaaaga tttaacacag actgcttcaa gcaccgcaag ggccatggag    3240
gaattgcaag accaagaggg ctgggaatat gcttctctaa ttggctggaa atttcactgg    3300
aaacaacgta gttcagatac cttccgccgc agacgctgga ggagaaaaat ggctccttca    3360
gaaacacatg gtgcagctgc catctttaaa cttgaaggtg cccttgggc agacactacc    3420 gaagatgggg atgagaagag cctggagaaa cagaagcaca gtgccaccac tgtgttcgga    3480
gcaaacaccc ccattgtttc ctgcaatttt gacagagtct acatctacca tctgcgctgc    3540
tatgtctatc aagccagaaa cctcttggct ttagataagg atagcttttc agatccatat    3600
gctcatatct gtttcctcca tcggagcaaa accactgaga tcatccattc aaccctgaat    3660
cccacgtggg accaaacaat tatattcgat gaagttgaaa tctatgggga accccaaaca    3720
gttctacaga atccacccaa agttatcatg gaacttttg acaatgacca agtgggcaaa    3780
gatgaatttt taggacgaag catttctct cctgtggtga aactgaactc agaaatggac    3840
```

-continued

```
atcacaccca aacttctctg gcacccagta atgaatggag acaaagcctg cggggatgtt     3900
cttgtaactg cagagctgat tctgaggggc aaggatggct ccaaccttcc cattcttccc     3960
cctcaaaggg cgccaaatct atacatggtc ccccagggga tcaggcctgt ggtccagctc     4020
actgccattg agattctagc ttggggctta agaaatatga aaaacttcca gatggcttct     4080
atcacatccc ccagtcttgt tgtggagtgt ggaggagaaa gggtggaatc ggtggtgatc     4140
aaaaacctta agaagacacc caactttcca agttctgttc tcttcatgaa agtgttcttg     4200
cccaaggagg aattgtacat gcccccactg gtgatcaagg tcatcgacca caggcagttt     4260
gggcggaagc ctgtcgtcgg ccagtgcacc atcgagcgcc tggaccgctt cgctgtgac      4320 ccttatgcag ggaaagagga catcgtccca cagctcaaag cctcccttct gtctgcccca     4380
ccatgccggg acatcgttat cgaaatggaa gacaccaaac cattactggc ttctaaggag     4440
gaagaaatcg tggactggtg gagtaaattt tatgcttcct caggggaaca tgaaaaatgc     4500
ggacagtata ttcagaaagg ctattccaag ctcaagatat ataattgtga actagaaaat     4560
gtagcagaat ttgagggcct gacagacttc tcagatacgt tcaagttgta ccgaggcaag     4620
tcggatgaaa atgaagatcc ttctgtggtt ggagagttta agggctcctt tcggatctac     4680
cctctgccgg atgaccccag cgtgccagcc cctcccagac agtttcggga attacctgac     4740
agcgtcccac aggaatgcac ggttaggatt tacattgttc gaggcttaga gctccagccc     4800
caggacaaca atggcctgtg tgacccttac ataaaaataa cactgggcaa aaaagtcatt     4860
gaagaccgag atcactacat tcccaacact ctcaacccag tctttggcag gatgtacgaa     4920
ctgagctgct acttacctca agaaaaagac ctgaaaattt ctgtctatga ttatgacacc     4980
tttacccggg atgaaaaagt aggagaaaca attattgatc tggaaaaccg attcctttcc     5040
cgctttgggt cccactgcgg cataccagag gagtactgtg tttctggagt caatacctgg     5100
cgagatcaac tgagaccaac acagctgctt caaaatgtcg ccagattcaa aggcttccca     5160
caacccatcc tttccgaaga tgggagtaga atcagatatg gaggacgaga ctacagcttg     5220
gatgaatttg aagccaacaa aatcctgcac cagcacctcg gggcccctga agagcggctt     5280
gctcttcaca tcctcaggac tcaggggctg gtccctgagc acgtggaaac aaggactttg     5340
cacagcacct tccagcccaa catttcccag ggaaaacttc agatgtgggt ggatgttttc     5400
cccaagagtt tggggccacc aggccctcct ttcaacatca caccccggaa agccaagaaa     5460
tactacctgc gtgtgatcat ctggaacacc aaggacgtta tcttggacga gaaaagcatc     5520
acaggagagg aaatgagtga catctacgtc aaaggctgga ttcctggcaa tgaagaaaac     5580
aaacagaaaa cagatgtcca ttacagatct ttggatggtg aagggaattt taactggcga     5640
tttgttttcc cgtttgacta ccttccagcc gaacaactct gtatcgttgc gaaaaagag      5700 catttctgga gtattgacca aacggaattt cgaatcccac ccaggctgat cattcagata     5760
tgggacaatg acaagttttc tctggatgac tacttgggtt tcctagaact tgacttgcgt     5820
cacacgatca ttcctgcaaa atcaccagag aaatgcaggt tggacatgat tccggacctc     5880
aaagccatga accccttaa agccaagaca gcctccctct ttgagcagaa gtccatgaaa      5940
ggatggtggc catgctacgc agagaaagat ggcgcccgcg taatggctgg aaagtggag      6000 atgacattgg aaatcctcaa cgagaaggag gccgacgaga ggccagccgg aaggggcgg     6060 gacgaaccca acatgaaccc caagctggac ttaccaaatc gaccagaaac ctccttcctc     6120
tggttcacca acccatgcaa gaccatgaag ttcatcgtgt ggcgccgctt taagtgggtc     6180
```

| | |
|---|---|
| atcatcggct tgctgttcct gcttatcctg ctgctcttcg tggccgtgct cctctactct | 6240 |
| ttgccgaact atttgtcaat gaagattgta agcccaaatg tgtaacaaag gcaaaggctt | 6300 |
| catttcaaga gtcatccagc aatgagagaa tcctgcctct gtagaccaac atccagtgtg | 6360 |
| attttgtgtc tgagaccaca ccccagtagc aggttacgcc atgtcaccga gccccattga | 6420 |
| ttcccagagg gtcttagtcc tggaaagtca ggccaacaag caacgtttgc atcatgttat | 6480 |
| ctcttaagta ttaaaagttt tattttctaa agtttaaatc atgttttttca aaatattttt | 6540 |
| caaggtggct ggttccattt aaaaatcatc ttttttatatg tgtcttcggt tctagacttc | 6600 |
| agcttttgga aattgctaaa tagaattcaa aaatctctgc atcctgaggt gatatacttc | 6660 |
| atatttgtaa tcaactgaaa gagctgtgca ttataaaatc agttagaata gttagaacaa | 6720 |
| ttcttattta tgcccacaac cattgctata ttttgtatgg atgtcataaa agtctattta | 6780 |
| acctctgtaa tgaaactaaa taaaaatgtt tcacctttt | 6818 |

<210> SEQ ID NO 109
<211> LENGTH: 6936
<212> TYPE: DNA
<213> ORGANISM: Homo sapiens

<400> SEQUENCE: 109

| | |
|---|---|
| actgggagag aacttctctc ccagggcggt gcgacccgga gctccagcgc ccgagtctcc | 60 |
| acttcgtttg ctgaaacttg ctttctacca gctaagaacc atgctgcgag tgattgtgga | 120 |
| atctgccagc aatatcccta aaacgaaatt tggcaagccg gatcctattg tttctgtcat | 180 |
| ttttaagggt tccatgagcc agatccgaat tgaggctgga gtgagtgcct gtgagccagg | 240 |
| ggtggccatt ctgccctaag ttccatgcgg acagccaggc tgtgaagctg aatctagctg | 300 |
| agattagact acacagacct ctgagaccaa tttcaactct gagacttgat gattcttcca | 360 |
| aacagtcctc caaacagaac agatgagaaa agaaaacaa agaaagttga taatgaattg | 420 |
| aaccctgtct ggaatgagat tttggagttt gacttgaggg gtataccact ggacttttca | 480 |
| tcttcccttg ggattattgt gaaagatttt gagacaattg dacaaaataa attaattggc | 540 |
| acggcgactg tagccctgaa ggacctgact ggtgaccaga gcagatccct gccgtacaag | 600 |
| ctgatctccc tgctaaatga aaagggcaa gatactgggg ccaccattga cttggtgatc | 660 |
| ggctatgatc cgccttctgc tccacatcca aatgacctga gcgggcccag cgtgccaggc | 720 |
| atggaggag atggggaaga agatgaaggt gatgaagaca ggttggacaa tgcagtcagg | 780 |
| ggccctgggc ccaaggggcc agttgggacg tgtgtcggaag ctcagcttgc tcggaggctc | 840 |
| accaaagtaa agaacagccg gcggatgctg tcaaataagc cacaggactt ccagatccgc | 900 |
| gtccgagtga ttgagggccg acagttaagt ggtaacaaca taaggcctgt ggtcaaagtt | 960 |
| cacgtctgtg gccagacaca ccgaacaaga atcaagagag gaaacaaccc ttttttttgat | 1020 |
| gagttgtttt tctacaatgt caacatgacc ccttctgaat tgatggatga gatcatcagc | 1080 |
| atccgggttt ataattctca ctctctgcgg gcagattgtc tgatgggga atttaagatt | 1140 |
| gatgttggat ttgttttatga tgaacctggc catgctgtca tgagaaagtg gcttcttctc | 1200 |
| aatgacccgg aagataccag ttcaggttct aaaggttata tgaaagtcag catgtttgtc | 1260 |
| ctgggaaccg gagatgagcc tcctcctgag agacgagatc gtgataatga cagtgatgat | 1320 |
| gtggagagta attttgttact ccctgctggc cattgcctcc ggtgggtgac cttcttgctg | 1380 |
| aaaatctacc gagctgagga catccccag atggatgatg ccttctcaca gacagtaaag | 1440 |
| gaaatatttg gaggcaatgc agataagaaa aatctcgtgg atccttttgt agaagtttcc | 1500 |

```
tttgctggaa aaaaggtttg tacaaacata attgagaaaa atgcaaaccc agagtggaat    1560
caggtcgtca atcttcagat caagtttcct tcagtgtgtg aaaaaataaa actaacaata    1620
tatgactggg accgtcttac taaaaatgat gtagttggaa caacatatct acacctctct    1680
aaaattgctg cctctggtgg ggaagtggaa gtaaacacag gagaaacaga ggtaggcttt    1740
gttccaacgt ttggaccttg ttacctgaat ctttatggaa gccccagaga gtacacggga    1800
ttcccagacc cctatgatga gctgaatact ggaaaggggg aaggagttgc ctacagaggc    1860
aggatcttgg ttgaattagc cacttttctt gagaagacac caccagataa aaagcttgag    1920
cccatttcaa atgatgacct gctggttgtt gagaaatacc agcgaaggcg gaagtacagc    1980
ctgtctgccg tgtttcattc agccaccatg ttgcaagatg ttggtgaggc cattcagttt    2040
gaagtcagca ttgggaacta tggcaacaag tttgacacca cctgtaagcc tttggcatca    2100
acaactcagt acagccgtgc tgtatttgat ggcaactact attattactt gccttgggcc    2160
cacaccaagc cagttgttac cctgacttca tactgggagg atattagtca tcgcctggat    2220
gcggtgaaca ctctcctagc tatggcagaa cggctgcaaa caaatataga agctctaaaa    2280
tcagggatac aaggtaaaat tcctgcaaac cagctggctg aattgtggct gaagctgata    2340
gatgaagtta tagaagacac gagatacacg ttgcctctca cagaaggaaa agccaacgtc    2400
acagttctcg atactcagat ccgaaagctg cggtccaggt ctctctccca aatacatgag    2460
gcggctgtga ggatgaggtc ggaagccaca gatgtgaagt ccacactggc agaaattgag    2520
gactggcttg ataaattaat gcagctgact gaagagccac agaacagcat gcctgacatc    2580
atcatctgga tgatccgggg agagaagaga ctggcctatg cacgaattcc cgcacatcag    2640
gtcttgtact ccaccagtgg tgagaatgca tctggaaaat actgtgggaa acccaaaacc    2700
atctttctga gtatccaca ggagaaaaac aacgggccaa aggtgcctgt ggagttgcga    2760
gtgaacatct ggctaggctt aagtgctgtg gagaagaagt ttaacagctt cgcagaagga    2820
actttcaccg tctttgctga aatgtatgaa aatcaagctc tcatgtttgg aaaatggggt    2880
acttctggat tagtaggacg tcataagttt tctgatgtca caggaaaaat aaaactcaag    2940
agggaatttt ttctgcctcc aaaaggctgg aatgggaag gagagtggat agttgatcct    3000
gaaagaagct tgctgactga ggcagatgca ggtcacacgg agttcactga tgaagtctat    3060
cagaacgaga gccgctaccc cgggggcgac tggaagccgg ccgaggacac ctacacggat    3120
gcgaacggca taaagcagc atcacccagc gagttgactt gtcctccagg ttgggaatgg    3180
gaagatgatg catggtctta tgacataaat cgagcggtgg atgagaaagg ctgggaatat    3240
ggaatcacca ttcctcctga tcataagccc aaatcctggg ttgcagcaga gaaaatgtac    3300
cacactcata gacggcgaag gctggtccga aaacgcaaga aagatttaac acagactgct    3360
tcaagcaccg caagggccat ggaggaattg caagaccaag agggctggga atatgcttct    3420
ctaattggct ggaaatttca ctggaaacaa cgtagttcag ataccttccg ccgcagacgc    3480
tggaggagaa aaatggctcc ttcagaaaca catggtgcag ctgccatctt taaacttgaa    3540
ggtgcccttg gggcagacac taccgaagat ggggatgaga gagcctgga gaaacagaag    3600
cacagtgcca ccactgtgtt cggagcaaac accccattg tttcctgcaa ttttgacaga    3660
gtctacatct accatctgcg ctgctatgtc tatcaagcca gaaacctctt ggctttagat    3720
aaggatagcc tttcagatcc atatgctcat atctgtttcc tccatcggag caaaaccact    3780
gagatcatcc attcaaccct gaatcccacg tgggaccaaa caattatatt cgatgaagtt    3840
```

```
gaaatctatg gggaacccca aacagttcta cagaatccac ccaaagttat catggaactt    3900
tttgacaatg accaagtggg caaagatgaa tttttaggac gaagcatttt ctctcctgtg    3960
gtgaaactga actcagaaat ggacatcaca cccaaacttc tctggcaccc agtaatgaat    4020
ggagacaaag cctgcgggga tgttcttgta actgcagagc tgattctgag gggcaaggat    4080
ggctccaacc ttcccattct tccccctcaa agggcgccaa atctatacat ggtccccag    4140 gggatcaggc ctgtggtcca gctcactgcc attgagattc tagcttgggg cttaagaaat    4200
atgaaaaact tccagatggc ttctatcaca tcccccagtc ttgttgtgga gtgtggagga    4260
gaaagggtgg aatcggtggt gatcaaaaac cttaagaaga cacccaactt ccaagttct    4320 gttctcttca tgaaagtgtt cttgcccaag gaggaattgt acatgccccc actggtgatc    4380
aaggtcatcg accacaggca gtttgggcgg aagcctgtcg tcggccagtg caccatcgag    4440
cgcctggacc gctttcgctg tgacccttat gcagggaaag aggacatcgt cccacagctc    4500
aaagcctccc ttctgtctgc cccaccatgc cgggacatcg ttatcgaaat ggaagacacc    4560
aaaccattac tggcttctaa gtgcttaagc agtatgtcaa cagcactcag caaaatggct    4620
tctccagcga cagtgcatct gacagaaaag gaggaagaaa tcgtggactg gtggagtaaa    4680
ttttatgctt cctcagggga acatgaaaaa tgcggacagt atattcagaa aggctattcc    4740
aagctcaaga tatataattg tgaactagaa aatgtagcag aatttgaggg cctgacagac    4800
ttctcagata cgttcaagtt gtaccgaggc aagtcggatg aaaatgaaga tccttctgtg    4860
gttggagagt ttaagggctc ctttcggatc taccctctgc cggatgaccc cagcgtgcca    4920
gcccctccca gacagtttcg ggaattacct gacagcgtcc cacaggaatg cacggttagg    4980
atttacattg ttcgaggctt agagctccag ccccaggaca caatggcct gtgtgacct    5040 tacataaaaa taacactggg caaaaaagtc attgaagacc gagatcacta cattcccaac    5100
actctcaacc cagtctttgg caggatgtac gaactgagct gctacttacc tcaagaaaaa    5160
gacctgaaaa tttctgtcta tgattatgac acctttaccc gggatgaaaa agtaggagaa    5220
acaattattg atctggaaaa ccgattcctt tcccgctttg ggtcccactg cggcatacca    5280
gaggagtact gtgtttctgg agtcaatacc tggcgagatc aactgagacc aacacagctg    5340
cttcaaaatg tcgccagatt caaaggcttc ccacaaccca tcctttccga agatgggagt    5400
agaatcagat atggaggacg agactacagc ttggatgaat ttgaagccaa caaaatcctg    5460
caccagcacc tcggggcccc tgaagagcgg cttgctcttc acatcctcag gactcagggg    5520
ctggtccctg agcacgtgga aacaaggact ttgcacagca ccttccagcc caacattata    5580
ctacctgcgt gtgatcatct ggaacaccaa ggacgttatc ttggacgaga aaagcatcac    5640
aggagaggaa atgagtgaca tctacgtcaa aggctggatt cctggcaatg aagaaaacaa    5700
acagaaaaca gatgtccatt acagatcttt ggatggtgaa gggaatttta actggcgatt    5760
tgtttccccg tttgactacc ttccagccga caactctgt atcgttgcga aaaagagca    5820 ttctggagt attgaccaaa cggaatttcg aatcccaccc aggctgatca ttcagatatg    5880
ggacaatgac aagttttctc tggatgacta cttgggtttc ctagaacttg acttgcgtca    5940
cacgatcatt cctgcaaaat caccagagaa atgcaggttg acatgattc cggacctcaa    6000 agccatgaac cccttaaag ccaagacagc ctcctctttt gagcagaagt ccatgaaagg    6060
atggtggcca tgctacgcag agaaagatgg cgcccgcgta atggctggga agtggagat    6120 gacattggaa atcctcaacg agaaggaggc cgacgagagg ccagccggga aggggcggga    6180
cgaacccaac atgaacccca agctggactt accaaatcga ccagaaacct ccttcctctg    6240
```

```
gttcaccaac ccatgcaaga ccatgaagtt catcgtgtgg cgccgcttta agtgggtcat    6300
catcggcttg ctgttcctgc ttatcctgct gctcttcgtg gccgtgctcc tctactcttt    6360
gccgaactat ttgtcaatga agattgtaaa gccaaatgtg taacaaaggc aaaggcttca    6420
tttcaagagt catccagcaa tgagagaatc ctgcctctgt agaccaacat ccagtgtgat    6480
tttgtgtctg agaccacacc ccagtagcag gttacgccat gtcaccgagc ccattgatt    6540 cccagagggt cttagtcctg gaaagtcagg ccaacaagca acgtttgcat catgttatct    6600
cttaagtatt aaaagttta ttttctaaag tttaaatcat gttttttcaaa atattttttca   6660 aggtggctgg ttccatttaa aaatcatctt tttatatgtg tcttcggttc tagacttcag    6720 ctttttggaaa ttgctaaata gaattcaaaa atctctgcat cctgaggtga tatacttcat    6780
atttgtaatc aactgaaaga gctgtgcatt ataaaatcag ttagaatagt tagaacaatt    6840
cttatttatg cccacaacca ttgctatatt ttgtatggat gtcataaaag tctatttaac    6900
ctctgtaatg aaactaaata aaaatgtttc accttt                              6936

<210> SEQ ID NO 110
<211> LENGTH: 2898
<212> TYPE: DNA
<213> ORGANISM: Homo sapiens

<400> SEQUENCE: 110
tccagtgccc tgccagtagc tcctagagag gcaggggtta ccaactggcc agcaggctgt      60
gtccctgaag tcagatcaac gggagagaag gaagtggcta aaacattgca caggagaagt     120
cggcctgagt ggtgcggcgc tcgggaccca ccagcaatgc tgctcttcgt gctcacctgc     180
ctgctggcgg tcttcccagc catctccacg aagagtccca tatttggtcc cgaggaggtg     240
aatagtgtgg aaggtaactc agtgtccatc acgtgctact acccacccac ctctgtcaac     300
cggcacaccc ggaagtactg gtgccggcag ggagctagag tggctgcat aaccctcatc     360 tcctcggagg gctacgtctc cagcaaatat gcaggcaggg ctaacctcac caacttcccg     420
gagaacggca catttgtggt gaacattgcc cagctgagcc aggatgactc cgggcgctac    480
aagtgtggcc tgggcatcaa tagccgaggc ctgtcctttg atgtcagcct ggaggtcagc    540
cagggtcctg ggctcctaaa tgacactaaa gtctacacag tggacctggg cagaacggtg    600
accatcaact gccctttcaa gactgagaat gctcaaaaga ggaagtcctt gtacaagcag    660
ataggcctgt accctgtgct ggtcatcgac tccagtggtt atgtgaatcc caactataca    720
ggaagaatac gccttgatat tcagggtact ggccagttac tgttcagcgt tgtcatcaac    780
caactcaggc tcagcgatgc tgggcagtat ctctgccagg ctggggatga ttccaatagt    840
aataagaaga atgctgacct ccaagtgcta aagcccgagc ccgagctggt ttatgaagac    900
ctgaggggct cagtgacctt ccactgtgcc ctgggccctg aggtggcaaa cgtgccaaa    960 tttctgtgcc gacagagcag tggggaaaac tgtgacgtgg tcgtcaacac cctggggaag   1020
agggccccag cctttgaggg caggatcctg ctcaaccccc aggacaagga tggctcattc   1080
agtgtggtga tcacaggcct gaggaaggag gatgcagggc gatacctgtg tggagcccat   1140
tcggatggtc agctgcagga aggctcgcct atccaggcct ggcaactctt cgtcaatgag   1200
gagtccacga ttccccgcag ccccactgtg gtgaagggg tggcaggaag ctctgtggcc   1260
gtgctctgcc cctacaaccg taaggaaagc aaaagcatca gtactggtg tctctgggaa   1320 ggggcccaga atggccgctg ccccctgctg gtggacagcg aggggtgggt taaggcccag   1380
```

```
tacgagggcc gcctctccct gctggaggag ccaggcaacg gcaccttcac tgtcatcctc   1440
aaccagctca ccagccggga cgccggcttc tactggtgtc tgaccaacgg cgatactctc   1500
tggaggacca ccgtggagat caagattatc gaaggagaac caaacctcaa ggtaccaggg   1560
aatgtcacgg ctgtgctggg agagactctc aaggtcccct gtcactttcc atgcaaattc   1620
tcctcgtacg agaaatactg gtgcaagtgg aataacacgg gctgccaggc cctgcccagc   1680
caagacgaag gccccagcaa ggccttcgtg aactgtgacg agaacagccg gcttgtctcc   1740
ctgaccctga acctggtgac cagggctgat gagggctggt actggtgtgg agtgaagcag   1800
ggccacttct atggagagac tgcagccgtc tatgtggcag ttgaagagag gaaggcagcg   1860
gggtcccgcg atgtcagcct agcgaaggca gacgctgctc ctgatgagaa ggtgctagac   1920
tctggttttc gggagattga gaacaaagcc attcaggatc ccaggctttt tgcagaggaa   1980
aaggcggtgg cagatacaag agatcaagcc gatgggagca gagcatctgt ggattccggc   2040
agctctgagg aacaaggtgg aagctccaga gcgctggtct ccaccctggt gcccctgggc   2100
ctggtgctgg cagtgggagc cgtggctgtg ggggtggcca gagcccggca caggaagaac   2160
gtcgaccgag tttcaatcag aagctacagg acagacatta gcatgtcaga cttcgagaac   2220
tccagggaat ttggagccaa tgacaacatg ggagcctctt cgatcactca ggagacatcc   2280
ctcggaggaa aagaagagtt tgttgccacc actgagagca ccacagagac caaagaaccc   2340
aagaaggcaa aaggtcatc caaggaggaa gccgagatgg cctacaaaga cttcctgctc   2400
cagtccagca ccgtggccgc cgaggcccag gacggccccc aggaagccta gacggtgtcg   2460
ccgcctgctc cctgcaccca tgacaatcac cttcagaatc atgtcgatcc tgggggccct   2520
cagctcctgg ggaccccact ccctgctcta acacctgcct aggttttcc tactgtcctc   2580 agaggcgtgc tggtcccctc ctcagtgaca tcaaagcctg gcctaattgt tcctattggg   2640
gatgagggtg gcatgaggag gtcccacttg caacttcttt ctgttgagag aacctcaggt   2700
acggagaaga atagaggtcc tcatgggtcc cttgaaggaa gagggaccag ggtgggagag   2760
ctgattgcag aaaggagaga cgtgcagcgc ccctctgcac ccttatcatg ggatgtcaac   2820 agaattttt ccctccactc catccctccc tcccgtcctt cccctcttct tctttcctta   2880
ccatcaaaag atgtattt                                                 2898
```

<210> SEQ ID NO 111
<211> LENGTH: 4242
<212> TYPE: DNA
<213> ORGANISM: Homo sapiens

<400> SEQUENCE: 111

```
tccagtgccc tgccagtagc tcctagagag gcaggggtta ccaactggcc agcaggctgt     60
gtccctgaag tcagatcaac gggagagaag gaagtggcta aaacattgca caggagaagt    120
cggcctgagt ggtgcggcgc tcggacccca ccagcaatgc tgctcttcgt gctcacctgc    180
ctgctggcgg tcttcccagc catctccacg aagagtccca tatttggtcc gaggaggtg     240 aatagtgtga aggtaactc agtgtccatc acgtgctact acccacccac ctctgtcaac    300
cggcacaccc ggaagtactg gtgccggcag ggagctagag gtggctgcat aaccctcatc    360
tcctcggagg gctacgtctc cagcaaatat gcaggcaggg ctaacctcac caacttcccg    420
gagaacggca catttgtggt gaacattgcc cagctgagcc aggatgactc cgggcgctac    480
aagtgtggcc tggcatcaa tagccgaggc ctgtcctttg atgtcagcct ggaggtcagc    540
cagggtcctg ggctcctaaa tgacactaaa gtctacacag tggacctggg cagaacggtg    600
```

-continued

```
accatcaact gcccttccaa gactgagaat gctcaaaaga ggaagtcctt gtacaagcag    660
ataggcctgt accctgtgct ggtcatcgac tccagtggtt atgtgaatcc caactataca    720
ggaagaatac gccttgatat tcagggtact ggccagttac tgttcagcgt tgtcatcaac    780
caactcaggc tcagcgatgc tgggcagtat ctctgccagg ctggggatga ttccaatagt    840
aataagaaga atgctgacct ccaagtgcta agcccgagc ccgagctggt ttatgaagac      900
ctgaggggct cagtgacctt ccactgtgcc ctgggccctg aggtggcaaa cgtggccaaa    960
tttctgtgcc gacagagcag tggggaaaac tgtgacgtgg tcgtcaacac cctggggaag   1020
agggccccag cctttgaggg caggatcctg ctcaaccccc aggacaagga tggctcattc   1080
agtgtggtga tcacaggcct gaggaaggag gatgcagggc gctacctgtg tggagcccat   1140
tcggatggtc agctgcagga aggctcgcct atccaggcct ggcaactctt cgtcaatgag   1200
gagtccacga ttccccgcag ccccactgtg gtgaagggg tggcaggagg ctctgtggcc    1260
gtgctctgcc cctacaaccg taaggaaagc aaaagcatca agtactggtg tctctgggaa   1320
ggggcccaga atggccgctg ccccctgctg gtggacagcg aggggtgggt taaggcccag   1380
tacgagggcc gcctctccct gctggaggag ccaggcaacg gcaccttcac tgtcatcctc   1440
aaccagctca ccagccggga cgccggcttc tactggtgtc tgaccaacgg cgatactctc   1500
tggaggacca ccgtggagat caagattatc gaaggagaac caaacctcaa ggtaccaggg   1560
aatgtcacgg ctgtgctggg agagactctc aaggtcccct gtcactttcc atgcaaattc   1620
tcctcgtacg agaaatactg gtgcaagtgg aataacacgg gctgccaggc cctgcccagc   1680
caagacgaag gccccagcaa ggccttcgtg aactgtgacg agaacagccg gcttgtctcc   1740
ctgacccctga acctggtgac cagggctgat gagggctggt actggtgtgg agtgaagcag   1800
ggccacttct atggagagac tgcagccgtc tatgtggcag ttgaagagag gaaggcagcg   1860
gggtcccgcg atgtcagcct agcgaaggca gacgctgctc ctgatgagaa ggtgctagac   1920
tctggttttc gggagattga gaacaaagcc attcaggatc ccaggctttt tgcagaggaa   1980
aaggcggtgg cagatacaag agatcaagcc gatgggagca gagcatctgt ggattccggc   2040
agctctgagg aacaaggtgg aagctccaga gcgctggtct ccaccctggt gcccctgggc   2100
ctggtgctgg cagtgggagc cgtggctgtg ggggtggcca gagcccggca caggaagaac   2160
gtcgaccgag tttcaatcag aagctacagg acagacatta gcatgtcaga cttcgagaac   2220
tccagggaat tggagccaa tgacaacatg ggagcctctt cgatcactca ggagacatcc    2280
ctcggaggaa aagaagagtt tgttgccacc actgagagca ccacagagac caaagaaccc   2340
aagaaggcaa aaaggtcatc caaggaggaa gccgagatgg cctacaaaga cttcctgctc   2400
cagtccagca ccgtggccgc cgaggcccag gacggccccc aggaagccta gacggtgtcg   2460
ccgcctgctc cctgcaccca tgacaatcac cttcagaatc atgtcgatcc tggggccctc   2520
agctcctggg gaccccactc cctgctctaa cacctgccta ggttttttcct actgtcctca   2580
gaggcgtgct ggtcccctcc tcagtgacat caaagcctgg cctaattgtt cctattgggg   2640
atgagggtgg catgaggagg tcccacttgc aacttctttc tgttgagaga acctcaggta   2700
cggagaagaa tagaggtcct catgggtccc ttgaaggaag agggaccagg gtgggagagc   2760
tgattgcaga aaggagagac gtgcagcgcc cctctgcacc cttatcatgg gatgtcaaca   2820
gaattttttcc ctccactcca tccctccctc ccgtccttcc cctcttcttc tttccttcca   2880
tcaaaagatg tatttgaatt catactagaa ttcaggtgct tgctagatg ctgtgacagg    2940
```

```
tatgccacca acactgctca cagcctttct gaggacacca gtgaaagaag ccacagctct    3000
tcttggcgta tttatactca ctgagtctta acttttcacc aggggtgctc acctctgccc    3060
ctattgggag aggtcataaa atgtctcgag tcctaaggcc ttaggggtca tgtatgatga    3120
gcatacacac aggtaattat aaacccacat tcttaccatt tcacacataa gaaaattgag    3180
gtttggaaga gtgaagcgtt tttcttttte tttttttttt ttgagacgga gtctctcact    3240
gtcgcccagg ctggagtgca gtggcgcaat ctcggctcac tgcaacctcc gcctcccagg    3300
ttgacaccat tctcctgcct caccctccca gtagctggg actacaggcg cctgccagca    3360
cgcctggcta atttttgta ttttagtag agacagggg tcaccgtgtt agccaggatg    3420
gtctcgatct cctgacctcg tgatccgcct gcctctgcct cccaaagtgc tgggattaca    3480
ggcgtgagcc accgcgtccg gcctcttttt ttcttttctt ttttttgaga caaagtctca    3540
ctgtgtcacc cagactggaa tgcagtgaca caatctcggc tcactgaaac ctctgccttc    3600
caggttcaag ctattctcat gcctcagcct ctcaagtagc tgggactaca gatgtgggcc    3660
accatgtctg gctaattttt tttttttttt ttttttttg tagagacagg gtttcgccat    3720
gttgacgaga ctggtctcga actcctggcc tcaagtgatc tgccgcctca gcttctcaaa    3780
gtactgggat tatataggca tgagccactg agcctggccc tgaagcgttt ttctcaaagg    3840
ccctcagtga gataaattag atttggcatc tcctgtcctg gccagggat ctctctacaa    3900 gagcccctgc ccctctgttg gaggcacagt tttagaataa ggaggaggag ggagaagaga    3960
aaatgtaaag gagggagatc tttcccaggc cgcaccattt ctgtcactca catggaccca    4020
agataaaaga atggccaaac cctcacaacc cctgatgttt gaagagttcc aagttgaagg    4080
gaaacaaaga agtgtttgat ggtgccgag aggggctgct ctccagaaag ctaaaattta    4140
atttcttttt tcctctgagt tctgtacttc aaccagccta caagctggca cttgctaaca    4200
aatcagaaat atgacaatta atgattaaag actgtgattg cc                      4242
```

<210> SEQ ID NO 112  
<211> LENGTH: 4266  
<212> TYPE: DNA  
<213> ORGANISM: Homo sapiens

<400> SEQUENCE: 112

```
agagtttcag ttttggcagc agcgtccagt gccctgccag tagctcctag agaggcaggg     60
gttaccaact ggccagcagg ctgtgtccct gaagtcagat caacgggaga gaaggaagtg    120
gctaaaacat tgcacaggag aagtcggcct gagtggtgcg gcgctcggga cccaccagca    180
atgctgctct tcgtgctcac ctgcctgctg gcggtcttcc cagccatctc cacgaagagt    240
cccatatttg gtcccgagga ggtgaatagt gtggaaggta actcagtgtc catcacgtgc    300
tactacccac ccacctctgt caaccggcac acccggaagt actggtgccg gcagggagct    360
agaggtggct gcataaccct catctcctcg gagggctacg tctccagcaa atatgcaggc    420
agggctaacc tcaccaactt cccggagaac ggcacatttg tggtgaacat tgcccagctg    480
agccaggatg actccgggcg ctacaagtgt ggcctgggca tcaatagccg aggcctgtcc    540
tttgatgtca gcctggaggt cagccagggt cctgggctcc taaatgacac taaagtctac    600
acagtggacc tgggcagaac ggtgaccatc aactgccctt tcaagactga gaatgctcaa    660
aagaggaagt ccttgtacaa gcagatuggc ctgtaccctg tgctggtcat cgactccagt    720
ggttatgtaa atcccaacta tacaggaaga tacgccttg atattcaggg tactggccag    780
ttactgttca gcgttgtcat caaccaactc aggctcagcg atgctgggca gtatctctgc    840
```

| | |
|---|---|
| caggctgggg atgattccaa tagtaataag aagaatgctg acctccaagt gctaaagccc | 900 |
| gagcccgagc tggtttatga agacctgagg ggctcagtga ccttccactg tgccctgggc | 960 |
| cctgaggtgg caaacgtggc caaatttctg tgccgacaga gcagtgggga aaactgtgac | 1020 |
| gtggtcgtca cacccctggg gaagagggcc ccagcctttg agggcaggat cctgctcaac | 1080 |
| ccccaggaca aggatggctc attcagtgtg gtgatcacag gcctgaggaa ggaggatgca | 1140 |
| gggcgctacc tgtgtggagc ccattcggat ggtcagctgc aggaaggctc gcctatccag | 1200 |
| gcctggcaac tcttcgtcaa tgaggagtcc acgattcccc gcagccccac tgtggtgaag | 1260 |
| ggggtggcag gaggctctgt ggccgtgctc tgcccctaca accgtaagga aagcaaaagc | 1320 |
| atcaagtact ggtgtctctg gaaggggcc cagaatggcc gctgccccct gctggtggac | 1380 |
| agcgaggggt gggttaaggc ccagtacgag ggccgcctct ccctgctgga ggagccaggc | 1440 |
| aacggcacct tcactgtcat cctcaaccag ctcaccagcc gggacgccgg cttctactgg | 1500 |
| tgtctgacca acggcgatac tctctggagg accaccgtgg agatcaagat tatcgaagga | 1560 |
| gaaccaaacc tcaaggtacc agggaatgtc acggctgtgc tgggagagac tctcaaggtc | 1620 |
| ccctgtcact ttccatgcaa attctcctcg tacgagaaat actggtgcaa gtggaataac | 1680 |
| acgggctgcc aggccctgcc cagccaagac gaaggcccca gcaaggcctt cgtgaactgt | 1740 |
| gacgagaaca gccggcttgt ctccctgacc ctgaacctgg tgaccagggc tgatgagggc | 1800 |
| tggtactggt gtggagtgaa gcagggccac ttctatggag agactgcagc cgtctatgtg | 1860 |
| gcagttgaag agaggaaggc agcggggtcc cgcgatgtca gcctagcgaa ggcagacgct | 1920 |
| gctcctgatg agaaggtgct agactctggt tttcgggaga ttgagaacaa agccattcag | 1980 |
| gatcccaggc tttttgcaga ggaaaaggcg gtggcagata caagagatca agccgatggg | 2040 |
| agcagagcat ctgtggattc cggcagctct gaggaacaag gtggaagctc cagagcgctg | 2100 |
| gtctccaccc tggtgcccct gggcctggtg ctggcagtgg gagccgtggc tgtgggggtg | 2160 |
| gccagagccc ggcacaggaa gaacgtcgac cgagtttcaa tcagaagcta caggacagac | 2220 |
| attagcatgt cagacttcga gaactccagg gaatttggag ccaatgacaa catgggagcc | 2280 |
| tcttcgatca ctcaggagac atccctcgga ggaaagaag agtttgttgc caccactgag | 2340 |
| agcaccacag agaccaaaga acccaagaag gcaaaaaggt catccaagga ggaagccgag | 2400 |
| atggcctaca aagacttcct gctccagtcc agcaccgtgg ccgccgaggc ccaggacggc | 2460 |
| ccccaggaag cctagacggt gtcgccgcct gctccctgca cccatgacaa tcaccttcag | 2520 |
| aatcatgtcg atcctggggc cctcagctcc tggggacccc actccctgct ctaacacctg | 2580 |
| cctaggttt tcctactgtc ctcagaggcg tgctggtccc ctcctcagtg acatcaaagc | 2640 |
| ctggcctaat tgttcctatt ggggatgagg gtggcatgag gaggtccac ttgcaacttc | 2700 |
| tttctgttga gagaacctca ggtacggaga agaatagagg tcctcatggg tcccttgaag | 2760 |
| gaagagggac cagggtggga gagctgattg cagaaggag agacgtgcag cgcccctctg | 2820 |
| cacccttatc atgggatgtc aacagaattt ttccctccac tccatccctc cctcccgtcc | 2880 |
| ttcccctctt cttctttcct tccatcaaaa gatgtatttg aattcatact agaattcagg | 2940 |
| tgctttgcta gatgctgtga caggtatgcc accaacactg ctcacagcct ttctgaggac | 3000 |
| accagtgaaa gaagccacag ctcttcttgg cgtatttata ctcactgagt cttaactttt | 3060 |
| caccaggggt gctcacctct gcccctattg ggagaggtca taaatgtct cgagtcctaa | 3120 |
| ggccttaggg gtcatgtatg atgagcatac acacaggtaa ttataaaccc acattcttac | 3180 |

-continued

```
catttcacac ataagaaaat tgaggtttgg aagagtgaag cgttttctt tttcttttt          3240 ttttttgaga cggagtctct cactgtcgcc caggctggag tgcagtggcg caatctcggc       3300
tcactgcaac ctccgcctcc caggttgaca ccattctcct gcctcaccct cccaagtagc       3360
tgggactaca ggcgcctgcc agcacgcctg gctaatttt tgtattttta gtagagacag        3420
ggtttcaccg tgttagccag gatggtctcg atctcctgac ctcgtgatcc gcctgcctct       3480
gcctcccaaa gtgctgggat tacaggcgtg agccaccgcg tccggcctct ttttttcttt      3540 tcttttttt gagacaaagt ctcactgtgt cacccagact ggaatgcagt gacacaatct        3600
cggctcactg aaacctctgc cttccaggtt caagctattc tcatgcctca gcctctcaag      3660
tagctgggac tacagatgtg gccaccatg tctggctaat ttttttttt ttttttttt         3720 tttgtagaga cagggtttcg ccatgttgac gagactggtc tcgaactcct ggcctcaagt      3780
gatctgccgc ctcagcttct caaagtactg ggattatata ggcatgagcc actgagcctg      3840 gcctgaagc gttttctca aaggccctca gtgagataaa ttagatttgg catctcctgt         3900
cctgggccag ggatctctct acaagagccc ctgcccctct gttggaggca cagttttaga      3960
ataaggagga ggagggagaa gagaaaatgt aaaggaggga gatctttccc aggccgcacc      4020
atttctgtca ctcacatgga cccaagataa agaatggcc aaaccctcac aaccctgat        4080 gtttgaagag ttccaagttg aagggaaaca agaagtgtt tgatggtgcc agagagggc        4140 tgctctccag aaagctaaaa tttaatttct ttttcctct gagttctgta cttcaaccag       4200
cctacaagct ggcacttgct aacaaatcag aaatatgaca attaatgatt aaagactgtg     4260
attgcc                                                                  4266
```

<210> SEQ ID NO 113
<211> LENGTH: 4189
<212> TYPE: DNA
<213> ORGANISM: Homo sapiens

<400> SEQUENCE: 113

```
tgtttggcct ataggactct gtagggagag cctgggtcag ccctgcacag cattgcacag         60
gagaagtcgg cctgagtggt gcggcgctcg ggacccacca gcaatgctgc tcttcgtgct        120
cacctgcctg ctggcggtct tcccagccat ctccacgaag agtcccatat ttggtcccga        180
ggaggtgaat agtgtggaag gtaactcagt gtccatcacg tgctactacc cacccacctc        240
tgtcaaccgg cacacccgga agtactggtg ccggcaggga gctagaggtg gctgcataac        300
cctcatctcc tcggagggct acgtctccag caaatatgca ggcagggcta acctcaccaa        360
cttcccggag aacggcacat tgtggtgaa cattgcccag ctgagccagg atgactccgg        420
gcgctacaag tgtggcctgg gcatcaatag ccgaggcctg tcctttgatg tcagcctgga      480
ggtcagccag ggtcctgggc tcctaaatga cactaaagtc tacacagtgg acctgggcag      540
aacggtgacc atcaactgcc cttttcaagac tgagaatgct caaaagagga agtccttgta      600
caagcagata ggcctgtacc ctgtgctggt catcgactcc agtggttatg tgaatcccaa      660
ctatacagga agaatacgcc ttgatattca gggtactggc cagttactgt tcagcgttgt      720
catcaaccaa ctcaggctca gcgatgctgg gcagtatctc tgccaggctg ggatgattc        780 caatagtaat aagaagaatg ctgacctcca agtgctaaag cccagcccg agctggttta       840 tgaagacctg aggggctcag tgaccttcca ctgtgccctg ggcctgagg tggcaaacgt        900 ggccaaattt ctgtgccgac agagcagtgg ggaaaactgt gacgtggtcg tcaacaccct       960
ggggaagagg gccccagcct ttgagggcag gatcctgctc aacccccagg acaaggatgg     1020
```

-continued

```
ctcattcagt gtggtgatca caggcctgag gaaggaggat gcagggcgct acctgtgtgg   1080
agcccattcg gatggtcagc tgcaggaagg ctcgcctatc caggcctggc aactcttcgt   1140
caatgaggag tccacgattc cccgcagccc cactgtggtg aaggggggtgg caggaggctc   1200 tgtggccgtg ctctgcccct acaaccgtaa ggaaagcaaa agcatcaagt actggtgtct   1260 ctggaaggg gcccagaatg gccgctgccc cctgctggtg gacagcgagg ggtgggttaa    1320
ggcccagtac gagggccgcc tctccctgct ggaggagcca ggcaacggca ccttcactgt   1380
catcctcaac cagctcacca gccgggacgc cggcttctac tggtgtctga ccaacggcga   1440
tactctctgg aggaccaccg tggagatcaa gattatcgaa ggagaaccaa acctcaaggt   1500
accagggaat gtcacggctg tgctgggaga gactctcaag gtccctgtc actttccatg    1560 caaattctcc tcgtacgaga atactggtg caagtggaat aacacgggct gccaggccct    1620
gcccagccaa gacgaaggcc ccagcaaggc cttcgtgaac tgtgacgaga cagccggct    1680 tgtctccctg accctgaacc tggtgaccag ggctgatgag ggctggtact ggtgtggagt   1740
gaagcagggc cacttctatg gagagactgc agccgtctat gtggcagttg aagagaggaa   1800
ggcagcgggg tcccgcgatg tcagcctagc gaaggcagac gctgctcctg atgagaaggt   1860
gctagactct ggttttcggg agattgagaa caaagccatt caggatccca ggcttttttgc   1920 agaggaaaag gcggtggcag atacaagaga tcaagccgat gggagcagag catctgtgga   1980
ttccggcagc tctgaggaac aaggtggaag ctccagagcg ctggtctcca ccctggtgcc   2040
cctgggcctg gtgctggcag tgggagccgt ggctgtgggg gtggcagag cccggcacag    2100 gaagaacgtc gaccgagttt caatcagaag ctacaggaca gacattagca tgtcagactt   2160
cgagaactcc agggaattg gagccaatga caacatggga gcctcttcga tcactcagga    2220
gacatccctc ggaggaaaag aagagtttgt tgccaccact gagagcacca cagagaccaa   2280
agaacccaag aaggcaaaaa ggtcatccaa ggaggaagcc gagatggcct acaaagactt   2340
cctgctccag tccagcaccg tggccgccga ggcccaggac ggcccccagg aagcctagac   2400
ggtgtcgccg cctgctccct gcacccatga caatcacctt cagaatcatg tcgatcctgg   2460
ggccctcagc tcctggggac cccactccct gctctaacac ctgcctaggt ttttcctact   2520
gtcctcagag gcgtgctggt cccctcctca gtgacatcaa agcctggcct aattgttcct   2580
attggggatg agggtggcat gaggaggtcc cacttgcaac ttctttctgt tgagagaacc   2640
tcaggtacgg agaagaatag aggtcctcat gggtcccttg aaggaagagg accagggtg    2700 ggagagctga ttgcagaaag gagagacgtg cagcgcccct ctgcaccctt atcatgggat   2760
gtcaacagaa ttttccctc cactccatcc ctccctcccg tccttcccct cttcttcttt    2820
ccttccatca aaagatgtat ttgaattcat actagaattc aggtgctttg ctagatgctg   2880
tgacaggtat gccaccaaca ctgctcacag cctttctgag gacaccagtg aaagaagcca   2940
cagctcttct tggcgtattt atactcactg agtcttaact tttcaccagg ggtgctcacc   3000
tctgccccta ttgggagagg tcataaaatg tctcgagtcc taaggcctta ggggtcatgt   3060
atgatgagca tacacacagg taattataaa cccacattct taccatttca cacataagaa   3120
aattgaggtt tggaagagtg aagcgttttt cttttttctt ttttttttg agacggagtc    3180 tctcactgtc gcccaggctg gagtgcagtg gcgcaatctc ggctcactgc aacctccgcc   3240
tcccaggttg acaccattct cctgcctcac cctcccaagt agctgggact acaggcgcct   3300
gccagcacgc ctggctaatt ttttgtattt ttagtagaga cagggtttca ccgtgttagc   3360
```

| caggatggtc tcgatctcct gacctcgtga tccgcctgcc tctgcctccc aaagtgctgg | 3420 |
| gattacaggc gtgagccacc gcgtccggcc tcttttttc ttttcttttt tttgagacaa | 3480 |
| agtctcactg tgtcacccag actggaatgc agtgacacaa tctcggctca ctgaaacctc | 3540 |
| tgccttccag gttcaagcta ttctcatgcc tcagcctctc aagtagctgg gactacagat | 3600 |
| gtgggccacc atgtctggct aatttttttt ttttttttt tttttgtag agacaggggtt | 3660 |
| tcgccatgtt gacgagactg gtctcgaact cctggcctca agtgatctgc cgcctcagct | 3720 |
| tctcaaagta ctgggattat ataggcatga gccactgagc ctggccctga gcgtttttc | 3780 |
| tcaaggccc tcagtgagat aaattagatt tggcatctcc tgtcctgggc cagggatctc | 3840 |
| tctacaagag cccctgcccc tctgttggag gcacagtttt agaataagga ggaggaggga | 3900 |
| gaagagaaaa tgtaaaggag ggagatcttt cccaggccgc accatttctg tcactcacat | 3960 |
| ggacccaaga taaagaatg gccaaaccct cacaaccct gatgtttgaa gagttccaag | 4020 |
| ttgaagggaa acaagaagt gtttgatggt gccagagagg ggctgctctc cagaaagcta | 4080 |
| aaatttaatt tcttttttcc tctgagttct gtacttcaac cagcctacaa gctggcactt | 4140 |
| gctaacaaat cagaaatatg acaattaatg attaaagact gtgattgcc | 4189 |

<210> SEQ ID NO 114
<211> LENGTH: 1089
<212> TYPE: DNA
<213> ORGANISM: Homo sapiens

<400> SEQUENCE: 114

| atgcgggtca cggcgccccg aaccctcctc ctgctgctct gggggggcagt ggccctgacc | 60 |
| gagacctggg ctggctccca ctccatgagg tatttccaca cctccgtgtc ccggcccggc | 120 |
| cgcggggagc cccgcttcat caccgtgggc tacgtggacg acacgctgtt cgtgaggttc | 180 |
| gacagcgacg ccgcgagtcc gagagaggag ccgcgggcgc cgtggataga gcaggagggg | 240 |
| ccggagtatt gggaccggga gacacagatc tgcaaggcca aggcacagac tgaccgagag | 300 |
| aacctgcgga tcgcgctccg ctactacaac cagagcgagg ccgggtctca caccctccag | 360 |
| aatatgtatg gctgcgacgt ggggccggac gggcgcctcc tccgcgggta ccaccaggac | 420 |
| gcctacgacg gcaaggatta catcgccctg aacgaggacc tgagctcctg gaccgccgcg | 480 |
| gacacggcgg ctcagatcac ccagcgcaag tgggaggcgg ccgtgtggc ggagcagctg | 540 |
| agagcctacc tggagggcga gtgcgtggag tggctccgca gatacctgga gaacgggaag | 600 |
| gagacgctgc agcgcgcgga ccccccaaag acacacgtga cccaccaccc catctctgac | 660 |
| catgaggcca ccctgaggtg ctgggccctg gcttctacc ctgcggagat cacactgacc | 720 |
| tggcagcggg atggcgagga ccaaactcag gacactgagc ttgtggagac cagaccagca | 780 |
| ggagatagaa ccttccagaa gtgggcagct gtggtggtgc cttctggaga agagcagaga | 840 |
| tacacatgcc atgtacagca tgagggggctg ccgaagcccc tcaccctgag atgggagccg | 900 |
| tcttcccagt ccaccgtccc catcgtgggc attgttgctg gcctggctgt cctagcagtt | 960 |
| gtggtcatcg gagctgtggt cgctgctgtg atgtgtagga ggaagagctc aggtggaaaa | 1020 |
| ggagggagct actctcaggc tgcgtgcagc gacagtgccc agggctctga tgtgtctctc | 1080 |
| acagcttga | 1089 |

<210> SEQ ID NO 115
<211> LENGTH: 1522
<212> TYPE: DNA
<213> ORGANISM: Homo sapiens

<400> SEQUENCE: 115

```
atgcgggtca tggagccccg aaccctcatc ctgctgctct cgggagccct ggccctgacc      60
gagacctggg cctgctccca ctccatgagg tatttctaca ccgctgtgtc ccggcccagc     120
cgcggagagc cccacttcat cgcagtgggc tacgtggacg acacgcagtt cgtgcggttc     180
gacagcgacg ccgcgagtcc aagaggggag ccgcggggcc gctgggtgga gcaggagggg     240
ccggagtatt gggaccggga gacacagaag tacaaccgcc aggcacagac tgaccgagtg     300
aacctgcgga aactgcgcgg ctactacaac cagagcgagg ccgggtctca cacccctcag     360
aggatgtacg gctgcgacct ggggcccgac gggcgcctcc tccgcgggta tgaccagtcc     420
gcctacgacg gcaaggatta catcgccctg aacgaggacc tgcgctcctg gaccgccgcg     480
gacacagcgg ctcagatcac ccagcgcaag tgggaggcgg cccgtgaggc ggaggagtgg     540
agagcctacc tggagggcga gtgcgtggag tggctccgca gatacctgga gaacgggaag     600
gagaagctgc agcgcgcgga cacccaaag acacacgtga cccaccatcc cgtctctgac      660
catgaggcca ccctgaggtg ctgggccctg gcttctacc ctacggagat cacactgacc       720
tggcagcggg atggcgagga ccaaactcag gacaccgagc ttgtggagac caggccagca     780
ggagatggaa ccttccagaa gtgggcagct gtggtggtgc cttctggaga agagcagaga     840
tacacgtgcc atgtgcagca cgaggggctg ccggagcccc tcaccctgag atgggagcca     900
tcttcccagc ccaccatccc catcgtgggc atcgttgctg gcctggctgt cctggctgtc     960
ctagctgtcc taggagctgt ggtggctgtt gtgatgtgta ggaggaagag ctcaggtgga    1020
aaaggaggga gctgctctca ggctgcgtcc agcaacagtg cccagggctc tgatgagtct    1080
ctcatcgctt ctaaagcctg agacagctgc ctgtgtggga ctgagatgca ggatttcctc    1140
acacctctcc tttgtgactt caagagcctc tggcatctct ttctacaaag catctgaat     1200
gtgtctgcgt ccctgttagc ataatgtgag gaggtggaga ccagccca ccccgtgtc       1260
caccgtgacc cctgtcccca cactgacctg tgttccctcc ccgatcatct ttcctgttcc    1320
agagaagtgg gctggatgtc tccatctctg tctcaacttt acgtggcctg acgtgcaact    1380
tacttcccta ctgaaaataa gaatctgaat ataaatttgt tttctcaaat atttgctatg    1440
agaggttgat ggattaatta aataagtcaa ttcctggaag ttgagagagc aaataaagac    1500
ctgagaacct tccagaatcc gc                                            1522
```

<210> SEQ ID NO 116
<211> LENGTH: 1089
<212> TYPE: DNA
<213> ORGANISM: Homo sapiens

<400> SEQUENCE: 116

```
atgctggtca tggcgccccg aaccgtcctc ctgctgctct cggcggccct ggccctgacc      60
gagacctggg ccggctccca ctccatgagg tatttctaca cctccgtgtc ccggcccggc     120
cgcggggagc cccgcttcat ctcagtgggc tacgtggacg acacccagtt cgtgaggttc     180
gacagcgacg ccgcgagtcc gagagaggag ccgcggggcg cgtggataga gcaggagggg     240
ccggagtatt gggaccggaa cacacagatc tacaaggccc aggcacagac tgaccgagag     300
agcctgcgga acctgcgcgg ctactacaac cagagcgagg ccgggtctca cacccttccag     360
agcatgtacg gctgcgacgt ggggccggac gggcgcctcc tccgcgggca tgaccagtac     420
gcctacgacg gcaaggatta catcgccctg aacgaggacc tgcgctcctg gaccgccgcg     480
```

```
gacacggcgg ctcagatcac ccagcgcaag tgggaggcgg cccgtgaggc ggagcagcgg      540
agagcctacc tggagggcga gtgcgtggag tggctccgca gatacctgga gaacgggaag      600
gacaagctgg agcgcgctga ccccccaaag acacacgtga cccaccaccc catctctgac      660
catgaggcca ccctgaggtg ctgggccctg ggtttctacc ctgcggagat cacactgacc      720
tggcagcggg atggcgagga ccaaactcag gacactgagc ttgtggagac cagaccagca      780
ggagatagaa ccttccagaa gtgggcagct gtggtggtgc cttctggaga agagcagaga      840
tacacatgcc atgtacagca tgagggggctg ccgaagcccc tcaccctgag atgggagccg      900
tcttcccagt ccaccgtccc catcgtgggc attgttgctg gcctggctgt cctagcagtt      960
gtggtcatcg gagctgtggt cgctgctgtg atgtgtagga ggaagagttc aggtggaaaa     1020
ggagggagct actctcaggc tgcgtgcagc gacagtgccc agggctctga tgtgtctctc     1080
acagcttga                                                              1089

<210> SEQ ID NO 117
<211> LENGTH: 1098
<212> TYPE: DNA
<213> ORGANISM: Homo sapiens

<400> SEQUENCE: 117
atgctggtca tggcgccccg aaccgtcctc ctgctgctct cggcggccct ggccctgacc       60
gagacctggg ccggctccca ctccatgagg tatttctaca cctccgtgtc ccggcccggc      120
cgcggggagc cccgcttcat ctcagtgggc tacgtggacg acacccagtt cgtgaggttc      180
gacagcgacg ccgcgagtcc gagagaggag ccgcgggcgc cgtggataga gcaggagggg      240
ccggagtatt gggaccggga gacacagatc tccaagacca cacacagac ttaccgagag       300 agcctgcgga acctgcgcgg ctactacaac cagagcgagg ccgggtctca caccctccag      360
agcatgtacg gctgcgacgt ggggccggac gggcgcctcc tccgcgggca taaccagtac      420
gcctacgacg gcaaggatta catcgccctg aacgaggacc tgcgctcctg gaccgccgcg      480
gacacggcgg ctcagatctc ccagcgcaag ttggaggcgg cccgtgtggc ggagcagctg      540
agagcctacc tggagggcga gtgcgtggag tggctccgca gatacctgga gaacgggaag      600
gacaagctgg agcgcgctga ccccccaaag acacacgtga cccaccaccc catctctgac      660
catgaggcca ccctgaggtg ctgggccctg ggtttctacc ctgcggagat cacactgacc      720
tggcagcggg atggcgagga ccaaactcag gacactgagc ttgtggagac cagaccagca      780
ggagatagaa ccttccagaa gtggacagct gtggtggtgc cttctggaga agagcagaga      840
tacacatgcc atgtacagca tgagggggctg ccgaagcccc tcaccctgag atgggagccg      900
tcttcccagt ccaccgtccc catcgtgggc attgttgctg gcctggctgt cctagcagtt      960
gtggtcatcg gagctgtggt cgctgctgtg atgtgtagga ggaagagttc aggtggaaaa     1020
ggagggagct actctcaggc tgcgtgcagc gacagtgccc agggctctga tgtgtctctc     1080
acagcttgaa agcctgag                                                    1098

<210> SEQ ID NO 118
<211> LENGTH: 1089
<212> TYPE: DNA
<213> ORGANISM: Homo sapiens

<400> SEQUENCE: 118
atgctggtca tggcgccccg aaccgtcctc ctgctgctct gggggggcagt ggccctgacc      60 gagacctggg ccggctccca ctccatgagg tatttctaca cctccgtgtc ccggcccggc     120
```

```
cgcggggagc ccgcttcat ctcagtgggc tacgtggacg acacccagtt cgtgaggttc      180
gacagcgacg ccgcgagtcc gagagaggag ccgcgggcgc cgtggataga gcaggagggg      240
ccggagtatt gggaccggaa cacacagatc tacaaggccc aggcacagac tgaccgagag      300
agcctgcgga acctgcgcgg ctactacaac cagagcgagg ccgggtctca caccctccag      360
agcatgtacg gctgcgacgt ggggccggac gggcgcctcc tccgcgggca taaccagtac      420
gcctacgacg gcaaggatta catcgccctg aacgaggacc tgcgctcctg gaccgccgcg      480
gacacggcgg ctcagatctc ccagcgcaag ttggaggcgg ccgtgtggc ggagcagctg       540 agagcctacc tggagggcga gtgcgtggag tggctccgca gatacctgga gaacgggaag      600
gacaagctgg agcgcgctga ccccccaaag acacacgtga cccaccaccc catctctgac      660
catgaggcca ccctgaggtg ctgggccctg ggtttctacc ctgcggagat cacactgacc      720
tggcagcggg atggcgagga ccaaactcag gacactgagc ttgtggagac cagaccagca      780
ggagatagaa ccttccagaa gtggacagct gtggtggtgc cttctggaga agagcagaga      840
tacacatgcc atgtacagca tgaggggctg ccgaagcccc tcaccctgag atgggagccg      900
tcttcccagt ccaccgtccc catcgtgggc attgttgctg gcctggctgt cctagcagtt      960
gtggtcatcg gagctgtggt cgctgctgtg atgtgtagga ggaagagttc tggtggaaaa     1020
ggagggagct actctcaggc tgcgtgcagc gacagtgccc agggctctga tgtgtctctc     1080
acagcttga                                                             1089

<210> SEQ ID NO 119
<211> LENGTH: 1241
<212> TYPE: DNA
<213> ORGANISM: Homo sapiens

<400> SEQUENCE: 119
gccaatcagt gtcgccgggg tcccagttct aaagtcccca cgcacccacc cggactcaga       60
atctcctcag acgccgagat gcgggtcacg gcgccccgaa ccctcctcct gctgctctgg      120
ggggcagtgg ccctgaccga gacctgggct ggtgagtgcg gggtgggcag ggaaatggcc      180
tctgtgggga ggagcgaggg gaccgcaggc ggggcgcagg aacccgggga gccgcgccgg      240
gaggagggtc gggcggctct ctgccccctcc tcgccccagg ctcccactcc atgaggtatt      300
tccacacctc cgtgtcccgg cccggccgcg gggagccccg cttcatcacc gtgggctacg      360
tggacgacac gctgttcgtg aggttcgaca cgcgacgccgc gagtccgaga gaggagccgc      420
gggcgccgtg gatagagcag gaggggccgg agtattggga ccggagaca cagatctgca      480 aggccaaggc acagactgac cgagaggacc tgcggaccct gctccgctac tacaaccaga      540
gcgaggccgg tgagtgaccc cggcccgggg cgcaggtcac gctccccatc ccccacgtac      600
ggcccgggtc gccccgagtc tccgggtccg agatccgccc ccgaggccgc ggggctcgct      660
cagccctcgc cggcgagagt cccaagcgcg tttacccggt ttcattttca gttgaggcca      720
aaatccccgc gggttggtcg gggcggggcg ggctcgggg gacggggct gaccgcgggg        780 ggacggggcc agggtctcac accctccaga atatgtatgg ctgcgacgtg gggccggacg      840
ggcgcctcct ccgcgggtac caccaggacg cctacgacgg caaggattac atcgccctga      900
acgaggacct gagctcctgg accgccgcgg acacggcggc tcagatcacc cagcgcaagt      960
gggaggcggc ccgtgtggcg gagcagctga gagcctacct ggagggcgag tgcgtggagt     1020
ggctccgcag atacccttgag aacgggaagg agacgctgca gcgcgcgggt accaggggca     1080
```

-continued

```
gtggggagcc ttccccatct cctataggtc gccggggatg gcctcccacg agaagaggaa    1140 aatgggtca gcgctgaatg tcgccctccc ttgaatggag aatggcatga gttttcctga     1200
gtttcctctg agggccccct cttctctcta ggcaattaag g                         1241
```

<210> SEQ ID NO 120
<211> LENGTH: 1093
<212> TYPE: DNA
<213> ORGANISM: Homo sapiens

<400> SEQUENCE: 120

```
atgcgggtca cggcgccccg aaccctcctc ctgctgctct gggggggcagt ggccctgacc    60 gagacctggg ctggctccca ctccatgagg tatttctaca ccgccatgtc ccggcccggc    120
cgcggggagc cccgcttcat caccgtgggc tacgtggacg acacgctgtt cgtgaggttc    180
gacagcgacg ccacgagtcc gaggaaggag ccgcgggcgc catggataga gcaggagggg    240
ccggagtatt gggaccggga gacacagatc tccaagacca cacacagac ttaccgagag     300 gacctgcgga ccctgctccg ctactacaac cagagcgagg ccgggtctca caccctccag    360
aggatgtttg ctgcgacgt ggggccggac gggcgcctcc tccgcgggta ccaccaggac     420
gcctacgacg gcaaggatta catcgccctg aacgaggacc tgagctcctg gaccgccgcg    480
gacacggcgg ctcagatcac ccagcgcaag tgggaggcgg cccgtgtggc ggagcagctg    540
agagcctacc tggagggcga gtgcgtggag tggctccgca gataccggga gaacgggaag    600
gagacgctgc agcgcgcgga cccccccaaag acacacgtga cccaccaccc catctctgac    660
catgaggcca ccctgaggtg ctgggccctg gcttctacc ctgcggagat cacactgacc     720
tggcagcggg atggcgagga ccaaaactcag gacactgagc ttgtggagac cagaccagca    780
ggagatagaa ccttccagaa gtgggcagct gtggtggtgc cttctggaga agagcagaga    840
tacacatgcc atgtacagca tgaggggctg ccgaagcccc tcaccctgag atgggagccg    900
tcttcccagt ccaccgtccc catcgtgggc attgttgctg gcctggctgt cctagcagtt    960
gtggtcatcg agctgtggt cgctgctgtg gtgtgtagga ggaagagctc aggtggaaaa    1020
ggagggagct actctcaggc tgcgtgcagc gacagtgccc agggctctga tgtgtctctc    1080
acagcttgaa aag                                                       1093
```

<210> SEQ ID NO 121
<211> LENGTH: 1092
<212> TYPE: DNA
<213> ORGANISM: Homo sapiens

<400> SEQUENCE: 121

```
atgctggtca tggcgccccg aaccgtcctc ctgctgctct cggcggccct ggccctgacc    60
gagacctggg ccggctccca ctccatgagg tatttccaca cctccgtgtc ccggcctggc    120
cgcggggagc cccgcttcat caccgtgggc tacgtggacg acacccagtt cgtgaggttc    180
gacagcgacg ccgcgagtcc gagagaggag ccgcgggcgc cgtggataga gcaggagggg    240
ccggagtatt gggaccggaa cacacagatc tgcaaggcca aggcacagac tgaccgagtg    300
ggcctgcgga acctgcgcgg ctactacaac cagagcgagg acgggtctca cacttggcag    360
acgatgtatg ctgcgacat ggggccggac gggcgcctcc tccgcgggta taaccagttc    420
gcctacgacg gcaaggatta catcgccctg aacgaggacc tgcgctcctg gaccgccgcg    480
gacacggcgg ctcagatcac ccagcgcaag tgggaggcgg cccgtgtggc ggagcagctg    540
agagcctacc tggagggcga gtgcgtggag tggctccgca gacacctgga gaacgggaag    600
```

```
gagacgctgc agcgcgcgga ccccccaaag acacacgtga cccaccaccc catctctgac    660
catgaggcca ccctgaggtg ctgggccctg gcttctacc ctgcggagat cacactgacc    720
tggcagcggg atggcgagga ccaaactcag gacaccgagc ttgtggagac caggccagca    780
ggagatggaa ccttccagaa gtgggcagct gtggtggtgc cttctggaca agaacagaga    840
tacacgtgcc atgtgcagca cgaggggctg caggagccct gcaccctgag atggaagcca    900
tcttcccagt ccaccatccc catcgtgggc attgttgctg gcctggctgt ccttgtggtc    960
accgtagctg tggtcgctgt ggtcgctgct gtgatgtgta ggaggaagag ctcaggtgga    1020
aaaggaggga gctactctca ggctgcgtcc agcgacagtg cccagggctc tgatgtgtct    1080
ctcacagctt ga                                                       1092
```

<210> SEQ ID NO 122
<211> LENGTH: 1101
<212> TYPE: DNA
<213> ORGANISM: Homo sapiens

<400> SEQUENCE: 122

```
atgcgggtca tggcgccccg aaccctcctc ctgctgctct cgggagccct ggccctgacc     60
gagacctggg cctgctccca ctccatgagg tatttctaca ccgctgtgtc ccggcccagc    120
cgcggagagc cccacttcat cgcagtgggc tacgtggacg acacgcagtt cgtgcggttc    180
gacagcgacg ccgcgagtcc aagagggag ccgcgggcgc cgtgggtgga gcaggagggg    240
ccggagtatt gggaccggga gacacagaag tacaagcgcc aggcacagac tgaccgagtg    300
aacctgcgga aactacgcgg ctactacaac cagagcgagg ccgggtctca caccctccag    360
aggatgtacg gctgcgacct ggggccgac ggcgcctcc tccgcgggta tgaccagtcc    420
gcctacgacg gcaaggatta catcgccctg aacgaggacc tgcgctcctg gaccgccgcg    480
gacacagcgg ctcagatcac ccagcgcaag tgggaggcgg cccgtgaggc ggagcagtgg    540
agagcctacc tggagggcga gtgcgtggag tggctccgca gatacctgga gaacgggaag    600
gagacgctgc agcgcgcgga acacccaaag acacacgtga cccaccatcc cgtctctgac    660
catgaggcca ccctgaggtg ctgggccctg gcttctacc ctacggagat cacactgacc    720
tggcagcggg atggcgagga ccaaactcag gacaccgagc ttgtggagac caggccagca    780
ggagatggaa ccttccagaa gtgggcagct gtggtggtgc cttctggaga agagcagaga    840
tacacgtgcc atgtgcagca cgaggggctg ccggagcccc tcaccctgag atgggagcca    900
tcttcccagc ccaccatccc catcgtgggc atcgttgctg gcctggctgt cctggctgtc    960
ctagctgtcc taggagctgt ggtggctgtt gtgatgtgta ggaggaagag ctcaggtgga   1020
aaaggaggga gctgctctca ggctgcgtcc agcaacagtg cccagggctc tgatgagtct   1080
ctcatcgctt gtaaagcctg a                                             1101
```

<210> SEQ ID NO 123
<211> LENGTH: 3649
<212> TYPE: DNA
<213> ORGANISM: Homo sapiens

<400> SEQUENCE: 123

```
ctagagaagc caatcagtgt cgccggggtc ccagttctaa agtccccacg cacccacccg     60
gactcagaat ctcctcagac gccgagatgc gggtcacggc gccccgaacc ctcctcctgc    120
tgctctgggg ggcagtggcc ctgaccgaga cctgggctgg tgagtgcggg gtcggcaggg    180
```

```
aaatggcctc tgtggggagg agcgagggga ccgcagcggg gcgcaggacc cggggagccg    240
cgccgggagg agggtcgggc gggtctcagc ccctcctcgc ccccaggctc ccactccatg    300
aggtatttcc acacctccgt gtcccggccc ggccgcgggg agcccgcctt catcaccgtg    360
ggctacgtgg acgacacgct gttcgtgagg ttcgacagcg acgccgcgag tccgagagag    420
gagccgcggg cgccgtggat agagcaggag gggccggagc attgggaccg ggagacacag    480
atctgcaagg ccaaggcaca gactgaccga gaggacctgc ggaccctgct ccgctactac    540
aaccagagcg aggccggtga gtgaccccgg ccgggcgc aggtcacgac tccccatccc      600
ccacgtacgg cccgggtcgc cccgagtctc cgggtccgag atccgccccc gaggccgcgg    660
gacccgccca ccctcgac cggcgagacg ccaggcgcgt ttacccggtt tcattttcag      720
ttgaggccaa atcccgcg ggttggtcgg ggcggggcgg ggctcggggg gacggggctg      780
acgcggggcg gggccaggt ctcacaccct ccagaatatg tatggctgcg acgtggggcc     840
ggacgggcgc ctcctccgcg gtaccacca ggacgcctac gacggcaagg attacatcgc    900
cctgaacgag gacctgagct cctggaccgc cgcggacacg gcggctcaga tcacccagcg    960
caagtgggag gcgcccgtg tggcggagca gctgagagcc tacctggagg gcgagtgcgt     1020
ggagtggctc cgcagatacc tggagaacgg gaaggagacg ctgcagcgcg cgggtaccag    1080
gggcagtggg gagccttccc catctcctat aggtcgccgg ggatggcctc ccacgagaag    1140
aggaggaaaa tgggatcagc gctagaatgt cgccctccct tgaatggaga atggcatgag    1200
tttcctgag tttcctctga gggccccctc ttctctctag acaattaag ggatgacgtc      1260
tctgaggaaa tggaggggaa gacagtccct agaatactga tcaggggtcc cctttgaccc    1320
ctgcagcagc cttgggaacc gtgacttttc ctctcaggcc ttgttctctg cctcacactc    1380
agtgtgtttg gggctctgat ccagcacttt ctgagtcact ttacctccac tcagatcagg    1440
agcagaagtc cctgttcccc gctcagagac tcgaactttc caatgaatag gagattatcc    1500
caggtgcctg cgtccaggct ggtgtctggg ttctgtgccc cttccccacc ccaggtgtcc    1560
tgtccattct caggctggtc acatgggtgg tcctagggtg tcccatgaga gatgcaaagc    1620
gcctgaattt tctgactctt cccatcagac ccccaaaga cacacgtgac ccaccacccc     1680
atctctgacc atgaggccac cctgaggtgc tgggccctgg gcttctaccc tgcggagatc    1740
acactgacct ggcagcggga tggcgaggac caaaactcagg acactgagct tgtggagacc    1800
agaccagcag gagatagaac cttccagaag tgggcagctg tggtggtgcc ttctggagaa    1860
gagcagagat acacatgcca tgtacagcat gaggggctgc cgaagcccct caccctgaga    1920
tggggtaagg aggggggatga gggtcatat ctcttctcag ggaaagcagg agcccttcag    1980
cagggtcagg gcccctcatc ttcccttcct ttcccagagc cgtcttccca gtccaccgtc    2040
cccatcgtgg gcattgttgc tggcctggct gtcctagcag ttgtggtcat cggagctgtg    2100
gtcgctgctg tgatgtgtag gaggaagagc tcaggtaggg aaggggtgag gggtggggtc    2160
tgagttttct tgtcccactg ggggtttcaa gccccaggta gaagtgttcc ctgcctcatt    2220
actgggaagc agcatccaca caggggctaa cgcagcctgg gaccctgtgt gccagcactt    2280
actcttttgt gcagcacatg tgacaatgaa tgacggatgt atcaccttgg tggttgtggt    2340
gttgggtcc tgattccagc attcatgagt caggggaagg tccctgctaa ggacagacct     2400
taggagggca gttggtccag gacccacact tgctttcctc gtgtttcctg atcctgcctt    2460
gggtctgtag tcatacttct ggaaattcct ttgggtcca agacgaggag gttcctctaa     2520
gatctcatgg ccctgcttcc tcccagtccc ctcacagggc attttcttcc cacaggtgga    2580
```

```
aaaggaggga gctactctca ggctgcgtgt aagtgatggg ggtgggagtg tggaggagct    2640
cacccacccc ctaattcctc ctgtcccacg tctcctgcgg gctctgacca ggtcctgttt    2700
ttgttctact ccaggcagcg acagtgccca gggctctgat gtgtctctca cagcttgaaa    2760
aggtgagatt cttggggtct agagtgggtg gggtggcagg tctggggggtg ggtggggcag    2820 tggggaaagg cctgggtaat ggagattctt tgattgggat gtttcgcgtg tggtgggctg    2880
tttagactgt catcacttac catgactaac cagaatttgt tcatgactgt tgttttctgt    2940
agcctgagac agctgtcttg tgagggactg agatgcagga tttcttcacg cctcccttt    3000 gtgacttcaa gagcctctgg catctctttc tgcaaaggca cctgaatgtg tctgcgtccc    3060
tgttagcata atgtgaggag gtggagagac cagcccaccc ccgtgtccac tgtgaccct    3120 gttcccatgc tgacctgtgt ttcctcccca gtcatctttc ctgttccaga gaggtggggc    3180
tggatgtctc catctctgtc tcaactttat gtgcactgag ctgcaacttc ttacttccct    3240
actgaaaata agaatctgaa tataaatttg ttttctcaaa tatttgctat gagaggttga    3300
tggattaatt aaataagtca attcctggaa tttgagagag caaataaaga cctgagaacc    3360
ttccagaatc tgcatgttgg ctgtgctgag tctgttgcag gtggggtgtg gagaaggctg    3420 tgggggccg agtgtggacg gggcctgtgc ccatttggtg ttgagtccat catgggcttt    3480
atgtggttag tcctcagctg ggtcaccttc actgctccat tgtccttgtc ccttcagtgg    3540
aaacttgtcc agcgggagct gtgaccacag aggctcacac atgccctggg cggcccctgc    3600
acacgggggt ctctgtgcat tctgagacaa attttcagag ccattcacc                3649

<210> SEQ ID NO 124
<211> LENGTH: 1098
<212> TYPE: DNA
<213> ORGANISM: Homo sapiens

<400> SEQUENCE: 124
atgcgggtca cggcgccccg aaccctcctc ctgctgctct gggggggcagt ggccctgacc      60 gagacctggg ctggctccca ctccatgagg tatttccaca cctccgtgtc ccggcccggc     120
cgcggggagc cccgcttcat caccgtgggc tacgtggacg acacgctgtt cgtgaggttc     180
gacagcgacg ccacgagtcc gaggaaggag ccgcgggcgc catggataga gcaggagggg     240
ccggagtatt gggaccggga gacacagatc tccaagacca acacacagac ttaccgagag     300
agcctgcgga acctgcgcgg ctactacaac cagagcgagg ccgggtctca caccctccag     360
agcatgtacg gctgcgacgt ggggccggac gggcgcctcc tccgcgggca tgaccagtcc     420
gcctacgacg gcaaggatta catcgccctg aacgaggacc tgcgctcctg gaccgccgcg     480
gacacggcgg ctcagatcac ccagcgcaag tgggaggcgg cccgtgtggc ggagcagctg     540
agagcctacc tggagggcga gtgcgtggag tggctccgca gatacctgga gaacgggaag     600
gagacgctgc agcgcgcgga ccccccaaag acacacgtga cccaccaccc catctctgac     660
catgaggcca ccctgaggtg ctgggccctg ggcttctacc ctgcggagat cacactgacc     720
tggcagcggg atggcgagga ccaaactcag gacactgagc ttgtggagac cagaccagca     780
ggagatagaa ccttccagaa gtgggcagct gtggtggtgc cttctggaga agagcagaga     840
tacacatgcc atgtacagca tgaggggctg ccgaagcccc tcaccctgag atgggagccg     900
tcttcccagt ccaccgtccc catcgtgggc attgttgctg gcctggctgt cctagcagtt     960
gtggtcatcg gagctgtggt cgctgctgtg atgtgtagga ggaagagctc aggtggaaaa    1020
```

```
ggagggagct actctcaggc tgcgtgcagc gacagtgccc agggctctga tgtgtctctc    1080
acagcttgaa agcctgag                                                   1098

<210> SEQ ID NO 125
<211> LENGTH: 1089
<212> TYPE: DNA
<213> ORGANISM: Homo sapiens

<400> SEQUENCE: 125
atgcgggtca cggcgccccg aaccctcctc ctgctgctct gggggcagt ggccctgacc      60 gagacctggg ccggctccca ctccatgagg tatttctaca ccgccatgtc ccggcccggc   120
cgcggggagc ccgcttcat caccgtgggc tacgtggacg acacccagtt cgtgaggttc    180
gacagcgacg ccacgagtcc gaggatggcg ccccgggcgc catggataga gcaggagggg   240
ccggagtatt gggaccggga gacacagatc tccaagacca cacacagac ttaccgagag    300 aacctgcgca ccgcgctccg ctactacaac cagagcgagg ccgggtctca cacttggcag   360
acgatgtatg gctgcgacct ggggccggac gggcgcctcc tccgcgggca taaccagtta   420
gcctacgacg gcaaggatta tatcgccctg aacgaggacc tgagctcctg gaccgcggcg   480
gacaccgcgg ctcagatcac ccagctcaag tgggaggcgg cccgtgtggc ggagcagctg   540
agagcctacc tggagggcga gtgcgtggag tggctccgca gatacctgga gaacgggaag   600
gagacgctgc agcgcgcgga ccccccaaag acacacgtga cccaccaccc catctctgac   660
catgaggcca ccctgaggtg ctgggccctg gcttctacc ctgcggagat cacactgacc    720
tggcagcggg atggcgagga ccaaactcag gacactgagc ttgtggagac cagaccagca   780
ggagatagaa ccttccagaa gtgggcagct gtggtggtgc cttctggaga agagcagaga   840
tacacatgcc atgtacagca tgagggggctg ccgaagcccc tcaccctgag atgggagcca   900
tcttcccagt ccaccgtccc catcgtgggc attgttgctg gctggctgt cctagcagtt   960 gtggtcatcg gagctgtggt cgctgctgtg atgtgtagga ggaagagctc aggtggaaaa  1020
ggagggagct actctcaggc tgcgtgcagc gacagtgccc agggctctga tgtgtctctc  1080
acagcttga                                                          1089

<210> SEQ ID NO 126
<211> LENGTH: 1017
<212> TYPE: DNA
<213> ORGANISM: Homo sapiens

<400> SEQUENCE: 126
ggctcccact ccatgaggta tttccacacc tccgtgtccc ggcccggccg cggggagccc     60
cgcttcatca ccgtgggcta cgtggacgac acgctgttcg tgaggttcga cagcgacgcc   120
gcgagtccga gaggagcc gcgggcgccg tggatagagc aggagggccc ggagtattgg    180
gaccgggaga cacagatctg caaggccaag gcacagactg accgagagga cctgcggacc   240
ctgctccgct actacaacca gagcgaggcc gggtctcaca ccctccagag catgtacggc   300
tgcgacgtgg ggccggacgg gcgcctcctc cgcgggcata accagtacgc ctacgacggc   360
aaggattaca tcgccctgaa cgaggacctg cgctcctgga ccgccgcgga cacggcggct   420
cagatcaccc agcgcaagtg ggaggcggcc cgtgtggcgg agcagctgag agcctacctg   480
gagggcgagt gcgtggagtg gctccgcaga tacctggaga cgggaaggga cgctgcag    540 cgcgcggacc ccccaaagac acacgtgacc caccacccca tctctgacca tgaggccacc   600
ctgaggtgct gggccctggg cttctaccct gcggagatca cactgacctg cagcgggat    660
```

```
ggcgaggacc aaactcagga cactgagctt gtggagacca gaccagcagg agatagaacc    720
ttccagaagt gggcagctgt ggtggtgcct tctggagaag agcagagata cacatgccat    780
gtacagcatg aggggctgcc gaagcccctc accctgagat gggagccgtc ttcccagtcc    840
accgtcccca tcgtgggcat tgttgctggc ctggctgtcc tagcagttgt ggtcatcgga    900
gctgtggtcg ctgctgtgat gtgtaggagg aagagctcag gtggaaaagg agggagctac    960
tctcaggctg cgtgcagcga cagtgcccag ggctctgatg tgtctctcac agcttga     1017

<210> SEQ ID NO 127
<211> LENGTH: 1098
<212> TYPE: DNA
<213> ORGANISM: Homo sapiens

<400> SEQUENCE: 127
atgcgggtca cggcgccccg aaccctcctc ctgctgctct gggggggcagt ggccctgacc     60 gagacctggg ctggctccca ctccatgagg tatttccaca cctccgtgtc ccggcccggc    120
cgcggggagc cccgcttcat caccgtgggc tacgtggacg acacgctgtt cgtgaggttc    180
gacagcgacg ccacgagtcc gaggaaggag ccgcgggcgc catggataga gcaggagggg    240
ccggagtatt gggaccggga gacacagatc tccaagacca acacacagac ttaccgagag    300
agcctgcgga acctgcgcgg ctactacaac cagagcgagg ccgggtctca catcatccag    360
aggatgtatg gctgcgacct ggggccggac gggcgcctcc tccgcgggca taaccagtac    420
gcctacgacg gcaaggatta catcgccctg aacgaggacc tgcgctcctg gaccgccgcg    480
gacacggcgg ctcagatcac ccagcgcaag tgggaggcgg cccgtgtggc ggagcagctg    540
agagcctacc tggagggcga gtgcgtggag tggctccgca gatacctgga gaacgggaag    600
gagacgctgc agcgcgcgga cccccccaaag acacacgtga cccaccaccc catctctgac    660
catgaggcca ccctgaggtg ctgggccctg gccttctacc tgcggagat cacactgacc    720 tggcagcggg atggcgagga ccaaaactcag gacactgagc ttgtggagac cagaccagca    780
ggagatagaa ccttccagaa gtgggcagct gtggtggtgc cttctggaga agagcagaga    840
tacacatgcc atgtacagca tgagggggctg ccgaagcccc tcaccctgag atgggagccg    900
tcttcccagt ccaccgtccc catcgtgggc attgttgctg gctggctgt cctagcagtt    960 gtggtcatcg gagctgtggt cgctgctgtg atgtgtagga ggaagagctc aggtggaaaa   1020
ggagggagct actctcaggc tgcgtgcagc gacagtgccc agggctctga tgtgtctctc   1080
acagcttgaa agcctgag                                                  1098

<210> SEQ ID NO 128
<211> LENGTH: 1089
<212> TYPE: DNA
<213> ORGANISM: Homo sapiens

<400> SEQUENCE: 128
atgcgggtca cggcgccccg aaccctcctc ctgctgctct gggggggcagt ggccctgacc     60 gagacctggg ctggctccca ctccatgagg tatttccaca cctccgtgtc ccggcccggc    120
cgcggggagc cccgcttcat caccgtgggc tacgtggacg acacgctgtt cgtgaggttc    180
gacagcgacg ccacgagtcc gaggaaggag ccgcgggcgc catggataga gcaggagggg    240
ccggagtatt gggaccggga gacacagatc tccaagacca acacacagac ttaccgagag    300
agcctgcgga acctgcgcgg ctactacaac cagagcgagg ccgggtctca caccctccag    360
```

```
agcatgtacg gctgcgacgt ggggccggac gggcgcctcc tccgcgggca taaccagtac      420
gcctacgacg gcaaggatta catcgccctg aacgaggacc tgcgctcctg gaccgccgcg      480
gacacggcgg ctcagatcac ccagcgcaag tgggaggcgg cccgtgtggc ggagcagctg      540
agagcctacc tggagggcga gtgcgtggag tggctccgca gatacctgga gaacgggaag      600
gagacgctgc agcgcgcgga ccccccaaag acacacgtga cccaccaccc catctctgac      660
catgaggcca ccctgaggtg ctgggccctg ggcttctacc ctgcggagat cacactgacc      720
tggcagcggg atggcgagga ccaaactcag gacactgagc ttgtggagac cagaccagca      780
ggagatagaa ccttccagaa gtgggcagct gtggtggtgc cttctggaga gagcagaga      840 tacacatgcc atgtacagca tgaggggctg ccgaagcccc tcaccctgag atgggagccg      900
tcttcccagt ccaccgtccc catcgtgggc attgttgctg gcctggctgt cctagcagtt      960
gtggtcatcg gagctgtggt cgctgctgtg atgtgtagga ggaagagctc aggtggaaaa     1020
ggagggagct actctcaggc tgcgtgcagc gacagtgccc agggctctga tgtgtctctc     1080
acagcttga                                                              1089

<210> SEQ ID NO 129
<211> LENGTH: 1119
<212> TYPE: DNA
<213> ORGANISM: Homo sapiens

<400> SEQUENCE: 129
atgcgggtca tggcgcccca agccctcctc ctgctgctct cgggagccct ggccctgatc       60
gagacctggg ccggctccca ctccatgagg tatttctaca ccgccgtgtc ccggcccggc      120
cgcggagagc cccgcttcat cgcagtgggc tacgtggacg acacgcagtt cgtgcggttc      180
gacagcgacg ccgcgagtcc gagaggggag ccgcgggcgc cgtgggtgga gcaggagggg      240
ccggagtatt gggaccggga gacacagaag tacaagcgcc aggcacaggc tgaccgagtg      300
aacctgcgga aactgcgcgg ctactacaac cagagcgagg ccggttctca caccatccag      360
aggatgtatg gctgcgacct ggggcccgac gggcgcctcc tccgcgggta taaccagttc      420
gcctacgacg gcaaggatta catcgccctg aacgaggacc tgcgctcctg gaccgcggcg      480
gacacggcgg ctcagatctc ccagcgcaag ttggaggcgg cccgtgaggc ggagcagctg      540
agagcctacc tggagggcga gtgcgtggag tggctccgcg gatacctgga gaacgggaag      600
gagacgctgc agcgcgcgga acgcccaaag acacacgtga cccaccatcc cgtctctgac      660
catgaggcca ccctgaggtg ctgggccctg ggcttctacc ctgcggagat cacactgacc      720
tggcagcggg atggggagga ccaaactcag gacaccgagc ttgtggagac caggccagca      780
ggagatggaa ccttccagaa gtgggcagct gtggtggtgc cttctggaca agaacagaga      840
tacacgtgcc atgtgcagca cgaggggctg caggagccct gcaccctgag atggaagccg      900
tcttcccagc ccaccatccc caacttgggc atcgtttctg gccagctgt cctggctgtc      960 ctggctgtcc tggctgtcct agctgtccta ggagctgtgg tcgctgctgt gatacatagg     1020
aggaagagct caggtggaaa aggagggagc tgctctcagg ctgcgtccag caacagtgcc     1080
cagggctctg atgagtctct catcgcttgt aaagcctga                            1119

<210> SEQ ID NO 130
<211> LENGTH: 12
<212> TYPE: PRT
<213> ORGANISM: Homo sapiens

<400> SEQUENCE: 130
```

Ala Tyr Leu Glu Gly Glu Cys Val Glu Trp Leu Arg
1               5                   10

<210> SEQ ID NO 131
<211> LENGTH: 12
<212> TYPE: PRT
<213> ORGANISM: Homo sapiens

<400> SEQUENCE: 131

Ala Tyr Leu Glu Gly Thr Cys Val Asp Gly Leu Arg
1               5                   10

<210> SEQ ID NO 132
<211> LENGTH: 10
<212> TYPE: PRT
<213> ORGANISM: Homo sapiens

<400> SEQUENCE: 132

Cys Leu Gly Leu Thr Glu Ala Gln Thr Arg
1               5                   10

<210> SEQ ID NO 133
<211> LENGTH: 11
<212> TYPE: PRT
<213> ORGANISM: Homo sapiens

<400> SEQUENCE: 133

Asp Gly Gly Val Cys Leu Leu Ser Gly Thr Lys
1               5                   10

<210> SEQ ID NO 134
<211> LENGTH: 16
<212> TYPE: PRT
<213> ORGANISM: Homo sapiens

<400> SEQUENCE: 134

Asp Ile Pro Phe Ser Ala Ile Tyr Phe Pro Cys Tyr Ala His Val Lys
1               5                   10                  15

<210> SEQ ID NO 135
<211> LENGTH: 17
<212> TYPE: PRT
<213> ORGANISM: Homo sapiens

<400> SEQUENCE: 135

Phe His Tyr Leu Pro Phe Leu Pro Ser Thr Glu Asp Val Tyr Asp Cys
1               5                   10                  15

Arg

<210> SEQ ID NO 136
<211> LENGTH: 10
<212> TYPE: PRT
<213> ORGANISM: Homo sapiens

<400> SEQUENCE: 136

Phe Tyr Ala Pro Trp Cys Gly His Cys Lys
1               5                   10

<210> SEQ ID NO 137
<211> LENGTH: 10
<212> TYPE: PRT
<213> ORGANISM: Homo sapiens

<400> SEQUENCE: 137

-continued

```
Ile Ala Glu Val Asp Cys Thr Ala Glu Arg
1               5                  10

<210> SEQ ID NO 138
<211> LENGTH: 25
<212> TYPE: PRT
<213> ORGANISM: Homo sapiens

<400> SEQUENCE: 138

Lys Gly Gly Ser Tyr Ser Gln Ala Ala Ser Ser Asp Ser Ala Gln Gly
1               5                  10                  15

Ser Asp Val Ser Leu Thr Ala Cys Lys
            20                  25

<210> SEQ ID NO 139
<211> LENGTH: 19
<212> TYPE: PRT
<213> ORGANISM: Homo sapiens

<400> SEQUENCE: 139

Leu Asp Leu Pro Asn Arg Pro Glu Thr Ser Phe Leu Trp Phe Thr Asn
1               5                  10                  15

Pro Cys Lys

<210> SEQ ID NO 140
<211> LENGTH: 8
<212> TYPE: PRT
<213> ORGANISM: Homo sapiens

<400> SEQUENCE: 140

Gln Ser Leu Leu Phe Cys Pro Lys
1               5

<210> SEQ ID NO 141
<211> LENGTH: 16
<212> TYPE: PRT
<213> ORGANISM: Homo sapiens

<400> SEQUENCE: 141

Gln Ser Ser Gly Glu Asn Cys Asp Val Val Asn Thr Leu Gly Lys
1               5                  10                  15

<210> SEQ ID NO 142
<211> LENGTH: 11
<212> TYPE: PRT
<213> ORGANISM: Homo sapiens

<400> SEQUENCE: 142

Ser Phe Gly Ala Glu Glu His Glu Val Cys Arg
1               5                  10

<210> SEQ ID NO 143
<211> LENGTH: 8
<212> TYPE: PRT
<213> ORGANISM: Homo sapiens

<400> SEQUENCE: 143

Thr Val Tyr Cys Asn Val His Lys
1               5

<210> SEQ ID NO 144
<211> LENGTH: 9
<212> TYPE: PRT
```

```
<213> ORGANISM: Homo sapiens

<400> SEQUENCE: 144

Val Val Ala Val Asp Cys Gly Ile Lys
 1               5

<210> SEQ ID NO 145
<211> LENGTH: 9
<212> TYPE: PRT
<213> ORGANISM: Homo sapiens

<400> SEQUENCE: 145

Tyr Lys Glu Ala Leu Glu Gln Cys Arg
 1               5
```

COLON DISEASE TARGETS AND USES THEREOF

FIELD OF THE INVENTION

This invention relates to the fields of molecular biology and oncology. Specifically, the invention provides a molecular marker and a therapeutic agent for use in the diagnosis and treatment of colon diseases.

BACKGROUND OF THE INVENTION

Cancer currently constitutes the second most common cause of death in the United States. Carcinomas of the colon are the eighth most prevalent form of cancer and fourth among the most common causes of cancer deaths in this country. The incidence of colon cancer has been increasing steadily in the past twenty years in most industrialized countries, exhibiting the characteristics of a growing epidemiological problem. In the year 2000, for example, an estimated 28,600 deaths will be ascribed to this type of cancer and approximately 28,600 new cases will be diagnosed.

Colon cancer is the second most frequently diagnosed malignancy in the United States as well as the second most common cause of cancer death. The five-year survival rate for patients with colorectal cancer detected in an early localized stage is 92%; unfortunately, only 37% of colorectal cancer is diagnosed at this stage. The survival rate drops to 64% if the cancer is allowed to spread to adjacent organs or lymph nodes, and to 7% in patients with distant metastases.

The prognosis of colon cancer is directly related to the degree of penetration of the tumor through the bowel wall and the presence or absence of nodal involvement, consequently, early detection and treatment are especially important. Currently, diagnosis is aided by the use of screening assays for fecal occult blood, sigmoidoscopy, colonoscopy and double contrast barium enemas. Treatment regimens are determined by the type and stage of the cancer, and include surgery, radiation therapy and/or chemotherapy. Recurrence following surgery (the most common form of therapy) is a major problem and is often the ultimate cause of death. In spite of considerable research into therapies for the disease, colon cancer remains difficult to diagnose and treat. In spite of considerable research into therapies for these and other cancers, colon cancer remains difficult to diagnose and treat effectively. Accordingly, there is a need in the art for improved methods for detecting and treating such cancers. The present invention fulfills these needs and further provides other related advantages.

In spite of considerable research into therapies for these and other cancers, colon cancer remains difficult to diagnose and treat effectively. Accordingly, there is a need in the art for improved methods for detecting and treating such cancers. The present invention fulfills these needs and further provides other related advantages such as other colon diseases.

SUMMARY OF THE INVENTION

The present invention is based on the identification of certain cell surface proteins or cytosolic proteins that are differentially expressed in colon cancer. A malignant cell often differs from a normal cell by a differential expression of one or more proteins. These differentially expressed proteins, and the fragments thereof, are important markers for the diagnosis of colon disease. The differentially expressed proteins of the present invention and the nucleic acids encoding said proteins and the fragments of said proteins are referred to herein as colon cancer associated target, CCAT proteins or CCAT nucleic acids or CCAT peptides, respectively.

The present invention provides peptides and protein differentially expressed in colon diseases (hereinafter CCAT). Based on the site of protein localization, e.g., surface or cytosolic, and protein characterization, e.g. receptor or enzyme, specific uses of these CCATs are provided. Some of the CCATs of the present invention serve as targets for one or more classes of therapeutic agents, while others may be suitable for antibody therapeutics.

Accordingly, the present invention provides a method for diagnosing or detecting colon disease in a subject comprising: determining the level of one or more CCAT proteins, or any fragment(s) thereof, in a test sample from said subject, wherein said CCAT protein comprises a sequence selected from a group consisting of SEQ ID NOS: 1-66; wherein a differential level of said CCAT protein(s) or fragment(s) in said sample relative to the level of said protein(s) or fragment(s) in a test sample from a healthy subject, or the level established for a healthy subject, is indicative of colon disease.

The present invention also provides a method for detecting colon cancer in a subject comprising: determining the level of one or more CCAT peptide(s) comprising a peptide sequence selected from a group consisting of SEQ ID NOS: 130-145 in a test sample from said subject, wherein a differential level of said CCAT peptide(s) in said sample to the level of said CCAT peptide(s) in a test sample from a healthy subject, or the level of said CCAT peptide(s) established for a healthy subject, is indicative of colon disease.

The present invention further provides a method for detecting colon disease in a subject comprising: determining the level of one or more CCAT nucleic acid(s), or any fragment(s) thereof, in a test sample from said subject, wherein said CCAT nucleic acid(s) encode a CCAT protein sequence selected from a group consisting of SEQ ID NOS: 1-66; wherein a differential level of said CCAT nucleic acids or fragment(s) in said sample relative to the level of said protein(s) or fragment(s) in a test sample from a healthy subject, or the level established for a healthy subject, is indicative of colon disease.

The invention also provides methods for detecting the CCAT peptides, gene or mRNA in a test sample for use in diagnosing the presence, absence or progression of a disease. The test sample includes but is not limited to a biological sample such as tissue, blood, serum or biological fluid.

The present invention further provides a purified antibody that binds specifically to a protein molecule, or any fragment thereof, selected from a group consisting of SEQ ID NOS: 1-66.

The present invention further provides a composition comprising an antibody that binds to a protein selected from a group consisting of SEQ ID NOS: 1-66, and an acceptable carrier.

The present invention further provides a method for treating colon disease, comprising administering to a patient in need of said treatment a therapeutically effective amount of one or more antibody(ies) of this invention.

The present invention further provides a method for treating colon disease comprising (i) identifying a subject having colon disease and (ii) administering to a said patient a therapeutically effective amount of one or more antibody(ies) of this invention.

The present invention further provides a method to screen for agents that modulate CCAT protein activity, comprising the steps of (i) contacting a test agent with a CCAT protein and (ii) assaying for CCAT protein activity, wherein a change in said activity in the presence of said agent relative to CCAT protein activity in the absence of said agent indicates said agent modulates said CCAT protein activity.

The present invention further provides a method to screen for agents that bind to CCAT protein, comprising the steps of (i) contacting a test agent with a CCAT protein and (ii) measuring the level of binding of agent to said CCAT protein.

The invention also provides diagnostic methods for human disease, in particular for colon diseases, its metastatic stage, and therapeutic potential.

The present invention further provides diagnostic method for epithelial-cell related cancers. In particular pancreas, lung, colon, prostate, ovarian, breast, bladder renal, hepatocellular, pharyngeal, and gastric cancer.

The invention also provides a method for monitoring the disease progression and the treatment progress.

The invention further provide a method of diagnosis by an array, wherein the array is immobilized with two or more CCAT proteins, peptides or nucleic acid molecules. The proteins, peptides or nucleic acid molecules include but are not limited to the SEQ ID NOS: 1-145.

The invention also provides monoclonal or polyclonal antibodies and composition thereof reactive with antigenic portion of CCAT protein, peptides or fragments thereof in a form for use in colon diseases diagnosis.

The invention further provides an immunogenic antibody for treating colon diseases disease or diseases associated with colon diseases.

The present invention provides a method for screening agents that modulate CCAT activity, comprising the steps of (a) contacting a sample comprising CCAT with an agent; and (b) assaying for CCAT activity, wherein a change in said CCAT activity in the presence of said agent relative to CCAT activity in the absence of said compound indicates said agent modulates CCAT. The agents include but are not limited to protein, peptide, antibody, nucleic acid such as antisense RNA, RNAi fragments, small molecules.

The present invention further provides a method for treating colon diseases, comprising: administering to a patient one or more agents in a therapeutically effective amount to treat colon diseases.

The present invention provides a method for treating colon diseases, comprising: identifying a subject having colon diseases; and administering to a patient to one or more antibodies in a therapeutically effective amount to treat colon diseases.

The present invention further provides therapeutic potential for epithelial-cell related cancers. In particular pancreas, lung, colon, prostate, ovarian, breast, bladder renal, hepatocellular, pharyngeal and gastric cancer.

DESCRIPTION OF THE FILES CONTAINED ON THE CD-R NAMED CL001535ORD

The CD-R named CL001535ORD contains the following three text (ASCII) files:

1) File SEQLIST_1535.txt provides the Sequence Listing. The Sequence Listing provides the protein sequences (SEQ ID NOS: 1-66); transcript sequences (SEQ ID NOS: 67-129) and peptide sequences (SEQ ID NOS: 130-145) as shown in Table 2. File SEQLIST_1535.txt is 553 KB in size.

2) File TABLE1_1535.txt provides Table 1. File TABLE1_1535.txt is 19 KB in size.

3) File TABLE2_1535.txt provides Table 2. File TABLE2_1535.txt is 263 KB in size.

The material contained on the CD-R labeled CL001535ORD is hereby incorporated by reference pursuant to 37 CFR 1.77(b)(4).

DESCRIPTION OF TABLE 1 AND TABLE 2

Table 1 (provided on the CD-R) discloses the peptides which correspond to the protein in the colon cancer tumor, the expression information, and the ratio compare to the control sample. The expression is based on measuring the level of the peptides. "N/A" represents the number of overexpression by more than two, whereas numerical representation of overexpression is also indicated. "S" which is overexpressed singleton indicates that the peptide peak in diseased sample was detected and there was no peak detected in control samples.

Table 2 (provided on the CD-R) discloses the CCAT proteins, transcripts, and peptides sequences that correlated to the Table 1.

The transcript/protein information includes:

a protein number (1 through 66)

a Celera protein internal identification number for the protein encoded by the Celera transcript (hCP and/or UID)

a public protein accession number (Genbank e.g., RefSeq NP number, Swiss-prot, or Derwent) for the protein an art-known gene/protein name a Celera transcript internal identification number (hCT and/or UID)

a public transcript accession number (Genbank e.g., RefSeq NM number, or Derwent)

a Celera hCG and UID internal identification numbers for the gene an art-known gene symbol Celera genomic axis position (indicating start nucleotide position-stop nucleotide position)

the chromosome number of the chromosome on which the gene is located an OMIM (Online Mendelian Inheritance in Man; Johns Hopkins University/NCBI) public reference number for obtaining further information regarding the medical significance of each gene alternative gene/protein name(s) and/or symbol(s) in the OMIM entry

DETAILED DESCRIPTION OF THE PREFERRED EMBODIMENTS

General Description

While the broadest definition of this invention is set forth in the Summary of the Invention, certain nucleic acids, peptides or proteins are preferred. For example a preferred method for detecting colon disease by determining the level of one or more CCAT protein(s) or any fragment(s) thereof is wherein the level of CCAT protein(s) are determined by contacting one or more antibody(ies) that specifically bind to the antigenic regions of the CCAT protein(s). Further preferred is a method wherein the level of two or more proteins are determined, more preferred wherein the level of four or more proteins are determined and most preferred wherein the level of eight or more proteins are determined.

A preferred method for detecting colon disease by determining the level of one or more CCAT peptide(s) is wherein the level of CCAT peptides(s) are determined by contacting one or more antibody(ies) that specifically bind to the antigenic regions of the CCAT peptide(s). Further preferred is a method wherein the level of five or more peptides are determined, more preferred wherein the level of ten or more peptides are determined and most preferred wherein the level of fifteen or more peptides are determined.

A preferred method for detecting colon disease by determining the level of one or more CCAT nucleic acid(s) is wherein the level of said CCAT nucleic acid(s) is determined by contacting one or more probes that specifically hybridize to said nucleic acid(s). Further preferred is a method wherein the level of two or more nucleic acids are determined, more preferred wherein the level of four or more nucleic acids are determined and most preferred wherein the level of eight or more nucleic acids are determined.

The methods for detecting colon disease provided by the present invention may be used for diagnosing the presence of disease in a patent, monitoring the presence of colon disease in patients undergoing treatment and testing for the reoccurrence of colon disease in patients that were successfully treated for colon disease; preferably wherein the colon disease is colon cancer. The test sample may be, but is not limited to, a biological sample such as tissue, blood, serum or biological fluid.

The present invention is based on the discovery of protein(s) and peptide(s) that are differentially expressed in colon cancer samples versus normal colon diseases samples. These proteins and peptide, and the encoding nucleic acid molecules are associated with colon diseases, hereinafter the CCAT protein, peptide or nucleic acids.

The discovery of disease specific target proteins is base on discoveries made using proteomics techniques. The method uses on MALDI-TOF TOF LC/MS analyses platform to generate protein expression profiles from colon diseases tissues or cell lines in an effort to discover and identify novel molecules associated with the disease.

Based on these discoveries, the present invention provides proteins, peptides, nucleic acids that are differential in colon diseases, as well as antibodies binds to the proteins or peptides. The present invention also provides methods for detection, monitoring, diagnosis, prognosis, preventive and treatment of colon diseases. The present invention provides a detection reagent, markers for colon diseases at various stages, comprises CCAT sequences isolated from human colon diseases tissue, sera, cell lines, blood or biological fluids.

The present invention provides a method for treating colon diseases targeting at CCAT. The treatment includes administration of a therapeutically effective amount of composition comprise, but not limit to, an antibody, an immunogentic peptide which induces T cell response, a small molecule, a protein or a nucleic acid molecule. The composition further comprises an agonist or antagonist to CCAT. A "Colon or colorectal disease" includes but not limited to colon cancer, colon tumor, diverticulosis, diverticulitis, Crohn's disease, ulcerative colitis, irritable bowel syndrome, inflammatory bowel disease, hemorrhoids, and anal fissure.

The present invention may further provide a diagnostic or therapeutic potential for epithelial-cell related cancers, which include but are not limited to pancreas, lung, colon; prostate, ovarian, breast, bladder renal, hepatocellular, pharyngeal and gastric cancers.

The present invention further provides the target for screening an agent for CCAT, wherein the agent is compounds of small molecules, proteins, peptides, nucleic acids, antibodies or other agonists or antagonists.

CCAT Peptide/Proteins and Peptides

The present invention provides isolated CCAT peptide and protein molecules that consisting of, consisting essentially of, or comprising the amino acid sequences of the CCAT peptides and proteins disclosed in the Tables 1 and 2, (encoded by the nucleic acid molecule shown in Table 2), as well as all obvious variants of these peptides that are within the art to make and use. Some of these variants are described in detail below.

In one embodiment CCAT peptides include, but are not limited to, the amino acid sequence of SEQ ID NOS: 130-145 and variants thereof. A CCAT protein includes, but is not limited to, the amino acid sequence of SEQ ID NOS: 1-66 and variants thereof. CCAT proteins may be differentially expressed in colon cell line, blood, tissue, serum or body fluids.

The peptide or protein or fragment thereof, to which the invention pertains, however, are not to be construed as encompassing peptide, protein or fragment that may be disclosed publicly prior to the present invention.

The CCAT proteins and peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

As used herein, a "peptide" is defined as amino acid sequences between 5-20 amino acids derived from CCAT proteins such as SEQ ID NOS: 1-66 or variants thereof. The peptide differentially expressed in either colon diseases cell line, blood, tissue, serum or body fluids. In one embodiment peptides include, but are not limited to, the amino acid sequence of SEQ ID NOS: 130-145, or variants thereof.

As used herein, a "protein" is full-length protein differentially expressed in colon diseases cell line, tissue, blood, serum or body fluids. A protein includes, but is not limited to, the amino acid sequence of SEQ ID NOS: 1-66.

A peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule are discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the CCAT peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated CCAT proteins and peptide can be purified from cells that naturally express it, purified from cells that have been altered to express it (recombinant), or synthesized using known protein synthesis methods. Sambrook et al., Molecular Cloning: A Laboratory Manual. 3rd. ed., Cold Spring Harbor Laboratory Press, Cold Spring Harbor, N.Y., (2001). Experimental data as provided in Table 1 indicates expression in human colon tumor tissues. For example, a nucleic acid molecule encoding the CCAT protein or peptide is cloned into an expression vector, the expression vector introduced into a host cell and the protein expressed in the host cell. The protein or peptide can then be isolated from the cells by an appropriate purification scheme using standard protein purification techniques. Many of these techniques are described in detail below.

A CCAT peptide or protein can be attached to heterologous sequences to form chimeric or fusion proteins. Such Schimeric and fusion proteins comprise a peptide operatively linked to a heterologous protein having an amino acid sequence not substantially homologous to the peptide. "Operatively linked" indicates that the peptide and the heterologous protein are fused in-frame. The heterologous protein can be fused to the N-terminus or C-terminus of the peptide.

In some uses, the fusion protein does not affect the activity of the peptide or protein per se. For example, the fusion protein can include, but is not limited to, fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant CCAT proteins or peptides. In certain host cells (e.g., mammalian host cells), expression and/or secretion of a protein can be increased by using a heterologous signal sequence.

A chimeric or fusion CCAT protein or peptide can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A CCAT-encoding nucleic acid can be cloned into such an expression vector such that the fusion moiety is linked in-frame to the CCAT protein or peptide.

As mentioned above, the CCAT peptide or the CCAT protein has obvious variants of the amino acid sequence, such as naturally occurring mature forms of the CCAT, allelic/sequence variants of the CCAT, non-naturally occurring recombinantly derived variants of the CCATs, and orthologs and paralogs of the CCAT proteins or peptides. Such variants can readily be generated using art-known techniques in the fields of recombinant nucleic acid technology and protein biochemistry.

It is understood, however, that CCAT and variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the CCAT peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48): 444-453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., Nucleic Acids Res. 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215: 403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the CCAT peptides of the present invention as well as being encoded by the same genetic locus as the CCAT peptide provided herein (See Table 2).

Allelic variants of a CCAT peptide can readily be identified as being a human protein having a high degree (significant) of sequence homology/identity to at least a portion of the CCAT peptide as well as being encoded by the same genetic locus as the CCAT peptide provided herein. Genetic locus can readily be determined based on the genomic information provided in Table 2, such as the genomic sequence mapped to the reference human. As used herein, two proteins (or a region of the proteins) have significant homology when the amino acid sequences are typically at least about 70-80%, 80-90%, and more typically at least about 90-95% or more homologous. A significantly homologous amino acid sequence, according to the present invention, will be encoded by a nucleic acid sequence that will hybridize to a CCAT peptide encoding nucleic acid molecule under stringent conditions as more fully described below.

Paralogs of a CCAT peptide can readily be identified as having some degree of significant sequence homology/identity to at least a portion of the CCAT peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a CCAT peptide encoding nucleic acid molecule under moderate to stringent conditions as more fully described below.

Orthologs of a CCAT peptide can readily be identified as having some degree of significant sequence homology/identity to at least a portion of the CCAT peptide as well as being encoded by a gene from another organism. Preferred orthologs will be isolated from mammals, preferably primates, for the development of human therapeutic targets and agents. Such orthologs will be encoded by a nucleic acid sequence that will hybridize to a CCAT peptide encoding nucleic acid molecule under moderate to stringent conditions, as more fully described below, depending on the degree of relatedness of the two organisms yielding the proteins.

Non-naturally occurring variants of the CCAT peptides of the present invention can readily be generated using recombinant techniques. Such variants include, but are not limited to deletions, additions and substitutions in the amino acid sequence of the CCAT peptide. For example, one class of substitutions is conserved amino acid substitution. Such substitutions are those that substitute a given amino acid in a CCAT peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

Variant CCAT peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081-1085 (1989)). The latter procedure introduces single alanine mutations at every residue in the molecule. The resulting mutant molecules are then tested for biological activity such as CCAT activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899-904 (1992); de Vos et al. Science 255:306-312 (1992)).

The present invention further provides fragments of the CCATs, in addition to proteins and peptides that comprise and consist of such fragments, particularly those comprising the residues identified in Tables 1 and 2. As used herein, a fragment comprises at least 8, 10, 12, 14, 16, 18, 20 or more contiguous amino acid residues from a CCAT. Such fragments can be chosen based on the ability to retain one or more of the biological activities of the CCAT or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the CCAT, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in CCATs are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T.E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (Meth. Enzymol. 182: 626-646 (1990)) and Rattan et al. (Ann. N.Y. Acad. Sci. 663:48-62 (1992)).

Accordingly, the CCATs of the present invention also encompass derivatives or analogs in which a substituted amino acid residue is not one encoded by the genetic code, in which a substituent group is included, in which the mature CCAT is fused with another compound, such as a compound to increase the half-life of the CCAT (for example, polyethylene glycol), or in which the additional amino acids are fused to the mature CCAT, such as a leader or secretory sequence or a sequence for purification of the mature CCAT or a proprotein sequence.

Protein/Peptide Uses

The proteins of the present invention can be used in substantial and specific assays related to the functional information provided in the Tables; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a CCAT-effector protein interaction or CCAT-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", Sambrook, J., E. F. Fritsch and T. Maniatis eds., 3rd. ed., Cold Spring Harbor Laboratory Press, Cold Spring Harbor, N.Y., (2001) and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, CCATs isolated from humans and their human/mammalian orthologs serve as targets for identifying agents for use in mammalian therapeutic applications, e.g. a human drug, particularly in modulating a biological or pathological response in a cell or tissue that expresses the CCAT. Experimental data as provided in Table 1 indicate that the CCAT of the present invention are overexpressed in colon tumor tissue. A large percentage of pharmaceutical agents are being developed that modulate the activity of CCAT proteins, particularly members of the CCAT subfamily (see Background of the Invention). The structural and functional information provided in the Background and Figures provide specific and substantial uses for the molecules of the present invention, particularly in combination with the expression information provided in Table 1. Experimental data as provided in Table 1 indicates expression in human colon tumor tissues. Such uses can readily be determined using the information provided herein, that which is known in the art, and routine experimentation.

The proteins of the present invention (including variants and fragments that may have been disclosed prior to the present invention) are useful for biological assays related to CCATs that are related to members of the CCAT subfamily. Such assays involve any of the known CCAT functions or activities or properties useful for diagnosis and treatment of CCAT-related conditions that are specific for the subfamily of CCATs that the one of the present invention belongs to, particularly in cells and tissues that express the CCAT. Experimental data as provided in Table 1 indicate that the CCAT of the present invention are overexpressed in colon tumor tissue The proteins of the present invention are also useful in drug screening assays, in cell-based or cell-free systems. Cell-based systems can be native, i.e., cells that normally express the CCAT, as a biopsy or expanded in cell culture. Experimental data as provided in Table 1 indicates expression in human colon tumor tissues. In an alternate embodiment, cell-based assays involve recombinant host cells expressing the CCAT protein.

The polypeptides can be used to identify compounds or agents that modulate CCAT activity of the protein in its natural state or an altered form that causes a specific disease or pathology associated with the CCAT. Both the CCATs of the present invention and appropriate variants and fragments can be used in high-throughput screens to assay candidate compounds for the ability to bind to the CCAT. These compounds can be further screened against a functional CCAT to determine the effect of the compound on the CCAT activity. Further, these compounds can be tested in animal or invertebrate systems to determine activity/effectiveness. Compounds can be identified that activate (agonist) or inactivate (antagonist) the CCAT to a desired degree.

Further, the proteins of the present invention can be used to screen a compound or an agent for the ability to stimulate or inhibit interaction between the CCAT protein and a molecule that normally interacts with the CCAT protein, e.g. a substrate or or an extracellular binding ligand or a component of the signal pathway that the CCAT protein normally interacts (for example, a cytosolic signal protein or another CCAT). Such assays typically include the steps of combining the CCAT protein with a candidate compound under conditions that allow the CCAT protein, or fragment, to interact with the target molecule, and to detect the formation of a complex between the protein and the target or to detect the biochemical consequence of the interaction with the CCAT protein and the target, such as any of the associated effects of signal transduction such as protein phosphorylation, cAMP turnover, and adenylate cyclase activation, etc.

Candidate compounds or agents include, for example, 1) peptides such as soluble peptides, including Ig-tailed fusion peptides and members of random peptide libraries (see, e.g., Lam et al., Nature 354:82-84 (1991); Houghten et al., Nature 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767-778 (1993)); 3) antibodies (e.g., polyclonal, monoclonal, humanized, anti-idiotypic, chimeric, and single chain antibodies as well as Fab, F(ab')2, Fab expression library fragments, and epitope-binding fragments of antibodies); and 4) small organic and inorganic molecules (e.g., molecules obtained from combinatorial and natural product libraries).

One candidate compound or agent is a soluble fragment of the CCAT that competes for substrate binding. Other candidate compounds include mutant CCATs or appropriate fragments containing mutations that affect CCAT function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) CCAT activity. The assays typically involve an assay of events in the signal transduction pathway that indicate CCAT activity. Thus, the phosphorylation of a substrate, activation of a protein, a change in the expression of genes that are up- or down-regulated in response to the CCAT protein dependent signal cascade can be assayed.

Any of the biological or biochemical functions mediated by the CCAT can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Tables, particularly Table 1. Specifically, a biological function of a cell or tissues that expresses the CCAT can be assayed. Experimental data as provided in Table 1 indicate that the CCAT of the present invention are overexpressed in colon tumor tissue.

Binding and/or activating compounds can also be screened by using chimeric CCAT proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native CCAT. Accordingly, a different set of signal transduction components is available as an endpoint assay for activation. This allows for assays to be performed in other than the specific host cell from which the CCAT is derived.

The proteins of the present invention are also useful in competition binding assays in methods designed to discover compounds that interact with the CCAT (e.g. binding partners and/or ligands). Thus, a compound is exposed to a CCAT polypeptide under conditions that allow the compound to bind or to otherwise interact with the polypeptide. Soluble CCAT polypeptide is also added to the mixture. If the test compound interacts with the soluble CCAT polypeptide, it decreases the amount of complex formed or activity from the CCAT. This type of assay is particularly useful in cases in which compounds are sought that interact with specific regions of the CCAT. Thus, the soluble polypeptide that competes with the target CCAT region is designed to contain peptide sequences corresponding to the region of interest.

To perform cell free drug screening assays, it is sometimes desirable to immobilize either the CCAT protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of CCAT-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a CCAT-binding protein and a candidate compound are incubated in the CCAT protein-presenting wells and the amount of complex trapped in the well can be quantitated. Methods for detecting such complexes, in addition to those described above for the GST-immobilized complexes, include immunodetection of complexes using antibodies reactive with the CCAT protein target molecule, or which are reactive with CCAT protein and compete with the target molecule, as well as CCAT-linked assays which rely on detecting an enzymatic activity associated with the target molecule.

Agents that modulate one of the CCATs of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of CCAT protein activity identified according to these drug screening assays can be used to treat a subject with a disorder mediated by the CCAT pathway, by treating cells or tissues that express the CCAT. Experimental data as provided in Table 1 indicates expression in human colon tumor tissues. These methods of treatment include the steps of administering a modulator of CCAT activity in a pharmaceutical composition to a subject in need of such treatment, the modulator being identified as described herein.

In yet another aspect of the invention, the CCAT proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with the CCAT and are involved in CCAT activity. Such CCAT-binding proteins are also likely to be involved in the propagation of signals by the CCAT proteins or CCAT targets as, for example, downstream elements of a CCAT-mediated signaling pathway. Alternatively, such CCAT-binding proteins are likely to be CCAT inhibitors.

The two-hybrid system is based on the modular nature of most transcription factors, which consist of separable DNA-binding and activation domains. Briefly, the assay utilizes two different DNA constructs. In one construct, the gene that codes for a CCAT protein is fused to a gene encoding the DNA binding domain of a known transcription factor (e.g., GAL-4). In the other construct, a DNA sequence, from a library of DNA sequences that encode an unidentified protein ("prey" or "sample") is fused to a gene that codes for the activation domain of the known transcription factor. If the "bait" and the "prey" proteins are able to interact, in vivo, forming a CCAT-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the CCAT protein.

This invention further pertains to novel agents identified by the above-described screening assays. Accordingly, it is within the scope of this invention to further use an agent identified as described herein in an appropriate animal model. For example, an agent identified as described herein (e.g., a CCAT-modulating agent, an antisense CCAT nucleic acid molecule, an CCAT-RNAi fragment, a CCAT-specific antibody, or a CCAT-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The CCAT proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in Table 1 indicates expression in human colon tumor tissues. The method involves contacting a biological sample with a compound capable of interacting with the CCAT protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered CCAT activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10-11): 983-985 (1996)), and Linder, M. W. (Clin. Chem. 43(2):254-266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the CCAT protein in which one or more of the CCAT functions in one population are different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and CCAT activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in Table 1 indicates expression in human colon tumor tissues. Accordingly, methods for treatment include the use of the CCAT protein or fragments.

Antibodies

The present invention provides antibodies specifically bind to CCAT proteins or fragments thereof, peptides, or antigenic portion thereof.

The invention also provides antibodies that selectively bind to one of the peptides of the present invention, a protein comprising such a peptide, as well as variants and fragments thereof as describe above.

The antibody of present invention selectively binds a target CCAT when it binds the target domain and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

The term "antibody" is used in the broadest sense, and specifically covers monoclonal antibodies (including full length monoclonal antibodies), polyclonal antibodies, multispecific antibodies (e.g., bispecific antibodies), humanized antibody and antibody fragments (e.g., Fab, F(ab').sub.2 and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules that lack antigen specificity.

As used herein, antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains. Chothia et al., J. Mol. Biol. 186, 651-63 (1985); Novotny and Haber, Proc. Natl. Acad. Sci. USA 82 4592-4596 (1985).

An "isolated" antibody is one which has been identified and separated and/or recovered from a component of the environment in which is produced. Contaminant components of its production environment are materials that would interfere with diagnostic or therapeutic uses for the antibody, and may include enzymes, hormones, and other proteinaceous or nonproteinaceous solutes. In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequentator; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

An "antigenic region" or "antigenic determinant" or an "epitope" includes any protein determinant capable of specific binding to an antibody. This is the site on an antigen to which each distinct antibody molecule binds. Epitopic determinants usually consist of active surface groupings of molecules such as amino acids or sugar side chains and usually have specific three-dimensional structural characteristics, as well as charge characteristics.

"Antibody specificity," is an antibody, which has a stronger binding affinity for an antigen from a first subject species than it has for a homologue of that antigen from a second subject species. Normally, the antibody "bind specifically" to a human antigen (i.e., has a binding affinity (Kd) value of no more than about $1\times10^{-7}$M, preferably no more than about $1\times10^{-8}$ M and most preferably no more than about $1\times10^{-9}$ M) but has a binding affinity for a homologue of the antigen from a second subject species which is at least about 50 fold, or at least about 500 fold, or at least about 1000 fold, weaker than its binding affinity for the human antigen. The antibody can be of any of the various types of antibodies as defined above, but preferably is a humanized or human antibody (Queen et al., U.S. Pat. Nos. 5,530,101, 5,585,089; 5,693,762; and 6,180,370).

The present invention provides an "antibody variant," which refers to an amino acid sequence variant of an antibody wherein one or more of the amino acid residues have been modified. Such variant necessarily have less than 100% sequence identity or similarity with the amino acid sequence having at least 75% amino acid sequence identity or similarity with the amino acid sequence of either the heavy or light chain variable domain of the antibody, more preferably at least 80%, more preferably at least 85%, more preferably at least 90%, and most preferably at least 95%. Since the method of the invention applies equally to both polypeptides, antibodies and fragments thereof, these terms are sometimes employed interchangeably.

The term "variable" in the context of variable domain of antibodies refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains. There are at least two techniques for determining CDRs: (1) an approach based on cross-species sequence variability (i.e., Kabat et al., Sequences of Proteins of Immunological Interest (National Institute of Health, Bethesda, Md. 1987); and (2) an approach based on crystallographic studies of antigen-antibody complexes (Chothia, C. et al. (1989), Nature 342: 877). The more highly conserved portions of variable domains are called the framework (FR). The variable domains of native heavy and light chains each comprise four FR regions, largely adopting a .beta.-Sheet configuration, connected by three CDRs, which form loops connecting, and in some cases forming part of, the .beta.-sheet structure. The CDRs in each chain are held together in close proximity by the FR regions and, with the CDRs from the other chain, contribute to the formation of the antigen-binding site of antibodies (see Kabat et al.) The constant domains are not involved directly in binding an antibody to an antigen, but exhibit various effector functions, such as participation of the antibody in antibody-dependent cellular toxicity.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of crosslinking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

An "Fv" fragment is the minimum antibody fragment that contains a complete antigen recognition and binding site.

This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment [also designated as F(ab)] also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

The present invention further provides monoclonal antibody, polyclonal antibody as well as humanized antibody. In general, to generate antibodies, an isolated peptide is used as an immunogen and is administered to a mammalian organism, such as a rat, rabbit or mouse. The full-length protein, an antigenic peptide fragment or a fusion protein of the CCAT protein can be used. Particularly important fragments are those covering functional domains, some but not all the examples of the domains are identified in Tables. Many methods are known for generating and/or identifying antibodies to a given target peptide. Several such methods are described by Harlow, Antibodies, Cold Spring Harbor Press, (1989).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" antibody indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol. Biol. 222: 581-597 (1991). For detailed procedure for making a monoclonal antibody, see the Example below.

"Humanized" forms of non-human (e.g. murine or rabbit) antibodies are chimeric immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-327 (1988) and Presta, Curr. Op. Struct. Biol. 2, 593-596 (1992).

Polyclonal antibodies may be prepared by any known method or modifications of these methods including obtaining antibodies from patients. For example, a complex of an immunogen such as CCAT protein, peptides or fragments thereof and a carrier protein is prepared and an animal is immunized by the complex according to the same manner as that described with respect to the above monoclonal antibody preparation and the description in the Example. A serum or plasma containing the antibody against the protein is recovered from the immunized animal and the antibody is separated and purified. The gamma globulin fraction or the IgG antibodies can be obtained, for example, by use of saturated ammonium sulfate or DEAE Sephadex, or other techniques known to those skilled in the art.

The antibody titer in the antiserum can be measured according to the same manner as that described above with respect to the supernatant of the hybridoma culture. Separation and purification of the antibody can be carried out according to the same separation and purification method of antibody as that described with respect to the above monoclonal antibody and in the Example.

The protein used here in as the immunogen is not limited to any particular type of immunogen. In one aspect, antibodies are preferably prepared from regions or discrete fragments of the CCAT proteins. Antibodies can be prepared from any region of the peptide as described herein. In particular, they are selected from a group consisting of SEQ ID NOS: 130-145 and fragments of SEQ ID NOS: 1-66. An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness.

Antibodies may also be produced by inducing production in the lymphocyte population or by screening antibody libraries or panels of highly specific binding reagents as disclosed in Orlandi et al. (1989; Proc Natl Acad Sci 86:3833-3837) or Winter et al. (1991; Nature 349:293-299). A protein may be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art. Smith G. P., 1991, Curr. Opin. Biotechnol. 2: 668-673.

The antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibody can be also made recombinantly. When using recombinant techniques, the antibody variant can be produced intracellularly, in the periplasmic space, or directly secreted into the medium. If the antibody variant is produced intracellularly, as a first step, the particulate debris, either host cells or lysed fragments, is removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibodies or antigen binding fragments may also be produced by genetic engineering. The technology for expression of both heavy and light chain genes in *E. coli* is the subject the following PCT patent applications; publication number WO 901443, WO901443, and WO 9014424 and in Huse et al., 1989 Science 246:1275-1281. The general recombinant methods are well known in the art.

The antibody composition prepared from the cells can be purified using, for example, hydroxylapatite chromatography, gel elecrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .delta.1, .delta.2 or .delta.4 heavy chains (Lindmark et al., J. Immunol. Meth. 62: 1-13 (1983)). Protein G is recommended for all mouse isotypes and for human .delta.3 (Guss et al., EMBO J. 5: 1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in Table 1 indicate that the CCAT of the present invention are overexpressed in colon tumor tissue. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in Table 1 indicates expression in human colon tumor tissues. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in Table 1 indicates expression in human colon tumor tissues. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy. More detection and diagnosis methods are described in detail below.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in Table 1 indicates expression in human colon tumor tissues. Thus, where a specific protein has been correlated with expression in a specific tissue, antibodies that are specific for this protein can be used to identify a tissue type.

The antibodies are also useful for inhibiting protein function, for example, blocking the binding of the CCAT peptide to a binding partner such as a substrate or another antibody. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. More therapeutics methods are described in detail below.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a CCAT peptide or protein of the present invention. Such nucleic acid molecules will consist of, consist essentially of, or comprise a nucleotide sequence that encodes one of the CCAT peptides of the present invention, an allelic variant thereof, or an ortholog or paralog thereof. The nucleic acid molecules and the fragments thereof of the present invention pertains, however, are not to be construed as encompassing fragments that may be disclosed publicly prior to the present invention.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

The present invention further provides nucleic acid molecules that comprise the nucleotide sequences shown in Table 2, (SEQ ID NOS: 67-129), or any nucleic acid molecule that encodes the protein provided in Table 2, (SEQ ID NOS: 1-66). A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In Table 2, human transcript sequences are provided. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the CCAT peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the CCAT proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in Tables 1 and 2. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60-70%, 70-80%, 80-90%, and more typically at least about 90-95% or more homologous to the nucleotide sequence shown in the Table 2 or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60-70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1-6.3.6. One example of stringent hybridization conditions are hybridization in 6× sodium chloride/sodium citrate (SSC) at about 45 C, followed by one or more washes in 0.2×SSC, 0.1% SDS at 50-65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in Tables 1 and 2 and to isolate cDNA and genomic clones that correspond to variants (alleles, orthologs, etc.) producing the same or related peptides shown in Tables 1 and 2.

The probe can correspond to any sequence along the entire length of the nucleic acid molecules provided in the Tables. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein. The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in Table 1 indicate that the CCAT of the present invention are overexpressed in colon tumor tissue. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in CCAT protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a CCAT protein, such as by measuring a level of a CCAT-encoding nucleic acid in a sample of cells from a subject e.g., mRNA or genomic DNA, or determining if a CCAT gene has been mutated. Experimental data as provided in Table 1 indicate that the CCAT of the present invention are overexpressed in colon tumor tissue. More detection and diagnosis methods are described in detail below.

Nucleic acid expression assays are useful for drug screening to identify compounds that modulate CCAT nucleic acid expression.

The invention thus provides a method for identifying a compound that can be used to treat a disorder associated with nucleic acid expression of the CCAT gene, particularly biological and pathological processes that are mediated by the CCAT in cells and tissues that express it. Experimental data as provided in Table 1 indicates expression in human colon tumor tissues. The method typically includes assaying the ability of the compound to modulate the expression of the CCAT nucleic acid and thus identifying a compound that can be used to treat a disorder characterized by undesired CCAT nucleic acid expression. The assays can be performed in cell-based and cell-free systems. Cell-based assays include cells naturally expressing the CCAT nucleic acid or recombinant cells genetically engineered to express specific nucleic acid sequences.

The assay for CCAT nucleic acid expression can involve direct assay of nucleic acid levels, such as mRNA levels, or on collateral compounds involved in the signal pathway. Further, the expression of genes that are up- or down-regulated in response to the CCAT protein signal pathway can also be assayed. In this embodiment the regulatory regions of these genes can be operably linked to a reporter gene such as luciferase.

Thus, modulators of CCAT gene expression can be identified in a method wherein a cell is contacted with a candidate compound or agent and the expression of mRNA determined. The level of expression of CCAT mRNA in the presence of the candidate compound or agent is compared to the level of expression of CCAT mRNA in the absence of the candidate compound or agent. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound or an agent identified through drug screening as a gene modulator to modulate CCAT nucleic acid expression in cells and tissues that express the CCAT. Experimental data as provided in Table 1 indicate that the CCAT of the present invention are overexpressed in colon tumor tissue. Modulation includes both up-regulation (i.e. activation or agonization) or down-regulation (suppression or antagonization) or nucleic acid expression.

Alternatively, a modulator for nucleic acid expression can be a small molecule or drug identified using the screening assays described herein as long as the drug or small molecule inhibits the CCAT nucleic acid expression in the cells and tissues that express the protein. Experimental data as provided in Table 1 indicates expression in human colon tumor tissues.

The nucleic acid molecules are also useful for monitoring the effectiveness of modulating compounds or agents on the expression or activity of the CCAT gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in CCAT nucleic acid expression, and particularly in qualitative changes that lead to pathology. The nucleic acid molecules can be used to detect mutations in CCAT genes and gene expression products such as mRNA. The nucleic acid molecules can be used as hybridization probes to detect naturally occurring genetic mutations in the CCAT gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the CCAT gene associated with a dysfunction provides a diagnostic tool for an active disease or susceptibility to disease when the disease results from overexpression, underexpression, or altered expression of a CCAT protein.

Individuals carrying mutations in the CCAT gene can be detected at the nucleic acid level by a variety of techniques. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077-1080 (1988); and Nakazawa et al., PNAS 91:360-364 (1994)), the latter of which can be particularly useful for detecting point mutations in the gene (see Abravaya et al., Nucleic Acids Res. 23:675-682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a CCAT gene can be directly identified, for example, by alterations in restriction enzyme digestion patterns determined by gel electrophoresis.

Further, sequence-specific ribozymes (U.S. Pat. No. 5,498, 531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and Si protection or the chemical cleavage method. Furthermore, sequence differences between a mutant CCAT gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127-162 (1996); and Griffin et al., Appl. Biochem. Biotechnol. 38:147-159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286-295 (1992)), electrophoretic mobility of mutant and wild type nucleic acid is compared (Orita et al., PNAS 86:2766 (1989); Cotton et al., Mutat. Res. 285:125-144 (1993); and Hayashi et al., Genet. Anal. Tech. Appl. 9:73-79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the CCAT gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control CCAT gene expression in cells, tissues, and organisms. A DNA antisense nucleic acid molecule is designed to be complementary to a region of the gene involved in transcription, preventing transcription and hence production of CCAT protein. An antisense RNA or DNA nucleic acid molecule would hybridize to the mRNA and thus block translation of mRNA into CCAT protein.

The nucleic acid of the present invention may also be used to specifically suppress gene expression by methods such as RNA interference (RNAi), which may also include cosuppression and quelling. This and antisense RNA or DNA of gene suppression are well known in the art. A review of this technique is found in Science 288:1370-1372, 2000. RNAi also operates on a post-transcriptional level and is sequence specific, but suppresses gene expression far more efficiently than antisense RNA. RNAi fragments, particularly double-stranded (ds) RNAi, can be also used to generate loss-of-function phenotypes.

Alternatively, a class of antisense molecules can be used to inactivate mRNA in order to decrease expression of CCAT nucleic acid. Accordingly, these molecules can treat a disorder characterized by abnormal or undesired CCAT nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the CCAT protein, such as substrate binding.

The nucleic acid molecules also provide vectors for gene therapy in patients containing cells that are aberrant in CCAT gene expression. Thus, recombinant cells, which include the patient's cells that have been engineered ex vivo and returned to the patient, are introduced into an individual where the cells produce the desired CCAT protein to treat the individual.

The invention also encompasses kits for detecting the presence of a CCAT nucleic acid in a biological sample. Experimental data as provided in Table 1 indicate that the CCAT of the present invention are overexpressed in colon tumor tissue. For example, the kit can comprise reagents such as a labeled or labelable nucleic acid or agent capable of detecting CCAT nucleic acid in a biological sample; means for determining the amount of CCAT nucleic acid in the sample; and means for comparing the amount of CCAT nucleic acid in the sample with a standard. The compound or agent can be packaged in a suitable container. The kit can further comprise instructions for using the kit to detect CCAT protein mRNA or DNA.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequences to which the nucleic acid molecules described herein can be operably linked include promoters for directing mRNA transcription. These include, but are not limited to, the left promoter from bacteriophage, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., Molecular Cloning: A Laboratory Manual. 3rd. ed., Cold Spring Harbor Laboratory Press, Cold Spring Harbor, N.Y., (2001).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 3rd. ed., Cold Spring Harbor Laboratory Press, Cold Spring Harbor, N.Y., (2001).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, E. coli, Streptomyces, and Salmonella typhimurium. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein; increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion E. coli expression vectors include pTrc (Amann et al., Gene 69:301-315 (1988)) and pET 11d (Studier et al., Gene Expression Technology: Methods in Enzymology 185:60-89 (1990)). Recombinant protein expression can be maximized in host bacteria by providing a genetic background wherein the host cell has an impaired capacity to proteolytically cleave the recombinant protein. (Gottesman, S., Gene Expression Technology: Methods in Enzymology 185, Academic Press, San Diego, Calif. (1990) 119-128). Alternatively, the sequence of the nucleic acid molecule of interest can be altered to provide preferential codon usage for a specific host cell, for example E. coli. (Wada et al., Nucleic Acids Res. 20:2111-2118 (1992)).

The nucleic acid molecules can also be expressed by expression vectors that are operative in yeast. Examples of vectors for expression in yeast e.g., S. cerevisiae include pYepSec1 (Baldari, et al., EMBO J. 6:229-234 (1987)), pMFa (Kurjan et al., Cell 30:933-943 (1982)), pJRY88 (Schultz et al., Gene 54:113-123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell. Biol. 3:2156-2165 (1983)) and the pVL series (Lucklow et al., Virology 170:31-39 (1989)).

In certain embodiments of the invention, the nucleic acid molecules described herein are expressed in mammalian cells using mammalian expression vectors. Examples of mammalian expression vectors include pCDM8 (Seed, B. Nature 329:840 (1987)) and pMT2PC (Kaufman et al., EMBO J. 6:187-195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. Molecular Cloning: A Laboratory Manual. 3rd. ed., Cold Spring Harbor Laboratory Press, Cold Spring Harbor, N.Y., (2001).

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (Molecular Cloning: A Laboratory Manual. 3rd. ed., Cold Spring Harbor Laboratory Press, Cold Spring Harbor, N.Y., (2001).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as CCATs, appropriate secretion signals are incorporated into the vector. The signal sequence can be endogenous to the peptides or heterologous to these peptides.

Where the peptide is not secreted into the medium, which is typically the case with CCATs, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a CCAT protein or peptide that can be further purified to produce desired amounts of CCAT protein or fragments. Thus, host cells containing expression vectors are useful for peptide production.

Host cells are also useful for conducting cell-based assays involving the CCAT protein or CCAT protein fragments, such as those described above as well as other formats known in the art. Thus, a recombinant host cell expressing a native CCAT protein is useful for assaying compounds that stimulate or inhibit CCAT protein function.

Host cells are also useful for identifying CCAT protein mutants in which these functions are affected. If the mutants naturally occur and give rise to a pathology, host cells containing the mutations are useful to assay compounds that have a desired effect on the mutant CCAT protein (for example, stimulating or inhibiting function) which may not be indicated by their effect on the native CCAT protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a CCAT protein and identifying and evaluating modulators of CCAT protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the CCAT protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the CCAT protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. PNAS 89:6232-6236 (1992). Another example of a recombinase system is the FLP recombinase system of *S. cerevisiae* (O'Gorman et al. Science 251: 1351-1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. Nature 385:810-813 (1997) and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, CCAT protein activation, and signal transduction, may not be evident from in vitro cell-free or cell-based assays. Accordingly, it is useful to provide non-human transgenic animals to assay in vivo CCAT protein function, including substrate interaction, the effect of specific mutant CCAT proteins on CCAT protein function and substrate interaction, and the effect of chimeric CCAT proteins. It is also possible to assess the effect of null mutations, that is, mutations that substantially or completely eliminate one or more CCAT protein functions.

Detection and Diagnosis

The present invention provides a method for detecting CCAT nucleic acids, proteins, peptides and fragments thereof that are differentially expressed in colon diseases in a test sample, preferably in a biological sample.

The present invention further provides a method for diagnosing the colon diseases, by detecting the nucleic acids, proteins, peptides and fragments thereof. The further embodiment includes but is not limited to, monintoring the disease prognosis (recurrance), diagnosing disease stage, preventing the disease and treating the disease.

As used herein, a "biological sample" can be collected from tissues, blood, sera, cell lines or biological fluids such as, plasma, interstitial fluid, urine, cerebrospinal fluid, and the like, containing cells. In preferred embodiments, a biological sample comprises cells or tissues suspected of having diseases (e.g., cells obtained from a biopsy).

As used herein, a "differential level" is defined as the level of CCAT protein or nucleic acids in a test sample either above or below the level of the ones in control samples, wherein the level of control samples is obtained either from a control cell line, a normal tissue or body fluids, or combination thereof, from a healthy subject.

As used herein, a "subject" can be a mammalian subject or non mammalian subject, preferably, a mammalian subject. A mammalian subject can be human or non-human, preferably human. A healthy subject is defined as a subject without detectable colon diseases or colon associated diseases by using conventional diagnostic methods.

As used herein the "diseases" include colon diseases and colon associated disease.

As used herein, "cancer" includes epithelial-cell related cancers, for example pancreatic, lung, colon, prostate, ovarian, breast, bladder renal, hepatocellular, pharyngeal and gastric cancers.

Nucleic Acid Detections

The present invention is not limited to the detection methods described above. Any suitable detection method that allows for the specific detection of colon diseases cells, tissues or organs may be utilized. For example, in some embodiments, the expression of RNA corresponding to a CCAT gene is detected by hybridization to an antisense oligonucleotide (described below). In other embodiments, RNA expression is detected by hybridization assays such as Northern blots, RNase assays, reverse transcriptase PCR amplification, and the like. One preferred detection method is using RT PCR by using TaqMan technology (ABI, Foster City, Calif.).

In another embodiment, the present invention provides a method for diagnosing or detecting colon diseases in a subject comprising: determining the level of one or more CCAT nucleic acid molecules or any fragment(s) thereof in a test sample from said subject, wherein said CCAT nucleic acid molecule(s) comprises a sequence selected from a group consisting of SEQ ID NOS: 67-129 and a combination thereof; wherein a differential level of said CCAT nucleic acid molecule(s) relative to the level of said nucleic acid molecule(s) in a test sample from a healthy subject, or the level established for a healthy subject, is indicative of colon diseases.

In another embodiment, the detecting or diagnosing method comprises determining level of differential expression of 2, 4, 8, 10, 20 or more nucleic acid molecules, preferably, the nucleic acid molecules comprise or consists of a sequence selected from the group consisting of SEQ ID NOS: 67-129 and combination thereof.

In further embodiments of the present invention, the presence of particular sequences in the genome of a subject is detected. Such sequences include CCAT sequences associated with abnormal expression of CCAT (e.g., overexpression or expression at a physiological inappropriate time). These sequences include polymorphisms, including polymorphisms in the transcribed sequence (e.g., that effect CCAT processing and/or translation) and regulatory sequences such as promoters, enhances, repressors, and the like. These sequences may also include polymorphisms in genes or control sequences associated with factors that affect expression such as transcription factors, and the like. Any suitable method for detecting and/or identifying these sequences is within the scope of the present invention including, but not limited to, nucleic acid sequencing, hybridization assays (e.g., Southern blotting), single nucleotide polymorphism assays (See e.g., U.S. Pat. No. 5,994,069, herein incorporated by reference in its entirety), and the like.

Protein Detections

The present invention provides methods for diagnosing or detecting the differential presence of CCAT protein. In some embodiments (e.g., where CCATs are overexpressed in diseased cells), CCAT proteins are detected directly. In other embodiments (e.g., where the presence of a CCATs are underexpressed), CCAT to the disease antigens are detected non-existence.

The diagnostic methods of the present invention find utility in the diagnosis and characterization of diseases. For example, the presence of an antibody to a specific protein may be indicative of a cancer or disease. In addition, certain CCAT may be indicative of a specific stage or sub-type of the same cancer or disease.

The information obtained is also used to determine prognosis and appropriate course of treatment. For example, it is contemplated that individuals with a specific CCAT expression or stage of colon diseases may respond differently to a given treatment that individuals lacking the CCAT expression. The information obtained from the diagnostic methods of the present invention thus provides for the personalization of diagnosis and treatment.

In one embodiment, the present invention provides a method for monitoring colon diseases treatment in a subject comprising: determining the level of one or more CCAT proteins or any fragment(s) or peptide(s) thereof in a test sample from said subject, wherein said CCAT protein(s) comprises a sequence selected from a group consisting of SEQ ID NOS: 1-66, SEQ ID NOS: 130-145 and a combination thereof; wherein an level of said CCAT protein(s) similar to the level of said protein(s) in a test sample from a healthy subject, or the level established for a healthy subject, is indicative of successful treatment.

In another embodiment, the present invention provides a method for diagnosing recurrence of colon diseases following successful treatment in a subject comprising: determining the level of one or more CCAT proteins or any fragment(s) or peptide(s) thereof in a test sample from said subject, wherein said CCAT protein(s) comprises a sequence selected from a group consisting of SEQ ID NOS: 1-66, SEQ ID NOS: 130-145 or a combination thereof; wherein a changed level of said CCAT protein(s) relative to the level of said protein(s) in a test sample from a healthy subject, or the level established for a healthy subject, is indicative of recurrence of colon diseases.

In yet another embodiment, the present invention provides a method for diagnosing or detecting colon diseases in a subject comprising: determining the level of one or more CCAT proteins or any fragment(s) or peptides thereof in a test sample from said subject, wherein said CCAT protein(s) comprises a sequence selected from a group consisting of SEQ ID NOS: 1-66, SEQ ID NOS: 130-145 and a combination thereof; wherein a differential level of said CCAT protein(s) relative to the level of said protein(s) in a test sample from a healthy subject, or the level established for a healthy subject, is indicative of colon diseases.

The detecting or diagnosing method comprises determining level of differential expression of 2, 4, 8, 10, 20 or more proteins, preferably, the proteins are selected from a group consisting of SEQ ID NOS: 1-66 and combination thereof.

Further, the detecting or diagnosing method comprises determining level of differential expression of 5, 10, 15, 20, 40, 60, 80, 100 or more CCAT peptides, preferably the peptides are selected from the group consisting of SEQ ID NOS: 130-145 and combination thereof.

These methods are also useful for diagnosing diseases that show differential protein expression. As describe earlier, normal, control or standard values or level established from a healthy subject for protein expression are established by combining body fluids or tissue, cell extracts taken from a normal healthy mammalian or human subject with specific antibodies to a protein under conditions for complex formation. Standard values for complex formation in normal and diseased tissues are established by various methods, often photometric means. Then complex formation as it is expressed in a subject sample is compared with the standard values. Deviation from the normal standard and toward the diseased standard provides parameters for disease diagnosis or prognosis while deviation away from the diseased and toward the normal standard may be used to evaluate treatment efficacy.

In yet another embodiment, the present invention provides a detection or diagnostic method of CCATs by using LC/MS. The proteins from cells are prepared by methods known in the art (R. Aebersold Nature Biotechnology Volume 21 Number 6 Jun. 2003). The differential expression of proteins in disease and healthy samples are quantitated using Mass Spectrometry and ICAT (Isotope Coded Affinity Tag) labeling, which is known in the art. ICAT is an isotope label technique that allows for discrimination between two populations of proteins, such as a healthy and a disease sample. The LC/MS spectra are collected for the labeled samples. The raw scans from the LC/MS instrument are subjected to peak detection and noise reduction software. Filtered peak lists are then used to detect 'features' corresponding to specific peptides from the original sample(s). Features are characterized by their mass/charge, charge, retention time, isotope pattern and intensity.

The intensity of a peptide present in both healthy and disease samples can be used to calculate the differential expression, or relative abundance, of the peptide. The intensity of a peptide found exclusively in one sample can be used to calculate a theoretical expression ratio for that peptide (singleton). Expression ratios are calculated for each peptide of each replicate of the experiment (Table 1). Thus overexpression or under expression of CCAT protein or peptide are similar to the expression pattern in Table 1 in a test subject indicates the likelihood of having colon diseases or diseases associated with colon.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art (Ausubel, supra, unit 10.1-10.6). A two-site, monoclonal-based immunoassay utilizing antibodies reactive to two non-interfering epitopes is preferred, but a competitive binding assay may be employed (Pound (1998) Immunochemical Protocols, Humana Press, Totowa N.J.). More immunological detections are described in section below.

Antibody Detections

Antibodies are useful to detect the presence of one of the proteins or fragments thereof, peptides of the present invention in cells or tissues to determine the pattern of expression of the protein among various tissues in an organism and over the course of normal development.

Further, as described above, the antibodies can be used to assess expression in disease states such as in active stages of the disease or in an individual with a predisposition toward disease related to the protein's function. The antibodies can also be used to assess normal and aberrant subcellular localization of cells in the various tissues in an organism.

Detection on a protein by an antibody can be facilitated by coupling (i.e., physically linking) the antibody to a detectable substance. Examples of detectable substances include various enzymes, prosthetic groups, fluorescent materials, luminescent materials, bioluminescent materials, and radioactive materials (see below). The antibodies may also be useful in diagnostic assays, e.g., for detecting expression of an antigen, for example CCAT protein, peptide or fragment thereof, in specific cells, tissues, blood, serum or body fluids.

For diagnostic applications, the antibody or its variant typically will be labeled with a detectable moiety. Numerous labels are available which can be generally grouped into the following categories:

(a) Radioisotopes, such as $^{36}S$, $^{14}C$, $^{125}I$, $^{3}H$, and $^{131}I$. The antibody variant can be labeled with the radioisotope using the techniques described in Current Protocols in Immunology, vol 1-2, Coligen et al., Ed., Wiley-Interscience, New York, Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques disclosed in Current Protocols in Immunology, supra, for example. Fluorescence can be quantified using a fluorimeter.

(c) Various enzyme-substrate labels are available and U.S. Pat. Nos. 4,275,149, 4,318,980 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digloxin) and one of the different types of labels mentioned above is conjugated with an anti-hapten antibody (e.g. anti-digloxin antibody). Thus, indirect conjugation of the label with the antibody can be achieved.

In another embodiment of the invention, the antibody need not be labeled, and the presence thereof can be detected using a labeled antibody, which binds to the antibody.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The biological samples can then be tested directly for the presence of CCAT by assays (e.g., ELISA or radioimmunoassay) and format (e.g., microwells, dipstick (e.g., as described in International Patent Publication WO 93/03367), etc). Alternatively, proteins in the sample can be size separated (e.g., by polyacrylamide gel electrophoresis (PAGE)), in the presence or absence of sodium dodecyl sulfate (SDS), and the presence of CCAT detected by immunoblotting (e.g., Western blotting). Immunoblotting techniques are generally more effective with antibodies generated against a peptide corresponding to an epitope of a protein, and hence, are particularly suited to the present invention.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay. In some embodiments, an automated detection assay is utilized. Methods for the automation of immunoassays are well known in the art (See e.g., U.S. Pat. Nos. 5,885,530, 4,981,785, 6,159,750, and 5,358,691, each of which is herein incorporated by reference). In some embodiments, the analysis and presentation of results is also automated. For example, in some embodiments, software that generates a prognosis based on the presence or absence of a series of antigens is utilized.

Competitive binding assays rely on the ability of a labeled standard to compete with the test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample, which remain unbound.

Sandwich assays involve the use of two antibodies, each capable of binding to a different immunogenic portion, or epitope, or the protein to be detected. In a sandwich assay, the test sample to be analyzed is bound by a first antibody, which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more CCAT targets and the affinity value (Kd) is less than $1 \times 10^8$ M.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art.

For immunohistochemistry, the disease tissue sample may be fresh or frozen or may be embedded in paraffin and fixed with a preservative such as formalin (see Example). The fixed or embedded section contains the sample are contacted with a labeled primary antibody and secondary antibody, wherein the antibody is used to detect the CCAT protein express in situ. The detailed procedure is shown in the Example.

Array:

Array technologies and quantitative PCR provide the means to explore the expression profiles of a large number of related or unrelated genes, and proteins. When an expression profile is examined, arrays provide a platform for examining which genes or proteins are tissue-specific, carrying out housekeeping functions, parts of a signaling cascade, or specifically related to a particular genetic predisposition, condition, disease, or disorder. The potential application of gene or protein expression profiling is particularly relevant to improving diagnosis, prognosis, and treatment of disease. For example, both the sequences and the amount of expression can be compared between tissues from subjects with different types of colon diseases and cytologically normal healthy tissue.

"Array" refers to an ordered arrangement of at least two transcripts, proteins or peptides, or antibodies on a substrate. At least one of the transcripts, proteins, or antibodies represents a control or standard, and the other transcript, protein, or antibody is of diagnostic or therapeutic interest. The arrangement of at least two and up to about 40,000 transcripts, proteins, or antibodies on the substrate assures that the size and signal intensity of each labeled complex, formed between each transcript and at least one nucleic acid, each protein and at least one ligand or antibody, or each antibody and at least one protein to which the antibody specifically binds, is individually distinguishable.

An "expression profile" is a representation of gene expression in a sample. A nucleic acid expression profile is produced using sequencing, hybridization, or amplification technologies using transcripts from a sample. A protein expression profile, although time delayed, mirrors the nucleic acid expression profile and is produced using gel electrophoresis, mass spectrometry, or an array and labeling moieties or antibodies which specifically bind the protein. The nucleic acids, proteins, or antibodies specifically binding the protein may be used in solution or attached to a substrate, and their detection is based on methods well known in the art.

A substrate includes but not limits to, paper, nylon or other type of membrane, filter, chip, glass slide, or any other suitable solid support.

The invention also provides an array with a cDNA or transcript encoding CCAT proteins or peptides or fragments thereof, antibodies which specifically bind CCAT proteins, peptides or fragments thereof. Preferably, two or more of the nucleic acid molecules (e.g., SEQ ID NOS: 67-129), proteins (e.g., SEQ ID NOS: 1-66) or peptides (e.g., SEQ ID NOS: 130-145) are immobilized on a substrate.

The present invention also provides an antibody array. Antibody arrays have allowed the development of techniques for high-throughput screening of recombinant antibodies. Such methods use robots to pick and grid bacteria containing antibody genes, and a filter-based ELISA to screen and identify clones that express antibody fragments. Because liquid handling is eliminated and the clones are arrayed from master stocks, the same antibodies can be spotted multiple times and screened against multiple antigens simultaneously. For more information, see de Wildt et al. (2000) Nat Biotechnol 18:989-94.

The array is prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), U.S. Pat. No. 5,807,522, Brown et al., all of which are incorporated herein in their entirety by reference.

In one embodiment, a nucleic acid array or a microarray, preferably composed of a large number of unique, single-stranded nucleic acid sequences, usually either synthetic antisense oligonucleotides or fragments of cDNAs, fixed to a solid support. The oligonucleotides are preferably about 6-60 nucleotides in length, more preferably 15-30 nucleotides in length, and most preferably about 20-25 nucleotides in length.

In order to produce oligonucleotides to a known sequence for an array, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on an array. The "pairs"

will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process, wherein the substrate may be paper, nylon or other type of membrane, filter, chip, glass slide or any other suitable solid support as described above.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference.

A gene expression profile comprises the expression of a plurality of transcripts as measured by after hybridization with a sample. The transcripts of the invention may be used as elements on an array to produce a gene expression profile. In one embodiment, the array is used to diagnose or monitor the progression of disease. Researchers can assess and catalog the differences in gene expression between healthy and diseased tissues or cells.

For example, the transcript or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human or nonmammal, with a transcript under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

By analyzing changes in patterns of gene expression, disease can be diagnosed at earlier stages before the patient is symptomatic. The invention can be used to formulate a prognosis and to design a treatment regimen. The invention can also be used to monitor the efficacy of treatment. For treatments with known side effects, the array is employed to improve the treatment regimen. A dosage is established that causes a change in genetic expression patterns indicative of successful treatment. Expression patterns associated with the onset of undesirable side effects are avoided.

In another embodiment, animal models which mimic a human disease can be used to characterize expression profiles associated with a particular condition, disease, or disorder; or treatment of the condition, disease, or disorder. Novel treatment regimens may be tested in these animal models using arrays to establish and then follow expression profiles over time. In addition, arrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

Treatment

The following terms, as used in the present specification and claims, are intended to have the meaning as defined below, unless indicated otherwise.

"Treat," "treating" or "treatment" of a disease includes:

(1) inhibiting the disease, i.e., arresting or reducing the development of the disease or its clinical symptoms, or (2) relieving the disease, i.e., causing regression of the disease or its clinical symptoms.

A "therapeutically effective amount" means the amount of an agent that, when administered to a subject for treating a disease, is sufficient to effect such treatment for the disease. The "therapeutically effective amount" will vary depending on the agent, the disease and its severity and the age, weight, etc., of the subject to be treated.

A "Colon or colorectal disease" includes but not limited to colon cancer, colon tumor, diverticulosis, diverticulitis, Crohn's disease, ulcerative colitis, irritable bowel syndrome, inflammatory bowel disease, hemorrhoids, and anal fissure.

A "cancer" is epithelial-cell related cancers include but not limited to pancreatic, lung, colon, prostate, ovarian, breast, bladder renal, hepatocellular, pharyngeal and gastric cancer.

The present invention provides an application of treatment by using antibody, immunogenic peptides as well as other CCAT agonists or antagonists.

CCATs are proteins differentially expressed in the colon diseases cell lines or tissues. The proteins are either cell surface proteins or cytosolic proteins (see the list in Table 2). These proteins are associated with the diseases especially colon diseases, particularly colon cancer; thus, they serve as candidate targets for the treatment of the diseases.

In one embodiment, when decreased expression or activity of the protein is desired, an inhibitor, antagonist, antibody and the like or a pharmaceutical agent containing one or more of these molecules may be delivered. Such delivery may be effected by methods well known in the art and may include delivery by an antibody specifically targeted to the protein. Neutralizing antibodies, which inhibit dimer formation, are generally preferred for therapeutic use.

In another embodiment, when increased expression or activity of the protein is desired, the protein, an agonist, an enhancer and the like or a pharmaceutical agent containing one or more of these molecules may be delivered. Such delivery may be effected by methods well known in the art and may include delivery of a pharmaceutical agent by an antibody specifically targeted to the protein.

Any of the transcripts, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Antibody Therapy

The antibody of the present invention can be used for therapeutic reason. It is contemplated that the antibody of the present invention may be used to treat a mammal, preferably human with colon diseases.

In general, the antibodies are also useful for inhibiting protein function, for example, blocking the binding of the CCAT protein or peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated within a cell or cell membrane. The function blocking assays are provided in detail in the Examples.

The antibodies of present invention can also be used as means of enhancing the immune response. The antibodies can be administered in amounts similar to those used for other therapeutic administrations of antibody. For example, pooled gamma globulin is administered at a range of about 1 mg to about 100 mg per patient. Thus, antibodies reactive with the protein or peptides of CCAT can be passively administered alone or in conjunction with other anti-cancer therapies to a mammal afflicted-with colon diseases or cancer. Examples of anti-cancer therapies include, but are not limited to, chemotherapy, radiation therapy, adoptive immunotherapy therapy with TIL (Tumor Infiltration Lymphocytes).

The selection of an antibody subclass for therapy will depend upon the nature of the disease tumor antigen. For example, an IgM may be preferred in situations where the antigen is highly specific for the diseased target and rarely occurs on normal cells. However, where the disease-associated antigen is also expressed in normal tissues, although at much lower levels, the IgG subclass may be preferred for the following reason: since the binding of at least two IgG molecules in close proximity is required to activate complement, less complement mediated damage may occur in the normal tissues which express smaller amounts of the antigen and, therefore, bind fewer IgG antibody molecules. Furthermore, IgG molecules by being smaller may be more able than IgM molecules to localize to the diseased tissue.

The mechanism for antibody therapy is that the therapeutic antibody recognizes a cell surface protein or a cytosolic protein that is overexpressed in diseased cells. By NK cell or complement activation, conjugation of the antibody with an immunotoxin or radiolabel, the interaction can abrogate ligand/receptor interaction or activation of apoptosis.

The potential mechanisms of antibody-mediated cytotoxicity of diseased cells are phagocyte (antibody dependent cellular cytotoxicity (ADCC)) (see Example), complement (Complement-mediated cytotoxicity (CMC)) (see Example), naked antibody (receptor cross-linking apoptosis and growth factor inhibition), or targeted payload labeled with radionuclide or immunotoxins or immunochemotherapeutics.

In one embodiment, the antibody is administered to a non-human mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

The antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody variant is suitably administered by pulse infusion, particularly with declining doses of the antibody variant. Preferably the dosing is given by injections, most preferably intravenous or subcutaneous injections, depending in part on whether the administration is brief or chronic.

For the prevention or treatment of a disease, the appropriate dosage of the antibody will depend on the type of disease to be treated, the severity and the course of the disease, whether the antibody is administered for preventive or therapeutic purposes, previous therapy, the patient's clinical history and response to the antibody, and the discretion of the attending physician.

Depending on the type and severity of the disease, about 1.mu.g/kg to 150 mg/kg (e.g., 0.1-20 mg/kg) of antibody is an initial candidate dosage for administration to the patient, whether, for example, by one or more separate administrations, or by continuous infusion. A typical daily dosage might range from about 1.mu.g/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutically effective amount of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question.

Antibodies of the present invention may also be used as therapeutic reagents, to diminish or eliminate cancer or tumors. For example, the antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be affected, for example, through amino groups, carboxyl groups, sulfhydryl groups or oxidized carbohydrate residues. There are numerous references describing such methodology, e.g. U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways as described above.

While it is possible for the immunogen to be administered in a pure or substantially pure form, it is preferable to present it as a pharmaceutical composition, formulation or preparation with a carrier.

The formulations of the present invention, both for veterinary and for human use, comprise an immunogen as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

Suitable pharmaceutical carriers include proteins such as albumins (e.g., U.S. Pat. No. 4,507,234, to Kato et al.), peptides and polysaccharides such as aminodextran (e.g., U.S. Pat. No. 4,699,784, to Shih et al.), or water. A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, metal oxide, radionuclide. For example, U.S. Pat. No. 4,673,562, to Davison et al. discloses representative chelating compounds and their synthesis.

All methods include the step of bringing into association the active ingredient with the carrier, which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions, which are preferably isotonic with the blood of the recipient. Such formulations may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids, which may be used either on their own or as admixtures. These stabilizers are preferably incorporated in an amount of 0.11-10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8. In formulating the antibody of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the CCAT antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The therapeutic antibody may be supplied in the form of a kit, alone, or in the form of a pharmaceutical composition as described above.

Other Immunotherapy

The CCAT proteins or peptides or fragments thereof of this invention are also intended for use in producing antiserum designed for pre- or post-disease prophylaxis. Here the protein, peptides or fragment thereof, is formulated with a suitable adjuvant and administered by injection to human volunteers, according to known methods for producing human antisera. Antibody response to the injected proteins is monitored, during a several-week period following immunization, by periodic serum sampling to detect the presence of antiserum antibodies, using an immunoassay as described herein.

The antiserum from immunized individuals may be administered as a prophylactic measure for individuals who are at risk of developing colon diseases or cancer. The antiserum is also useful in treating an individual afflicted with colon diseases or cancer for post-disease prophylaxis.

Alternatively, peptides derived form the CCAT protein sequence may be modified to increase their immunogenicity by enhancing binding of the peptide to the MHC molecules in which the peptide is presented. The peptide or modified peptide may be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites, D. P. and Terr A. I. (eds) Appleton and Lange, Norwalk Conn., San Mateo, Calif.).

An "immunogenic peptide" is a peptide, which comprises an allele-specific motif such that the peptide will bind the MHC allele (HLA in human) and be capable of inducing a CTL (cytoxic T-lymphocytes) response. Thus, immunogenic peptides are capable of binding to an appropriate class I or II MHC molecule and inducing a cytotoxic T cell or T helper cell response against the antigen from which the immunogenic peptide is derived.

Alternatively, amino acid sequence variants of the peptide can be prepared by mutations in the DNA, which encodes the peptide, or by peptide synthesis.

At the genetic level, these variants ordinarily are prepared by site-directed mutagenesis of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

T-lymphocytes recognize antigen in association with Class I or Class II MHC molecules in the form of a peptide fragment bound to an MHC molecule. The degree of peptide binding to a given MHC allele is based on amino acids at particular positions within the peptide (Parker et al. (1992) Journal of Immunology 149:3580; Kubo, et al. (1994) Journal of Immunology 52:3913-3924; Ruppert J. et al. (1993) Cell 74:929-937; Falk et al. (1991) Nature 351:290-296). The peptides of the present invention are useful as an epitope for immunogenic response (see more detailed description below).

In human, MHC is called HLA, wherein class I molecules are encoded by the HLA-A, B, and C loci. HLA-A and B antigens are expressed at the cell surface at approximately equal densities, whereas the expression of HLA-C is significantly lower (about 10-fold lower). Each of these loci has a number of alleles. MHC class II molecules are encoded by three pairs of MHC II alpha- and beta-chain genes, called HLA DR, -DP, and -DQ in human. In many haplotypes the HLA-DR cluster contains an extra beta-chain gene whose product can pair with the DR alpha chain. Each MHC class I and II molecule binds a different rage of peptides. The present of several loci means that any one individual is equipped to present a much broader ranger of different peptides than if only one MHC protein of each class were expressed at the cell surface. The peptide binding motifs of the present invention are designed to be specific for each allelic subtype.

The peptides of the present invention are used for treatment of the colon diseases. Treatment involves administration of the protective composition after the appearance of the disease.

The present invention is also applied to prevent and suppress the disease. It is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

The peptides are used for treating T cell-mediated pathology. The term "T cell-mediated pathology" refers to any condition in which an inappropriate T cell response is a component of the pathology. The term is intended to encompass both T cell mediated colon diseases and diseases resulting from unregulated clonal T cell replication.

Therefore, the present invention relates to peptides or modified peptides derived from the protein sequences of the CCAT proteins that differentially expressed in the colon diseases. By way of example, modification may include substitution, deletion or addition of an amino acid in the given immunogenic peptide sequence or mutation of existing amino acids within the given immunogenic peptide sequence, or derivatization of existing amino acids within the given immunogenic peptide sequence. Any amino acid comprising the immunogenic peptide sequence may be modified in accordance with this invention. In one aspect, at least one amino acid is substituted or replaced within the given immunogenic peptide sequence. Any amino acid may be used to substitute or replace a given amino acid within the immunogenic peptide sequence. Modified peptides are intended to include any immunogenic peptide obtained from differentially expressed proteins, which has been modified and exhibits enhanced binding to the MHC molecule with which it associates when presented to the T-cell. These modified peptides may be synthetically or recombinantly produced by conventional methods.

In another embodiment, the peptides of the present invention comprise, or consisting sequences of about 5-8, 8-10, 10-15 or 15-30 amino acids which are immunogenic, that is, capable of inducing an immune response when injected into a subject.

The recombinant or natural protein, peptides, or fragment thereof of CCAT, or modified peptides, may be used as a vaccine either prophylactically or therapeutically. When provided prophylactically the vaccine is provided in advance of any evidence of colon diseases, particularly, cancer. The prophylactic administration of the colon diseases vaccine should serve to prevent or attenuate colon diseases, preferably cancer, in a mammal.

Preparation of vaccine is using recombinant protein or peptide expression vectors comprising all or part of nucleic acid sequence of CCAT proteins encoding peptides.

Examples of vectors that may be used in the aforementioned vaccines include, but are not limited to, defective retroviral vectors, adenoviral vectors vaccinia viral vectors, fowl pox viral vectors, or other viral vectors (Mulligan, R. C., (1993) Science 260:926-932). The viral vectors carrying all or part of nucleic sequence of SEQ ID NOS: 67-129 can be introduced into a mammal either prior to any evidence of colon diseases or to mediate regression of the disease in a mammal afflicted with colon diseases. Examples of methods for administering the viral vector into the mammals include, but are not limited to, exposure of cells to the virus ex vivo, or injection of the retrovirus or a producer cell line of the virus into the affected tissue or intravenous administration of the virus. Alternatively the viral vector carrying all or part of the CCAT nucleic acid sequence that encode peptides may be administered locally by direct injection into the cancer lesion or topical application in a pharmaceutically acceptable carrier. The quantity of viral vector, carrying all or part of the CCAT nucleic acid sequence, to be administered is based on the titer of virus particles. A preferred range of the immunogen to be administered may be about 106 to about 1011 virus particles per mammal, preferably a human. After immunization the efficacy of the vaccine can be assessed by production of antibodies or immune cells that recognize the antigen, as assessed by specific lytic activity or specific cytokine production or by tumor regression. One skilled in the art would know the conventional methods to assess the aforementioned parameters. If the mammal to be immunized is already afflicted with cancer, the vaccine can be administered in conjunction with other therapeutic treatments. Examples of other therapeutic treatments includes, but are not limited to, adoptive T cell immunotherapy, coadministration of cytokines or other therapeutic drugs for cancer.

Alternatively all or parts thereof of a substantially or partially purified the CCAT protein or their peptides may be administered as a vaccine in a pharmaceutically acceptable carrier. Ranges of the protein that may be administered are about 0.001 to about 100 mg per patient, preferred doses are about 0.01 to about 100 mg per patient. In a preferred embodiment, the peptides or modified peptides thereof is administered therapeutically or prophylactically to a mammal in need of such treatment. The peptide may be synthetically or recombinantly produced. Immunization is repeated as necessary, until a sufficient titer of anti-immunogen antibody or immune cells has been obtained.

In yet another alternative embodiment a viral vector, such as a retroviral vector, can be introduced into mammalian cells. Examples of mammalian cells into which the retroviral vector can be introduced include, but are not limited to, primary mammalian cultures or continuous mammalian cultures, COS cells, NIH13T3, or 293 cells (ATTC #CRL 1573), dendritic cells. The means by which the vector carrying the gene may be introduced into a cell includes, but is not limited to, microinjection, electroporation, transfection or transfection using DEAE dextran, lipofection, calcium phosphate or other procedures known to one skilled in the art (Sambrook et al. (EDS) (2001) in "Molecular Cloning. A laboratory manual", Cold Spring Harbor Press Plainview, N.Y.).

The vaccine formulation of the present invention comprises an immunogen that induces an immune response directed against the cancer associated antigens such as the CCATs, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, cancer patients can be tested. Conventional methods would be used to evaluate the immune response of the patient to determine the efficiency of the vaccine.

Measurement of candidate disease tumor antigen or vaccine expression in patients is the first step of the present invention. Subsequent steps will focus on measuring immune responses to these candidate antigens or vaccine. Sera from disease patients, particularly cancer patients, and healthy donors will be screened for antibodies to the candidate antigens as well as for levels of circulating tumor derived antigens. antigen. The vaccine formulations may be evaluated first in animal models, initially rodents In one embodiment mammals, preferably human, at high risk for colon diseases, particularly cancer, are prophylactically treated with the vaccines of this invention. Examples of such mammals include, but are not limited to, humans with a family history of colon diseases, humans with a history of colon diseases, particular cancer, or humans afflicted with colon cancer previously resected and therefore at risk for reoccurrence. When provided therapeutically, the vaccine is provided to enhance the patient's own immune response to the diseased antigen present on the colon diseases or advanced stage of colon diseases. The vaccine, which acts as an immunogen, may be a cell, cell lysate from cells transfected with a recombinant expression vector, cell lysates from cells transfected with a recombinant expression vector, or a culture supernatant containing the expressed protein. Alternatively, the immunogen is a partially or substantially purified recombinant protein, peptide or analog thereof or modified peptides or analogs thereof. The proteins or peptides may be conjugated with lipoprotein or administered in liposomal form or with adjuvant.

While it is possible for the immunogen to be administered in a pure or substantially pure form, it is preferable to present it as a pharmaceutical composition, formulation or preparation. The formulations of the present invention are described in the previous section.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen also may be coupled with lipoproteins or administered in liposomal form or with adjuvants. The immunogen can be administered by any route-appropriate for antibody production such as intravenous, intraperitoneal, intramuscular, subcutaneous, and the like. The immunogen may be administered once or at periodic intervals until a significant titer of anti-CCAT immune cells or anti-CCAT antibody is produced. The presence of anti-CCAT immune cells may be assessed by measuring the frequency of precursor CTL (cytoxic T-lymphocytes) against CCAT antigen prior to and after immunization by a CTL precursor analysis assay (Coulie, P. et al., (1992) International Journal Of Cancer 50:289-297). The antibody may be detected in the serum using the immunoassay described above.

The safety of the immunization procedures is determined by looking for the effect of immunization on the general health of the immunized animal (weight change, fever, appetite behavior etc.) and looking for pathological changes on autopsies. After initial testing in animals, colon diseases patients can be tested. Conventional methods would be used to evaluate the immune response of the patient to determine the efficiency of the vaccine.

In yet another embodiment of this invention all, part, or parts of the CCAT proteins or peptides or fragments thereof, or modified peptides, may be exposed to dendritic cells cultured in vitro. The cultured dendritic cells provide a means of producing T-cell dependent antigens comprised of dendritic cell modified antigen or dendritic cells pulsed with antigen, in which the antigen is processed and expressed on the antigen activated dendritic cell. The CCAT antigen activated dendritic cells or processed dendritic cell antigens may be used as immunogens for vaccines or for the treatment of colon diseases, particularly colon cancer. The dendritic cells should be exposed to antigen for sufficient time to allow the antigens to be internalized and presented on the dendritic cells surface. The resulting dendritic cells or the dendritic cell process antigens can than be administered to an individual in need of therapy. Such methods are described in Steinman et al. (WO93/208185) and in Banchereau et al. (EPO Application 0563485A1).

In yet another aspect of this invention T-cells isolated from individuals can be exposed to the CCAT proteins, peptides or fragment thereof, or modified peptides in vitro and then administered to a patient in need of such treatment in a therapeutically effective amount. Examples of where T-lymphocytes can be isolated include but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami, Y. et al. (1989) J. Immunol. 142: 2453-3461). Lymphocytes are cultured in media such as RPMI or RPMI 1640 or AIM V for 1-10 weeks. Viability is assessed by trypan blue dye exclusion assay. Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A. et al. (1992) Human Gene Therapy, 3: 75-90; Rosenberg, S. A. et al. (1992) Human Gene Therapy, 3: 57-73).

The present invention is further described by the following example. The example is provided solely to illustrate the invention by reference to specific embodiments. This exemplification, while illustrating certain aspects of the invention, does not offer the limitations or circumscribe the scope of the disclosed invention.

All examples outlined here were carried out using standard techniques, which are well known and routine to those of skill in the art. Routine molecular biology techniques of the following example can be carried out as described in standard laboratory manuals, such as Sambrook et al., Molecular Cloning: A laboratory Manual, 3rd. ed., Cold Spring Harbor Laboratory Press, Cold Spring Harbor, N.Y., (2001).

Working Examples

1. Colon Tissues

Tissue Processing

All tissues were procured as fresh specimens. Tissues were collected as remnant tissues following surgical resection of colorectal tissues. Remnant tissues were supplied following processing for pathological diagnosis according to proper standards of patient care. Procurement of all tissues was performed in an anonymised manner in strict compliance with Federal mandated ethical and legal guidelines (HIPAA) and in accordance with clinical institution ethical review board as well as the internal institutional review board. Tissues were transported on ice in ice-cold transport buffer by courier for processing.

i) Enrichment of Epithelial Cells from Normal Colorectal Mucosa

Normal colorectal tissue was transferred from the transport vessel to a sterile dish containing 25 ml of ice-cold transport buffer. The tissue was measured, weighed and photographed. The tissue was dissected to isolate colorectal mucosa which was transferred to a fresh dish containing 25 ml ice-cold Hanks buffered saline solution. The tissue section was washed by vigorous shaking and the HBSS replaced. This was repeated 2 further times or until all visible mucus was removed. Mucosa was measured, weighed and diced into 1 mm2 sections. The tissues sections were transferred to a 50 ml polypropylene centrifuge tube containing 50 ml of A52 media (Biosource) supplemented with 2 mM L-glutamine and 1.5 mg/ml dispase (Roche Biochemicals). The digest was incubated for 1 h at 37° C. with frequent agitation. Following the incubation, the suspension was poured through a 40-mesh cell sieve situated in the base of a 15 cm culture dish. The filtrate was diluted to 50 ml using A52 media supplemented with 2 mM L-glutamine and passed through a 200-mesh cell sieve. The filtrate was collected into a 50 ml polypropylene centrifuge tube and the suspension was triturated several times followed by vortexing for 2 min at setting 6. The density and viability of nucleated cells was determined by flow cytometry using propidium iodide as a negative stain for viability (Guava system). Erythrocytes were lysed using a standard ammonium chloride lysis protocol with incubation at room temperature for 10 s. Cells were harvested by centrifugation at 500 g for 5 min at 4° C. The cell pellet was resuspended in 50 ml of ice-cold HBSS and recentrifuged. The final cell pellet was resuspended in 3 ml of ice-cold HBSS supplemented with 0.1% BSA and 0.25M EDTA. Cell density and viability were estimated using the Guava system and the density adjusted to $1 \times 10^7$ cells per ml. Epithelial cells were stained with a FITC-labeled anti-EpCAM murine monoclonal antibody and enriched by cell sorting using flow cytometry.

ii) Enrichment of Tumor Cells from Colorectal Tumor Tissue

Colorectal tumor tissue was transferred from the transport vessel to a sterile dish containing 25 ml of ice-cold transport buffer. The tissue was measured, weighed and photographed. The tissue was dissected to remove necrotic and fibrotic tissue plaques and the tumour tissue transferred to a fresh dish containing 25 ml ice-cold Hanks buffered saline solution. The tissue section was washed by vigorous shaking and the HBSS replaced. This was repeated 2 further times or until all visible mucus was removed. Tumour tissue was measured, weighed and extensively diced. The tissues slurry was transferred to a 50 ml polypropylene centrifuge tube containing 50 ml of A52 media (Biosource) supplemented with 2 mM L-glutamine and 1.5 mg/ml dispase (Roche Biochemicals). The digest was incubated for 1 h at 37° C. with frequent agitation. Following the incubation, the suspension was poured through a 40-mesh cell sieve situated in the base of a 15 cm culture dish. The filtrate was diluted to 50 ml using A52 media supplemented with 2 mM L-glutamine and passed through a 200-mesh cell sieve. The filtrate was collected into a 50 ml polypropylene centrifuge tube and the suspension was triturated several times followed by vortexing for 2 min at setting 6. The density and viability of nucleated cells was determined by flow cytometry using propidium iodide as a negative stain for viability (Guava system). Erythrocytes were lysed using a standard ammonium chloride lysis protocol with incubation at room temperature for 10 s. Cells were harvested by centrifugation at 500 g for 5 min at 4° C. The cell pellet was resuspended in 50 ml of ice-cold HBSS and recentrifuged. The final cell pellet was resuspended in 3 ml of ice-cold HBSS supplemented with 0.1% BSA and 0.25M EDTA. Cell density and viability were estimated using the Guava system and the density adjusted to $1 \times 10^7$ cells per ml. Epithelial cells were stained with a FITC-labeled anti-EpCAM murine monoclonal antibody and enriched by cell sorting using flow cytometry.

iii) Enrichment of Cell Surface Proteins from Sorted Epithelial and Tumor Cells

Sorted cells were centrifuged at 500 g at 4° C. for 5 min and resuspended in 50 ml of ice-cold DPBS. The cell suspension was washed by 2 further cycles of centrifugation 500 g at 4° C. for 5 min and resuspension of the cell pellet in 50 ml of ice-cold DPBS. Finally, the cell pellet was resuspended in 9.5 ml of ice-cold DPBS and sodium metaperiodate added to a final concentration of 1 mM. The cell suspension was incubated on ice for 10 min with frequent agitation in the dark. Cells were centrifuged at 500 g at 4° C. for 5 min and resuspended in 50 ml of ice-cold DPBS. The cell suspension was washed by 2 further cycles of centrifugation 500 g at 4° C. for 5 min and resuspension of the cell pellet in 50 ml of ice-cold DPBS. Finally, the cell pellet was resuspended in lysis buffer (1% SDS [w/v]; 0.1M HEPES; 10 mM $MgCl_2$; 0.1% Non ionic detergent P40; 10 μl/ml protease inhibitor cocktail [P8340, Sigma]) and homogenisation performed by passage of lysate through a 18G syringe needle 10 times. Protein concentrations were assayed relative to a Bovine serum albumin standard by a modified Lowry assay (DC assay, Bio-RAD) and 1 mg of total cellular protein transferred to a fresh tube and diluted to 1 mg/ml in acetate buffer (0.1M, pH 5.0).

2. Cloning and Expression of Target Proteins cDNA Retrieval

Peptide sequences were searched by BlastP against the Celera Discovery System (CDS) and public database to identify the corresponding full-length open reading frames (ORFs). Each ORF sequence was then searched by BlastN against the Celera in-house human cDNA clone collection. For each sequence of interest, up to three clones are pulled and streaked onto LB/Ampicillin (100 ug/ml) plates. Plasmid DNA is isolated using Qiagen spin mini-prep kit and verified by restriction digest. Subsequently, the isolated plasmid DNA is sequence verified against the ORF reference sequence. Sequencing reactions are carried out using Applied Biosystems BigDye Terminator kit followed by ethanol precipitation. Sequence data is collected using the Applied Biosystems 3100 Genetic Analyzer and analyzed by alignment to the reference sequence using the Clone Manager alignment tool.

PCR

PCR primers are designed to amplify the full-length ORF as well as any regions of the ORF that are interest for expression (antigenic or hydrophilic regions as determined by the Clone Manager sequence analysis tool). Primers also contain 5' and 3' overhangs to facilitate cloning (see below). PCR reactions contain 2.5 units Platinum Taq DNA Polymerase High Fidelity (Invitrogen), 50 ng cDNA plasmid template, 1 uM forward and reverse primers, 800 uM dNTP cocktail (Applied Biosystems) and 2 mM $MgSO_4$. After 20-30 cycles (94° C. for 30 seconds, 55° C. for 1 minutes and 73° C. for 2 minutes), product is verified and quantitated by agarose gel electrophoresis.

Construction of Entry Clones

PCR products are cloned into an entry vector for use with the Gateway recombination based cloning system (Invitrogen). These vectors include pDonr221, pDonr201, pEntr/D-TOPO or pEntr/SD/D-TOPO and are used as described in the cloning methods below.

TOPO Cloning into pEntr/D-TOPO or pEntr/SD/D-TOPO

For cloning using this method, the forward PCR primer contained a 5' overhang containing the sequence "CACC". PCR products are generated as described above and cloned into the entry vector using the Invitrogen TOPO cloning kit. Reactions are typically carried out at room temperature for 10 minutes and subsequently transformed into TOP10 chemically competent cells (Invitrogen, CA). Candidate clones are picked, plasmid DNA is prepared using Qiagen spin mini-prep kit and screened using restriction digest. Inserts are subsequently sequence verified as described above.

Gateway Cloning into pDonr201 or pDonr221

For cloning using this method, PCR primers contained the following overhangs:

Forward 5' Overhang:
   5'-GGGGACAAGTTTGTACAAAAAAGCAGGCTTC-3'

Reverse 5' Overhang:
   5'-GGGGACCACTTTGTACAAGAAAGCTGGGT-3'

PCR products are generated as described above. ORFs are recombined into the entry vector using the Invitrogen Gateway BP Clonase enzyme mix. Reactions are typically carried out at 25° C. for 1 hour, treated with Proteinase K at 37° C. for 10 minutes and transformed into Library Efficiency DH5a chemically competent cells (Invitrogen, CA). Candidate clones are picked, plasmid DNA is prepared using Qiagen spin mini-prep kit and screened using restriction digest. Inserts are subsequently sequence verified as described above.

Construction of Expression Clones

ORFs are transferred from the entry construct into a series of expression vectors using the Gateway LR Clonase enzyme mix. Reactions are typically carried out for 1 hour at 25° C., treated with Proteinase K at 37° C. for 10 minutes and subsequently transformed into Library Efficiency DH5a chemically competent cells (Invitrogen). Candidate clones are picked, plasmid DNA is prepared using Qiagen spin mini-prep kit and screened using restriction digest. Expression vectors include but are not limited to pDest14, pDest15, pDest17, pDest8, pDest10 and pDest20. These vectors allow expression in systems such as *E. coli* and recombinant baculovirus. Other vectors not listed here allow expression in yeast, mammalian cells, or in vitro.

Expression of Recombinant Proteins in *E. coli*

Constructs are transformed into one or more of the following host strains: BL21 SI, BL21 AI, (Invitrogen); Origami B (DE3), Origami B (DE3) pLysS, Rosetta (DE3), Rosetta (DE3) pLysS, Rosetta-Gami (DE3), Rosetta-Gami (DE3) pLysS, or Rosetta-Gami B (DE3) pLysS (Novagen). The transformants are grown in LB with or without NaCl and with appropriate antibiotics, at temperatures in the range of 20-37° C., with aeration. Expression is induced with the addition of IPTG (0.03-0.3 mM) or NaCl (75-300 mM) when the cells are in mid-log growth. Growth is continued for one to 24 hours post-induction. Cells are harvested by centrifugation in a Sorvall RC-3C centrifuge in a H6000A rotor for 10 minutes at 3000 rpm, at 4° C. Cell pellets are stored at −80° C.

Expression of Recombinant Proteins Using Baculovirus

Recombinant proteins are expressed using baculovirus in Sf21 fall army worm ovarian cells. Recombinant baculoviruses are prepared using the Bac-to-Bac system (Invitrogen) per the manufacturer's instructions. Proteins are expressed on the large scale in SP900II serum-free medium (Invitrogen) in a 10 L bioreactor tank (27° C., 130 rpm, 50% dissolved oxygen for 48 hours).

3. Recombinant Protein Purification

Recombinant proteins are purified from *E. coli* and/or insect cells using a variety of standard chromatography methods. Briefly, cells are lysed using sonication or detergents. The insoluble material is pelleted by centrifugation at 10,000×g for 15 minutes. The supernatant is applied to an appropriate affinity column, e.g. His-tagged proteins are separated using a pre-packed chelating sepharose column (Pharmacia) or GST-tagged proteins are separated using a glutathione sepharose column (Pharmacia). After using the affinity column, proteins are further separated using various techniques, such as ion exchange chromatography (columns from Pharmacia) to separate on the basis of electrical charge or size exclusion chromatography (columns from Tosohaas) to separate on the basis of molecular weight, size and shape.

Expression and purification of the protein are also achieved using either a mammalian cell expression system or an insect cell expression system. The pUB6/V5-His vector system (Invitrogen, CA) is used to express GSCC in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6.times.His) sequence for rapid purification on PROBOND resin (Invitrogen, CA). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6xhis which enables purification as described above. Purified protein is used in the following activity and to make antibodies

4. Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds .alpha.-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-a-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20). Automated synthesis may also be carried out on machines such as the 431A peptide synthesizer (ABI). A protein or portion thereof may be purified by preparative high performance liquid chromatography and its composition confirmed by amino acid analysis or by sequencing (Creighton (1984) Proteins, Structures and Molecular Properties, W H Freeman, New York N.Y.).

5. Antibody Development

Polyclonal Antibody Preparations

Polyclonal antibodies against recombinant proteins are raised in rabbits (Green Mountain Antibodies, Burlington, Vt.). Briefly, two New Zealand rabbits are immunized with 0.1 mg of antigen in complete Freund's adjuvant. Subsequent immunizations are carried out using 0.05 mg of antigen in incomplete Freund's adjuvant at days 14, 21 and 49. Bleeds are collected and screened for recognition of the antigen by solid phase ELISA and western blot analysis. The IgG fraction is separated by centrifugation at 20,000×g for 20 minutes followed by a 50% ammonium sulfate cut. The pelleted protein is resuspended in 5 mM Tris and separated by ion exchange chromatography. Fractions are pooled based on IgG content. Antigen-specific antibody is affinity purified using Pierce AminoLink resin coupled to the appropriate antigen.

Isolation of Antibody Fragments Directed Against CCATs from a Library of scFvs

Naturally occurring V-genes isolated from human PBLs are constructed into a library of antibody fragments which contain reactivities against CCAT to which the donor may or may not have been exposed (see e.g., U.S. Pat. No. 5,885,793 incorporated herein by reference in its entirety).

Rescue of the Library: A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100.mu.g/ml of ampicillin (2.times.TY-AMP-GLU) and grown to an O.D. of 0.8 with shaking. Five ml of this culture is used to innoculate 50 ml of 2.times.TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100.mu.g/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100.mu.g ampicillin/ml and 25.mu.g kanamycin/ml (2×TY-AMP-KAN) and grown overnight, shaking at 37° C. Phagre particles are purified and concentrated from the culture medium by two PEG-precipitations (Sambrook et al., 2001), resuspended in 2 ml PBS and passed through a 0.45.mu.m filter (Minisart NML; Sartorius) to give a final concentration of approximately 1013 transducing units/ml (ampicillin-resistant clones).

Panning of the Library: Immunotubes (Nunc) are coated overnight in PBS with 4 ml of either 100.mu.g/ml or 10.mu.g/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phages are then used to infect 10 ml of mid-log *E. coli* TG1 by incubating eluted phage with bacteria for 30 minutes at 37° C. The *E. coli* are then plated on TYE plates containing 1% glucose and 100.mu.g/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders: Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10.mu.g/ml of the polypeptide of the present invention in 50 mM bicarbonate pH 9.6. Clones positive in ELISA are further characterized by PCR fingerprinting (see, e.g., PCT publication WO 92/01047) and then by sequencing.

Monoclonal Antibody Generation i) Materials:

1) Complete Media No Sera (CMNS) for washing of the myeloma and spleen cells; Hybridoma medium CM-HAT {Cell Mab (BD), 10% FBS (or HS); 5% Origen HCF (hybridoma cloning factor) containing 4 mM L-glutamine and antibiotics} to be used for plating hybridomas after the fusion.

2) Hybridoma medium CM-HT (NO AMINOPTERIN) (Cell Mab (BD), 10% FBS 5% Origen HCF containing 4 mM L-glutamine and antibiotics) to be used for fusion maintenance are stored in the refrigerator at 4-6° C. The fusions are fed on days 4, 8, and 12, and subsequent passages. Inactivated and pre-filtered commercial Fetal Bovine serum (FBS) or Horse Serum (HS) are thawed and stored in the refrigerator at 4° C. and must be pretested for myeloma growth from single cells.

3) The L-glutamine (200 mM, 100× solution), which is stored at −20° C. freezer, is thawed and warmed until completely in solution. The L-glutamin is dispensed into media to supplement growth. L-glutamin is added to 2 mM for myelomas, and 4 mM for hybridoma media. Further the Penicillin, Streptomycin, Amphotericin (antibacterial-antifungal stored at −20° C.) is thawed and added to Cell Mab Media to 1%.

4) Myeloma growth media is Cell Mab Media (Cell Mab Media, Quantum Yield from BD is stored in the refrigerator at 4° C. in the dark) which are added L-glutamine to 2 mM and antibiotic/antimycotic solution to 1% and is called CMNS.

5) 1 bottle of PEG 1500 in Hepes (Roche, NJ)

6) 8-Azaguanine is stored as the dried powder supplied by SIGMA at −700° C. until needed. Reconstitute 1 vial/500 ml of media and add entire contents to 500 ml media (eg. 2 vials/liter).

7) Myeloma Media is CM which has 10% FBS (or HS) and 8-Aza (1×) stored in the refrigerator at 4° C.

8) Clonal cell medium D (Stemcell, Vancouver) contains HAT and methyl cellulose for semi-solid direct cloning from the fusion. This comes in 90 ml bottles with a CoA and must be "melted at 37° C. in a waterbath in the morning of the day of the fusion. Loosen the cap and leave in CO2 incubator to sufficiently gas the medium D and bring the pH down.

9) Hybridoma supplements HT [hypoxanthine, thymidine] are to be used in medium for the section of hybridomas and maintenace of hybridomas through the cloning stages respectively.

10) Origen HCF can be obtained directly from Igen and is a cell supernatant produced from a macrophage-like cell-line. It can be thawed and aliqouted to 15 ml tubes at 5 ml per tube and stored frozen at −20° C. Positive Hybridomas are fed HCF through the first subcloning and are gradually weaned. It is not necessary to continue to supplement unless you have a particularly difficult hybridoma clone. This and other additives have been shown to be more effective in promoting new hybridoma growth than conventional feeder layers.

ii) Procedure

To generate monoclonal antibodies, mice are immunized with 5-50 ug of antigen either intra-peritoneally (i.p.) or by intravenous injection in the tail vein (i.v.). Typically, the antigen used is a recombinant protein that is generated as described above. The primary immunization takes place 2 months prior to the harvesting of splenocytes from the mouse and the immunization is typically boosted by i.v. injection of 5-50 ug of antigen every two weeks. At least one week prior to expected fusion date, a fresh vial of myeloma cells is thawed and cultured. Several flasks at different densities are maintained in order that a culture at the optimum density is ensured at the time of fusion. The optimum density is determined to be $3-6\times10^5$ cells/ml. Two to five days before the scheduled fusion, a final immunization is administered of ~5 ug of antigen in PBS i.p. or i.v.

Myeloma cells are washed with 30 ml serum free media by centrifugation at 500 g at 4° C. for 5 minutes. Viable cell density is determined in resuspended cells using hemocytometry and vital stains. Cells resuspended in complete growth medium are stored at 37° C. during the preparation of splenocytes. Meanwhile, to test aminopterin sensitivity, $1\times10^6$ myeloma cells are transferred to a 15 ml conical tube and centrifuged at 500 g at 4° C. for 5 minutes. The resulting pellet is resuspended in 15 ml of HAT media and cells plated at 2 drops/well on a 96 well plate.

To prepare splenocytes from immunized mice, the animals are euthanised and submerged in 70% ETOH. Under sterile conditions, the spleen is surgically removed and placed in 10 ml of RPMI medium supplemented with 20% fetal calf serum in a Petri dish. Cells are extricated from the spleen by infusing the organ with medium >50 times using a 21 g syringe.

Cells are harvested and washed by centrifugation (at 500 g at 4° C. for 5 minutes) with 30 ml of medium. Cells are resuspended in 10 ml of medium and the density of viable cells determined by hemocytometry using vital stains. The splenocytes are mixed with myeloma cells at a ratio of 5:1 (spleen cells: myeloma cells). Both the myeloma and spleen cells are washed 2 more times with 30 ml of RPMI-CMNS. Spin at 800 rpm for 12 minutes.

Supernatant is removed and cells are resuspended in 5 ml of RPMI-CMNS and are pooled to fill volume to 30 ml and spin down as before. Then, the pellet is broken up by gently tapping on the flow hood surface and resuspended in 1 ml of BMB REG1500 (prewarmed to 37° C.) dropwise with 1 cc needle over 1 minute.

RPMI-CMNS to the PEG cells and RPMI-CMNS are added to slowly dilute out the PEG. Cells are centrifuged and diluted in 5 ml of Complete media and 95 ml of Clonacell Medium D (HAT) media (with 5 ml of HCF). The cells are plated out 10 ml per small petri plate.

Myeloma/HAT control. P is prepared as follows: dilute about 1000 P3X63 Ag8.653 myeloma cells into 1 ml of medium D and transfer into a single well of a 24 well plate. Plates are placed in incubator, with two plates inside of a large petri plate, with an additional petri plate full of distilled water, for 10-18 days under 5% CO2 overlay at 37° C. Clones are picked from semisolid agarose into 96 well plates containing 150-200 ul of CM-HT. Supernatants are screened 4 days later in ELISA, and positive clones are moved up to 24 well plates. Heavy growth will require changing of the media at day 8 (+/−150 ml). One should further decrease the HCF to 0.5% (gradually-2%, then 1%, then 0.5%) in the cloning plates.

For further references see Kohler G, and C. Milstein Continuous cultures of fused cells secreting antibody of pre-defined specificity. 1975. Nature 256: 495-497; Lane, R. D. A short duration polyethylene glycol fusion technique for increasing production of monoclonal antibody-secreting hybridomas. 1985. J. Immunol. Meth. 81:223-228;

Harlow, E. and D. Lane. Antibodies: A laboratory manual. Cold Spring Harbour Laboratory Press. 1988; Kubitz, D. The Scripps Research Institute. La Jolla. Personal Communication; Zhong, G., Berry, J. D., and Choukri, S. (1996) Mapping epitopes of *Chlamydia trachomatis* neutralizing monoclonal antibodies using phage random peptide libraries. J. Indust. Microbiol. Biotech. 19, 71-76; Berry, J. D., Licea, A., Popkov, M., Cortez, X., Fuller, R., Elia, M., Kerwin, L., and C. F. Barbas III. (2003) Rapid monoclonal antibody generation via dendritic cell targeting in vivo. Hybridoma and Hybridomics 22 (1), 23-31.

6. mRNA Expression

Validation in Tissues by Taqman

Expression of mRNA is quantitated by RT-PCR using Taq-Man® technology. The Taqman system couples a 5' fluorogenic nuclease assay with PCR for real time quantitation. A probe is used to monitor the formation of the amplification product.

Total RNA is isolated from cancer model cell lines using the RNEasy Kit® (Qiagen) per manufacturer's instructions and included DNase treatment. Normal human tissue RNAs are acquired from commercial vendors (Ambion, Austin, Tex.; Stratagene, La Jolla, Calif., BioChain Institute, Newington, N.H.) as were RNAs from matched disease/normal tissues.

Target transcript sequences are identified for the differentially expressed peptides by searching the BlastP database. TaqMan assays (PCR primer/probe set) specific for those transcripts are identified by searching the Celera Discovery System™ (CDS) database. The assays are designed to span exon-exon borders and do not amplify genomic DNA.

The TaqMan primers and probe sequences are as designed by Applied Biosystems (AB) as part of the Assays on Demand™ product line or by custom design through the AB Assays by Design[SM] service.

RT-PCR is accomplished using AmpliTaqGold and Multi-Scribe reverse transcriptase in the One Step RT-PCR Master Mix reagent kit (AB) according to the manufacturer's instructions. Probe and primer concentrations are 250 nM and 900 nM, respectively, in a 15 µl reaction. For each experiment, a master mix of the above components is made and aliquoted into each optical reaction well. Eight nanograms of total RNA is the template. Each sample is assayed in triplicate. Quantitative RT-PCR is performed using the ABI Prism® 7900HT Sequence Detection System (SDS). Cycling parameters follow: 48° C. for 30 min. for one cycle; 95° C. for 10 min for one cycle; 95° C. for 15 sec, 60° C. for 1 min. for 40 cycles.

The SDS software calculates the threshold cycle ($C_T$) for each reaction, and $C_T$ values are used to quantitate the relative amount of starting template in the reaction. The $C_T$ values for each set of three reactions are averaged for all subsequent calculations Data are analyzed for fold difference in expression using an endogenous control for normalization and is expressed relative to a normal tissue or normal cell line reference. The choice of endogenous control is determined empirically by testing various candidates against the cell line and tissue RNA panels and selecting the one with the least variation in expression. Relative changes in expression are quantitated using the $2^{-\Delta\Delta C_T}$ Method. Livak, K. J. and Schmittgen, T. D. (2001) Methods 25: 402-408; User bulletin #2: ABI Prism 7700 Sequence Detection System.

Validation by Tissue Flow Cytometry Analysis

Post tissue processing, cells are sorted by flow cytometry known in the art to enrich for epithelial cells. Alternatively, cells isolated from lung tissue are stained directly with EpCAM (for epithelial cells) and the specific antibody to CCAT. Cell numbers and viability are determined by PI exclusion (GUAVA) for cells isolated from both normal and tumor lung tissue. A minimum of $0.5 \times 10^6$ cells are used for each analysis. Cells are washed once with Flow Staining Buffer (0.5% BSA, 0.05% NaN3 in D-PBS). To the cells, 20 ul of each antibody for CCAT are added. An additional 5 ul of EpCAM antibody conjugated to APC were added when unsorted cells are used in the experiment. Cells are incubated with antibodies for 30 minutes at 4° C. Cells are washed once with Flow Staining Buffer and either analyzed immediately on the LSR flow cytometry apparatus or fixed in 1% formaldehyde and store at 4° C. until LSR analysis. The antibodies used to detect CCAT targets are all purchased by BD Biosciences and PE-conjugated. The isotype control antibody used for these experiments is PE-conjugated mouse IgG1k.

7. Detection and Diagnosis of CCAT by Liquid Chromatography and Mass Spectrometry (LC/MS)

The proteins from cells can be prepared by methods known in the art (R. Aebersold Nature Biotechnology Volume 21 Number 6 Jun. 2003).

The differential expression of proteins in disease and healthy samples are quantitated using Mass Spectrometry and ICAT (Isotope Coded Affinity Tag) labeling, which is known in the art. ICAT is an isotope label technique that allows for discrimination between two populations of proteins, such as a healthy and a disease sample that are pooled together for experimental purposes or two acquisitions of the same sample for classification of true sample peptides from LC/MS noise artifacts. The LC/MS spectra are collected for the labeled samples and processed using the following steps:

The raw scans from the LC/MS instrument are subjected to peak detection and noise reduction software. Filtered peak lists are then used to detect 'features' corresponding to specific peptides from the original sample(s). Features are characterized by their mass/charge, charge, retention time, isotope pattern and intensity.

Similar experiments are repeated in order to increase the confidence in detection of a peptide. These multiple acquisitions are computationally aggregated into one experiment. Experiments involving healthy and disease samples used the known effects of the ICAT label to classify the peptides as originating from a particular sample or from both samples. The intensity of a peptide present in both healthy and disease samples is used to calculate the differential expression, or relative abundance, of the peptide. The intensity of a peptide found exclusively in one sample is used to calculate a theoretical expression ratio for that peptide (singleton). Expression ratios are calculated for each peptide of each replicate of the experiment (see Table 1).

Statistical tests are performed to assess the robustness of the data and select statistically significant differentials. To assess general quality of the data, one: a) ensured that similar features are detected in all replicates of the experiment; b) assessed the distribution of the log ratios of all peptides (a Gaussian is expected); c) calculated the overall pair wise correlations between ICAT LC/MS maps to ensure that the expression ratios for peptides are reproducible across the multiple replicates; d) aggregated multiple experiments in order to compare the expression ratio of a peptide in multiple diseases or disease samples.

8. Expression Validation by IHC in Tissue Sections

Tissue Sections

Paraffin embedded, fixed tissue sections are obtained from a panel of normal tissues (Adrenal, Bladder, Lymphocytes, Bone Marrow, Breast, Cerebellum, Cerebral cortex, Colon, Endothelium, Eye, Fallopian tube, Small Intestine, Heart, Kidney [glomerulus, tubule], Liver, Lung, Testes and Thyroid) as well as 30 tumor samples with matched normal adjacent tissues from pancreas, lung, colon, prostate, ovarian and breast. In addition, other tissues are selected for testing such as bladder renal, hepatocellular, pharyngeal and gastric tumor tissues. Replicate sections are also obtained from numerous tumor types (Bladder Cancer, Lung Cancer, Breast Cancer, Melanoma, Colon Cancer, Non-Hodgkins Lymphoma, Endometrial Cancer, Ovarian Cancer, Head and Neck Cancer, Prostate Cancer, Leukemia [ALL and CML] and Rectal Cancer). Sections are stained with hemotoxylin and eosin and histologically examined to ensure adequate representation of cell types in each tissue section.

An identical set of tissues will be obtained from frozen sections and are used in those instances where it is not possible to generate antibodies that are suitable for fixed sections. Frozen tissues do not require an antigen retrieval step.

Paraffin Fixed Tissue Sections

Hemotoxylin and Eosin staining of paraffin embedded, fixed tissue sections.

Sections are deparaffinized in 3 changes of xylene or xylene substitute for 2-5 minutes each. Sections are rinsed in 2 changes of absolute alcohol for 1-2 minutes each, in 95% alcohol for 1 minute, followed by 80% alcohol for 1 minute. Slides are washed well in running water and stained in Gill solution 3 hemotoxylin for 3 to 5 minutes. Following a vigorous wash in running water for 1 minute, sections are stained in Scott's solution for 2 minutes. Sections are washed for 1 min in running water then counterstained in Eosin solution for 2-3 minutes depending upon development of desired staining intensity. Following a brief wash in 95% alcohol, sections are dehydrated in three changes of absolute alcohol for 1 minute each and three changes of xylene or xylene substitute for 1-2 minutes each. Slides are coverslipped and stored for analysis.

Optimisation of Antibody Staining

For each antibody, a positive and negative control sample are generated using data from the ICAT analysis of the colon cancer cell lines/tissues. Cells are selected that are known to express low levels of a particular target as determined from the ICAT data. This cell line is the reference normal control. Similarly, a colon tumor line is selected that is determined to overexpress the target is selected.

Antigen Retrieval

Sections are deparaffinized and rehydrated by washing 3 times for 5 minutes in xylene; two times for 5 minutes in 100% ethanol; two times for 5 minutes in 95% ethanol; and once for 5 minutes in 80% ethanol. Sections are then placed in endogenous blocking solution (methanol+2% hydrogen peroxide) and incubated for 20 minutes at room temperature. Sections are rinsed twice for 5 minutes each in deionized water and twice for 5 minutes in phosphate buffered saline (PBS), pH 7.4. Alternatively, where necessary sections are deparrafinized by High Energy Antigen Retrieval as follows: sections are washed three times for 5 minutes in xylene; two times for 5 minutes in 100% ethanol; two times for 5 minutes in 95% ethanol; and once for 5 minutes in 80% ethanol. Sections are placed in a Coplin jar with dilute antigen retrieval solution (10 mM citrate acid, pH 6). The Coplin jar containing slides is placed in a vessel filled with water and microwaved on high for 2-3 minutes (700 watt oven). Following cooling for 2-3 minutes, steps 3 and 4 are repeated four times (depending on tissue), followed by cooling for 20 minutes at room temperature. Sections are then rinsed in deionized water, two times for 5 minutes, placed in modified endogenous oxidation blocking solution (PBS+2% hydrogen peroxide) and rinsed for 5 minutes in PBS.

Blocking and Staining

Sections are blocked with PBS/1% bovine serum albumin (PBA) for 1 hour at room temperature followed by incubation in normal serum diluted in PBA (2%) for 30 minutes at room temperature to reduce non-specific binding of antibody. Incubations are performed in a sealed humidity chamber to prevent air-drying of the tissue sections. (The choice of blocking serum is the same as the species of the biotinylated secondary antibody). Excess antibody is gently removed by shaking and sections covered with primary antibody diluted in PBA and incubated either at room temperature for 1 hour or overnight at 4° C. (Care is taken that the sections do not touch during incubation). Sections are rinsed twice for 5 minutes in PBS, shaking gently. Excess PBS is removed by gently shaking. The sections are covered with diluted biotinylated secondary antibody in PBA and incubated for 30 minutes to 1 hour at room temperature in the humidity chamber. If using a monoclonal primary antibody, addition of 2% rat serum is used to decrease the background on rat tissue sections. Following incubation, sections are rinsed twice for 5 minutes in PBS, shaking gently. Excess PBS is removed and sections incubated for 1 hour at room temperature in Vectastain ABC reagent (as per kit instructions). The lid of the humidity chamber is secured during all incubations to ensure a moist environment. Sections are rinsed twice for 5 minutes in PBS, shaking gently.

Develop and Counterstain

Sections are incubated for 2 minutes in peroxidase substrate solution that is made up immediately prior to use as follows:

10 mg diaminobenzidine (DAB) dissolved in 10 ml 50 mM sodium phosphate buffer, pH 7.4.
12.5 microliters 3% CoCl2/NiCl2 in deionized water
1.25 microliters hydrogen peroxide Slides are rinsed well three times for 10 min in deionized water and counterstained with 0.01% Light Green acidified with 0.01% acetic acid for 1-2 minutes depending on intensity of counterstain desired.

Slides are rinsed three times for 5 minutes with deionized water and dehydrated two times for 2 minutes in 95% ethanol; two times for 2 minutes in 100% ethanol; and two times for 2 minutes in xylene. Stained slides are mounted for visualization by microscopy.

9. IHC Staining of Frozen Tissue Sections

Fresh tissues are embedded carefully in OCT in plastic mold, without trapping air bubbles surrounding the tissue. Tissues are frozen by setting the mold on top of liquid nitrogen until 70-80% of the block turns white at which point the mold is placed on dry ice. The frozen blocks were stored at $-80°$ C. Blocks are sectioned with a cryostat with care taken to avoid warming to greater than $-10°$ C. Initially, the block is equilibrated in the cryostat for about 5 minutes and 6-10 mm sections are cut sequentially. Sections are allowed to dry for at least 30 minutes at room temperature. Following drying, tissues are stored at 4° C. for short term and $-80°$ C. for long term storage.)

Sections are fixed by immersing in acetone jar for 1-2 minutes at room temperature, followed by drying at room temp. Primary antibody is added (diluted in 0.05 M Tris-saline [0.05 M Tris, 0.15 M NaCl, pH 7.4], 2.5% serum) directly to the sections by covering the section dropwise to cover the tissue entirely. Binding is carried out by incubation a chamber for 1 hour at room temperature. Without letting the sections dry out, the secondary antibody (diluted in Tris-saline/2.5% serum) is added in a similar manner to the primary and incubated as before (at least 45 minutes).

Following incubation, the sections are washed gently in Tris-saline for 3-5 minutes and then in Tris-saline/2.5% serum for another 3-5 minutes. If a biotinylated primary antibody is used, in place of the secondary antibody incubation, slides are covered with 100 ul of diluted alkaline phosphatase conjugated streptavidin, incubated for 30 minutes at room temperature and washed as above. Sections are incubated with alkaline phosphatase substrate (1 mg/ml Fast Violet; 0.2 mg/ml Napthol AS-MX phosphate in Tris-Saline pH 8.5) for 10-20 minutes until the desired positive staining is achieved at which point the reaction is stopped by washing twice with Tris-saline. Slides are counter-stained with Mayer's hematoxylin for 30 seconds and washed with tap water for 2-5 minutes. Sections are mounted with Mount coverslips and mounting media.

10. Assay for Antibody Dependent Cellular Cytotoxicity

Cultured tumor cells are labeled with 100 µCi 51Cr for 1 hour; Livingston, P. O., Zhang, S., Adluri, S., Yao, T.-J., Graeber, L., Ragupathi, G., Helling, F., & Fleischer, M. (1997). Cancer Immunol. Immunother. 43, 324-330. After being washed three times with culture medium, cells are resuspended at $10^5$/ml, and 100 µl/well are plated onto 96-well round-bottom plates. A range of antibody concentrations are applied to the wells, including an isotype control together with donor peripheral blood mononuclear cells that are plated at a 100:1 and 50:1 ratio. After an 18-h incubation at 37° C., supernatant (30 µl/well) is harvested and transferred onto Lumaplate 96 (Packard), dried, and read in a Packard Top-Count NXT γ counter. Each measurement is carried out in triplicate. Spontaneous release is determined by cpm of tumor cells incubated with medium and maximum release by cpm of tumor cells plus 1% Triton X-100 (Sigma). Specific lysis is defined as: % specific lysis=[(experimental release–spontaneous release)/(maximum release–spontaneous release)]×100. The percent ADCC is expressed as peak specific lysis postimmune subtracted by preimmune percent specific lysis. A doubling of the ADCC to >20% is considered significant.

11. Assay for Complement Dependent Cytotoxicity

Chromium release assays to assess complement-mediated cytotoxicity are performed for each patient at various time points; Dickler, M. N., Ragupathi, G., Liu, N. X., Musselli, C., Martino, D. J., Miller, V. A., Kris, M. G., Brezicka, F. T., Livingston, P. O. & Grant, S. C. (1999) Clin. Cancer Res. 5, 2773-2779. Cultured tumor cells are washed in FCS-free media two times, resuspended in 500 µl of media, and incubated with 100 µCi $^{51}$Cr per 10 million cells for 2 h at 37° C. The cells are then shaken every 15 min for 2 h, washed 3 times in media to achieve a concentration of approximately 20,000 cells/well, and then plated in round-bottom plates. The plates contain either 50 µl cells plus 50 µl monoclonal antibody, 50 µl cells plus serum (pre- and posttherapy), or 50 µl cells plus mouse serum as a control. The plates are incubated in a cold room on a shaker for 45 min. Human complement of a 1:5 dilution (resuspended in 1 ml of ice-cold water and diluted with 3% human serum albumin) is added to each well at a volume of 100 µl. Control wells include those for maximum release of isotope in 10% Triton X-100 (Sigma) and for spontaneous release in the absence of complement with medium alone. The plates are incubated for 2 h at 37° C., centrifuged for 3 min, and then 100 µl of supernatant is removed for radioactivity counting. The percentage of specific lysis is calculated as follows: % cytotoxicity=[(experimental release–spontaneous release)/(maximum release–spontaneous release)]×100. A doubling of the CDC to >20% is considered significant.

12. In Vitro Assays In Cell Lines

Lipofectamine is purchased from Invitrogen (Carlsbad, Calif.) and GeneSilencer from Gene Therapy Systems (San Diego, Calif.). Synthetic siRNA oligonucleotides are from Dharmacon (Lafayette, Colo.), Qiagen (Valencia, Calif.) or Ambion (Austin, Tex.) RNeasy 96 Kit is purchased from Qiagen (Valencia, Calif.). Apop-one homogeneous caspase-3/7 kit and CellTiter 96 AQueous One Solution Cell Proliferation Assay are both purchased from Promega (Madison, Wis.). Function blocking antibodies are purchased from Chemicon (Temecula, Calif.), Biotrend (Cologne, Germany) or Alexis Corporation (San Diego, Calif.). Cell invasion assay kits from purchased from Chemicon (Temecula, Calif.). RiboGreen RNA Quantitation Kit is purchased from Molecular probes (Eugene, Oreg.).

RNAi

RNAi is performed by using Smartpools (Dharmacon), 4—for Silencing siRNA duplexes (Qiagen) or scrambled negative control siRNA (Ambion). Transient transfections are carried out in triplicate by using either Lipofectamine 2000 from Invitrogen (Carlsbad, Calif.) or by using GeneSilencer from Gene Therapy Systems (San Diego, Calif.) in methods described below. 1 to 4 days after transfections, total RNA is isolated by using the RNeasy 96 Kit (Qiagen) according to manufacturer's instructions and expression of mRNA is quantitated by using TaqMan technology. Protein expression levels are examined by flow cytometry and apoptosis and proliferation assays are performed daily using Apop-one homogeneous caspase-3/7 kit and CellTiter 96 AQueous One Solution Cell Proliferation Assay (see protocols below).

i) RNAi Transfections—Lipofectamine 2000

Transient transfections are carried out on sub-confluent colon cancer cell lines as previously described. Elbashir, S. M. et al. (2001) Nature 411: 494-498; Caplen, N. J. et al. (2001) Proc Natl Acad Sci USA 98: 9742-9747; Sharp, P. A. (2001) Genes and Development 15: 485-490. Synthetic RNA to gene of interest or scrambled negative control siRNA is transfected using lipofectamine according to manufacturer's instructions. Cells are plated in 96 well plates in antibiotics free medium. The next day, the transfection reagent and siRNA are prepared for transfections as follows: Each 0.1-1 ul of lipofectamine 2000 and 10-150 mM siRNA are resuspended 25 ul serum-free media and incubated at room temperature for 5 minutes. After incubation, the diluted siRNA and the lipofectamine 2000 are combined and incubated for 20 minutes at room temperature. The cells are then washed and the combined siRNA-Lipofectamine 2000 reagent added. After further 4 hours incubation, 50 ul serum containing medium is added to each well. 1 and 4 days after transfection, expression of mRNA is quantitated by RT-PCR using TaqMan technology and protein expression levels are examined by flow cytometry. Apoptosis and proliferation assays are performed daily using Apop-one homogeneous caspase-3/7 kit and CellTiter 96 AQueous One Solution Cell Proliferation Assay (see protocols below).

ii) RNAi Transfections—GeneSilencer

Transient transfections are carried out on sub-confluent colon cancer cell lines as previously described. Elbashir, S. M. et al. (2001) Nature 411: 494-498; Caplen, N. J. et al. (2001) Proc Natl Acad Sci USA 98: 9742-9747; Sharp, P. A. (2001) Genes and Development 15: 485-490. Synthetic RNA to gene of interest or scrambled negative control siRNA is transfected using GeneSilencer according to manufacturer's instructions. Cells are plated in 96 well plates in antibiotics free medium. The next day, the transfection reagent and the synthetic siRNA are prepared for transfections as follows: predetermined amount of Gene Silencer is diluted in serum-free media to a final volume of 20 ul per well. After resuspending 10-150 mM siRNA in 20 ul serum-free media, the reagents are combined and incubated at room temperature for 5-20 minutes. After incubation, the siRNA-Gene Silencer reagent is added to each well and incubated in a 37° C. incubator for 4 hours before an equal volume of serum containing media is added back to the cultured cells. The cells are then incubated for 1 to 4 days before mRNA, protein expression and effects on apoptosis and proliferation are examined.

Testing of Function Blocking Antibodies

Sub-confluent colon cancer cell lines are serum-staved overnight. The next day, serum-containing media is added back to the cells in the presence of 5-50 ng/ml of function blocking antibodies. After 2 or 5 days incubation at 37° C. 5% $CO_2$, antibody binding is examined by flow cytometry and apoptosis and proliferation are examined by using protocols described below.

Apoptosis

Apoptosis assay is performed by using the Apop-one homogeneous caspase-3/7 kit from Promega. Briefly, the caspase-3/7 substrate is thawed to room temperature and diluted 1:100 with buffer. The diluted substrate is then added 1:1 to cells, control or blank. The plates are then placed on a plate shaker for 30 minutes to 18 hours at 300-500 rpm. The fluorescence of each well is then measured at using an excitation wavelength of 485+/−20 nm and an emission wavelength of 530+/−25 nm.

Proliferation

Proliferation assay is performed by using the CellTiter 96 AQueous One Solution Cell Proliferation Assay kit from Promega. 20 ul of CellTiter 96 AQueous One Solution is added to 100 ul of culture medium. The plates are then incubated for 1-4 hours at 37° C. in a humidified 5% $CO_2$ incubator. After incubation, the change in absorbance is read at 490 nm.

The target corresponding to, for example, protein number 49 (protein SEQ ID NO:49/transcript SEQ ID NO:112) gives a positive result for colon cancer in a proliferation assay.

Cell Invasion

Cell invasion assay is performed by using the 96 well cell invasion assay kit available from Chemicon. After the cell invasion chamber plates are adjusted to room temperature, 100 ul serum-free media is added to the interior of the inserts. 1-2 hours later, cell suspensions of $1 \times 10^6$ cells/ml are prepared. Media is then carefully removed from the inserts and 100 ul of prepared cells are added into the insert +/−0 to 50 ng function blocking antibodies. The cells are pre-incubated for 15 minutes at 37° C. before 150 ul of media containing 10% FBS is added to the lower chamber. The cells are then incubated for 48 hours at 37° C. After incubation, the cells from the top side of the insert are discarded and the invasion chamber plates are then placed on a new 96-well feeder tray containing 150 ul of pre-warmed cell detachment solution in the wells. The plates are incubated for 30 minutes at 37° C. and are periodically shaken. Lysis buffer/dye solution (4 ul CyQuant Dye/300 ul 4× lysis buffer) is prepared and added to each well of dissociation buffer/cells on feeder tray. The plates are incubated for 15 minutes at room temperature before 150 ul is transferred to a new 96-well plate. Fluorescence of invading cells is then read at 480 excitation and 520 emission.

Receptor Internalization

For quantification of receptor internalization, ELISA assays are performed essentially as described by Daunt et al. Daunt, D. A., Hurtz, C., Hein, L., Kallio, J., Feng, F., and Kobilka, B. K. (1997) Mol. Pharmacol. 51, 711-720. The cell lines are plated at $6 \times 10^5$ cells per in a 24-well tissue culture dishes that have previously been coated with 0.1 mg/ml poly-L-lysine. The next day, the cells are washed once with PBS and incubated in DMEM at 37° C. for several minutes. Agonist to the cell surface target of interest is then added at a pre-determined concentration in prewarmed DMEM to the wells. The cells are then incubated for various times at 37° C. and reactions are stopped by removing the media and fixing the cells in 3.7% formaldehyde/TBS for 5 min at room temperature. The cells are then washed three times with TBS and nonspecific binding blocked with TBS containing 1% BSA for 45 min at room temperature. The first antibody is added at a pre-determined dilution in TBS/BSA for 1 h at room temperature. Three washes with TBS followed, and cells are briefly reblocked for 15 min at room temperature. Incubation with goat anti-mouse conjugated alkaline phosphatase (Bio-Rad) diluted 1:1000 in TBS/BSA is carried out for 1 h at room temperature. The cells are washed three times with TBS and a colorimetric alkaline phosphatase substrate is added. When the adequate color change is reached, 100-μl samples are taken for colorimetric readings.

mRNA Expression

Expression of mRNA is quantitated by RT-PCR using Taq-Man® technology. Total RNA is isolated from cancer model cell lines using the RNEasy 96 kit (Qiagen) per manufacturer's instructions and included DNase treatment. Target transcript sequences are identified for the differentially expressed peptides by searching the BlastP database. TaqMan assays (PCR primer/probe set) specific for those transcripts are identified by searching the Celera Discovery System™ (CDS) database. The assays are designed to span exon-exon borders and do not amplify genomic DNA. The TaqMan primers and probe sequences are as designed by Applied Biosystems (AB) as part of the Assays on Demand™ product line or by custom design through the AB Assays by Design$^{SM}$ service. RT-PCR is accomplished using AmpliTaqGold and MultiScribe reverse transcriptase in the One Step RT-PCR Master Mix reagent kit (AB) according to the manufacturers instructions. Probe and primer concentrations are 900 nM and 250 nM, respectively, in a 25 μl reaction. For each experiment, a master mix of the above components is made and aliquoted into each optical reaction well. 5 μl of total RNA is the template. Each sample is assayed in triplicate. Quantitative RT-PCR is performed using the ABI Prism® 7900HT Sequence Detection System (SDS). Cycling parameters follow: 48° C. for 30 min. for one cycle; 95° C. for 10 min for one cycle; 95° C. for 15 sec, 60° C. for 1 min. for 40 cycles.

The SDS software calculates the threshold cycle ($C_T$) for each reaction, and $C_T$ values are used to quantitate the relative amount of starting template in the reaction. The $C_T$ values for each set of three reactions are averaged for all subsequent calculations.

Total RNA is quantitated by using RiboGreen RNA Quantitation Kit according to manufacturer's instructions and the % mRNA expression is calculated using total RNA for normalization. % knockdown is then calculated relative to the no addition control.

13. In Vivo Studies by Using Antibodies

Treatment of Colon Cancer Cells with Monoclonal Antibodies colon cancer cells are seeded at a density of 4×10$^4$ cells per well in 96-well microtiter plates and allowed to adhere for 2 hours. The cells are then treated with different concentrations of anti-CCAT monoclonal antibody (Mab) or irrelevant isotype matched (anti-rHuIFN-.gamma.Mab) at 0.05, 0.5 or 5.0 mug/ml. After a 72 hour incubation, the cell monolayers are stained with crystal violet dye for determination of relative percent viability (RPV) compared to control (untreated) cells. Each treatment group consists of replicates. Cell growth inhibition is monitored.

Treatment of NIH 3T3 Cells Overexpression CCAT Protein with Monoclonal Antibodies.

NIH 3T3 expressing CCAT protein are treated with different concentrations of anti-CCAT MAbs. Cell growth inhibition is monitored.

In Vivo Treatment of NIH 3T3 Cells Overexpressing CCAT with Anti-CCAT Monoclonal Antibodies.

NIH 3T3 cells transfected with either a CCAT expression plasmid or the neo-DHFR vector are injected into nu/nu (athymic) mice subcutaneously at a dose of 10$^6$ cells in 0.1 ml of phosphate-buffered saline. On days 0, 1, 5 and every 4 days thereafter, 100 mug (0.1 ml in PBS) of either an irrelevant or anti-CCAT monoclonal antibody of the IG2A subclass is injected intraperitoneally. Tumor occurrence and size are monitored for 1 month period of treatment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. A method of diagnosing colon cancer in an individual, the method comprising detecting an elevated level of CI-MPR protein in a colon sample from the individual relative to a control CI-MPR protein level of a non-cancerous colon sample, wherein the elevated level of CI-MPR protein indicates that the individual has colon cancer, and wherein the amino acid sequence of the CI-MPR protein comprises SEQ ID NO:16.

2. The method of claim 1, wherein the elevated level of CI-MPR protein is detected by contacting the colon sample with an isolated antibody that selectively binds to the CI-MPR protein and detecting binding of the antibody to the CI-MPR protein.

3. The method of claim 2, wherein the antibody is coupled to a detectable substance.

* * * * *